United States Patent
Segal et al.

(10) Patent No.: US 9,597,394 B2
(45) Date of Patent: *Mar. 21, 2017

(54) LECTIN COMPOSITIONS AND METHODS FOR MODULATING AN IMMUNE RESPONSE TO AN ANTIGEN

(71) Applicant: OpSaniTx LLC, Racine, WI (US)

(72) Inventors: Andrew H. Segal, Cambridge, MA (US); Elihu Young, Sharon, MA (US)

(73) Assignee: OpSaniTx LLC, Racine, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,357

(22) Filed: Jan. 26, 2015

(65) Prior Publication Data

US 2015/0297715 A1 Oct. 22, 2015

Related U.S. Application Data

(60) Continuation of application No. 10/666,833, filed on Sep. 19, 2003, now Pat. No. 8,940,307, which is a division of application No. 10/645,000, filed on Aug. 20, 2003, now abandoned.

(60) Provisional application No. 60/404,823, filed on Aug. 20, 2002, provisional application No. 60/487,407, filed on Jul. 15, 2003.

(51) Int. Cl.
| | | |
|---|---|---|
| *A61K 39/39* | (2006.01) | |
| *A61K 39/145* | (2006.01) | |
| *C07K 14/535* | (2006.01) | |
| *A61K 38/00* | (2006.01) | |
| *A61K 39/00* | (2006.01) | |

(52) U.S. Cl.
CPC .......... *A61K 39/39* (2013.01); *A61K 39/0011* (2013.01); *A61K 39/145* (2013.01); *C07K 14/535* (2013.01); *A61K 38/00* (2013.01); *A61K 2039/5152* (2013.01); *A61K 2039/55516* (2013.01); *A61K 2039/55522* (2013.01); *A61K 2039/55527* (2013.01); *C07K 2319/00* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 5,376,367 A | 12/1994 | Williams | 424/85.2 |
| 5,866,131 A | 2/1999 | Ramshaw et al. | 424/186.1 |
| 5,891,432 A | 4/1999 | Hoo | 424/93.21 |
| 6,015,709 A | 1/2000 | Natesan | 435/366 |
| 6,277,368 B1 | 8/2001 | Hiserodt et al. | 424/93.21 |
| 6,277,369 B1 | 8/2001 | Gordon et al. | 424/93.21 |
| 6,911,317 B2 | 6/2005 | Meyers et al. | 435/15 |
| 7,629,440 B2 | 12/2009 | Segal et al. | 530/350 |
| 8,940,307 B2 * | 1/2015 | Segal | A61K 39/145 424/1.41 |
| 2003/0091640 A1 | 5/2003 | Ramanathan et al. | 424/486 |
| 2003/0129197 A1 | 7/2003 | Fiers et al. | 424/186.1 |
| 2003/0206917 A1 | 11/2003 | Tykocinski et al. | 424/185.1 |
| 2004/0122217 A1 | 6/2004 | Segal et al. | 530/395 |
| 2004/0126357 A1 | 7/2004 | Segal et al. | 424/85.1 |
| 2004/0126793 A1 | 7/2004 | Segal et al. | 435/6 |
| 2004/0142889 A1 | 7/2004 | Segal et al. | 514/44 |
| 2004/0151728 A1 | 8/2004 | Segal et al. | 424/184.1 |
| 2004/0180389 A1 | 9/2004 | Segal et al. | 435/7.23 |
| 2004/0241137 A1 | 12/2004 | Segal et al. | 424/85.1 |
| 2007/0269455 A1 | 11/2007 | Segal | 424/204.1 |

FOREIGN PATENT DOCUMENTS

| | | | | |
|---|---|---|---|---|
| CA | 2375619 | 12/2000 | | C07K 14/535 |
| WO | WO 99/61051 | 12/1999 | | A61K 39/00 |

OTHER PUBLICATIONS

Barker, E., et al., "Effect of a Chimeric Anti-Ganglioside $G_{D2}$ Antibody on Cell-mediated Lysis of Human Neuroblastoma Cells," *Cancer Research*, 51:144-149, 1991.

Batova, A., et al., "The Ch 14.18-GM-CSF Fusion Protein Is Effective at Mediating Antibody-dependent Cellular Cytotoxicity and Complement-dependent Cytotoxicity in Vitro," *Clinical Cancer Research*, 5:4259-4263, (1999).

Deliyannis, G., et al., "A fusion DNA vaccine that targets antigen-presenting cells increases protection from viral challenge," *PNAS*, 97(12):6676-6680, 2000.

Faulkner, L., et al., "IL-2 linked to a peptide from influenza hemagglutinin enhances T cell activation by affecting the antigen-presentation function of bone marrow-derived dendritic cells," *International Immunology*, 13( 6): 713-721, 2001.

Frankel, A., et al., "IL2-Ricin Fusion Toxin Is Selectively Cytotoxic in Vitro to IL2 Receptor-Bearing Tumor Cells," *Bioconjugate Chem.*, 6:666-672, 1995.

Gillies, S.D., et al., "Expression of Genetically Engineered Immunoconjugates of Lymphotoxin and a Chimeric Anti-Ganglioside GD2 Antibody," *Hybridoma*, 10(3):347-356, 1991.

Gillies, S.D., et al., "Antibody-targeted interleukin 2 stimulates T-cell killing ofautologous tumor cells," *Proc. Natl. Acad. Sci. USA*, 89:1428-1432, 1992.

\* cited by examiner

*Primary Examiner* — Benjamin P Blumel
(74) *Attorney, Agent, or Firm* — Sunstein Kann Murphy & Timbers LLP

(57) ABSTRACT

The present invention provides a fusion polypeptide which can bind to a cell surface binding moiety (e.g., a carbohydrate) and serve as a ligand for a cell surface polypeptide, as well as a vector comprising a nucleic acid encoding for such a fusion polypeptide, and a host cell comprising such nucleic acid. The present invention also provides a composition comprising an antigen bearing target and such a fusion polypeptide, as well as a composition comprising a virus or a cell and such a fusion polypeptide. The present invention further relates to a method of modulating an immune response in an animal using such compositions.

8 Claims, No Drawings

LECTIN COMPOSITIONS AND METHODS FOR MODULATING AN IMMUNE RESPONSE TO AN ANTIGEN

RELATED APPLICATIONS

The present application is a divisional application to U.S. Utility application with Ser. No. 10/645,000, filed Aug. 20, 2003, which claims priority to U.S. Provisional applications 60/404,823, filed Aug. 20, 2002 and 60/487,407, filed Jul. 15, 2003, the entirety of each is hereby incorporated by reference.

BACKGROUND OF THE INVENTION

Typically, the specific modulation of an immune response to an antigen in a subject requires the administration of another substance, e.g. an adjuvant, in admixture with the antigen in order to initiate and/or direct the modulation. Traditional adjuvants, though, have a number of weaknesses. For example, many are crude, heterogeneous preparations. In addition, many are relatively weak immunomodulators, and some cause severe local inflammation that is unacceptable in humans. Purified soluble polypeptides, such as cytokines, have some advantages over crude adjuvants, but their value is limited because they diffuse away from the antigen upon administration. While certain cell-surface molecules may be potential immunomodulators as components of cell-based vaccines, their application generally involves gene transfer into the cells, which is often problematic.

The invention therefore fills heretofore unmet needs by providing molecules that can bind to antigen bearing targets, such as cells, viruses, and isolated antigens, and that can serve as immunomodulators when administered with an antigen bearing target. In addition, the invention provides compositions comprising these molecules and related methods. The compositions and methods of the invention are also useful for other applications, e.g. any application in which it is desirable to attach a biological effeector, such as a polypeptide ligand for a cell surface receptor, to a target structure, such as a virus or a cell.

SUMMARY OF THE INVENTION

The present invention relates to a multifunctional molecule, e.g. a fusion polypeptide, comprising a first part which is capable of binding to an antigen bearing target and a second part which is capable of binding to a cell. In a preferred embodiment, the first part is a first cell surface binding moiety and the second part is a second cell surface binding moiety. In this embodiment, the first cell surface binding moiety can attach to a virus or cell, e.g. a tumor cell, which comprises an antigen. It is also particularly preferred that the second cell surface binding moiety can bind to a cell-surface polypeptide, e.g. a non-immunoglobulin polypeptide, of an antigen presenting cell (APC). Thus, in some embodiments, a multifunctional molecule of the invention can serve as a bridge or link between an antigen bearing target and an APC.

As used herein an "antigen bearing target" is an entity which comprises an antigen. As used herein an "antigen bearing target" includes, for example, a whole cell which expresses an antigen a cell fraction comprising an antigen, a membrane fraction comprising an antigen, a virus comprising an antigen, a viral particle comprising an antigen, or an antigen, e.g. a polypeptide antigen, which may be free of any other cell-derived or virus-derived material. Cellular fractions may be prepared using methods known to those of skill in the art such as those taught in *Cell Biology A Laboratory Handbook* (Academic Press 1994 Editor J. E. Cells ISBN 0-12-164715-3)

The term "antigen" as used herein refers to a molecule against which a subject can initiate a humoral and/or cellular immune response. Antigens can be any type of biologic molecule including, for example, simple intermediary metabolites, sugars, lipids, and hormones as well as macromolecules such as complex carbohydrates, phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens. In the compositions and methods of the invention, it is preferred that the antigen is a polypeptide, e.g., one comprising at least seven amino acids.

As used herein, "antigen presenting cell" or "APC" refers to cells that ingest and present antigen to T cells. These cells include phagocytic leukocytes, macrophages, and dendritic cells, B lymphocytes, and endothelial cells. A "professional APC" is an APC that is constitutively able to activate a T lymphocyte. Professional APCs typically constitutively express class II major histocompatibility molecules and costimulatory molecules such as B7-1 and/or B7-2.

In one embodiment, the invention encompasses a multifunctional molecule, the first part of which is a lectin. Thus, the multifunctional molecule can bind to one or more carbohydrates of an antigen bearing target. In a preferred embodiment of the invention, the first part of the multifunctional molecule is a lectin and the second portion is a ligand for a cell surface protein (e.g., a ligand for a cell surface receptor). Preferably, the cell surface protein is a cell surface receptor of an APC. Ligands for a cell surface receptor include any ligand which will bind to a cell surface protein, and preferably include, but are not limited to, an opsonin, cytokine, adhesion molecule, counterreceptor of a T cell costimulatory molecule, a defensin, a ligand for a CD40 molecule, or a heat shock protein, or a portion of any of these ligands, including about (or at least about) 5, 8, 10, 12, 15, 20, 25, 35, 50, 60, 70, 80, 100, or 120 contiguous amino acids of such a ligand. Preferably, the multifunctional molecule which comprises first and second parts comprises an amino acid sequence which can bind to a cell surface protein (e.g., a cell surface receptor) including, but not limited to an adhesion molecule, a costimulatory molecule for a T cell, or a receptor for at least one of the following types of molecules: a cytokine, a defensin, a heat shock protein, a CD40 molecule, or an opsonin.

A cell surface protein (e.g., a cell surface receptor) useful in the present invention is any cell surface molecule which can bind the ligand portion of a multifunctional molecule of the invention. Preferably, the cell surface receptor is a CD40 molecule, a T cell costimulatory molecule, an adhesion molecule, or a receptor for a cytokine, a defensin, a heat shock protein, an opsonin, or an adhesion molecule. Cell surface proteins, useful in the invention include, but are not limited to the cell surface molecules identified by GenBank Accession number in Appendix I and II, or those cell surface molecules which are encoded by a nucleic acid molecule identified by GenBank Accession number in Appendix I or II.

The term "cytokine" as used herein refers to a polypeptide molecule that is naturally secreted by mammalian cells and that binds to a cell surface protein on a leukocyte, inducing a change (e.g., a change in the proliferative state, a change in the transcriptional profile or a change in the propensity to migrate) in the leukocyte (other than mere occupancy of the leukocyte's receptors for the cytokine). "Change" refers to at least about a 5% increase or decrease as compared to in the absence of a cytokine. The term "cytokine" also refers herein to a polypeptide molecule that is a ligand for a receptor for a naturally occurring cytokine.

Examples of cytokines which are useful in the methods and compositions of the invention include the following: GM-CSF, IL-2, IL-4, IL-6, IL-12, ligands for hematopoietin receptors, ligands for immunoglobulin superfamily receptors, ligands for interferon receptors, ligands for TNF receptors, and ligands for chemokine receptors. An antibody against a cytokine receptor can also be a cytokine.

In one embodiment of the invention, it is preferred that a cytokine comprised by a composition of the invention promote a Th1 immune response, i.e., the generation of T cells that express Th1 cytokines such as IL-2 and IFN-γ. In another embodiment, it is preferred that a cytokine comprised by a composition of the invention promote a Th2 immune response, i.e., the generation of T cells that express Th2 cytokines such as IL-4 and IL-10.

"Engineered cytokines" as described herein are cytokines which comprise a heterologous cell surface binding moiety.

The term "opsonin" as used herein refers to naturally occurring and non-naturally occurring molecules which are capable, by virtue of being contemporaneously bound or attached to both an antigen-containing cell and an antigen-presenting cell (APC), of acting as a link or coupling agent (an adapter) between the antigen and the APC to allow more efficient binding, engulfment, and internalization of the antigen-containing cell by the APC. An opsonin useful according to the invention, also includes non-naturally occurring opsonins capable of binding to APCs via receptors that can bind naturally occurring opsonins.

The term "opsonin" as used herein can also refer to molecules which can be processed such that at least one product of the processing step or steps is capable of, by virtue of being contemporaneously bound or attached to both an antigen-containing cell and an APC, acting as a link or coupling agent to allow more efficient binding, engulfment, and internalization of other antigen-containing cells by the APC. An opsonin can also be any polypeptide chain of a multichain opsonin.

Examples of opsonins which are useful in the methods and compositions of the invention include the following: vitronectin, fibronectin, complement components such as C1q (including any of its component polypeptide chains A, B and C), complement fragments such as C3d, C3b and C4b, mannose binding protein, conglutinin, surfactant proteins A and D, C-reactive protein (CRP), alpha-2-macroglobulin, and immunoglobulins, for example, the Fc portion of an immunoglobulin.

"Innate opsonins" are opsonins of the innate immune system and are known in the art as secreted polypeptide molecules of the innate immune system and are believed to bind contemporaneously to an antigen and to the surface of an APC. They can thus act as "bridges", and are thought, by virtue of this property, to promote internalization of antigens by APCs. The mode in which opsonins bind to antigens varies among opsonins, and can be covalent or noncovalent. In general, the antigen-binding moieties of innate opsonins differ from the antigen-binding moieties of immunoglobulins in that the former are relatively invariant among members of the same species, and do not undergo diversification during the ontogeny of an individual.

A molecule containing a naturally occurring APC-binding moiety shall be considered an opsonin if it contains a moiety through which it can be stably bound or attached to a cell such that the APC-binding moiety is located in the extracellular space, whether or not the opsonin molecule contains its natural antigen-binding domain.

"Engineered opsonins", as described herein, include molecules in which a cell surface binding moiety is substituted for the natural antigen-binding domain of an opsonin or where a cell surface binding moiety is linked to the opsonin without modification or removal of the natural antigen-binding domain of the opsonin.

A "cell surface binding moiety" is a moiety through which a molecule can be stably bound to a cell surface, e.g. a cell wall, a polysaccharide capsule, or the lipid or protein component of a plasma membrane, or to the surface of a virus. Such moieties include but are not limited to cross-linking moieties and lipid moieties. It is preferred that the cell surface binding moiety bind to a cell by a means other than interaction of a polypeptide with its cognate cell-surface polypeptide. It is further preferred that the cell surface binding moiety comprise a non-polypeptide moiety. In a preferred embodiment, a lipid moiety is linked to the engineered molecule via a glycosylphosphatidylinositol (GPI) moiety. In another preferred embodiment, the lipid comprises a fatty acid, e.g. palmitate. In yet another preferred embodiment of the invention, the cell surface binding moiety is linked to an opsonin or an antigen-binding domain-truncated opsonin at the antigen-binding end of the opsonin. In another preferred embodiment, the multifunctional molecule comprises an idiotypic portion of an immunoglobulin which can bind to an APC. Preferably, the opsonin of an opsonin-enhanced cell is one of alpha' chain C3b or mannose binding protein.

If the opsonin is a fragment of C3, it is preferred hat it bind to CR1 with a greater affinity than to CR2. It is further preferred that the fragment of C3 not be a ligand for CR2. Preferably, the opsonin is neither C3bi, C3d, nor C3dg.

It is preferred that the opsonins bind to receptors that trigger phagocytosis and that are non-clonotypic and thus do not vary from cell to cell as, for example, clonotypic receptors do. Non-clonotypic receptors are present on cells which play a role in innate immunity, and include, e.g., non-idiotypic receptors. Examples of such receptors include CR1, CR2, CR3, CR4, and C1q receptor, receptors containing a component of the C1q receptor, collectin receptors, receptors for α2m, receptors for CRP, and Fc receptors for immunoglobulins.

"Exogenous" refers to something which is introduced from or produced outside the cell.

"Endogenous" refers to something which is expressed or present naturally in a cell.

"Heterologous" refers to something which is not naturally expressed in a cell.

Preferably, the multifunctional molecule which comprises first and second parts can bind, via the second part, to the surface or plasma membrane of an antigen presenting cell (APC), i.e. a cell that can present antigen to a T cell, e.g. a cell that can activate a T cell, at least in part by presenting antigen to the T cell. The APC may be a leukocyte, e.g. a cell of monocytic lineage and/or a dendritic cell. Preferably, binding of the multifunctional molecule is independent of expression of an idiotype, e.g. a clonotypic determinant of an immunoglobulin, on the APC. Most preferably, the multifunctional molecule comprises a first end which can bind to a cell that comprises an antigen and second end which can bind to a APC.

The multifunctional molecule may bind to an antigen bearing target cell by, e.g., inserting into the lipid portion of a cell membrane or by binding to a structure, e.g. a polypeptide or a carbohydrate, that is physically associated with the lipid portion of the membrane. The structure need not be directly in contact with the lipid portion of the membrane, but may be indirectly attached, e.g. a carbohydrate that is part of a cell-surface glycoprotein. Preferably the multifunctional molecule can bind via a first part to an antigen bearing target, preferably a mammalian cell that comprises an antigen, and via a second part to an APC. The invention also encompasses the use of a molecule that can bind via a first part to a virus or to a non-mammalian cell, e.g. a fungal or bacterial cell, and via a second part to an APC.

In the latter cases, the first part may bind, e.g., to a component of a cell wall or a capsule.

In a preferred embodiment, the multifunctional molecule which comprises first and second parts comprise a first part which comprises a lectin and a second part that can bind to a leukocyte, e.g. an APC, e.g. a cell of monocytic lineage or a dendritic cell (which may itself be of monocytic lineage). A "lectin", according to the invention, is a molecule or part of a molecule, e.g. an amino acid sequence, which can bind to a carbohydrate, e.g. a polysaccharide. Families of naturally occurring lectins include:

1) Galectins, a rapidly growing family of animal lectins. All of them share galactose-specificity.
2) Calcium-dependent (C-type) animal lectins, an extremely large family composed of members having diverse structures and functions.
3) Among this C-type lectin family, selectins form a distinguishable subfamily by their specific function in leukocyte adhesion to endothelial cells through sialyl-LewisX recognition.
4) Collectins, another subfamily of C-type lectins specific for mannose, which have a unique structure consisting of a C-type lectin domain and a collagen-like domain. They are involved in innate immunity.
5) Invertebrates are known to contain various lectins in their body fluids, probably as body-protection factors. Recently, some lectins from an echinoderm were found to show hemolytic activity.
6) Annexins, a group of proteins having affinity to lipids that were recently shown to be lectins showing binding to glycosaminoglycans.
7) The legume lectin family, which consists of a large number of members, such as ConA, with variable saccharide specifically comparable to C-type lectins.
8) Ricin, the first lectin investigated in Russia more than 100 years ago. It is now evident that the ricin family has many other homologous members which differ in either toxicity or sugar-binding specificities.

Thus, a multifunctional molecule of the invention may bind to one or more carbohydrates. Carbohydrates to which lectins may bind also include, for example, carbohydrates comprising lactose, D-mannose, D-glucose, D-fucose, L-fucose (e.g. alpha-L-fucose), D-galactose, blood group A oligosaccharides, blood group B oligosaccharides, saccharides comprising alpha-D-Gal (1->3)[alpha-Lfuc(1->2)]-beta-D-Gal(1->3/4-beta-D-GlcNAc, saccharides comprising alpha-sialyl[2->3]-lactose, alpha-D-mannosyl glycoconjugates, alpha-NeuNAc-[2->6]-Gal, alpha-NeuNAc-[2->6]-GalNAc, alpha-NeuNAc-[2->3]-Gal, N-acetyl-beta-D-glucosamine, terminal alpha-D-galactosyl residues, terminal beta-D-galactosyl residues, N-acetyllactosamine, terminal alpha-D-mannosyl residues, N-acetyl-beta-D-glucosamine, terminal N-acetyl-D-galactosamine, N-acetylneuraminic acid, and terminal alpha-D-galactosaminyl residues.

The multifunctional molecule which comprises a lectin may comprise, for example, the whole of a naturally occurring lectin or a portion of a naturally occurring lectin, e.g. about (or at least about) 5, 8, 10, 12, 15, 20, 25, 35, 50, 60, 70, 80, 100, or 120 contiguous amino acids of a naturally occurring polypeptide lectin. In one embodiment the multifunctional molecule comprises a carbohydrate-binding domain of a naturally occurring lectin, i.e., a portion of a lectin that can bind to a carbohydrate in the absence of the remainder of the lectin. In another embodiment the lectin may be non-naturally occurring, e.g. identified from an artificial library of molecules or designed by modifying the structure of a naturally occurring lectin.

Lectins known as "hemagglutinins" bind to carbohydrates on erythrocytes, e.g. blood group antigens, and when incubated with these cells cause them to aggregate. The influenza virus hemagglutinin, for example, binds to sialic acid (as does the human parainfluenza virus 3. hemagglutinin/neuraminidase). There are at least 15 known influenza hemagglutinin subtypes, defined by their distinct antigenic properties. Any of these subtypes, designated, e.g., H1, H2, H3, H4, H5, H6, H7, H8, H9, H10, H11, H12, H13, H14, and H15, may provide amino acid sequences useful in the compositions and methods of the invention. In one embodiment of the invention, the hemagglutinin is of a subtype from a virus that infects humans, e.g. H1, H2, or H3. In another embodiment, the hemagglutinin is of a subtype from a virus that does not infect humans, e.g. one of H4 through H15. Amino acid sequences can vary up to about 20% for influenza hemagglutinins within a given subtype, and can vary between about 30% and about 70% for influenza hemagglutinins from different subtypes.

Influenza hemagglutinin is expressed as a single polypeptide chain, designated HA0, which trimerizes post-translationally. HA0 is proteolytically cleaved to yield two domains, HA1 and HA2, which are disulfide-bonded to each other. HA1 comprises significant sialic acid binding activity, while HA2 is anchored to the viral membrane and facilitates fusion of this membrane with a host cell membrane. In preferred embodiments of the invention, the multifunctional molecule comprising first and second parts comprises an amino acid sequence of an HA1 domain.

The molecule may be a fusion polypeptide which comprises one or more amino acids interposed between the first and second parts which bind to cells, e.g. a fusion polypeptide which comprises a first amino acid sequence which can bind to an antigen bearing target and a second amino acid sequence which can bind to a leukocyte, and which further comprises at least one amino acid interposed between the first and second parts. The interposed amino acids may comprise, e.g., a linker sequence intended to lessen steric hindrance or other undesirable interactions between the aforementioned first and second parts. For, example, one such type of sequence takes the form $(Gly_3Ser)_n$. Additional useful linkers include, but are not limited to $(Arg\text{-}Ala\text{-}Arg\text{-}Asp\text{-}Pro\text{-}Arg\text{-}Val\text{-}Pro\text{-}Val\text{-}Ala\text{-}Thr)_{1\text{-}5}$ (Xu et al., 1999, Proc. Natl. Acad. Sci. U.S.A. 96: 151-156), $(Gly\text{-}Ser)_n$ (Shao et al., 2000, Bioconjug. Chem. 11: 822-826), $(Thr\text{-}Ser\text{-}Pro)_n$ (Kroon et al., 2000, Eur. J. Biochem. 267: 6740-6752), $(Gly\text{-}Gly\text{-}Gly)_n$ (Kluczyk et al., 2000, Peptides 21: 1411-1420), and $(Glu\text{-}Lys)_n$ (Klyczyk et al., 2000, supra), wherein n is 1 to 15 (each of the preceding references is also incorporated herein by reference). In another embodiment, no amino acids are interposed between the first and second parts.

The present invention further provides a nucleic acid molecule, preferably a recombinant nucleic acid molecule which encodes a multifunctional polypeptide of the present invention. The nucleic acid molecule may be, for example, DNA, RNA, cDNA, or mRNA. The nucleic acid molecule may be naturally occurring or may be partially or wholly synthesized using techniques known to those of skill in the art. In a preferred embodiment, the nucleic acid molecule is a DNA molecule comprising a first nucleic acid sequence encoding a first amino acid sequence which can bind to an antigen bearing target, and a second nucleic acid sequence encoding a second amino acid sequence which can bind to a cell surface receptor on an APC.

The present invention still further provides a vector comprising the nucleic acid molecule encoding a multifunctional polypeptide of the invention, e.g. an expression vector suitable for expressing in a host cell, wherein the host cell is preferably a eukaryotic cell, more preferably an animal cell, more preferably a mammalian cell, and still more preferably a human cell. In another preferred embodiment the host cell is a yeast cell, e.g. *Saccharomyces cerevesiae*.

The invention also provides a host cell comprising a nucleic acid vector which comprises a sequence encoding the multifunctional molecule of the present invention. Preferably, the host cell is a eukaryotic cell, such as a yeast cell- or an animal cell, preferably a human cell. The host cell may also be a prokaryotic cell.

The invention also encompasses a molecule, e.g. a polypeptide, e.g. a fusion polypeptide, which comprises a first part that can bind to an antigen bearing target, e.g. a cell, e.g. a cell that comprises an antigen, and a second part that can bind to a cell, e.g. a leukocyte, e.g. an APC. The molecule may have any of the characteristics taught in the descriptions of methods and compositions herein. Preferably the first and second parts are heterologous to each other. The molecule may be, e.g., a recombinant polypeptide expressed in a mammalian cell, an insect cell, a plant cell, a yeast cell, or a bacterial cell.

The invention also encompasses a method of modulating an immune response in an animal comprising the step of expressing in an animal, e.g. expressing in a host cell of the animal, a multifunctional molecule of the invention, e.g. a polypeptide which comprises a first part that can bind to a antigen bearing target and a second part that can bind to a cell. According to the invention, "expressing in an animal" means "causing to be present in an animal". When the molecule is a polypeptide, it is preferably expressed by introducing into the host cell, in vivo or ex vivo, a nucleic acid encoding the polypeptide. If the nucleic acid is introduced into the host cell ex vivo, the host cell may subsequently be administered to the animal. In a preferred embodiment, the method further comprises administering to the animal the antigen to which the immune response is modulated. For example, the antigen may be administered to the animal as part of a composition which further comprises a nucleic acid that encodes the multifunctional molecule. In another preferred embodiment, the antigen is already present in the animal at the time the multifunctional molecule is expressed. In yet another preferred embodiment, the antigen is administered to the animal after administration of the multifunctional molecule. In still other preferred embodiments, the antigen is expressed in the animal, e.g. by administering to the animal a composition comprising a nucleic acid encoding the antigen, either before or after expression of the multifunctional molecule in the animal. In another embodiment, nucleic acid sequences encoding the multifunctional molecule and the antigen are introduced into one or more host cells of the animal, e.g. by administering to the animal a composition comprising those nucleic acid sequences.

As used herein, the term "modulating an immune response" to a selected antigen using the methods and compositions of the invention means rendering the response more or less efficient, more or less rapid, greater or lesser in magnitude, and/or more or less easily induced than the response obtained from administration of a composition which is identical in every respect except that it does not comprise a multifunctional molecule of the invention. In a preferred embodiment, the response is between about 5 and 100%, or preferably between about 5 and 50% or more preferably between about 5 and 25% more or less efficient, more or less rapid, greater or lesser in magnitude, and/or more or less easily induced than the response obtained from administration of a composition which is identical in every respect except that it does not comprise a multifunctional molecule of the invention.

The term "modulate the immune response" may refer to stimulation/activation of an immune response to a selected antigen, or it may refer to suppression, elimination, or attenuation of an immune response to a selected antigen. In a preferred embodiment, modulating the immune response results in stimulation/activation of an immune response to a selected antigen by about at least 5%, or preferably between 5 and 50% or more preferably between 50 and 100%, as compared to an immune response in the absence of vaccination, or it may result in suppression, elimination, or attenuation of an immune response to a selected antigen by about at least 5%, or preferably between 5 and 50% or more preferably between 50 and 100%, as compared to an immune response in the absence of vaccination. In some cases, one immune response to an antigen (e.g. a Th1 response) may be increased while another immune response to the same antigen (e.g. a Th2 response) may be diminished.

The invention also encompasses a composition comprising a multifunctional molecule of the invention and antigen bearing target, e.g. a virus, a prion, or a cell. Preferably, when the antigen bearing target is a cell, the multifunctional molecule is exogenous to the cell. The multifunctional molecule may be heterologous to the cell. In one embodiment, the multifunctional molecule is expressed within the cell, e.g. from a recombinant nucleic acid within the cell. The invention also encompasses a cell comprising a nucleic acid encoding a multifunctional molecule of the invention. The multifunctional molecule may have any of the characteristics set forth herein. An antigen bearing target (e.g., a cell) useful in the invention includes, for example, malignant cells, benign tumor cells, lymphocytes, e.g. B or T lymphocytes which may be pathogenic and/or autoreactive, cells expressing an antigen from an exogenously introduced nucleic acid molecule, eukaryotic cells such as mammalian cells, human cells, fibroblasts, insect and fungal cells, and prokaryotic cells such as bacterial cells. Examples of viruses useful in the invention include, e.g., retroviruses such as human immunodeficiency viruses 1 and 2; herpesviruses such as herpes simplex viruses 1 and 2, cytomegalovirus, and varicella zoster virus; human papilloma virus; rabies virus; rotavirus; influenza viruses A, B, and C; hepatitis viruses A, B, C, and E or delta agent; adenoviruses; measles virus; mumps virus; polio virus; rubella virus; parainflunza viruses; coxsackie viruses A and B; variola virus; yellow fever virus; dengue and other hemorrhagic fever viruses; West Nile fever virus; Eastern equine encephalitis virus; Western equine encephalitis virus; Venezuelan equine encephalitis virus; Japanese encephalitis virus; rhinoviruses;

and foot and mouth disease virus. Prions include the agents of scrapie, kuru, and bovine spongiform encephalitis. The cell, virus, or prion may be attenuated, i.e. rendered non-pathogenic, by, e.g., killing, irradiation, chemical fixation, passaging in culture with selection for diminished pathogenicity, or genetic manipulation. Preferably, the composition further comprises a leukocyte, e.g. a monocyte, a cell of monocytic lineage, a macrophage, or a dendritic cell or another APC.

Preferably, in the inventive methods and compositions, the cell is substantially unable to divide in vitro. "Substantially unable to divide in vitro" means that the cell divides at a rate that is less than about 50% of the rate of division of corresponding cells which are not treated to prevent cell division. In a preferred embodiment, the cell divides at a rate that is less than about 30-50% of the rate of division of corresponding cells which are not treated to prevent cell division.

Preferably, the composition is substantially free of culture medium. As used herein, "culture medium" refers to medium that is used in cell culture containing at least 2% animal serum, such as fetal calf serum.

More particularly, the present invention provides a multifunctional molecule which is a fusion polypeptide comprising: a lectin which comprises at least about 10 contiguous amino acids of an influenza virus hemagglutinin, and at least about 5 contiguous amino acids of a naturally occurring GM-CSF molecule.

In one embodiment, the lectin is N-terminal to the contiguous amino acids of a naturally occurring GM-CSF molecule.

In an alternate embodiment, the lectin is C-terminal to the contiguous amino acids of a naturally occurring GM-CSF molecule.

In one embodiment, the lectin comprises at least about 10 contiguous amino acids of the HA1 domain of an influenza virus hemagglutinin.

In one embodiment, the lectin is the HA1 domain of an influenza virus hemagglutinin.

Preferably, the influenza virus hemagglutinin is a hemagglutinin of an influenza A virus. In other preferred embodiments the influenza virus hemagglutinin is a hemagglutinin of an influenza B or influenza C virus.

In one embodiment, the influenza virus hemagglutinin is of a subtype from a virus that infects humans. Preferably, the influenza virus hemagglutinin is of an H1 subtype. Still more preferably, the influenza virus hemagglutinin is from the influenza A strain PR/8/34.

In one embodiment, the influenza virus hemagglutinin is of an H2 subtype.

In one embodiment, the influenza virus hemagglutinin is of an H3 subtype.

In one embodiment, the influenza virus hemagglutinin is of a subtype from a virus that does not infect humans.

In one embodiment the fusion polypeptide comprises the entire amino acid sequence of a naturally occurring GM-CSF molecule.

Preferably, the GM-CSF molecule is a murine GM-CSF. Still more preferably, the GM-CSF molecule is a human GM-CSF.

In one aspect, the invention encompasses a method of reducing the number of metastases, e.g. tumor metastases, in a subject, e.g. a mammal, e.g. a human, comprising the step of administering to the subject any of the compositions described herein, e.g. a composition comprising a multifunctional molecule of the invention or a nucleic acid molecule encoding a multifunctional molecule of the invention. Typically, such a composition will further comprise an antigen associated with the disease, or a nucleic acid encoding such an antigen. The method may comprise any of the methods of administering a composition, modulating an immune response, or treating a disease described herein.

The invention provides, a method of reducing the number of metastasis in an animal comprising administering to said animal a composition comprising a cell comprising an antigen, said composition further comprising a fusion protein comprising a lectin and a ligand for a cell surface protein.

As used herein, a "metastasis" refers to a focus of disease that is caused by a malignant cell or infectious organism which has traveled from one site in a host to a second site in the host (e.g., from one site to a non-contiguous site; e.g., from a first organ to a second organ). More specifically, "metastasis" refers to a detectable focus of malignant tumor or infection that is derived from, and spread from, and is distinct from the primary site of disease. Accordingly, "metastases" refers to a plurality of foci either in a single organ or tissue in a subject, or in two or more organs or tissues in a subject. A "focus" as used herein may be at least a single malignant or infectious cell, or may be a detectable focus, which is detectable by one or more of the methods described hereinbelow. Metastases is said to be detected where a metastases is able to be detected by one of skill in the art using one or more of the assay methods described hereinbelow.

According to the invention, "reducing the number of metastases" may mean either causing there to be fewer (e.g., at least 10% fewer, 20%, 30%, 50%, 70%, 90%, and up to at least 100% fewer) metastases than expected (where the number or severity of metastases expected is based on the observations made in a set (e.g., more than one) or similar subjects which has not received the multifunctional molecule of the invention). In one embodiment "reducing the number of metastases" may encompass preventing metastases (e.g. a subject does not develop any detectable foci of disease), e.g. in a subject with a tumor, or causing one or more preexisting metastases to become undetectable, e.g. by radiologic, non-invasive imaging techniques, or other techniques as described herein. Those skilled in the art will recognize that a metastasis itself may become undetectable even though residual scarring or fibrosis may be detectable. Metastases may be, for example, to bone, brain, liver, lung, or spinal cord, or any other organ or tissue.

In another aspect, the invention encompasses a method of reducing the number of metastases in a population of subjects comprising the step of administering to one or more subjects any of the compositions described herein e.g. a composition comprising a multifunctional molecule of the invention or a nucleic acid molecule encoding a multifunctional molecule of the invention. Typically, such a composition will further comprise an antigen associated with the disease, or a nucleic acid encoding such an antigen. The method may comprise any of the methods of administering a composition, modulating an immune response, or treating a disease described herein.

In another aspect, the invention encompasses a method of reducing the size of a metastasis in a subject comprising the step of administering to the subject any of the compositions described herein, e.g. a composition comprising a multifunctional molecule of the invention or a nucleic acid molecule encoding a multifunctional molecule of the invention. Typically, such a composition will further comprise an antigen associated with the disease, or a nucleic acid encoding such an antigen. The method may comprise any of the methods of administering a composition, modulating an immune response, or treating a disease described herein. The "size" of a metastasis, as used herein refers to the one, two or three dimensional area encompassed by a metastasis, or alternatively, refers to the number of malignant or infectious cells present in a metastasis. The size of the metastasis, which may be measured by direct visualization or by non-invasive imaging, may be reduced by, e.g., at least about 10%, at least about 20%, 30%, 50%, 70%, 90%, and up to at least 100%.

The invention provides a method of reducing the size of a metastasis in an animal comprising administering to said animal a composition comprising a cell comprising an antigen, said composition further comprising a fusion protein comprising a lectin and a ligand for a cell surface protein.

In another aspect, the invention encompasses a method of reducing the average size of metastases in a subject comprising the step of administering to the subject any of the compositions described herein. The method may comprise any of the methods of administering a composition, modulating an immune response, or treating a disease described herein. According to the invention, "reducing the average size of metastases" may mean either causing metastases to be smaller on average than expected, e.g. by preventing one or more of them from growing to the expected size, or causing one or more preexisting metastases to become smaller, thus decreasing the mean size of the metastases. The average size of the metastases, which may be determined by direct visualization or by noninvasive imaging, may be reduced by, e.g., at least about 10%, at least about 20%, 30%, 50%, 70%, 90%, and up to at least 100%.

In another aspect, the invention encompasses a method of reducing the average size of metastases in a population comprising the step of administering to one or more subjects any of the compositions described herein, e.g. a composition comprising a multifunctional molecule of the invention or a nucleic acid molecule encoding a multifunctional molecule of the invention. The method may comprise any of the methods of administering a composition, modulating an immune response, or treating a disease described herein.

Thus, in another aspect the invention encompasses preventing or treating a disease in a subject by administering to the subject any of the compositions described herein, e.g. a composition comprising a multifunctional molecule of the invention or a nucleic acid molecule encoding a multifunctional molecule of the invention. Typically, such a composition will further comprise an antigen associated with the disease, or a nucleic acid encoding such an antigen. The disease may be, for example, a benign or malignant tumor, an infectious disease, an allergy, or an autoimmune disease. "Treating a disease" means decreasing morbidity or mortality associated with the disease in a patient or population afflicted with the disease. For example, survival, relapse-free survival, or disease-free survival may be prolonged by, e.g., at least about 10%, at least about 20%, 30%, 50%, 70%, 90%, and up to at least 100%, or the number of metastases may be reduced by, e.g., at least about 10%, at least about 20%, 30%, 50%, 70%, 90%, and up to at least 100%. For preventive applications, the incidence of the targeted disease may be reduced by, e.g., at least about 10%, at least about 20%, 30%, 50%, 70%, 90%, and up to at least 100%.

In yet another aspect, the invention encompasses a method of modulating an immune response to an antigen in a subject, e.g. a mammal, e.g. a human, comprising the steps of 1) administering to the subject a composition comprising the antigen and further comprising a multifunctional molecule of the invention and 2) administering to the subject a composition comprising the antigen and not comprising (i.e. free of) the multifunctional molecule administered in step 1. Generally, the two steps will be performed sequentially, e.g. at least 1 day apart, or at least 1 week apart, or at least 1 month apart, or at least 6 months apart, or at least 1 year apart. In one embodiment, the composition comprising the multifunctional molecule is administered to the subject prior to the composition which is free of the multifunctional molecule. In another embodiment, the composition which is free of the multifunctional molecule is administered to the subject prior to the composition which comprises the multifunctional molecule. The antigen of the composition may be comprised by an antigen bearing target such as a cell, a cell fraction, a virus, or a viral particle.

In yet another aspect, the invention encompasses a method of modulating an immune response to an antigen in a subject, e.g. a mammal, e.g. a human, comprising the steps of 1) administering to the subject a composition comprising the antigen and further comprising a nucleic acid molecule encoding a multifunctional molecule of the invention and 2) administering to the subject a composition comprising the antigen and not comprising (i.e. free of) the nucleic acid molecule administered in step 1. Again, the two steps will generally be performed sequentially, e.g. at least 1 day apart, or at least 1 week apart, or at least 1 month apart, or at least 6 months apart, or at least 1 year apart. In one embodiment, the composition comprising the nucleic acid molecule is administered to the subject prior to the composition which is free of the nucleic acid molecule. In another embodiment, the composition which is free of the nucleic acid molecule is administered to the subject prior to the composition which comprises the nucleic acid molecule. The antigen of the composition may be comprised by an antigen bearing target such as a cell, a cell fraction, a virus, or a viral particle. The nucleic acid molecule may be comprised by an expression vector.

In yet another aspect, the invention encompasses a method of modulating an immune response to an antigen in a subject, e.g. a mammal, e.g. a human, comprising the steps of 1) administering to the subject a composition comprising a nucleic acid molecule encoding the antigen and further comprising a multifunctional molecule of the invention and 2) administering to the subject a composition comprising a nucleic acid molecule encoding the antigen and not comprising (i.e. free of) the multifunctional molecule administered in step 1. Generally, the two steps will be performed sequentially, e.g. at least 1 day apart, or at least 1 week apart, or at least 1 month apart, or at least 6 months apart, or at least 1 year apart. In one embodiment, the composition comprising the multifunctional molecule is administered to the subject prior to the composition which is free of the multifunctional molecule. In another embodiment, the composition which is free of the multifunctional molecule is administered to the subject prior to the composition which comprises the multifunctional molecule. The antigen of the composition may be comprised by an antigen bearing target such as a cell, a cell fraction, a virus, or a viral particle. One or more of the nucleic acid molecules may be comprised by an expression vector.

In yet another aspect, the invention encompasses a method of modulating an immune response to an antigen in a subject, e.g. a mammal, e.g. a human, comprising the steps of 1) administering to the subject a composition comprising the antigen and further comprising a multifunctional molecule of the invention and 2) administering to the subject a composition comprising a nucleic acid molecule encoding the antigen and not comprising (i.e. free of) the multifunctional molecule administered in step 1. Generally, the two steps will be performed sequentially, e.g. at least 1 day apart, or at least 1 week apart, or at least 1 month apart, or at least 6 months apart, or at least 1 year apart. In one embodiment, the composition comprising the multifunctional molecule is administered to the subject prior to the composition which is free of the multifunctional molecule. In another embodiment, the composition which is free of the multifunctional molecule is administered to the subject prior to the composition which comprises the multifunctional molecule. The antigen of the composition may be comprised by an antigen bearing target such as a cell, a cell fraction, a virus, or a viral particle. The nucleic acid molecule may be comprised by an expression vector.

In yet another aspect, the invention encompasses a method of modulating an immune response to an antigen in a subject, e.g. a mammal, e.g. a human, comprising the steps of 1) administering to the subject a composition comprising a nucleic acid molecule encoding the antigen and further comprising a multifunctional molecule of the invention and 2) administering to the subject a composition comprising the antigen and not comprising (i.e. free of) the multifunctional molecule administered in step 1. Generally, the two steps will be performed sequentially, e.g. at least 1 day apart, or at least 1 week apart, or at least 1 month apart, or at least 6 months apart, or at least 1 year apart. In one embodiment, the composition comprising the multifunctional molecule is administered to the subject prior to the composition which is free of the multifunctional molecule. In another embodiment, the composition which is free of the multifunctional molecule is administered to the subject prior to the composition which comprises the multifunctional molecule. The antigen of the composition may be comprised by an antigen bearing target such as a cell, a cell fraction, a virus, or a viral particle. The nucleic acid molecule may be comprised by an expression vector.

In yet another aspect, the invention encompasses a method of modulating an immune response to an antigen in a subject, e.g. a mammal, e.g. a human, comprising the steps of 1) administering to the subject a composition comprising a nucleic acid molecule encoding the antigen and further comprising a nucleic acid molecule encoding a multifunctional molecule of the invention and 2) administering to the subject a composition comprising a nucleic acid molecule encoding the antigen and not comprising (i.e. free of) the nucleic acid molecule encoding the multifunctional molecule, which was administered in step 1. Again, the two steps will generally be performed sequentially, e.g. at least 1 day apart, or at least 1 week apart, or at least 1 month apart, or at least 6 months apart, or at least 1 year apart. In one embodiment, the composition comprising the nucleic acid molecule is administered to the subject prior to the composition which is free of the nucleic acid molecule encoding the multifunctional molecule. In another embodiment, the composition which is free of the nucleic acid molecule encoding the multifunctional molecule is administered to the subject prior to the composition which comprises the nucleic acid molecule encoding the multifunctional molecule. One or more of the nucleic acid molecules may be comprised by an expression vector.

In yet another aspect, the invention encompasses a method of modulating an immune response to an antigen in a subject, e.g. a mammal, e.g. a human, comprising the steps of 1) administering to the subject a composition comprising a nucleic acid molecule encoding the antigen and further comprising a nucleic acid molecule encoding a multifunctional molecule of the invention and 2) administering to the subject a composition comprising a nucleic acid molecule encoding the antigen and further comprising a multifunctional molecule of the invention. The multifunctional molecules of step 1 and step 2 may be the same or different. Again, the two steps will generally be performed sequentially, e.g. at least 1 day apart, or at least 1 week apart, or at least 1 month apart, or at least 6 months apart, or at least 1 year apart. In one embodiment, the composition comprising the nucleic acid molecule is administered to the subject prior to the composition which is free of the nucleic acid molecule encoding the multifunctional molecule. In another embodiment, the composition which is free of the nucleic acid molecule encoding the multifunctional molecule is administered to the subject prior to the composition which comprises the nucleic acid molecule encoding the multifunctional molecule. One or more of the nucleic acid molecules may be comprised by an expression vector.

In yet another aspect, the invention encompasses a method of modulating an immune response to an antigen in a subject, e.g. a mammal, e.g. a human, comprising the steps of 1) administering to the subject a composition comprising a nucleic acid molecule encoding the antigen and further comprising a multifunctional molecule of the invention and 2) administering to the subject a composition comprising a nucleic acid molecule encoding the antigen and further comprising a nucleic acid molecule encoding a multifunctional molecule of the invention. The multifunctional molecules of step 1 and step 2 may be the same or different. Again, the two steps will generally be performed sequentially, e.g. at least 1 day apart, or at least 1 week apart, or at least 1 month apart, or at least 6 months apart, or at least 1 year apart. In one embodiment, the composition comprising the nucleic acid molecule is administered to the subject prior to the composition which is free of the nucleic acid molecule encoding the multifunctional molecule. In another embodiment, the composition which is free of the nucleic acid molecule encoding the multifunctional molecule is administered to the subject prior to the composition which comprises the nucleic acid molecule encoding the multifunctional molecule. One or more of the nucleic acid molecules may be comprised by an expression vector.

The present invention encompasses a method of modulating an immune response in an animal comprising the step of administering a composition comprising a multifunctional molecule, e.g. a polypeptide, e.g. a fusion polypeptide, which comprises a first part that can bind to a antigen bearing target and a second part that can bind to a cell. In a preferred embodiment, the composition further comprises an antigen, an immune response to which is modulated by administration of the composition. The antigen may be, for example, a polypeptide (e.g. a recombinant polypeptide), a lipid (e.g. a glycolipid), or a carbohydrate (e.g. a polysaccharide or a component of a bacterial or fungal cell wall). The composition therefore comprises an antigen bearing target, whether, e.g., a homogeneous antigen or a heterogeneous structure such as a cell or a virus. When the antigen bearing target is a cell, it may be autologous, syngeneic, allogeneic, or xenogeneic to the animal. In other preferred embodiments, the antigen is already present in the animal at the time the molecule is administered, and/or the antigen is administered to the animal prior to administration of the molecule. In yet another preferred embodiment, the antigen is administered to the animal after administration of the molecule.

Preferably, the composition comprises multifunctional molecules which are not bound to an antigen bearing target.

In a preferred embodiment, the composition further comprises an antigen bearing target, e.g. a cell. In one embodiment of the invention, the composition comprises multifunctional molecules, some of which are bound to a antigen bearing target, e.g. to the surface of a cell, and some of which are external to and not bound to any target. In another embodiment, the composition comprises a multifunctional molecule and further comprises a portion of a cell, e.g. a membrane fraction of a cell (i.e., an antigen bearing target). In yet another embodiment, the composition comprises a multifunctional molecule and further comprises a multiplicity of different molecules derived from a cell, as is found, e.g., in a cell lysate. Cells may be lysed, for example, by freezing and thawing, preferably repeatedly. In a preferred embodiment, the composition is cell-free.

The present invention further encompasses a method of vaccinating a mammal to a selected antigen comprising administering to the animal a vaccine composition comprising a multifunctional molecule of the invention comprising a first part which is a lectin, and a second part which is a ligand for a cell surface protein, e.g. a cell surface receptor of an APC. Preferably, the lectin can bind to an antigen bearing target which comprises the antigen.

In one embodiment, the invention provides a method of vaccinating a mammal to a selected antigen comprising removing at least one cell from the mammal, wherein the cell comprises the antigen, contacting the cell ex vivo with a multifunctional molecule comprising a first part which is a lectin and is capable of binding to at least one carbohydrate molecule on the surface of the antigen bearing cell, and a second part which is a ligand for a cell surface protein of an APC, so as to form an antigen bearing cell/multifunctional molecule complex; and placing the complex back into the mammal.

In a preferred embodiment, the composition comprises an antigen, an immune response to which is modulated by administration of the composition.

The invention provides a method of modulating an immune response to a selected antigen in a mammal comprising administering to said animal a composition comprising a cell comprising said antigen, and a multifunctional molecule comprising a lectin and a ligand for a cell surface protein.

The invention also relates to a method of vaccinating an animal to a selected antigen comprising removing at least one cell from said animal, wherein the cell comprises said antigen; contacting said cell ex vivo with a fusion polypeptide comprising a lecting and a ligand for a cell surface protein of an antigen presenting cell so as to form a complex; and placing said complex back in said animal.

The present invention provides a method for juxtaposing an APC with an antigen bearing target comprising: contacting an APC and antigen bearing target with a multifunctional molecule comprising a first part comprising a lectin which is able to bind to at least one carbohydrate moiety on the antigen bearing target and a second part comprising a ligand for a cell surface protein on the APC. Preferably, the multifunctional molecule is first contacted with the antigen bearing target and the resulting antigen bearing target/multifunctional molecule complex is subsequently contacted with the APC. In one embodiment the antigen bearing target is a cell from an animal comprising an antigen, and is contacted with the multifunctional molecule ex vivo under conditions which permit the binding of the lectin to at least one carbohydrate moiety of the cell. The resulting multifunctional molecule/antigen bearing cell complex is then administered back to the animal from which the antigen bearing cell was derived wherein it is able to bind to a cell surface receptor on an APC via the ligand portion of the multifunctional molecule, thereby juxtaposing the antigen bearing target and the APC.

"Juxtaposition", in the context of the present invention, includes but is not limited to physical contact. An APC and antigen bearing target are "juxtaposed" with one another if they are sufficiently close for the APC to internalize the antigen bearing target. An APC and antigen bearing target are also "juxtaposed" if they are separated by no more that 20 µm, preferably no more than 10 µm, and still more preferably no more than 5 µm, and more preferably no more than 1 µm.

As used herein, "contacting" refers to admixing in vitro or in vivo.

The invention also encompasses a method of modulating an immune response to an antigen comprising contacting in vitro an antigen bearing target, a multifunctional molecule of the invention, and an APC and administering the resultant composition to a subject. In one embodiment the antigen bearing target/multifunctional molecule complex is contacted with an APC for a time sufficient to permit internalization of the antigen bearing target by the APC. In other embodiments the antigen bearing target/multifunctional molecule complex is contacted with an APC for a time that allows internalization of less than about 80%, less than about 60%, less than about 40%, less than about 20%, less than about 10%, or less than about 5% of the antigen bearing target by the APC. Methods for determining the amount of target internalized, e.g. by measuring the amount remaining outside the APC and subtracting from the starting amount, are well-known in the art. Preferably, the antigen bearing target/multifunctional molecule complex is contacted with an APC for less than about 10 minutes, less than about 30 minutes, less than about 60 minutes, less than about 90 minutes, less than about 120 minutes, or less than about 180 minutes.

As used herein, "time sufficient to permit internalization" refers to a period of time that is of a sufficient duration to allow internalization of the selected antigen or antigen bearing target by the APC (for example, no more than about fourteen days, or seven days, or five or three days, or as little as about 24, 12, 6, 3, 2 or 1 hour, or even as little as about 30, 20, 10, 5, or 1 minute).

The invention also encompasses a method of attaching a ligand for a cell surface polypeptide to an antigen bearing target comprising admixing the antigen bearing target with a multifunctional molecule which comprises the ligand. The invention also encompasses a method of attaching an amino acid sequence to an antigen bearing target comprising admixing the antigen bearing target with a fusion polypeptide which comprises the amino acid sequence and further comprises a lectin. The invention also encompasses a composition comprising an antigen bearing target admixed with a fusion polypeptide which comprises a first amino acid sequence which is not a lectin and a second amino acid sequence which comprises a lectin.

The invention also comprises methods of producing a multifunctional molecule of the invention in each of the following cell types: a yeast cell, a mammalian cell, a bacterial cell, an insect cell. Each of these methods comprises the step of introducing a nucleic acid encoding a multifunctional molecule into the respective cell type, as taught hereinbelow.

The invention also encompasses methods of detecting or quantifying a multifunctional molecule of the invention comprising contacting the multifunctional molecule with an antibody or other ligand that binds to the multifunctional molecule. Such methods include ELISA assays and flow cytometry, as described hereinbelow. Preferably, the multifunctional molecule to be detected or quantitated is bound to an antigen bearing target.

DETAILED DESCRIPTION

The present invention is based, in part, on the discovery that a multifunctional fusion protein comprising a first polypeptide which is a lectin and a second polypeptide which is a ligand of a cell surface receptor of an APC, can effectively target an antigen bearing target, such as a cell bearing an antigen of interest, to an APC, wherein the antigen is engulfed by the APC, and an appropriate immune response to the antigen is mounted by an animal to which the multifunctional molecule is administered.

Accordingly, the present invention provides a method for vaccinating a mammal comprising administering to the animal a vaccine composition comprising a multifunctional molecule of the invention comprising a first part which is a lectin and which can bind to a target bearing the antigen, and a second part which is a ligand for a cell surface protein of an APC. In one embodiment, the method comprises removing at least one cell from the mammal, wherein the cell comprises the antigen, contacting the cell ex vivo with a multifunctional molecule comprising a first part which is a lectin and is capable of binding to at lease one carbohydrate molecule on the surface of the antigen bearing cell, and a second part which is a ligand for a cell surface protein of an APC, so as to form an antigen bearing cell/multifunctional molecule complex; and placing the complex back into the mammal.

Multifunctional Molecules

The present invention encompasses a multifunctional molecule comprising a first part which can bind to an antigen bearing target, and a second part which is a ligand for a cell surface protein of a cell, e.g. an antigen presenting cell. Preferably, the first part which can bind to an antigen bearing target is a lectin which binds to at least one carbohydrate molecule present on the antigen bearing target. Preferably the lectin is an influenza hemagglutinin and binds to sialic acid residues present on the antigen bearing target. Preferably, the ligand of a cell surface protein of an antigen presenting cell is selected from an opsonin, a cytokine, a ligand for a CD40 molecule, an adhesion molecule, a defensin, a heat shock protein, or a counterreceptor for a T cell costimulatory molecule. Cell surface molecules which can act as receptors for the second part of the multifunctional molecule include CD40 molecules and specific receptors for an opsonin, a cytokine, an adhesion molecule, a defensin, a heat shock protein, or a counterreceptor for a T cell costimulatory molecule, and also include, but are not limited to the cell surface molecules listed in Appendix I and II.

Lectins

The multifunctional molecule which comprises first and second parts can comprise a first part which comprises a lectin and a second part that can bind to a leukocyte, e.g., an APC, e.g. a cell of monocytic lineage or a dendritic cell (which may itself be of monocytic lineage). A "lectin", according to the invention, is a molecule or part of a molecule, e.g. an amino acid sequence, which can bind to a carbohydrate, e.g. a polysaccharide. Families of naturally occurring lectins include:

1) Galectins, a rapidly growing family of animal lectins. All of them share galactose-specificity.
2) Calcium-dependent (C-type) animal lectins, an extremely large family composed of members having diverse structures or functions
3) Among this C-type lectin family, selectins form a distinguishable subfamily by their specific function in leukocyte adhesion to endothelial cells through sialyl-LewisX recognition.
4) Collectins, another subfamily of C-type lectins specific for mannose, which have a unique structure consisting of a C-type lectin domain and a collagen-like domain. They are involved in innate immunity.
5) Invertebrates are known to contain various lectins in their body fluids, probably as body-protection factors. Recently, some lectins from an echinoderm were found to show hemolytic activity.
6) Annexins, a group of proteins having affinity to lipids that were recently shown to be lectins showing binding to glycosaminoglycans.
7) The legume lectin family, which consists of a large number of members, such as ConA, with variable saccharide specificity comparable to C-type lectins.
8) Ricin, the first lectin investigated in Russia more than 100 years ago. It is now evident that the ricin family has many other homologous members which differ in either toxicity or sugar-binding specificities.

Thus, a multifunctional molecule of the invention may bind to one or more carbohydrates. Carbohydrates to which lectins may bind also include, for example, carbohydrates comprising lactose, D-mannose, D-glucose, D-fucose, L-fucose (e.g. alpha-L-fucose), D-galactose, blood group A oligosaccharides, blood group B oligosaccharides, saccharides comprising alpha-D-Gal(1->3)[alpha-Lfuc(1->2)]-beta-D-Gal(1->3/4-beta-D-GlcNAc, saccharides comprising alpha-sialyl-[2->3]-lactose, alpha-D-mannosyl glycoconjugates, alpha-NeuNAc-[2->6]-Gal, alpha-NeuNAc-[2->6]-GalNAc, alpha-NeuNAc-[2->3]-Gal, N-acetyl-beta-D-glucosamine, terminal alpha-D-galactosyl residues, terminal beta-D-galactosyl residues, N-acetyllactosamine, terminal alpha-D-mannosyl residues, N-acetyl-beta-D-glucosamine, terminal N-acetyl-D-galactosamine, N-acetylneuraminic acid, and terminal alpha-D-galactosaminyl residues.

The multifunctional molecule which comprises a lectin may comprise, for example, the whole of a naturally occurring lectin or a portion of a naturally occurring lectin, e.g. about (or at least about) 5, 8, 10, 12, 15, 20, 25, 35, 50, 60, 70, 80, 100, or 120 contiguous amino acids of a naturally occurring polypeptide lectin. In one embodiment the multifunctional molecule comprises a carbohydrate-binding domain of a naturally occurring lectin, i.e., a portion of a lectin that can bind to a carbohydrate in the absence of the remainder of the lectin. In another embodiment the lectin may be non-naturally occurring, e.g. identified from an artificial library of molecules or designed by modifying the structure of a naturally occurring lectin.

Lectins known as "hemagglutinins" bind to carbohydrates on erythrocytes, e.g. blood group antigens, and when incubated with these cells cause them to aggregate. The influenza virus hemagglutinin, for example, binds to sialic acid. There are at least 15 known influenza hemagglutinin subtypes, defined by their distinct antigenic properties. Any of these subtypes, designated, e.g., H1, H2, H3, H4, H5, H6, H7, H8, H9, H10, H11, H12, H13, H14, and H15, may provide amino acid sequences useful in the compositions and methods of the invention. In one embodiment of the invention, the hemagglutinin is of a subtype from a virus that infects humans, e.g. H1, H2, or H3. In another embodiment, the hemagglutinin is of a subtype from a virus that does not infect humans, e.g. one of H4 through H15. Amino acid sequences can vary up to about 20% for influenza hemagglutinins within a given subtype, and can vary between about 30% and about 70% for influenza hemagglutinins from different subtypes. Methods for determining amino acid sequence homology are known to those of skill in the art. Examples of other software that can perform sequence comparisons to determine the % identity between hemagglutinin variants (or variants of any portion of the multifunctional molecules disclosed herein) include, but are not limited to, the BLAST package (Ausubel et al., 1995, *Short Protocols in Molecular Biology*, 3rd Edition, John Wiley & Sons), FASTA (Atschul et al., 1990, J. Mol. Biol., 403-410) and the GENEWORKS suite of comparison tools. Both BLAST and FASTA are available for offline and online searching.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The BLAST algorithm is described in detail in Altschul et al., (1990) *J. Mol. Biol.* 215:403-410, which is incorporated herein by reference. The search parameters are defined as follows, and can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264-68; Karlin and Altschul, 1993, *Proc. Natl. Acad. Sci. USA* 90:5873-7) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available through the National Institutes of Health (NIH; Bethesda, Md.) perform the following tasks: blastp compares an amino acid query sequence against a protein sequence database; blastn compares a nucleotide query sequence against a nucleotide sequence database; blastx compares the six-frame conceptual translation products of a nucleotide query sequence (both strands) against a protein sequence database; tblastn compares a protein query sequence against a nucleotide sequence database dynamically translated in all six reading frames (both strands); tblastx compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States (1993) Computers and Chemistry 17:191-201, or, for BLASTN, by the DUST program of Tatusov and Lipman (NIH). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided by the NIH. In some embodiments of the present invention, no gap penalties are used when determining sequence identity.

Influenza hemagglutinin is expressed as a single polypeptide chain, designated HA0, which trimerizes post-translationally. HA0 is proteolytically cleaved to yield two domains, HA1 and HA2, which are disulfide-bonded to each other. HA1 comprises significant sialic acid binding activity, while HA2 is anchored to the viral membrane and facilitates fusion of this membrane with a host cell membrane. In preferred embodiments of the invention, the multifunctional molecule comprising first and second parts comprises an amino acid sequence of an HA1 domain.

Additional examples of lectin molecules useful in the present invention include, but are not limited to, those lectins shown in Table 1, and variants thereof having at least 50%, 70%, 90%, and up to 99% sequence homology with the sequences of the lectins shown in Table 1.

TABLE 1

| KEY | NAME | ABBREVIATION | CLASS | LECTIN CODE |
|---|---|---|---|---|
| [1] | / . . . /— | Quail Intestinal Lectin. | — | LECa.Ggg.Sss.xx.Xxxx. |
| [2] | / . . . /— | Porcine Heart Lectin (PHL). | — | LECa.Ggg.Sss.xx.Xxxx. |
| [3] | / . . . /— | Hepatic beta-galactoside binding lectins. | S-lectin or Galectin. | GLTa.Ggg.Sss.xx.Xxxx. |
| [4] | / . . . /— | Mammalian Brain Beta-Galactoside-binding Lectin. | S-lectin or Galectin. | GLTa.Ggg.Sss.xx.Xxxx. |
| [5] | *Aaptos papillata.* | — | — | LECi.Ada.Pap.xx.Xxxx. |
| [6] | *Abelmoschus esculentus.* | — | — | LECp.Abe.Esc.xx.Xxxx. |
| [7] | *Abramis brana.* | — | — | LECp.Abr.Bra.xx.Xxxx. |
| [8] | *Abrus precatorius.* | APA; APA-A; APA-C; Abrin. | beta-trefoil lectin (APA); Type 2 RIP. | LECp.AbrPre.se.Cga1 (abrin) LECp.AbrPre.se.Cga2 (APA). |
| [10] | *Achatina fulica.* | *Achatina fulica* Cold Aggltutinin; achatinin-H. | — | LECi.Ach.ful.xx.Xsi1. |
| [13] | *Actinomyces viscosus.* | — | — | LECf.Act.Vis.xx.Xga1. |
| [14] | *Adenia digitata.* | Modeccin. | Type 2 RIP. | LECp.AdeDig.ro.Cga1. |
| [15] | *Adenia volksensii.* | Volkensin. | Type 2 RIP. | LECp.AdeVol.ro.Cga1. |
| [16] | *Aegilops geniculata.* | — | Hevein domain lectin, chitin binding. | LECp.Aeg.Gen.se.Hch1. |
| [19] | *Aegopodium podagraria.* | APA. | — | LECp.Aeg.Pod.rh.Hga1. |
| [20] | *Aeromonas salmonicida.* | — | — | LECb.Aer.Sal.xx.Xxxx. |
| [21] | *Afzelia africana.* | — | — | LECz.Afz.Afr.xx.Xxxx. |
| [22] | *Agardhiella tenera.* | — | — | LECz.Aga.Ten.xx.Xxxx. |
| [23] | *Agaricales.* | — | — | LECz.Aga.sss.xx.Xxxx. |
| [24] | *Agaricus bisporus.* | ABA-I, ABA-II, ABA-III, ABA-IV. | — | LECf.Aga.Bis.xx.Xga1. |
| [25] | *Agaricus blazei.* | — | — | LECf.Aga.Bla.xx.Xxxx. |
| [26] | *Agaricus campestris.* | — | — | LECf.Aga.Cam.xx.Xxxx. |
| [27] | *Agaricus edulis.* | — | — | LECf.Aga.Edu.xx.Xxxx. |
| [28] | *Agrobacterium radiobacter.* | — | — | LECu.Agr.Rad.xx.Xxxx. |
| [29] | *Agrocybe aegerita.* | — | — | LECf.Agr.Aeg.xx.Xxxx. |
| [30] | *Agropyrum repens.* | AREL, ARLL. | Hololectin; Monocot mannose-binding lectins. | LECp.Agr.Rep.se.Hch1 (AREL) LECp.Agr.Rep.le.Hch1 (ARLL). |
| [31] | *Aleuria aurantia.* | — | — | LECf.Ale.Aur.xx.Xfu1. |
| [32] | *Allium ascalonicum.* | AAA. | Monocot mannose-binding lectins. | LECp.All.Asc.bu.Hma1. |
| [36] | *Allium cepa.* | ACA. | Monocot mannose-binding lectins. | LECp.All.Cep.bu.Hma1. |
| [37] | *Allium moly.* | AMA. | Monocot mannose-binding lectins. | LECp.All.Mol.bu.Hma1. |

TABLE 1-continued

| KEY | NAME | ABBREVIATION | CLASS | LECTIN CODE |
|---|---|---|---|---|
| [38] | *Allium porrum.* | APA. | Monocot mannose-binding lectins. | LECp.All.Por.le.Hma1. |
| [39] | *Allium sativum.* | ASA. | Monocot Mannose-binding lectin. | LECp.All.Sat.bu.Hma1 (ASA-I) LECp.All.Sat.bu.Hma1 (ASA-I) LECp.All.Sat.bu.Hma1 (ASA-I) LECp.All.Sat.bu.Hma1 (ASA-I) LECp.All.Sat.bu.Hma2 (ASA-II) LECp.All.Sat.le.Hma1 (ASA-III) LECp.All.Sat.ro.Hma1 (ASA-IV). |
| [40] | *Allium ursinum.* | AUA-I, AUA-II, AUA-III, AUA-Ir, AUA-L, AUA-Iir. | Monocot Mannose-binding lectin. | LECp.All.Urs.bu.Hma1 (AUA-I) LECp.All.Urs.bu.Hma2 (AUA-II) LECp.All.Urs.le.Hma1 (AUA-L) LECp.All.Urs.ro.Hma1 (AUA-Ir) LECp.All.Urs.ro.Hma2 (AUA-IIr). |
| [42] | *Allium vineale.* | AVA. | Monocot Mannose-binding lectin. | LECp.All.Vin.bu.Hma1. |
| [43] | *Allomyrina dichotoma.* | — | — | LECi.All.Dic.xx.Xxxx. |
| [44] | *Alocasia indica.* | — | — | LECp.Alo.Ind.tu.Hcu1. |
| [45] | *Aloe arborescens.* | Aloctin, AAA. | AAA: Monocot Mannose-binding proteins Aloctin-A: u. | LECp.Alo.Arb.le.? (Aloctin-A) LECp.Alo.Arb.le.Hma1 (AAA). |
| [46] | *Amaranthus caudatus.* | ACA, Amaranthin, ACL. | beta-trefoil lectin, Amaranthin group. | LECp.Ama.Cau.se.Hga1. |
| [47] | *Amaranthus cruentus.* | — | Amaranthin group. | LECp.Ama.Cru.se.Hga1. |
| [48] | *Amaranthus hypochondriacus.* | AHML, Amaranthin. | Amaranthin group. | LECp.Ama.Hyp.xx.Xgal1. |
| [49] | *Amranthus leucocarpus.* | — | Amaranthin group. | LECp.Ama.Leu.se.Hga1. |
| [50] | *Amaranthus spinosus.* | ASL. | Amaranthin group. | LECp.Ama.Spi.se.Hga1. |
| [51] | *Amphicarpaea bracteata.* | ABrA. | Legume lectins. | LECp.Amp.Bra.se.Hma1. |
| [52] | *Anadara granosa.* | Anadarin MS. | — | LECi.Ana.Gra.xx.Xsi1. |
| [53] | *Anguilla anguilla.* | AAL. | — | LECi.Ang.Ang.xx.Xfu1. |
| [54] | *Anthocidaris crassispina.* | — | Novel, unique lectin class. | LECi.Ant.Cra.xx.Xxxx. |
| [55] | *Anthocidaris crassispina Ovum.* | — | — | LECi.Ant.Cra.xx.Xxxx. |
| [57] | *Apium graveolens.* | — | — | LECp.Api.Gra.xx.Xxxx. |
| [58] | *Aplysia dactylomela.* | — | — | LECi.Apl.Dac.xx.Xxxx. |
| [59] | *Aplysia depilans.* | — | — | LECi.Apl.Dep.xx.Xga1. |
| [60] | *Aplysina archeria.* | — | — | LECu.Apl.Arc.xx.Xxxx. |
| [61] | *Arachis hypogea.* | PNA, GNL, MNL, PRA-I, PRA-II. | All Arachnis lectins are classed as legume lectins. | LECp.Ara.Hyp.se.Hga1 (PNA) LECp.Ara.Hyp.no.Hga1 (GNL) LECp.Ara.Hyp.se.Hga1 (MNL) LECp.Ara.Hyp.se.Hga1 (PRA-I) LECp.Ara.Hyp.se.Hga1 (PRA-II). |
| [62] | *Araucaria brasiliensis.* | Lectin I, Lectin II. | — | LECp.Ara.Bra.se.Hmg1 (Lectin I) LECp.Ara.Bra.se.Hmg2 (Lectin II). |
| [63] | *Arion empiricorum.* | — | — | LECi.Ari.Emp.xx.Xxxx. |

TABLE 1-continued

| KEY NAME | ABBREVIATION | CLASS | LECTIN CODE |
|---|---|---|---|
| [64] *Arisaema consanguineum.* | ACA. | — | LECp.Ari.Con.tu.Hcu1. |
| [65] *Arisaema curvatum.* | ACmA. | — | LECz.Ari.Cur.tu.Hcu1. |
| [66] *Arthrobotrys oligospora.* | AOL. | — | LECf.Art.Oli.xx.Xxxx. |
| [68] *Artocarpus hirsuta.* | — | — | LECp.Art.Hir.xx.Xxxx. |
| [69] *Artocarpus incisa.* | — | — | LECp.Art.Inc.xx.Xxxx. |
| [70] *Artocarpus integrifolia.* | Jacalin, AIA, KM+, Artocarpin. | beta-prism plant lectin, Jacalin-related lectins. | LECp.Art.Int.se.Hga1. |
| [71] *Artocarpus lakoocha.* | Artocarpin, ALA-I, ALA-II. | Jacalin-related lectins. | LECp.Art.Lak.se.Hga1. |
| [72] *Arum maculatum.* | AMA. | Monocot binding lectins. | LECp.Aru.Mac.tu.Hma1. |
| [73] *Ascaris lumbricoides.* | — | — | LECi.Asc.Lum.xx.Xxxx. |
| [74] *Asparagus officinalis.* | — | — | LECp.Asp.Off.xx.Xxxx. |
| [75] *Bacillus polymyxa.* | — | — | LECb.Bac.Pols.xx.Xxxx. |
| [76] *Bacterioides fragilis.* | — | — | LECb.Bac.Fra.xx.Xxxx. |
| [77] *Bandeiraea simplicifolia.* | BS-I, BS-I-A4, BS-I-B4, BS-II. | — | LECp.Ban.Sim.xx.Xxxx. |
| [78] *Basidiomycotina.* | — | — | LECf.Bas.Sss.xx.Xxxx. |
| [79] *Bauhinia purpurea.* | BPA. | Legume lectin. | LECp.Bau.Pur.se.Hga1. |
| [80] *Bauhinia tomentosa.* | — | — | LECz.Bau.Tom.xx.Xxxx. |
| [81] *Beauveria bassiana.* | — | — | LECf.Bea.Bas.xx.Xsi1. |
| [82] *Beta vulgaris.* | — | — | LECp.Bet.Vul.xx.Xxxx. |
| [83] *Beta vulgaris.* | — | — | LECp.Bet.Vul.xx.Xxxx. |
| [84] *Biomphalaria glabrata.* | BGL-I, BGL-II. | — | LECp.Bio.Gla.xx.Xxxx. |
| [85] *Biomphalaria glabrata.* | — | — | LECi.Bio.Gla.xx.Xxxx. |
| [86] *Birgus latro.* | — | — | LECz.Bir.Lat.xx.Xxxx. |
| [87] *Blaberus discoidalis.* | BDL1, BDL2, BDL3. | — | LECi.Bla.Dis.xx.Xxxx. |
| [88] *Bordetella pertussis.* | Pertussis toxin 1PRT. | — | LECz.Ggg.Sss.xx.Xxxx. |
| [89] *Bos Taurus.* | Mannose 6-phosphate receptor (1C39). | P-lectin. | LECa.Bos.Tau.xx.Xxxx. |
| [90] *Bos taurus.* | Bovine Conglutinin. | C-lectin or Collectin. | LECa.Bos.Tau.xx.Xxxx. |
| [91] *Bos taurus.* | Bovine collectin-43 (CL-43). | C-lectin or Collectin. | Leca.Bos.Tau.xx.Xxxx. |
| [92] *Botryllus schlosseri.* | — | S-lectin. | LECi.Bot.Sch.xx.Xxxx. |
| [93] *Botrytis cinerea.* | — | — | LECz.Bot.Cin.xx.Xxxx. |
| [94] *Bowringia milbraedii.* | BMA. | Legume lectins. | LECp.Bow.Mil.se.Hmg1. |
| [95] *Brachypodium sylvaticum.* | BsyL. | Chitin-binding lectins. | LECp.Bra.Syl.se.Hch1. |
| [96] *Bradyrhizobium japonicum.* | — | — | LECp.Bra.Jap.xx.Xga1. |
| [97] *Branchiostoma lanceolatum.* | — | — | LECi.Bra.Lan.xx.Xxxx. |
| [98] *Brassica campetsris.* | — | — | LECp.Bra.Cam.xx.Xxxx. |
| [99] *Brassica napobrassica.* | — | — | LECp.Bra.Nap.xx.Xxxx. |
| [100] *Brassica napus.* | — | — | LECp.Bra.Nap.xx.Xxxx. |
| [101] *Bryonia dioica.* | BDA. | — | LECp.Bry.Dio.tu.Hga1. |
| [113] *Cancer antennarius.* | — | — | LECi.Can.Ant.xx.Xsi1. |
| [114] *Candida albican* adhesin. | Adhesins. | — | LECf.Can.Alb.xx.Xfu1. |
| [115] *Canna generalis.* | — | — | LECp.Can.Gen.rh.Hma1. |
| [116] *Capnocytophaga gingivalis Actinomyces Israelii* Coaggregation agglutinin. | — | — | LECu.Cap.Gin.xx.Xxxx. |

TABLE 1-continued

| KEY NAME | ABBREVIATION | CLASS | LECTIN CODE |
|---|---|---|---|
| [117] *Capsicum annum.* | — | — | LECp.Cap.Ann.xx.Xxxx. |
| [118] *Caragana arborescens.* | CAA-I, CAA-II. | — | LECp.Car.Arb.se.Hga1 (CAA-I) LECp.Car.Arb.se.Hga2 (CAA-II). |
| [119] *Carcharhinus springeri.* | — | — | LECa.Car.Spr.xx.Xxxx. |
| [120] *Carcinoscorpious rotundacauda.* | L10; carcinoscorpin. | — | LECi.Car.Rot.xx.Xsi1. |
| [121] *Carica papya.* | — | — | LECp.Car.Pap.xx.Xxxx. |
| [123] *Carum carvia.* | — | — | LECp.Car.Car.xx.Xxxx. |
| [124] *Carybdea alata* Hemolysin. | — | — | LECi.Car.Ala.xx.Xxxx. |
| [125] *Castanea crenata.* | CCA. | — | LECp.Cas.Cre.xx.Xxxx. |
| [126] *Cepaea hortensis.* | CHA-I. | — | LECi.Cep.Hor.xx.Xxxx. |
| [127] *Channa punctatus.* | — | — | LECa.Cha.Pun.xx.Xxxx. |
| [129] *Chelidonium majus.* | — | — | LECp.Che.Maj.se.Hch1. |
| [132] *Chicorium intybus.* | — | — | LECp.Chi.Int.xx.Xxxx. |
| [133] *Cholla opuntia.* | — | — | LECp.Cho.Opu.xx.Xxxx. |
| [134] *Cicer arietinum.* | CAA. | — | LECp.Cic.Ari.se.Hcu1. |
| [135] *Cinachyrella alloclada.* | — | — | LECi.Cin.All.xx.Xxxx. |
| [136] *Cinnamonum camphora.* | — | — | LECp.Cin.Cam.xx.Xxxx. |
| [137] *Citrullus vulgaris.* | — | — | LECp.Cit.Vul.xx.Xxxx. |
| [139] *Citrus aurantium.* | — | — | LECp.Cit.Aur.se.Cnd1. |
| [140] *Citrus aurantium.* | — | — | LECp.Cit.Aur.xx.Xxxx. |
| [141] *Citrus medica.* | — | — | LECp.Cit.Med.xx.Xxxx. |
| [142] *Cladrastis lutea.* | CLA-I, CLA-II. | — | LECp.Cla.Lut.ba.Hmg1 (CLA-I) LECp.Cla.Lut.ba.Hmg2 (CLA-II). |
| [143] *Clerodendron trichotomum.* | CTA. | — | LECp.Cle.Tri.fr.Hga1. |
| [144] *Clitocyba nebularis.* | — | — | LECf.Cli.Neb.xx.Xxxx. |
| [145] *Clivia miniata.* | CMA. | — | LECp.Cli.Min.le.Hma1. |
| [146] *Clostridium botulinum.* | — | — | LECb.Clo.Bot.xx.Xxxx. |
| [147] *Clostridium tetani.* | Tetanus toxin (1A8D). | — | LECb.Ggg.Sss.xx.Xxxx. |
| [148] *Clupea harengus.* | — | — | LECa.Clu.Har.xx.Xxxx. |
| [149] *Coccinia grandis.* | CIA. | — | LECp.Coc.Gra.fr.Hch1. |
| [151] *Cocus nucifera.* | — | — | LECp.Coc.Nuc.xx.Xxxx. |
| [152] *Codium fragilis.* | — | — | LECu.Cod.Fra.xx.Xxxx. |
| [153] *Cofea arabica.* | — | — | LECp.Cof.Ara.xx.Xxxx. |
| [154] *Colchicum autumnale.* | CAA. | — | LECp.Col.Aut.bu.Hcu1. |
| [155] *Collybia velutipes.* | — | — | LECf.Col.Vels.xx.Xxxx. |
| [156] *Colocasia esculentum.* | CEA. | — | LECp.Col.Esc.tu.Hma1. |
| [157] *Conger myriaster.* | Congerin I, Congerin II. | S-lectin. | LECi.Con.Myr.xx.Xga1. |
| [159] *Conidiobolus obscurus.* | — | — | LECf.Con.Obs.xx.Xga1. |
| [160] *Coprinus cinereus.* | Cg1, Cg2. | Galectin. | LECf.Cop.Cin.xx.Xxxx. |
| [161] *Corbicula fluminea* Hemolysin. | — | — | LECi.Cor.Flu.xx.Xxxx. |
| [163] *Corylus avellania.* | — | — | LECp.Cor.Ave.xx.Xxxx. |
| [164] *Cratylia mollis.* | — | — | LECz.Cra.Mol.xx.Xxxx. |
| [165] *Crenomytilus grayanus.* | CGL. | — | LECi.Cre.Gra.xx.Xxxx. |
| [166] *Crocus sativum.* | — | — | LECp.Cro.Sat.bu.Hma1. |
| [167] *Crocus vernus.* | CVA. | — | LECp.Cro.Ver.xx.Xxxx. |
| [169] *Crotolaria striata.* | — | — | LECp.Cro.Str.se.Hga1. |
| [170] *Crotolaria aegyptica.* | — | — | LECz.Cro.Aeg.xx.Xxxx. |
| [171] *Crotolaria falcata.* | — | — | LECz.Cro.Fal.xx.Xxxx. |
| [172] *Crotolaria juncea.* | — | — | LECp.Cro.Jun.se.Hga1. |
| [174] *Croton tiglium.* | — | — | LECp.Cro.Tig.se.Hcu1. |
| [175] *Cucumaria echinata.* | CEL-III. | — | LECi.Cuc.Ech.xx.Xxxx. |
| [176] *Cucumis catalupensis.* | — | — | LECp.Cuc.Cat.xx.Xxxx. |

TABLE 1-continued

| KEY NAME | ABBREVIATION | CLASS | LECTIN CODE |
|---|---|---|---|
| [177] *Cucumis melo.* | — | — | LECp.Cuc.Mel.xx.Xch1. |
| [178] *Cucumis sativus.* | — | — | LECp.Cuc.Sat.xx.Xch1. |
| [180] *Cucurbita ficifolia.* | — | — | LECp.Cuc.Fic.xx.Xxxx. |
| [181] *Cucurbita maxima.* | CMA, PP2. | — | LECp.Cuc.Max.ps.Hch1. |
| [182] *Cucurbita pepe.* | — | — | LECp.Cuc.Pep.xx.Xxxx. |
| [183] *Cucurbita pepo.* | CPA. | — | LECp.Cuc.Pep.fr.Hch1. |
| [184] *Cucurbita sativus.* | — | — | LECp.Cuc.Sat.xx.Xxxx. |
| [185] *Cydonia oblonja.* | — | — | LECp.Cyd.Obl.xx.Xxxx. |
| [186] *Cymbidium hybrid.* | — | — | LECz.Cym.Hyb.le.Hma1. |
| [187] *Cyphomandra betacea.* | — | — | LECp.Cyp.Bet.xx.Xxxx. |
| [188] *Cytisis multiflorus.* | CMA-I, CMA-II. | — | LECp.Cyt.Mul.se.Hch1 (CMA-I) LECp.Cyt.Mul.se.Hfu1 (CMA-II). |
| [189] *Cytisus scoparius.* | CSA-I, CSA-II, CMH-I, CMH-II. | — | LECp.Cyt.Sco.se.Hga1 (CS-I) LECp.Cyt.Sco.se.Hga2 (CS-II). |
| [190] *Cytisus sessilfolius.* | — | — | LECp.Cyt.Ses.se.Hch1 (CSA-I) LECp.Cyt.Ses.se.Hga1 (CSA-II). |
| [191] *Dacrymycetales.* | — | — | LECz.Dac.sss.xx.Xxxx. |
| [192] *Dalbergia.* | — | — | LECz.Dal.sss.xx.Xxxx. |
| [193] *Datura innoxia.* | — | — | LECp.Dat.Inn.xx.Xxxx. |
| [194] *Datura stramonium.* | DSA. | Chitin-bindng lectins. | LECp.Dat.Str.se.Hch1. |
| [195] *Daucus carrota.* | — | — | LECp.Dau.Car.xx.Xxxx. |
| [196] *Dendroaspis jamesoni.* | JML, Jameson's Mamba Venon. | — | LECi.Den.Jam.xx.Xga1. |
| [198] *Deuteromycetes.* | — | — | LECz.Deu.sss.xx.Xxxx. |
| [199] *Dicolea lehmani.* | — | — | LECz.Dio.Leh.xx.Xxxx. |
| [200] *Dictyostelium discoideum.* | Discoidin I. | — | LECu.Dic.Dis.xx.Xxxx. |
| [201] *Dictyostelium purpureum.* | Purpurin. | — | LECu.Dic.Pur.xx.Xxxx. |
| [202] *Didemnum candidum.* | DTL, DCL-I, DCL-II. | — | LECi.Did.Sss.xx.Xga1. |
| [203] *Dieffenbachia sequina.* | — | — | LECp.Dif.Seq.xx.Xxxx. |
| [204] *Dioclea grandifolia.* | — | Legume lectin. | LECp.Dio.Gra.xx.Xxxx. |
| [205] *Dioclea guianensis.* | DLL-I, DLL-II, DLL-III. | Legume lectin. | LECp.Dio.Gui.xx.Xmg1. |
| [206] *Dioclea virgata.* | — | Legume lectin. | LECz.Dio.Vir.xx.Xxxx. |
| [207] *Dolichos biflorus.* | DBA-S, DBA-R, DB-58, DB-57, DB46. | Legume lectin. | LECp.Dol.Bif.se.Hga1 (DBA) LECp.Dol.Bif.pl.Hcu1 (DB58) LECp.Dol.Bif.pl.Hcu2 (DB57) LECp.Dol.Bif.ro.?ga1 (DB46). |
| [208] *Drosophila.* | — | — | LECi.Dro.Meg.xx.Xxxx. |
| [209] *Dumasia.* | — | — | LECz.Dum.sss.xx.Xxxx. |
| [210] *Echinocereus engelmanii.* | — | — | LECp.Echi.Eng.xx.Xxxx. |
| [211] *Echis multisquamatus.* | EMS16. | — | LECi.Ech.Mul.xx.Xxxx. |
| [212] *Electrophorus electricus.* | Electrolectin. | — | LECi.Ele.Ele.xx.Xxxx. |
| [213] *Elymus canadensis.* | — | Hevein domain lectin, chitin binding. | LECp.Ely.Can.se.Hch1. |
| [223] *Erythrina velutina.* | — | — | LECp.Ery.Vel.xx.Xxxx. |
| [224] *Escherichia coli.* | Pili mannose-specific FimH adhesin (1QUN),. | Verotoxin-1: ADP-ribosylating toxins. | LECb.Ech.Col.xx.Xxxx. |
| [225] *Euhadra callizoma.* | — | — | LECz.Euh.Cal.xx.Xxxx. |
| [226] *Euphorbia characias.* | — | — | LECp.Eup.Sss.xx.Xxxx. |
| [227] *Euphorbia heterophylla.* | — | — | LECp.Eup.Het.xx.Xga1. |
| [228] *Evonymus europaea.* | — | — | LECp.Evo.Eur.se.Hcu1. |

TABLE 1-continued

| KEY NAME | ABBREVIATION | CLASS | LECTIN CODE |
|---|---|---|---|
| [229] *Falcata japonica.* | — | — | LECp.Fal.Jap.se.Hga1. |
| [230] *Ficus cunia.* | — | — | LECp.Fic.Cun.xx.Xxxx. |
| [231] *Flammulina veltipes.* | — | — | LECf.Fla.Vel.xx.Xxxx. |
| [232] *Fomes fomentarius.* | — | — | LECz.Fom.Fom.xx.Xxxx. |
| [233] *Fragaria vesca.* | — | — | LECp.Fra.Ves.xx.Xxxx. |
| [234] *Fucus serratus.* | — | — | LECu.Fuc.Ser.xx.Xxxx. |
| [235] *Fucus vesiculosis.* | — | — | LECu.Fuc.Ves.xx.Xxxx. |
| [236] *Galactia tashiroi.* | — | — | LECp.Gal.Tas.se.Hga1. |
| [237] *Galactia tenuiflora.* | — | — | LECp.Gal.Ten.se.Hga1. |
| [238] *Galanthus nivalis.* | — | Monocot lectin. | LECp.Gal.Niv.bu.Hma1. |
| [239] *Galleria mellonella.* | — | — | LECi.Gal.Mel.xx.Xxxx. |
| [240] *Gallus gallus.* | GGL. | S-lectin or Galectin. | GLTa.Gal.Gal.xx.Xxxx. |
| [241] *Gallus gallus.* | Chicken Hepatic lectins (CHL). | — | LECa.Gal.Gal.xx.Xxxx. |
| [242] *Gallus gallus.* | Chicken egg agglutinins. | — | LECa.Gal.Gal.xx.Xxxx. |
| [243] *Gallus gallus.* | Chick Beta-galactoside-Binding lectins. | S-lectin or Galectin. | LECa.Gal.Gal.xx.Xxxx. |
| [244] *Gallus gallus.* | Chicken Serum Mannose-Binding Protein. | C-lectin or Collectin. | LECa.Gal.Gal.xx.Xxxx. |
| [245] *Gallus gallus.* | Chicken Liver Mannose-Binding Protein. | C-lectin or Collectin. | LECa.Gal.Gal.xx.Xxxx. |
| [246] *Gallus gallus.* | Chicken Thymic Electrolectin (CTE). | S-lectin or Galectin. | GLTa.Gal.Gal..xx.Xxxx. |
| [247] *Gallus gallus.* | Chick Embryonic Skin Lectins. | S-lectin or Galectin. | GLTa.Gal.Gal.xx.Xxxx. |
| [248] *Genypterus blacodes.* | — | — | LECi.Epi.Tre.xx.Xxxx. |
| [249] *Geodia cydonium.* | — | — | LECi.Geo.Cyd.xx.Xga1. |
| [250] *Giardia lambia* Surface lectin. | Taglin. | — | LECu.Gia.Lam.xx.Xxxx. |
| [251] *Gliricida sepium.* | Lectin A, Lectin B. | — | LECp.Gli.Sep.se.Hga1 (Lectin A) LECp.Gli.Sep.se.Hga2 (Lectin B). |
| [252] *Glossina longipennis* lectin. | — | — | LECi.Glo.Lon.xx.Xxxx. |
| [253] *Glycine max.* | SBA. | Legume lectin. | LECp.Gly.Max.se.Hga1. |
| [254] *Gonatanthus pumilus.* | — | — | LECz.Gon.Pum.ti.Hcu1. |
| [256] *Grateulopia filicina.* | — | — | LECu.Gra.Fil.xx.Xxxx. |
| [257] *Griffithsia flosculosa.* | — | — | LECu.Gri.Flo.xx.Xxxx. |
| [258] *Griffonia Simplicifolia* lectins. | GS-I-A4, GS-I-A4, GS-I-B4, GS-II, GS-IV. | Legume lectin. | LECp.Gri.Sim.se.Hga1 (GS-I-A4) LECp.Gri.Sim.se.Hga2 (GS-I-B4) LECp.Gri.Sim.se.Hch1 (GS-II) LECp.Gri.Sim.se.Hfu1 (GS-IV) LECp.Gri.Sim.le.Hga1 (GS-I-A4) LECp.Gri.Sim.le.Hga2 (GS-I-B4) LECp.Gri.Sim.le.Hch1 (GS-II) LECp.Gri.Sim.le.Hfu1 (GS-IV). |
| [260] *Grifola frondosa.* | GFL. | — | LECf.Gri.Fro.xx.Xga1. |
| [261] *Haemonchus contortus.* | — | — | LECz.Xxx.Xxx.xx.Xxxx. |
| [262] *Halidrys siliquosa.* | — | — | LECu.Hal.Sil.xx.Xxxx. |
| [263] *Halimeda opuntia.* | — | — | LECu.Hal.Opu.xx.Xxxx. |
| [264] *Halocynthia pyriformis.* | — | — | LECi.Hal.Pyr.xx.Xxxx. |
| [265] *Halocynthia roretzi.* | — | — | LECi.Hal.Ror.xx.Xga1. |
| [266] *Haynaldia villosa.* | — | Hevein domain lectin, chitin binding. | LECp.Hay.Vil.se.Hch1. |

TABLE 1-continued

| KEY NAME | ABBREVIATION | CLASS | LECTIN CODE |
|---|---|---|---|
| [269] *Helianthus annus.* | — | beta-prism plant lectin. | LECp.Hel.Ann.xx.Xxxx. |
| [270] *Helianthus tuberosus.* | HTA. | Jacalin-related lectins. | LECp.Hel.Tub.tu.Hmmm1. |
| [271] *Helicobacter pylori.* | HP-SAL. | — | LECb.Hel.Pyl.xx.Xxxx. |
| [272] *Helix aspersa.* | — | — | LECi.Hel.Asp.xx.Xxxx. |
| [273] *Helix pomatia.* | HPA. | — | LECi.Hel.Pom.xx.Xxxx. |
| [274] *Herpetomonas.* | — | — | LECz.Her.xx.Xxxx. |
| [276] *Heteranthelium piliferum.* | — | Hevein domain lectin, chitin binding. | LECp.Het.Pil.se.Hch1. |
| [277] *Heterometrus granulomanus.* | — | — | LECi.Het.gra.xx.Xsi1. |
| [279] *Hevea brasiliensis.* | HBA, Hevein. | Chitin-binding lectin with hevein domain. | LECp.Hev.Bra.la.Mch1. |
| [280] *Hippeastrum hybrid.* | HHA. | Monocot lectin. | LECp.Hip.Hyb.bu.Hma1. |
| [281] *Hippopus hippopus.* | Tridacnin. | C-lectin. | LECi.Hip.Hip.xx.Xxxx. |
| [282] *Hizoctonia solani.* | — | — | LECz.Hiz.Sol.xx.Xxxx. |
| [283] *Hohenbuehelia serotina.* | — | — | LECf.Hoh.Ser.xx.Xxxx. |
| [284] *Homarus americanus.* | HAA. | — | LECi.Hom.Ame.xx.Xxxx. |
| [285] *Homo sapiens.* | P-selectin (1KJD). | C-lectin. | LECh.Hom.Sap.xx.Xxxx. |
| [286] *Homo sapiens.* | Human Mannose Binding Protein (MBP) (1HUP). | C-lectin. | LECh.Hom.Sap.xx.Xxxx. |
| [287] *Homo sapiens.* | Gut Mucus Anti-*Salmonella* Lectin. | — | LECh.Hom.Sap.xx.Xxxx. |
| [288] *Homo sapiens.* | Human Membrane Lectins (HKML, HCCML). | — | LECh.Hom.Sap.Xxxx. |
| [289] *Homo sapiens.* | Human Synovial Tissue Lectins. | — | LECh.Hom.Sap.xx.Xxxx. |
| [290] *Homo sapiens.* | Human Placenta Lectins (HPL-H, HPL-BG). | — | LECh.Hom.Sap.xx.Xxxx. |
| [291] *Homo sapiens.* | Human Brain Galactoside-binding Lectin. | — | LECh.Hom.Sap.xx.Xxxx. |
| [292] *Homo sapiens.* | Human 14-kDa Lectins. | — | LECh.Hom.Sap.xx.Xxxx. |
| [293] *Homo sapiens.* | Human Core-specific Lectin (HCSL). | — | LECh.Hom.Sap.xx.Xxxx. |
| [294] *Homo sapiens.* | Cell Membrane Lectins. | — | LECh.Hom.Sap.xx.Xxxx. |
| [295] *Homo sapiens.* | Tumoricidal Macrophage Lectin. | — | LECh.Hom.Sap.xx.Xga1. |
| [296] *Homo sapiens.* | Tumor-associated Vertebrate Lectin. | — | LECa.Ggg.Sss.xx.Xxxx. |
| [297] *Homo sapiens.* | Human Conglutinin-like Protein. | — | LECh.Hom.Sap.xx.Xxxx. |
| [298] *Homo sapiens.* | Mannose-Specific Endocytosis Receptor. | — | LECh.Hom.Sap.xx.Xma1. |
| [299] *Homo sapiens.* | Human Penultimate Galactose Lectin. | — | LECh.Hom.Sap.xx.Xxxx. |
| [300] *Homo sapiens.* | Thrombospondin. | — | LECh.Hom.Sap.xx.Xxxx. |
| [301] *Homo sapiens.* | Tetranectin. | — | LECh.Hom.Sap.xx.Xxxx. |
| [302] *Homo sapiens.* | Human Dendritic Cell Immunoreceptor (DCIR). | — | LECh.Hom.Sap.xx.Xxxx. |
| [303] *Homo sapiens.* | Human Seminal Lectin (HSL). | — | LECh.Hom.Sap.xx.Xxxx. |
| [304] *Homo sapiens.* | Charcot-Leyden crystal protein (1LCL). | S-lectin or Galectin. | GLTh.Hom.Sap.xx.Xxxx. |
| [305] *Homo sapiens.* | Galectin II L-14-II (1HLC). | Proto S-lectin or Galectin. | GLTh.Hom.Sap.xx.Xxxx. |
| [306] *Homo sapiens.* | Human Lung Surfactant Protein (1B08). | C-lectin or Collectin. | GLTh.Hom.Sap.xx.Xxxx. |
| [307] *Homo sapiens.* | Galectin III. | Chimera S-lectin or Galectin. | GLTh.Hom.Sap.xx.Xxxx. |

TABLE 1-continued

| KEY | NAME | ABBREVIATION | CLASS | LECTIN CODE |
|---|---|---|---|---|
| [308] | Homo sapiens. | Galectin VII, hGal-7. | Proto S-lectin or Galectin. | GLTh.Hom.Sap.xx.Xxxx. |
| [309] | Homo sapiens. | Pentraxin (1CRV). | Pentraxin, S-lectin or Galectin. | GLTh.Hom.Sap.xx.Xxxx. |
| [310] | Homo sapiens. | Sialoadhesin. | I-lectin. | LECz.Ggg.Sss.xx.Xxxx. |
| [311] | Homo sapiens. | Serum Amyloid P Component. | Pentraxin. | LECh.Hom.Sap.xx.Xxxx. |
| [312] | Homo sapiens. | E-Selectin (1ESL). | C-lectin. | SELh.Hom.Sap.xx.Xxxx. |
| [313] | Homo sapiens. | L-Selectin (1KJB). | C-lectin. | SELh.Hom.Sap.xx.Xxxx. |
| [314] | Homo sapiens. | C-Reactive protein (1CRV). | Pentraxin, S-lectin or Galectin. | GLTh.Hom.Sap.xx.Xxxx. |
| [315] | Homo sapiens. | Galectin XII. | S-lectin or Galectin. | GLTh.Hom.Sap.xx.Xxxx. |
| [316] | Homo sapiens. | Galectin I. | Proto S-lectin or Galectin. | GLTh.Hom.Sap.xx.Xxxx. |
| [317] | Homo sapiens. | Galectin IX, Ecalectin. | Tandem Repeat S-lectin or Galectin. | GLTh.Hom.Sap.sr.Xxxx. |
| [318] | Homo sapiens. | Galectin VIII. | Tandem Repeat S-lectin or Galectin. | GLTh.Hom.Sap.xx.Xxxx. |
| [319] | Homo sapiens. | Galectin IV. | Tandem Repeat S-lectin or Galectin. | GLTh.Hom.Sap.xx.Xxxx. |
| [320] | Homo sapiens. | Alpha-1/Beta-1 integrin. | Integrin A (or I) domain. | INTh.Hom.Sap.xx.Xxxx. |
| [321] | Homo sapiens. | Alpha-2/Beta-1 integrin. | Integrin A (or I) domain. | INTh.Hom.Sap.xx.Xxxx. |
| [322] | Homo sapiens. | Alpha-3/Beta-1 integrin. | Integrin A (or I) domain. | INTh.Xxx.Xxx.xx.Xxxx. |
| [323] | Homo sapiens. | Alpha-4/Beta-1 integrin. | Integrin A (or I) domain. | INTh.Xxx.Xxx.xx.Xxxx. |
| [338] | Homo sapiens. | Alpha-5/Beta-8 integrin. | Integrin A (or I) domain. | INTh.Hom.Sap.xx.Xxxx. |
| [339] | Homo sapiens. | Alpha-4/Beta-7 Integrin. | Integrin. | INTh.Hom.Sap.xx.Xxxx. |
| [340] | Homo sapiens. | Alpha-E/Beta-7. | Integrin. | INTh.Hom.Sap.xx.Xxxx. |
| [341] | Homo sapiens. | Mucosal addressin cell adhesion molecule-1 (MADCAM-1). | Addressin. | LECh.Xxx.Xxx.xx.Xxxx. |
| [342] | Homo sapiens. | Vascular Adhesion Molecule (VCAM-1. | — | LECh.Xxx.Xxx.xx.Xxxx. |
| [343] | Homo sapiens. | P-Selectin. | Selectin. | SELh.Xxx.Xxx.xx.Xxxx. |
| [344] | Homo sapiens. | Intercellular Adhesion Molecule (ICAM-1, ICAM-2). | Addressin?. | LECh.Xxx.Xxx.xx.Xxxx. |
| [345] | Homo sapiens. | Peripheral Lymph Node Addressin (PNAd). | Addressin. | LECh.Xxx.Xxx.xx.Xxxx. |
| [346] | Homo sapiens. | Vascular Adhesion Protein (VAP-1). | — | LECh.Xxx.Xxx.xx.Xxxx. |
| [347] | Homo sapiens. | LFA-3. | Addressin?. | LECh.Xxx.Xxx.xx.Xxxx. |
| [348] | Homo sapiens. | Versican. | Soluble C-lectin ('Lecticans'). | LECh.Xxx.Xxx.xx.Xxxx. |
| [349] | Homo sapiens. | Aggrecan. | Soluble C-lectin ('Lecticans'). | LECh.Xxx.Xxx.xx.Xxxx. |
| [350] | Homo sapiens. | Neurocan. | Soluble C-lectin ('Lecticans'). | LECh.Xxx.Xxx.xx.Xxxx. |
| [351] | Homo sapiens. | Brevican. | Soluble C-lectin ('Lecticans'). | LECh.Xxx.Xxx.xx.Xxxx. |
| [352] | Homo sapiens. | Annexin V. | Annexin. | ANNh.Hom.Sap.xx.Xxx5. |
| [353] | Homo sapiens. | Annexin II. | Annexin. | ANNh.Hom.Sap.xx.Xxx2. |
| [354] | Homo sapiens. | Annexin IV. | Annexin. | ANNh.Hom.Sap.xx.Xxx4. |
| [355] | Homo sapiens. | Annexin I (Lipocortin-1), ANX1. | Annexin. | ANNh.Hom.Sap.xx.Xxx1. |
| [356] | Homo sapiens. | Annexin VII, Synexin. | — | ANNh.Hom.Sap.xx.Xxx7. |
| [357] | Homo sapiens. | Activated Leukocyte Adhesion Molecule (ALCAM). | — | LECh.Hom.Sapxx. |
| [358] | Homo sapiens. | E-cadherin. | — | CDHh.Hom.Sap.xx.XxxE. |
| [360] | Homo sapiens. | N-cadherin (uvomorulin). | — | CDHh.Hom.Sap.xx.XxxN. |
| [361] | Homo sapiens. | VE-cadherin (Vascular Endothelial Cadherin). | — | CDHh.Hom.Sap.xx.XxxVE. |

TABLE 1-continued

| KEY NAME | ABBREVIATION | CLASS | LECTIN CODE |
|---|---|---|---|
| [362] *Homo sapiens.* | P-cadherin. | — | CDHh.Hom.Sap.xx.XxxP. |
| [363] *Homo sapiens.* | Annexin XI (CAP-50). | — | ANNh.Hom.Sap.xx.Xxx9. |
| [364] *Homo sapiens.* | Endothelial Cell-Selective Adhesion Molecule (ESAM). | — | CDHh.Hom.Sapxxx. |
| [365] *Homo sapiens.* | ELAM-1. | — | CDHh.Xxx.Xxx.xx.Xxxx. |
| [366] *Homo sapiens.* | GMP-140. | — | CDHh.Xxx.Xxx.xx.Xxxx. |
| [367] *Homo sapiens.* | Cutaneous Lymphocyte Antigen (CLA). | — | LECh.Xxx.Xxx.xx.Xxxx. |
| [369] *Homo sapiens.* | Lymphocyte Function-Associated Antigen-1 (LFA-1). | — | LECh.Xxx.Xxx.xx.Xxxx. |
| [370] *Homo sapiens.* | Very Late Antigen 4 (VLA-4). | — | LECh.Xxx.Xxx.xx.Xxxx. |
| [371] *Hordeum vulgare.* | HVA. | — | LECp.Hor.Vul.se.Hch1. |
| [372] *Hura crepitans.* | HCA. | Type 2 RIP. | LECp.Hur.Cre.se.Cga1 (HCA) LECp.Hur.Cre.la.Cga1. |
| [373] *Hygrophorus hypothejus.* | — | — | LECf.Hyg.Hyp.xx.Xxxx. |
| [374] *Hypnea cervicornis.* | — | — | LECu.Hyp.Cer.xx.Xxxx. |
| [375] *Hyptos suaveolens.* | — | — | LECz.Hyp.Sua.xx.Xxxx. |
| [376] *Iberis amara.* | — | — | LECp.Ibe.Ama.xx.Xxxx. |
| [377] *Influenza virus.* | Hemagglutinin. | Hemagglutinin. | LECv.Inf.Vir.xx.Xxxx. |
| [378] *Ipomoea batatas.* | — | — | LECp.Ipo.Bat.xx.Xxxx. |
| [379] *Iris hollandica.* | — | — | LECp.Iri.Hol.xx.Xxxx. |
| [380] *Iris hybrid.* | IRA. | Type 2 RIP. | LECp.Iri.Hyb.bu.Cga1. |
| [381] *Juglans regia.* | — | — | LECp.Jug.Reg.xx.Xxxx. |
| [382] *Klyveromyces bulgaricus.* | — | — | LECz.Kly.Bul.xx.Xxxx. |
| [383] *Kuehneromyces mutabilis.* | — | — | LECu.Kue.Mut.xx.Xxxx. |
| [384] *Labiaceae origanum.* | — | — | LECp.Lab.Ori.xx.Xxxx. |
| [385] *Lablab purpureus.* | DLA, LPA. | Legum lectin. | LECp.Lab.Pur.se.Hmg1. |
| [386] *Laburnum alpinum.* | LAA-I, LAA-II. | Legume lectin. | LECp.Lab.Alp.se.Hch1 (LAA-I) LECp.Lab.Alp.se.Hga1 (LAA-II). |
| [387] *Laccaria amethystina.* | — | — | LECz.Lac.Ame.xx.Xxxx. |
| [389] *Lachesis huta.* | BML. | — | LECi.Lac.Jut.xx.Xxxx. |
| [390] *Lactarius deliciosus.* | LDL. | — | LECf.Lac.Del.xx.Xgal1. |
| [391] *Lactarius lignyotus.* | — | — | LECz.Lac.Lig.xx.Xxxx. |
| [392] *Lactuca scariole.* | PLA-I, PLA-II. | — | LECa.Lac.Sca.xx.Xxxx. |
| [393] *Laelia autumnalis.* | — | — | LECp.Lae.Aut.xx.Xxxx. |
| [394] *Laetiporus sulfureus.* | PSL. | — | LECf.Lae.Sul.xx.Xxxx. |
| [395] *Lathyrus cicera.* | LcLI, LcLII. | — | LECp.Lat.Cic.xx.Xxxx. |
| [396] *Lathyrus nissolia.* | — | — | LECp.Lat.Nis.xx.Xxxx. |
| [397] *Lathyrus ochrus.* | LOL-I, LOL-II. | Legume lectin. | LECp.Lat.Och.xx.Xxxx. |
| [398] *Lathyrus odoratus.* | — | — | LECp.Lat.Odo.xx.Xxxx. |
| [399] *Lathyrus silvestris.* | — | — | LECp.Lat.Sil.xx.Xxxx. |
| [400] *Lathyrus tuberosus.* | — | — | LECp.Lat.Tub.xx.Xxxx. |
| [401] *Lens culinaris.* | LCA, LcH. | Legume lectins. | LECp.Len.Cul.se.Hmg1. |
| [402] *Lepidium sativuum.* | — | — | LECp.Lep.Sat.xx.Xxxx. |
| [403] *Leptonychotes weddelli.* | — | — | LECz.Lep.Wed.xx.Xxxx. |
| [404] *Leptospermum archinoides.* | LAA. | — | LECp.Lep.Arc.xx.Xxxx. |
| [405] *Leucojum.* | — | — | LECz.Leu.sss.xx.Xxxx. |
| [406] *Leucojum aestivum.* | LAA. | Monocot mannose-binding lectins. | LECp.Leu.Aes.bu.Hma1. |
| [407] *Leucojum vernum.* | LVA. | Monocot mannose-binding lectins. | LECp.Leu.Ver.bu.Hma1. |
| [408] *Limulus polyphemus.* | Limulin. | Pentraxin. | LECi.Lim.Pol.xx.Xsi1. |

TABLE 1-continued

| KEY NAME | ABBREVIATION | CLASS | LECTIN CODE |
|---|---|---|---|
| [409] *Liocarcinus depurator.* | — | — | LECi.Lio.Dep.xx.Xxxx. |
| [410] *Listeria ovata.* | LOA, LOMBP. | Monocot mannose binding proteins. | LECp.Lis.Ova.le.Hma1 (LOA) LECp.Lis.Ova.le.Mma1 (LMOBP). |
| [411] *Litchi chinensis.* | LCL. | — | LECp.Lit.Chi.xx.Xxxx. |
| [412] *Lonchocarpus capassa.* | — | Legume lectin. | LECp.Lon.Cap.se.Hga1 |
| [413] *Lontonis bainesii.* | — | Legum lectins. | LECp.Lon.Bai.se.Hga1 LECp.Lon.Bai.ro.Hga1. |
| [414] *Lophocereus shotti.* | — | — | LECp.Lop.Sho.xx.Xxxx. |
| [415] *Lotus tetragonolobus.* | LTA. | Legume lectins. | LECp.Lot.Tet.se.Hfu1. |
| [416] *Luffa acutangula.* | LAA. | Cucurbtaceae phloem lectins. | LECp.Luf.Acu.fr.Hch1. |
| [417] *Lumbricus terrestris.* | EW29. | — | LECi.Lum.Ter.xx.Xxxx. |
| [418] *Lycopersicon esculentum.* | LEA, TL, LEL. | Chitin-binding lectins. | LECp.Lyc.Esc.fr.Hch1. |
| [419] *Lycoris aurea.* | — | Monocot mannose-binding lectins. | LECp.Lyc.Aur.bu.Hma1. |
| [420] *Maackia amurensis.* | MALb, MAHb, MAL, MAHs. | Legume lectins. | LECp.Maa.Amu.se.Hsi1 (MAHs, MAH) LECp.Maa.Amu.se.Hsi2 (MAHs, MAH) LECp.Maa.Amu.ba.Hsi1 (MAHb) LECp.Maa.Amu.ba.Hsi1 (MALb). |
| [421] *Machaerocereus eruca.* | MEA-I, MEA-II. | ?. | LECp.Mac.Eru.st.Hga1. |
| [422] *Machaerocereus gummosus.* | — | Hevein domain lectin, chitin binding. | LECp.Mac.Gum.xx.Xxxx. |
| [423] *Maclura pomifera.* | MPA. | beta-prism plant lectin. | LECi.Mac.Pom.xx.Xxxx. |
| [424] *Macrobdella decora.* | LL1-63. | — | LECi.Mac.Dec.xx.Xxxx. |
| [425] *Macrobrachium rosenbergii.* | MrL. | — | LECi.Mac.Ros.xx.Xxxx. |
| [426] *Macrotyloma axillare.* | — | — | LECp.Mac.Axi.xx.Xxxx. |
| [427] *Malus officinalis.* | — | — | LECp.Mal.Off.xx.Xxxx. |
| [428] *Manduca sexta.* | Immulectin. | C-lectin. | LECi.Man.Sex.xx.Xxxx. |
| [429] *Mangifera indica.* | MIA. | — | LECp.Man.Ind.xx.Xxxx. |
| [430] *Marah macrocarpus.* | — | — | LECp.Mar.Mac.xx.Xxxx. |
| [431] *Marasmius oreades.* | — | — | LECf.Mar.Ore.xx.Xxxx. |
| [432] *Medicago sativa.* | — | — | LECp.Med.Sat.xx.Xxxx. |
| [433] *Medicago truncatula.* | — | — | LECp.Med.Tru.xx.Xxxx. |
| [434] *Megabalanus rosa.* | — | — | LECi.Mag.Ros.xx.Xxxx. |
| [435] *Megapitaria squalida.* | — | — | LECi.Meg.Squ.xx.Xxxx. |
| [436] *Melanoleuca melaleuca.* | — | — | LECf.Mel.Mel.xx.Xxxx. |
| [437] *Melastiza chateri.* | — | — | LECf.Mel.Cha.xx.Xxxx. |
| [438] *Mesocricetus auratus.* | — | Pentraxin. | LECz.Ggg.Sss.xx.Xxxx. |
| [474] *Orchidaceae.* | — | — | LECp.Orc.Sss.xx.Xxxx. |
| [475] *Ornithodoros moubata.* | Dorin-M. | — | LECi.Orn.Mou.xx.Xxxx. |
| [476] *Oryza sativa.* | OSA. | Chitin binding lectins. | LECp.Ory.Sat.see.Hch1. |
| [477] *Oscillatoria agardhii.* | — | — | LECu.Osc.Aga.xx.Xxxx. |
| [478] *Otala lactea.* | — | — | LECi.Ota.Lac.xx.Xxxx. |
| [480] *Pachyderus pringleii.* | — | — | LECp.Pac.Pri.se.Hch1. |
| [481] *Pacifastacus leniusculus.* | — | — | LECi.Pac.Len.xx.Xxxx. |
| [482] *Palmaria palmata.* | — | — | LECz.Pal.Pal.xx.Xxxx. |
| [483] *Paracentrotus lividus.* | — | — | LECi.Par.Liv.xx.Xxxx. |

TABLE 1-continued

| KEY NAME | ABBREVIATION | CLASS | LECTIN CODE |
|---|---|---|---|
| [484] *Parkia biglandulosa.* | — | — | LECp.Par.Big.xx.Xxxx. |
| [485] *Parkia discolor.* | — | — | LECz.Par.Dis.xx.Xxxx. |
| [486] *Parkia platycephala.* | — | — | LECz.Par.Pla.xx.Xxxx. |
| [487] *Parkia speciosa.* | — | — | LECp.Park.Spe.xx.Xxxx. |
| [488] *Paxillus atrotomentosus.* | — | — | LECz.Pax.Atr.xx.Xxxx. |
| [489] *Paxillus panuoides.* | — | — | LECf.Pax.Pan.Sss.xx.Xxxx. |
| [490] *Penaeus californiensis.* | — | — | LECp.Pen.Cal.xx.Xxxx. |
| [492] *Penaeus stylirostris.* | — | — | LECi.Pen.Sty.xx.Xxxx. |
| [494] *Penaeus vannamei.* | — | — | LECi.Pen.Van.xx.Xxxx. |
| [495] *Perca fluviatilis.* | — | — | LECa.Per.Flu.xx.Xxxx. |
| [496] *Peresea gratissima.* | — | — | LECz.Per.Gra.xx.Xxxx. |
| [497] *Persea americana.* | PAA. | — | LECp.Per.Ame.xx.Xxxx. |
| [498] *Petromyzon marinus.* | — | — | LECz.Pet.Mar.xx.Xxxx. |
| [499] *Petrosecinum hortense.* | — | — | LECp.Pet.Hor.xx.Xxxx. |
| [500] *Peziza badia.* | — | — | LECp.Pez.Bad.xx.Xxxx. |
| [501] Phage p22. | Phage P22 TailspikeProteins (1TSP). | — | LECb.Ggg.Sss.xx.Xxxx. |
| [502] *Phalera flavescens.* | PFA. | — | LECi.Pha.Fla.xx.Xxxx. |
| [503] *Phallus impudicus.* | — | — | LECf.Pha.Imp.xx.Xxxx. |
| [504] *Phallusia mamillata.* | — | — | LECi.Pha.Mam.xx.Xxxx. |
| [505] *Phaseolus acutifolius.* | — | Legume lectins. | LECp.Pha.Acu.se.Hcu1 (erythroagglutinin) LECp.Pha.Acu.se.Hcu2 (lymphoagglutinin). |
| [506] *Phaseolus aureus.* | — | — | LECp.Pha.Aur.xx.Xxxx. |
| [507] *Phaseolus coccineus.* | PCA. | Legume lectin. | LECp.Pha.Coc.se.Hcu1 (PCA) LECp.Pha.Coc.se.Hcu2. |
| [508] *Phaseolus coccineus.* | — | — | LECp.Pha.Coc.xx.Xxxx. |
| [509] *Phaseolus limenesis.* | PLA, LBA, LBL. | Legume lectins. | LECp.Pha.Lim.se.Hga1. |
| [510] *Phaseolus lunatus.* | — | — | LECp.Pha.Lun.se.Xxxx. |
| [511] *Phaseolus vulgaris.* | PHA-E, PHA-L. | Legume lectin. | LECp.Pha.Vul.xx.Xxxx. |
| [512] *Phaseolus vulgaris.* | GNlL, GNpL, GNsL. | — | LECp.Pha.Vul.xx.Xxxx. |
| [513] *Phaseolus vulgaris.* | Pinto III. | — | LECa.Pha.Vul.xx.Xxxx. |
| [514] *Phaseolus vulgaris.* | — | — | LECp.Pha.Vul.xx.Xxxx. |
| [515] *Phaseolus vulgaris.* | — | — | LECp.Pha.Vul.xx.Xxxx. |
| [516] *Phaseolus vulgaris.* | — | — | LECp.Pha.Vul.xx.Xxxx. |
| [517] *Phaseolus vulgaris.* | — | — | LECp.Pha.Vul.xx.Xxxx. |
| [518] *Phaseolus vulgaris.* | — | — | LECp.Pha.Vul.xx.Xxxx. |
| [519] *Phaseolus vulgaris.* | — | — | LECf.Pha.Vul.xx.Xxxx. |
| [520] *Phlomis fructicosa.* | — | — | LECz.Phl.Fru.xx.Xxxx. |
| [521] *Pholiota aurivella.* | PAA. | — | LECf.Ggg.Sss.xx.Xxxx. |
| [522] *Pholiota squarrosa.* | — | — | LECf.Pho.Squ.xx.Xxxx. |
| [524] *Phoradendron californicum.* | — | — | LECz.Pjo.Cal.xx.Xxxx. |
| [525] *Phragmites.* | — | — | LECz.Phr.sss.xx.Xxxx. |
| [526] *Phragmites austalis.* | — | — | LECp.Phr.Aus.xx.Xxxx. |
| [527] *Physalia physalis.* | Physalitoxin. | — | LECi.Phy.Phy.xx.Xxxx. |
| [528] *Physalis angulata.* | PA-VII-A, PA-VII-B and PA-VII-C. | — | LECz.Phy.Ang.xx.Xxxx. |
| [529] *Physarum polycephalum.* | — | — | LECu.Phy.Pol.xx.Xxxx. |

TABLE 1-continued

| KEY | NAME | ABBREVIATION | CLASS | LECTIN CODE |
|---|---|---|---|---|
| [530] | *Phytolacca americana.* | PWM, Pa-1, Pa-2 (PL-A) Pa-3, Pa-4 (PL-C), Pa-5. | — | LECp.Phy.Ame.ro.Hch1(Pa-1) LECp.Phy.Ame.ro.Hch2(Pa-2) LECp.Phy.Ame.ro.Hch3(Pa-3) LECp.Phy.Ame.ro.Hch4(Pa-4) LECp.Phy.Ame.ro.Hch5(Pa-5) LECp.Phy.Ame.ro.Hch6(PL-B). |
| [531] | *Pimenta officinalis.* | — | — | LECp.Pim.Off.xx.Xxxx. |
| [532] | *Pisum sativum.* | PSA, PsA. | Legume lectins. | LECp.Pis.Sat.se.Hmg1 (PSA, PsA) LECp.Pis.Sat.ro.Hmg1. |
| [533] | *Plecoglossus altivelis.* | PAL. | — | LECa.Ple.Alt.xx.Xxxx. |
| [535] | *Pleurocybella porrigens.* | — | — | LECf.Ggg.Sss.xx.Xxxx. |
| [536] | *Pleurotus ostreatus.* | — | — | LECf.Ple.Ost.xx.Xxxx. |
| [537] | *Plumaria elegans.* | — | — | LECu.Plu.Ele.xx.Xxxx. |
| [538] | *Polyandrocarpa misakiensis.* | — | C-lectin. | LECi.Pol.Mis.xx.Xga1. |
| [539] | *Polygonum multiformum.* | — | — | LECp.Pol.Mul.xx.Xxxx. |
| [540] | *Polyomavirus.* | 1VPN. | — | LECV.Pol.Vir.xx.Xxxx. |
| [541] | *Polyporus fomentarius.* | — | — | LECf.Pol.Fom.xx.Xxxx. |
| [542] | *Polyporus squamosus.* | — | — | LECf.Pol.Squ.xx.Xxxx. |
| [543] | *Polysphondylium pallidum.* | — | — | LECu.Pol.Pal.xx.Xxxx. |
| [544] | *Potamon potamios.* | — | — | LECi.Pot.Pot.xx.Xxxx. |
| [545] | *Prunus Americana.* | — | — | LECp.Pru.Ame.xx.Xxxx. |
| [546] | *Prunus avium.* | — | — | LECp.Pru.Avi.xx.Xxxx. |
| [547] | *Psathyrostachys juncea.* | — | Hevein domain lectin, chitin binding. | LECp.Psa.Jun.se.Hch1. |
| [548] | *Pseudomonas aeruginosa.* | — | — | LECb.Pse.Aer.xx.Xga1. |
| [549] | *Pseudomonas aplysia.* | — | — | LECb.Pse.Apl.xx.Xxxx. |
| [550] | *Psophocarpus tetragonolobus.* | PTL-I (WBA-I), PTL-II (WBA-II), WBTL, L-I, L-II. | — | LECp.Pso.Tet.se.Hga1 (PTL-I) LECp.Pso.Tet.se.Hga2 (PTL-II) LECp.Pso.Tet.ro.Hga1 (WBTL) LECp.Pso.Tet.so.Hga2 LECp.Pso.Tet.le.Hga1 (L-I) LECp.Pso.Tet.le.Hga2 (L-II). |
| [551] | *Ptilota serrata.* | — | — | LECu.Pxx.Ser.xx.Xxxx. |
| [552] | *Punica granatum.* | — | — | LECp.Pun.Gra.xx.Xxxx. |
| [553] | *Rana catesbeiana.* | — | Lectins Displaying RNase Activity (Leczymes). | LECa.Ran.Cat.xx.Xxxx. |
| [554] | *Rana catesbeiana* ovum lectin. | cSBL. | Lectins Displaying RNase Activity (Leczymes). | LECa.Ran.Cat.xx.Xxxx. |
| [555] | *Rana japonica.* | jSBL. | Lectins Displaying RNase Activity (Leczymes). | LECa.Ran.Jap.xx.Xxxx. |
| [557] | *Rana nigromaculata.* | — | — | LECa.Ran.Nig.xx.Xxxx. |
| [558] | *Raphanus sativus.* | — | — | LECp.Rap.Sat.xx.Xxxx. |
| [559] | *Ratus norvegicus.* | Mannan Binding Protein (MBP-A). | C-lectin or Collectin. | LECa.Rat.Nor.xx.Xxxx. |
| [560] | *Ratus ratus.* | Rat peritoneal macrophage lectin. | — | LECa.Rat.Rat.xx.Xfu1 LECa.Rat.Rat.xx.Xga1. |

TABLE 1-continued

| KEY NAME | ABBREVIATION | CLASS | LECTIN CODE |
|---|---|---|---|
| [561] *Ratus ratus.* | — | — | LECa.Rat.Rat.xx.Xxxx. |
| [562] *Ratus ratus.* | Galectin II. | S-lectin or Galectin. | GLT2.Rat.Rat.xx.Xxxx. |
| [563] *Ratus ratus.* | Galectin IV. | Tandem Repeat S-lectin or Galectin. | GLTa.Rat.Rat.xx.Xxxx. |
| [564] *Rheum rhapontium.* | — | — | LECp.Rhe.Rhas.xx.Xxxx. |
| [565] *Ribes rubrum.* | — | — | LECp.Rib.Rubs.xx.Xxxx. |
| [566] *Ricinus communis.* | RCA-I, RCA-II, Ricin. | beta-trefoil lectin. | LECp.Ric.Com.se.Cga1 (Ricin D) LECp.Ric.Com.se.Cga2 (Ricin E) LECp.Ric.Com.se.Cga2 (RCA, RSL). |
| [567] *Robinia pseudoacacia.* | RPA-I, RCA-III. | — | LECp.Rob.Pse.se.Hcu1 (RPsA-I) LECp.Rob.Pse.se.Hcu2 (RPsA-II) LECp.Rob.Pse.se.Hcu1 (RPbA-I) LECp.Rob.Pse.se.Hcu2 (RPbA-II). |
| [568] *Rubus fructicosus.* | RFA. | ?. | LECp.Rub.Fru.tc.Xga1. |
| [569] *Rubus idaeus.* | — | — | LECp.Rub.Ida.xx.Xxxx. |
| [570] *Rutilus rutilus.* | — | — | LECv.Rut.Rut.xx.Xxxx. |
| [571] *Salmo gairdneri.* | — | — | LECa.Sal.Gai.xx.Xxxx. |
| [572] *Salmo salar* v. Atlantica. | — | — | LECa.Sal.Sal.xx.Xma1. |
| [573] *Salmo salar* v. Chinook. | — | — | LECa.Sal.Sal.xx.Xxxx. |
| [574] *Salmo trutta.* | — | — | LECa.Sal.Tru.xx.Xxxx. |
| [618] *Tetragonolobus pupurea.* | — | — | LECp.Tet.Pur.xx.Xxxx. |
| [619] *Thermopsis.* | — | — | LECz.The.sss.xx.Xxxx. |
| [621] *Toxopneustes pileolu.* | — | C-lectin. | LECi.Xxx.Xxx.xx.Xxxx. |
| [622] *Trichoderma.* | — | — | LECf.Tri.Sss.xx.Xxxx. |
| [623] *Tricholoma mongolicum.* | — | — | LECf.Tri.Mon.xx.Xxxx. |
| [624] Tricholomataceae 93-138. | — | — | LECf.Tri.Sss.xx.Xxxx. |
| [625] Tricholomataceae 93-34. | — | — | LECz.Tri.Sss.xx.Xxxx. |
| [626] *Trichosanthes japonica.* | TJA-II, TJA-I, TK-I, TK-II. | — | LECp.Tri.Jap.xx.Xxxx. |
| [627] *Trifolium repens.* | — | — | LECp.Tri.Rep.xx.Xxxx. |
| [628] *Triticum aestivium.* | WGA. | Hevein domain lectin, chitin binding lectin. | LECp.Tri.Aes.se.Hch1. |
| [629] *Tulipa gesneriana.* | TGA. | — | LECp.Tul.Ges.xx.Xxxx. |
| [630] *Udotea petiolata.* | — | — | LECp.Udo.Pet.xx.Xxxx. |
| [631] *Ulex europaeus.* | UEA-I, UEA-II, UEA-III. | Legume lectin. | LECp.Ule.Eur.xx.Xxxx. |
| [632] *Ulva lactuca.* | — | — | LECu.Ulv.Lac.xx.Xxxx. |
| [633] *Ulva laetevirens.* | — | — | LECu.Ulv.Lae.xx.Xxxx. |
| [635] *Ulva rigida.* | — | — | LECz.Ulv.Rig.xx.Xxxx. |
| [637] *Urtica dioica.* | UDA. | Chitin-binding lectins. | LECp.Urt.Dio.rh.Hch1. |
| [638] *Vaejovis confuscius.* | — | — | LECi.Vae.Con.xx.Xxxx. |
| [639] *Vatairea macrocarpa.* | VML. | — | LECp.Vat.Mac.xx.Xxxx. |
| [640] *Vibrio alginolyticus.* | — | — | LECb.Vib.Alg.xx.Xch1. |
| [641] *Vibrio chlolera.* | VPCV; Chitovibrin. | — | LECb.Vib.Cho.xx.Xxxx. |
| [642] *Vicia cracca.* | — | — | LECp.Vic.Cra.xx.Xxxx. |
| [643] *Vicia ervilia.* | — | — | LECp.Vic.Erv.xx.Xxxx. |
| [644] *Vicia faba.* | VFA, Favin. | Legume lectin. | LECp.Vic.Fab.xx.Xxxx. |
| [645] *Vicia graminea.* | VGA. | — | LECp.Vic.Gra.xx.Xxxx. |
| [646] *Vicia hyrcanica.* | — | — | LECp.Vic.Hyr.xx.Xxxx. |
| [647] *Vicia sativa.* | — | — | LECp.Vic.Sat.xx.Xxxx. |
| [648] *Vicia unijuga.* | VUA. | — | LECp.Vic.Unj.xx.Xxxx. |
| [649] *Vicia villosa.* | VVA-A4, VVL-A4. | Legume lectin. | LECp.Vic.Vil.xx.Xxxx. |
| [650] *Vigna radiata.* | MBL-I, MBL-II. | — | LECp.Vig.Rad.xx.Xxxx. |
| [651] *Vigna unguiculata.* | — | — | LECp.Vig.Ung.xx.Xxxx. |

TABLE 1-continued

| KEY | NAME | ABBREVIATION | CLASS | LECTIN CODE |
|---|---|---|---|---|
| [652] | Viscum album. | ML-I, ML-II, ML-III, Viscumin, VisAlbCBA. | Beta-trefoil lectin (ML-I). | LECp.Vis.Alb.pl.Cga1 (ML-I, viscumin) LECp.Vis.Alb.pl.Cga2 (ML-II, viscumin) LECp.Vis.Alb.pl.Cga3 (ML-III, VAA-II) LECp.Vis.Alb.pl.Hch1 (VisAlbCBA). |
| [653] | Vitis vinifera. | — | — | LECp.Vit.Vin.xx.Xxxx. |
| [654] | Volvariella volvacea. | VVL. | — | LECf.Vol.Vol.xx.Xxxx. |
| [655] | Wistaria floribunda. | WFA. | — | LECp.Wis.Flo.xx.Xxxx. |
| [656] | Wistaria floribunda. | — | — | LECp.Wis.Flo.xx.Xxxx. |
| [657] | Wistaria sinensis. | — | — | LECp.Wis.Sin.xx.Xxxx. |
| [658] | Wistaris brachbotrys. | — | — | LECz.Wis.Bra.xx.Xxxx. |
| [659] | Xanthosoma sagittifolium. | — | — | LECp.Xan.Sag.xx.Xxxx. |
| [660] | Xenopus laevis ovum. | — | — | LECa.Xen.Lae.xx.Xga1. |
| [661] | Xeromus chrysenteron. | — | — | LECz.Xer.Chr.xx.Xxxx. |
| [662] | Xylaria polymorpha. | — | — | LECf.Xyl.Pol.xx.Xxxx. |
| [663] | Zea mays. | ZMA-I, ZMA-II, ZMEA. | — | LECp.Zea.May.xx.Xxxx. |
| [664] | Cannabis sativa. | CSA. | — | LECp.CanSat.se.Glu. |
| [665] | Smilax glabra. | Sarparilla. | — | LECp.SmiGla.rh.xxx. |
| [666] | Trichosanthes anguina. | Snake gourd. | — | — |

Lectin codes take the following form:

LLLx.Ggg.Sss.ti.TspN

An explanation of each index variable follows.

LLL refers to the general category of agglutinin. At this point six general categories are recognized: lectins (LEC), integrins (INT), cadherins (CDH), annexins (ANN), selectins (SEL) and galectins (GLT). The x value refers to the taxonomic groups of the agglutinin, Table 1 summarizes these categories:

| Category | Taxonomic group |
|---|---|
| LECa, GLTa | Lectin or galectin from higher animal, typically vertebrates. |
| LECh, GLTh | Lectin or galectin from humans |
| LECi, GLTi | Lectin or galectin from invertebrates |
| LECp. | Plant lectins |
| LECf. | Lectin from fungi |
| LECu. | Lectin from unicellular organisms |
| LECb. | Lectin from Bacteria |
| LECv. | Viral lectins |

Ggg stands for the three first letters of the plant genus name (in Latin).

Sss stands for the three first letters of the plant species name (in Latin).

ti refers to the tissue from which the lectin has been isolated. Table 2 summarizes the indices used for the various tissues:

| Tissue, cell or organ | Taxonomic grouping | Index |
|---|---|---|
| Bark | Plant | Ba |
| Bulb | Plant | Bu |
| Cell membrane | Bacteria, Unicellular | Cm |
| Epidermis | Human, vertebrates | Ep |
| Fruit | Plant | Fr |
| Hemolymph | Invertebrates | He |
| Latex | Plant | La |
| Leaf | Plant | Le |
| Nodule | Plant | No |
| Organ or cell type | Human, vertebrates, Invertebrates | Oc |
| Phloem sap | Plant | Ps |
| Rhizome | Plant | Rh |
| Root | Plant | Ro |
| Seed | Plant | Se |
| Serum or plasma | Human, vertebrates, Invertebrates | Sr |
| Spores or fruiting bodies | Fungi | Sp |
| Stem | Plant | St |
| Tentacles | Invertebrates | Te |
| Tuber | Plant | Tu |
| Whole body homogenate | Invertebrates | Wb |
| Venom | Invertebrates | Ve |
| Undefined | Human, vertebrates, Invertebrates, Bacteria, Unicellular, Virus, Fungal | Un |

T refers to the lectin subtype. Hololectins, merolectins, chimerolectins and superlectins are indicated by the letters H, M, C and S, respectively.

sp refers to the specificity group. Each group is indicated by the index given in Table 3:

| Specificity | Index of group |
| --- | --- |
| Mannose-binding lectins | ma |
| Mannose/maltose-binding lectins | mm |
| Mannose/glucose-binding lectins | mg |
| GlcNAc/(GlcNAc)-binding lectins | ch |
| Gal/GalNAc-binding lectins | ga |
| Fucose-binding lectins | fu |
| Sialic acid-binding lectins | si |
| Lectins with a complex but known specificity | co |
| Lectins with a complex and unknown specificity | cu |
| Lectins with a dual specificity | du |
| Lectins with an undetermined specificity | nd |

Lipids

A multifunctional molecule of the invention can also be a molecule that comprises a first part which comprises a lipid and a second part which comprises an amino acid sequence which can bind to a cell surface molecule, e.g. a cell surface molecule of an APC. The attachment of a lipid, e.g. a long-chain fatty acid, to a molecule, e.g. a polypeptide, can permit the complex to become stably associated With the plasma membrane when the complex is admixed with a cell (Nagarajan et al, 1995, J Immunol Methods 184:241-51; McHugh et al, 1995, PNAS 92:8059-63; van den Berg et al, 1995, J Cell Biol, 131:669-77). This is believed to occur through intercalation of the lipid into the membrane. A convenient method of producing a lipid-associated polypeptide comprises expressing, in a suitable host cell, a nucleic acid encoding, in part, a signal sequence directing the post-translational addition of a GPI moiety. Using recombinant DNA technology, a naturally non-GPI linked protein can be expressed as a GPI-linked protein by constructing a nucleic acid that encodes the protein linked to a heterologous GPI signal sequence. Nucleotide sequences encoding GPI signal sequences useful for this purpose include, for example, those comprised by decay accelerating factor (e.g., sequences encoding amino acid sequence "22" in Table 1 of Bucht and Hjalmarsson, 1996, Biochim Biophys Acta 1292: 223-32; sequences encoding signal sequences disclosed in Caras et al, U.S. Pat. No. 5,109,113); brevican (e.g., nt 1982-2047 of Genbank accession number X86406), mesothelin (e.g., nt 1858-1983 of Genbank U40434), coccidioides immitis antigen 2 (e.g., sequences encoding amino acids 172-194 of NCBI Entrez protein database accession #1256444, Zhu et al, 1996, Gene 181:121-5), acetylcholinesterase (e.g., sequences encoding the peptide "HC" as described in Duval et al, 1992, EMBO J 11:3255-61; (e.g., sequences encoding amino acid sequence "19" in Table 1 of Bucht and Hjalmarsson, 1996, Biochim Biophys Acta 1292: 223-32)), human folate receptors alpha and beta (e.g., sequences encoding amino acids 230-257 of NCBI Entrez protein database accession #182416 or amino acids 228-255 of NCBI Entrez protein database accession #1655592, Yan and Ratnam, 1995, Biochemistry 34:14594-600), 5' nucleotidase (e.g., sequences encoding amino acids 547-570 or 547-574 of NCBI Entrez protein database accession #404502, Furukawa et al, 1994, Biochim Biophys Acta 1190:273-8; (e.g., sequences encoding amino acid sequences "5" or "6" in Table 1 of Bucht and Hjalmarsson, 1996, Biochim Biophys Acta 1292:223-32)), CD59 (e.g. encoded by nt 393-473 of Genbank U48255; sequences encoding amino acid sequence "20" in Table 1 of Bucht and Hjalmarsson, 1996, Biochim Biophys Acta 1292:223-32; sequences encoding amino acids 74-101 of FIG. 2 of Powell et al, 1997, J Immunol 158:1692-1702), T-cadherin (e.g., sequences encoding the 76 C-terminal amino acids of chick T cadherin as described by Koller and Ranscht, 1996, J Biol Chem 271:30061-7), aminopeptidase P (e.g., sequences encoding amino acids 649-673 of NCBI Entrez protein database accession #1517942, Hyde et al, 1996, Biochem J 319:197-201), carboxypeptidase M, CD16B, Thy 1, carbonic anhydrase IV (e.g., sequences encoding amino acids 284-312 of NCBI Entrez protein database accession #179791, Okuyama et al, 1995, Arch Biochem Biophys 320:315-22), placental alkaline phosphatase (e.g., sequences encoding amino acids 498-529 of NCBI Entrez protein database accession #178464, Oda et al, 1994, Biochem J 301:577-83), neuronal glycoprotein F3, carcinoembryonic antigen (e.g., sequences encoding amino acid sequence "28" in Table 1 of Bucht and Hjalmarsson, 1996, Biochim Biophys Acta 1292:223-32), MRC-OX45 (e.g., sequences encoding amino acid sequence "2" in Table 1 of Bucht and Hjalmarsson, 1996, Biochim Biophys Acta 1292:223-32), RT 6.2 (e.g., sequences encoding amino acid sequence "3" in Table 1 of Bucht and Hjalmarsson, 1996, Biochim Biophys Acta 1292:223-32), D. discoideum prespore-specific antigen (e.g., sequences encoding amino acid sequence "4" in Table 1 of Bucht and Hjalmarsson, 1996, Biochim Biophys Acta 1292:223-32), microsomal dipeptidase (e.g., sequences encoding amino acid sequence "8" in Table 1 of Bucht and Hjalmarsson, 1996, Biochim Biophys Acta 1292: 223-32), CAMPATH-1 (e.g., sequences encoding amino acid sequence "9" in Table 1 of Bucht and Hjalmarsson, 1996, Biochim Biophys Acta 1292:223-32), T. brucei PARP (e.g., sequences encoding amino acid sequence "10" in Table 1 of Bucht and Hjalmarsson, 1996, Biochim Biophys Acta 1292:223-32), T. brucei VSG Mit 118a (e.g., sequences encoding amino acid sequence "11" in Table 1 of Bucht and Hjalmarsson, 1996, Biochim Biophys Acta 1292:223-32), T. brucei VSG Mit 117a (e.g., sequences encoding amino acid sequence "12" in Table 1 of Bucht and Hjalmarsson, 1996, Biochim Biophys Acta 1292:223-32), T. brucei VSG MITat 1.1000 BC (e.g., sequences encoding amino acid sequence "13" in Table 1 of Bucht and Hjalmarsson, 1996, Biochim Biophys Acta 1292:223-32), T. brucei VSG MITat 1.5b (e.g., sequences encoding amino acid sequence "14" in Table 1 of Bucht and Hjalmarsson, 1996, Biochim Biophys Acta 1292:223-32), T. brucei VSG ILTat 1.1 (e.g., sequences encoding amino acid sequence "15" in Table 1 of Bucht and Hjalmarsson, 1996, Biochim Biophys Acta 1292:223-32), T. brucei VSG TxTat 1 (e.g., sequences encoding amino acid sequence "16" in Table 1 of Bucht and Hjalmarsson, 1996, Biochim Biophys Acta 1292:223-32), T. brucei VSG Mit 221 (e.g., sequences encoding amino acid sequence "17" in Table 1 of Bucht and Hjalmarsson, 1996, Biochim Biophys Acta 1292:223-32), prion proteins (e.g., sequences encoding amino acid sequence "18" in Table 1 of Bucht and Hjalmarsson, 1996, Biochim Biophys Acta 1292:223-32), urokinase receptor (e.g., sequences encoding amino acid sequence "21" in Table 1 of Bucht and Hjalmarsson, 1996, Biochim Biophys Acta 1292:223-32), T. congolense VSG YNat 1.1 (e.g., sequences encoding amino acid sequence "23" in Table 1 of Bucht and Hjalmarsson, 1996, Biochim Biophys Acta 1292:223-32), S. cerevesiae GAS-1 (e.g., sequences encoding amino acid sequence "24" in Table 1 of Bucht and Hjalmarsson, 1996, Biochim Biophys Acta 1292: 223-32), Thy-1 (e.g., sequences encoding amino acid sequences "25" or "26" in Table 1 of Bucht and Hjalmarsson, 1996, Biochim Biophys Acta 1292:223-32), L. major PSP (e.g., sequences encoding amino acid sequence "29" in Table 1 of Bucht and Hjalmarsson, 1996, Biochim Biophys Acta 1292:223-32), *D. discoideum* contact site A glycoprotein (e.g., sequences encoding the 25 C-terminal amino acids as described in Barth et al, 1996, Biochem J 317:533-40) CD24, and synthetic sequences (e.g. as described by Coyne et al, 1993, J Biol Chem 268:6689-93).

GPI-linked polypeptides can be extracted from cells using the following method. $5 \times 10^6$ cells are spun down and frozen at −80° C. The pellet is thawed in 14 ml of 0.15M NaCl/10 mM Tris 7.4/0.1 mM primaquine/2% Trito X-114 with stirring at 0° C. for 1 h, then centrifuged at 8800 g at 0° C. for 10 min. The supernatant is maintained at −20° C. overnight, thawed at room temperature, and then placed at 32° C. for 12 min. It is then centrifuged at 3000 g for 3 min at 32° C. The top layer is decanted and 11 ml of cold Buffer A (0.15M NaCl/10 mM Tris 7.4/0.1 mM primaquine/0.06% Triton X-114) is added to the bottom layer. This is incubated on ice for 10 min. The 12 min 32° C. incubation, 32° C. 3000 g centrifugation, decanting of top layer, and addition of 11 ml cold Buffer A to bottom layer are repeated. The solution is centrifuged at 18000 g for 10 min at 0° C. The 12 min 32° C. incubation, 32° C. 3000 g centrifugation, and decanting of top layer are repeated. 3 vol of cold acetone are added to the final bottom phase. The solution is centrifuged at 12,000 RPM for 30 min, the supernatant removed, and the protein pellet containing the GPI fraction dried under vacuum. Specific proteins can be purified by methods well-known to those skilled in the art, e.g. immunoaffinity purification.

Another method of producing a lipid-linked polypeptide is to chemically link the polypeptide to a fatty acid such as palmitate. 1.5 mg/ml of the polypeptide is suspended in PBS, pH 7.8, containing 0.3% deeoxycholic acid, 0.1% sodium bicarbonate, and 0.1% sodium azide. The optimal final pH of the solution is 7.6-8.0. The mixture is warmed to 37° C. and the N-hydroxysuccinimide ester of palmitic acid (Research Organics, Cleveland, Ohio) is added to a final concentration of 0.1 mg/ml. The solution is incubated overnight at room temperature. The polypeptide is purified by passage through a 16×250 mm Sephadex G-75 chromatography column equilibrated with 0.15% deoxycholic acid in PBS, pH 7.6.

Crosslinking Moieties Useful According to the Invention

Another convenient method of linking a ligand to an antigen bearing target is to use a crosslinking agent. A "crosslinking agent" is a chemical entity that can react with functional groups on at least two other molecules, e.g. two polypeptides or a polypeptide and a lipid, such that upon reaction with the crosslinking agent the two molecules become covalently linked. Thus, a ligand for CD40 can be crosslinked to a molecule on the surface of a cell.

A wide variety of crosslinking agents, both bifunctional and polyfunctional, are known in the art and are commercially available, e.g. from Sigma (St. Louis, Mo.). These include, for example, S-acetylmercaptosuccinic anhydride, S-acetylthioglycolic acid N-hydroxysuccinimide ester, S-acetylthiopropionic acid N-hydroxysuccinimide ester, adipic acid dihydrazide, 4-azidobenzoic acid N-hydroxysuccinimide ester, N-(5-azido-2-nitrobenzyloxy)succinimide, 6-(4-azido-2-nitrophenylamino)hexanoic acid N-hydroxysuccinimide ester, p-azidophenacyl bromide, N-(4-azidophenylthio)phthalimide, 4-azidosalicylic acid N-hydroxysuccinimide ester, bromoacetic acid N-hydroxysuccinimide ester, 1,4-butanediol diglycidyl ether, carbonyl-bis(L-methionine p-nitrophenyl ester), 2-diazo-3,3,3-trifluoropropionic acid p-nitrophenyl ester, diethyl malonimidate, 1,5-difluoro-2,4-dinitrobenzene, 4,4'-diisothiocyanatostilbene-2,2'-disulfonic acid, dimethyl adipimidate, dimethyl 3,3'-dithiobispropionimidate, dimethyl pimelimidate, dimethyl suberimidate, 4,4'-dithiobisphenyl azide, dithiobis (propionic acid N-hydroxysuccinimide ester), ethylene glycol bis-(succinic acid N-hydroxysuccinimide ester), 4-fluoro-3-nitrophenyl azide, bis-(4-fluoro-3-nitrophenyl) sulfone, p-formylbenzoic acid N-hydroxysuccinimide ester, glutaraldehyde, 2-iminothiolane, 6-(iodoacetamido)caproic acid N-hydroxysuccinimide ester, iodoacetic acid N-hydroxysuccinimide ester, 3-malemidoacetic acid N-hydroxysuccinimide ester, 3-malemidobenzoic acid N-hydroxysuccinimide ester, 4-(N-malemido)benzophenone, gamma-malemidobutyric acid N-hydroxysuccinimide ester, epsilon-malemidocaproic acid N-hydroxysuccinimide ester, 4-(N-malemidomethyl)cyclohexanecarboxylic acid N-hydroxysuccinimide ester, 4-(N-malemidomethyl)cyclohexanecarboxylic acid 3-sulfo-N-hydroxysuccinimide ester, beta-malemidopropionic acid N-hydroxysuccinimide ester, N,N'-bis(3-malemidopropionyl)-2-hydroxy-1,3-propanediamine, 1,4-phenylene diisothiocyanate, N,N'-o-phenylene dimalemide, N,N'-p-phenylene dimalemide, polyoxyethylene bis(glycidyl ether), bis(polyoxyethylene bis(glycidyl ether)), polyoxyethylene bis(imidazolylcarbonyl), bis(polyoxyethylene bis(imidazolylcarbonyl)), polyoxyethylene bis (p-nitrophenyl carbonate), 3-(2-pyridyldithio)propionic acid N-hydroxysuccinimide ester, suberic acid bis(N-hydroxysuccinimide) ester, succinic acid malemidoethyl N-hydroxysuccinimide ester, 1,5 bis(succinimidooxycarbonyloxy)-pentane, and bis(N-succinimidyl) carbonate.

Ligands of a Cell Surface Protein

The multifunctional molecules of the present invention comprise one part which is a lectin and is capable of binding to at least one carbohydrate molecule on an antigen bearing target, and a second part comprising a ligand for a cell surface protein of an antigen presenting cell. The ligand can be any ligand which binds to one or more of the cell surface molecules indicated by GenBank Accession number in Appendix I or II. More preferably, however, the ligand includes, but is not limited to an opsonin, a cytokine, a heat shock protein, an adhesion molecule. a defensin, or a counterreceptor for a T cell costimulatory molecule; or a portion of any of these molecules, e.g., about (or at least about) 5, 8, 10, 12, 15, 20, 25, 35, 40, 50, 60, 70, 80, 100, or 120 contiguous amino acid residues, up to the full length of such a molecule.

Cytokines Useful According to the Invention

The term "cytokine" as defined hereinabove refers to a polypeptide molecule that is naturally secreted by mammalian cells and that binds to a cell surface receptor on a leukocyte. The term "cytokine" also refers herein to a polypeptide molecule that is a ligand for a receptor for a naturally occurring cytokine. Unlike an opsonin, a cytokine does not naturally contemporaneously bind an antigen and a cell-surface receptor.

Leukocytes which bear receptors for cytokines include, for example, monocytes, macrophages, dendritic cells, neutrophils, eosinophils, basophils, platelets, lymphocytes, T lymphocytes, B lymphocytes, NK cells, myeloma cells, lymphoma cells, and leukemic cells.

Without being bound by any one mechanism, it is believed that cell-surface associated cytokines provide an advantage over freely diffusible cytokines by allowing stable juxtaposition of the cytokine to the cell, thus increasing the concentration of cytokine in the vicinity of the cell.

Preferred cytokines are non-rodent cytokines, e.g. primate, e.g. human cytokines.

Some cytokines can be regarded as belonging to one or more families of cytokines based on structural and/or functional properties. One such family consists of the interleukins. Interleukins are structurally diverse, but share the property of both being expressed by and acting on leukocytes. Examples of interleukins include IL-1 (e.g. polypeptides encoded by Genbank Accession No. M15330, M28983, E04743, M15131) IL-2 (e.g. polypeptides encoded by Genbank Accession No. E01108, K02797), IL-3 (e.g. polypeptides encoded by Genbank Accession No. A02046, M14743), IL-4 (e.g. polypeptides encoded by M13982, M25892), IL-5 (e.g. polypeptides encoded by X06270, J03478), IL-6 (e.g. polypeptides encoded by E02772, M20572), IL-7 (e.g. polypeptides encoded by J04156, M29054-29057), IL-8 (e.g. polypeptides encoded by M28130), IL-9 (e.g. sequences disclosed in Kelleher et al, Blood. 1991; 77: 1436-1441, Immunogenetics 1990;31(4): 265-270), IL-10 (e.g. polypeptides encoded by M84340, U16720), IL-11 (e.g. sequences disclosed in Paul et al, Proc Natl Acad Sci USA. 1990; 87: 7512-7516, Morris et al, Exp Hematol. 1996; 24: 1369-1376), IL-12 (e.g. polypeptides encoded by Genbank Accession No. M86671, S82412; Genbank protein P29459, P29460), IL-13 (e.g. polypeptides encoded by U31120, L3028), IL-14 (e.g. sequences disclosed in Ambrus et al, Proceedings of the National Academy of Science (USA) 1993; 90: 6330-4), IL-15 (e.g. polypeptides encoded by AF031167, U22339), 1L-16 (e.g. polypeptides encoded by AF006001, M90391), IL-17 (e.g. polypeptides encoded by U32659, U43088), IL-18 (e.g. polypeptides encoded by D49949, D49950), IL-19 (e.g. polypeptides encoded by AY040367), IL-20 (e.g. polypeptides encoded by NM02130, NM018724), IL-21 (e.g. polypeptides encoded by AF254069, AF254070), IL-22 (e.g. polypeptides encoded by AF279437), IL-23 (e.g. polypeptides encoded by AF301619, AF301620, AY055379 [p19 alpha chain combines with IL-12 p40 chain to form IL-23]), IL-24 (e.g. polypeptides encoded by AF276916, NM053095), IL-25 (e.g. polypeptides encoded by NM080837), TNF-alpha (e.g. polypeptides encoded by M16441, Y00467), and GM-CSF (e.g. polypeptides encoded by X03019, M11220) and their homologues among species. Nucleotide sequences encoding homologues will hybridize to each other under moderate- to high-stringency conditions.

Another family consists of the hematopoietins. Members of this family comprise helical regions, known as helices A, B, C, and D. Helices A and B and helices C and D run roughly parallel to each other, respectively. Examples of hematopoietins include IL-2, IL-3, IL-4, IL-5, IL-6, IL-7, IL-9, IL-11, IL-12, IL-13, IL-15, GM-CSF, G-CSF (e.g. polypeptides encoded by Genbank Accession No. E01219, M13926), oncostatin M (e.g. polypeptides encoded by Genbank Accession No. D31942, sequences disclosed in Malik et al, Mol Cell Biol 1989, 9:2847-2853), LIF (e.g. polypeptides encoded by Genbank Accession No. X13967, X06381), CNTF (e.g. polypeptides encoded by Genbank Accession No. U05342, X60542), and their homologues among species. Nucleotide sequences encoding homologues will hybridize to each other under moderate- to high-stringency conditions.

Human IL2 is a protein of 133 amino acids (15.4 kDa) with a slightly basic pI. Murine and human IL2 display a homology of approximately 65%. IL2 is synthesized as a precursor protein of 153 amino acids with the first 20 amino-terminal amino acids functioning as a hydrophobic secretory signal sequence. The protein contains a single disulfide bond (positions Cys58/105) essential for biological activity.

IL2 is O-glycosylated at threonine at position 3. Variants with different molecular masses and charges are due to variable glycosylation. Non-glycosylated IL2 is also biologically active. Glycosylation appears to promote elimination of the factor by hepatocytes.

A dimeric form of human IL2, produced by the action of a transglutaminase isolated from regenerating fish optic nerves, has been shown to be a cytotoxic factor for rat brain oligodendrocytes in culture.

The human IL2 gene contains four exons. The IL2 gene maps to human chromosome 4q26-28 (murine chromosome 3). The homology of murine and human IL2 is 72% at the nucleotide level in the coding region.

The biological activities of IL2 are mediated by a membrane receptor that is expressed almost exclusively on activated, but not on resting, T-cells at densities of $4-12\times10^3$ receptors/cell. Activated B-cells and resting mononuclear leukocytes rarely express this receptor. The expression of the IL2 receptor is modulated by IL5 and IL6. Three different types of IL2 receptors are distinguished that are expressed differentially and independently. The high affinity IL2 receptor (Kdis ~10 pM) constitutes approximately 10% of all IL2 receptors expressed by a cells. This receptor is a membrane receptor complex consisting of the two subunits IL2R-alpha (TAC antigen=T-cell activation antigen; p55) and IL2R-beta (p75; CD122) as the ligand binding domains and a gamma chain as a signaling component. p75 is expressed constitutively on resting T-lymphocytes, NK-cells, and a number of other cell types while the expression of p55 is usually observed only after cell activation. p55 is, however, synthesized constitutively by a number of tumor cells and by HTLV-1-infected cells.

IL2 receptor expression of monocytes is induced by IFN-gamma, so that these cells become tumor-cytotoxic. In T-cells the expression of p75 can be reduced by IL3. An intermediate affinity IL2 receptor (Kdis=100 pM) consists of the p75 subunit and a gamma chain (see below) while a low affinity receptor (Kdis=10 nM) is formed by p55 alone.

p55 (e.g. polypeptides encoded by Genbank Accession No. X01057) has a length of 251 amino acids with an extracellular domain of 219 amino acids an a very short cytoplasmic domain of 13 amino acids. The p55 gene maps to human chromosome 10p14-p15.

p75 (e.g. polypeptides encoded by Genbank Accession No. M26062, M28052) has a length of 525 amino acids with an extracellular domain of 214 amino acids and a cytoplasmic domain of 286 amino acids. The p75 gene contains 10 exons and has a length of approximately 24 kb. It maps to human chromosome 22q11. 2-q12 and to murine chromosome 15 (band E).

A third 64 kDa subunit of the IL2 receptor, designated gamma, has been described (e.g. polypeptides encoded by Genbank Accession No. D13821, D11086). Murine and human gamma subunits of the receptor have approximately 70% sequence identity at the nucleotide and amino acid levels. This subunit is required for the generation of high and intermediate affinity IL2 receptors but does not bind IL2 by itself. These two receptor types consist of an alpha-beta-gamma heterotrimer and a beta-gamma heterodimer, respectively. The gene encoding the gamma subunit of the IL2 receptor maps to human chromosome Xq13, spans approximately 4.2 kb and contains eight exons. The gamma subunit of the IL2 receptor has been shown recently to be a component of the receptors for IL4 and IL7. It is also believed to be a component of the IL13 receptor.

The amino acids at positions 267-317 lying directly adjacent to the transmembrane region of p75 are involved in IL2-mediated signal transduction. In addition the IL2 receptor is associated with a number of other proteins (p22, p40, p100) which are thought to be involved in mediating conformational changes in the receptor chains, receptor-mediated endocytosis, and further signal transduction processes. One of the identified proteins is the 95 kDa cell adhesion molecule ICAM-1 which probably focuses IL2 receptors at regions of cell-to-cell contacts and thus may mediate paracrine activities, for example, during IL2-mediated stimulation of T-cells. Another protein associated with p75 is a tyrosine-specific protein kinase called lck. The observation that proliferation of cells induced by IL2 is inhibited by specific inhibitors of protein tyrosine kinases in an lck negative cell line suggests that other kinases may also be associated with IL2 receptors. Two such kinases, called fyn and lyn, have been identified. In addition, IL2 receptor signaling may also be mediated by vav.

Activated lymphocytes continuously secrete a 42 kDa fragment of the TAC antigen. This fragment circulates in the serum and plasma and functions as a soluble IL2 receptor (sIL2R). The concentrations of this soluble receptor vary markedly in different pathological situations, for example, infections, autoimmune diseases, leukemias, or after organ transplantation. Levels may increase up to 100-fold. The levels of sIL2R appear to correlate with the severity of HIV-induces diseases and may be of diagnostic value also in other settings.

Mouse and human IL2 both cause proliferation of T-cells of the homologous species at high efficiency. Human IL2 also stimulates proliferation of mouse T-cells at similar concentrations, whereas mouse IL2 stimulates human T-cells at a lower (sixfold to 170-fold) efficiency.

IL2 is a growth factor for all subpopulations of T-lymphocytes. It is an antigen-unspecific proliferation factor for T-cells that induces cell cycle progression in resting cells and thus allows clonal expansion of activated T-lymphocytes. This effect is modulated by hormones such as prolactin.

IL2 also promotes the proliferation of activated B-cells also this requires the presence of additional factors, for example, IL4.

Due to its effects on T-cells and B-cells IL2 is a central regulator of immune responses. It also plays a role in anti-inflammatory reactions, in hematopoiesis and in tumor surveillance. IL2 stimulates the synthesis of IFN-gamma in peripheral leukocytes and also induces the secretion of IL1, TNF-alpha and TNF-beta.

It is believed that he induction of the secretion of tumoricidal cytokines apart from the activity in the expansion of LAK cells (lymphokine-activated killer cells) are probably the main factors responsible for the antitumor activity of IL2.

IL2 can be assayed in bioassays employing cell lines that respond to the factor (e.g., ATH8, CT6, CTLL-2, FDCPmix, HT-2, NKC3, TALL-103). Specific ELISA assays for IL2 and enzyme immunoassays for the soluble receptor are also available. The soluble receptor can be detected also by employing biotinylated IL2 and flow-through cytometry or ELISA assays.

IL2 displays significant anti-tumor activity for a variety of tumor cell types since it supports the proliferation and clonal expansion of T-cells that specifically attack certain tumors. IL2 is increasingly used to treat patients with cancers refractory to conventional treatment. Combination therapy with systemically administered IL2 has resulted in long-term remissions in 30% of patients with metastatic renal cell carcinoma, for which there is no standard treatment. Objective and long-lived clinical responses have been documented also in a proportion of patients with melanoma or acute myeloid leukemia.

High dose systemic IL2 therapy is also associated with a great number of unwanted toxic side-effects. IL2 has additional effects on other components of the cellular immune system, including B-cells and macrophages, and induces the secretion of other soluble mediators, including TNF-alpha, TNF-beta, and IFN-gamma. These effects may contribute to the antitumor activity of IL2 as well as to its dose-related toxicity.

The transduction of murine tumor cells with a functional IL2 gene has been shown to lead to the rejection of the genetically modified cells by syngeneic hosts. Altered tumor cells expressing IL2 also increase systemic immunity.

Human IL4 is a protein of 129 amino acids (20 kDa) that is synthesized as a precursor containing a hydrophobic secretory signal sequence of 24 amino acids. IL4 is glycosylated at two arginine residues (positions 38 and 105) and contains six cysteine residues involved in disulfide bond formation. The disulfide bonds are essential for biological activity. Some glycosylation variants of IL4 have been described that differ in their biological activities. A comparison of murine and human IL4 shows that both proteins only diverge at positions 91-128.

An IL4 variant, Y124D, in which Tyr124 of the recombinant human protein is substituted by an aspartic acid residue, binds with high affinity to the IL4 receptor (Kd=310 pM). This variant is a powerful antagonist for the IL4 receptor system. It retains no detectable proliferative activity for T-cells and competitively inhibits IL4-dependent T-cell proliferation (K(i)=620 pM). The existence of this mutant demonstrates that high affinity binding and signal generation can be uncoupled efficiently in a ligand. Y124D also acts as a powerful antagonist for the IL13 receptor.

The human IL4 gene contains four exons and has a length of approximately 10 kb. It maps to chromosome 5q23-31. The murine gene maps to chromosome 11. The IL4 gene is in close proximity to other genes encoding hematopoietic growth factors (e.g., GM-CSF, M-CSF, IL3, IL5). The distance between the IL4 and the IL5 gene is approximately 90-240 kb.

At the nucleotide level the human and the murine IL4 gene display approximately 70% homology. The 5' region of the IL4 contains several sequence elements, designated CLE (conserved lymphokine element), that are binding sites for transcription factors controlling the expression of this and other genes. A sequence motif, called P sequence (CGAAAATTTCC; SEQ ID NO: 1) in the 5' region of the human IL4 gene (positions −79-69) is the binding site for a nuclear factor, called NF(P), mediating the response to T-cell activation signals.

The biological activities of IL4 are mediated by a specific receptor (Kdis=20-100 pM) which is expressed at densities of 100-5000 copies/cell (e.g. polypeptides encoded by Genbank Accession No. M29854, X52425). The extracellular domain of the IL4 receptor is related to the receptors for erythropoietin (Epo), IL6, and the beta chain of the IL2 receptor. It has been given the name CD124.

The cDNA for the murine IL4 receptor encodes a transmembrane protein of 810 amino acids (including a secretory signal sequence). This receptor has a large intracellular domain of 553 amino acids. The human receptor has an extracellular domain of 207 amino acids, a transmembrane domain of 24 residues, and a large intracellular domain of 569 amino acids.

The IL4 receptor has been shown recently to contain the gamma subunit of the IL2 receptor as a signaling component. This gamma subunit is also associated with the receptors for IL4 and IL7 and probably also of IL13. Two forms of the receptor have been described, one of which is secreted. The secreted receptor only contains the extracellular IL4 binding domain and is capable of blocking IL4 activities. An IL4 binding protein (IL4-BP) that binds IL4 with the same affinity as the IL4 receptor has been shown also to be a soluble IL4 receptor variant. These soluble receptors probably function as physiological regulators of cytokine activities by inhibiting receptor binding or act as transport proteins. Soluble receptors or binding proteins have been described also for IL1 (IL1 receptor antagonist), IL2, IL6, IL7, TNF-alpha, IGF, and IFN-gamma.

The biological activities of IL4 are species-specific; mouse IL4 is inactive on human cells and human IL4 is inactive on murine cells. IL4 promotes the proliferation and differentiation of activated B-cells, the expression of class II MHC antigens, and of low-affinity IgE receptors in resting B-cells. IL4 enhances expression of class II MHC antigens on B-cells. It can promote their capacity to respond to other B-cell stimuli and to present antigens for T-cells. This may be one way to promote the clonal expansion of specific B-cells and the immune system may thus be able to respond to very low concentrations of antigens. The production of IL4 by non-B non-T-cells is stimulated if these cells interact with other cells via their Fc receptors for IgE or IgG. This effect can be enhanced by IL3. IL2 and PAF (platelet activating factor) induce the synthesis of IL4 while TGF-beta inhibits it.

IL3 antagonizes the IL2-induced effects in B-cells and causes a slow decrease of the expression of IL2 receptors, thus inhibiting the proliferation of human B-cells stimulated by IL2. In activated B-cells IL4 stimulates the synthesis of IgG1 and IgE and inhibits the synthesis of IgM, IgG3, IgG2a and IgG2b. This isotype switching induced by IL4 in B-cells is antagonized by IFN-gamma. The growth of multiple myelomas can be suppressed by IL4 which inhibits the synthesis of IL6, a myeloma growth factor. IL4 also inhibits the synthesis of IL6 in human alveolar macrophages.

Pretreatment of macrophages with IL4 prevents the production of IL1, TNF-alpha and prostaglandins in response to activation of the cells by bacterial endotoxins or IFN-gamma.

IL4 synergises with Epo and G-CSF/Epo in the generation of colonies containing granulocytes or erythroid progenitor cells in a colony formation assay.

The classical detection method for IL4 is a B-cell costimulation assay measuring the enhanced proliferation of stimulated purified B-cells. IL4 can be detected also in bioassays, employing IL4-responsive cells (e.g., BALM-4; BCL1; CT.4S; CTL44; CTLL-2; Da; FDCPmix; HT-2; L4; L138.8A; MO7E; MC/9; NFS-60; Ramos, Sez627, TF-1; TS1). A specific detection method for human IL4 is the induction of CD23 in a number of B-cell lines with CD23 detected either by flow-through cytometry or by a fluorescence immunoassay. An immunoassay that allows rapid determination of the rate of IL4 production under conditions preventing consumption/degradation is cytokine immunotrapping.

IL4 inhibits the growth of colon and mammary carcinomas. It has been shown to augment the development of LAK cells. The transduction of murine tumor cells with a functional IL4 gene has been shown to lead to the rejection of the genetically modified cells by syngeneic hosts. Altered tumor cells expressing IL4 also increase systemic immunity. Mice vaccinated with transduced cells reject a subsequent challenge of non-transduced cells, and, in some cases, a pre-existing tumor.

Human IL6 is a protein of 185 amino acids glycosylated at positions 73 and 172. It is synthesized as a precursor protein of 212 amino acids. Monocytes express at least five different molecular forms of IL6 with molecular masses of 21.5-28 kDa. They mainly differ by post-translational alterations such as glycosylation and phosphorylation.

IL6 isolated from various cell types shows some microheterogeneity in its N terminus. A 42-45 kDa form has been observed in plasma that is probably complexed with a carrier protein, alpha-2-macroglobulin ($\alpha$2M). Murine and human IL6 show 65% sequence homology at the DNA level and 42% homology at the protein level.

IL6 is a member of a family of cytokines which also includes LIF, CNTF, Oncostatin M, IL11, and CT-1. All known members of the IL6 cytokine family induce hepatic expression of acute phase proteins.

A stable and highly bioactive designer cytokine consisting of a fusion protein between IL6 and a soluble IL6 receptor, designated H-IL6, has been used for human hematopoietic progenitor cell expansion and is useful in cases in which cells do not respond to IL6 but require a stable complex consisting of IL6 and a soluble IL6 receptor.

The human IL6 gene has a length of approximately 5 kb and contains five exons. It maps to human chromosome 7p21-p14 between the markers D7S135 and D7S370. The murine gene maps to chromosome 5. The nucleotide sequences of IL6 and G-CSF genes resemble each other in a way suggesting a possible evolutionary relationship.

The IL6 receptor (e.g. polypeptides encoded by Genbank Accession No. M20566, E03515) is expressed on T-cells, mitogen-activated B-cells, peripheral monocytes and some macrophage- and B-cell-derived tumor cell types. It is not expressed in resting B-cells but is in resting T-cells. In hepatocytes the IL6 receptor expression is enhanced after treatment with IL6 or IL1. In several cell types the expression of the IL6 receptor is also enhanced by glucocorticoids. The IL6 receptor gene maps to human chromosome 1q21.

The IL6 receptor is a strongly glycosylated protein of 80 kDa and a length of 449 amino acids. It has been designated CD126. It is synthesized as a precursor of 468 amino acids. The molecular structure resembles that of receptors for M-CSF, PDGF and IL1 in that the receptor contains an immunoglobulin-like sequence domain in the aminoterminal region of the extracellular receptor domain.

The intracellular domain of the IL6 receptor has a length of approximately 82 amino acids and does not show any homology to other proteins involved in intracellular signal transduction. Two different forms of the receptor have been described that bind IL6 with different affinities (Kdis=$10^{-9}$ and $10^{-11}$ M) and most likely arise by post-translational modification of the same receptor protein. Biological activities of IL6 have been found also at concentrations of $10^{-13}$-$10^{-15}$ M suggesting either the existence of other high-affinity receptor conformations or the existence of further receptor molecules with higher affinities.

IL6 receptor-mediated signal transduction involves protein kinase C and also adenylate cyclase.

The complex formed between IL6 and its receptor associates with a transmembrane glycoprotein, gp130 (918 amino acids; cytoplasmic domain of 277 amino acids), that is involved in signal transduction. Binding of IL6 to its receptor leads to disulfide-linked homodimerization of gp130 and the associated activation of a tyrosine kinase as the first step of signal transduction. gp130 is expressed also in cells that do not express IL6 receptors. It has been found to be a component of other receptors, including those for IL11, LIF, Oncostatin M, and CNTF, and CT-1. This explains why LIF, CNTF, and IL6 share many biological activities although the factors themselves are not related to each other. A factor resembling STAT proteins, termed LIL factor, has been found to be involved in signaling pathways of IL6, and also of IL1 and bacterial lipopolysaccharides.

A soluble form of the IL6 receptor (IL6R-SUP (IL6 receptor soluble urinary protein)) has been described also that also interacts with gp130. These soluble receptors probably function as physiological regulators of cytokine activities by inhibiting receptor binding or act as transport proteins. Similar soluble receptors or binding proteins have been described also for IL1 (IL1ra, IL1 receptor antagonist), IL2, IL4, IL7, TNF-alpha, IGF, and IFN-gamma.

Some cells, including hematopoietic progenitor cells and neuronal cells, are only responsive towards a combination of IL6 and soluble IL6 receptor but not to IL6 alone.

Human IL6 is biologically active in monkeys, rats, and mice. Murine IL6 is not active in human cells. The plethora of biological activities is exemplified by the many different acronyms under which IL6 has been described. IL6 is a pleiotropic cytokine influencing antigen-specific immune responses and inflammatory reactions. It is one of the major physiological mediators of cute phase reaction. In hepatocytes IL6 in combination with glucocorticoids induces the synthesis of metallothioneins and increases intracellular zinc levels, thus preventing CCL4-induced hepatotoxicity. IL6 is a neurotrophic factor for cholinergic neurons that promotes their survival in culture. Some neuronal cell lines can be induced to differentiate by IL6.

IL6, like IL1, stimulates the synthesis of ACTH (Corticotropin) in the pituitary. Glucocorticoids synthesized in response to ACTH inhibit the production of IL6, IL1 and TNF in vivo, thus establishing a sort of negative feedback loop between the immune system and neuroendocrine functions. In astrocytes IL6 induces the synthesis of Nerve Growth Factor (NGF).

IL6 is a B-cell differentiation factor in vivo and in vitro and an activation factor for T-cells. In the presence of IL2 IL6 induces the differentiation of mature and immature T-cells into cytotoxic T-cells. IL6 also induces the proliferation of thymocytes and probably plays a role in the development of thymic T-cells.

IL6 is capable of inducing the final maturation of B-cells into immunoglobulin-secreting plasma cells if the cells have been pre-activated by IL4. In B-cells IL6 stimulates the secretion of antibodies to such a degree that serum IgG1 levels can rise 120-400-fold.

IL6 at concentrations of only 0.002 ng/mL is one of the major autocrine growth modulator for many human myelomas. The growth of these cells can be inhibited by monoclonal antibodies directed against IL6. It can be inhibited also by the introduction of antisense oligonucleotides against IL6 or by IL4. The growth-inhibitory effects of corticosteroids on myeloma cells is probably due to the steroid-induced reduction in the expression of IL6. The growth of human IL6 dependent myeloma cells can be inhibited also by IFN-gamma. IL6 may also function as an autocrine growth modulator for other tumor types, some of which have been found to secrete IL6 constitutively. IL6 has been shown to be an autocrine modulator of growth for in vitro cervical tumor cell growth. On the other hand IL6 blocks the growth of some solid tumors such as mammary carcinomas, cervical carcinomas, human lung cancer cell lines, histiocytic lymphomas, and melanomas.

IL6 and IL3 synergise in vitro in promoting the proliferation of multipotent hematopoietic progenitor cells. IL6 is also a thrombopoietin that induces the maturation of megakaryocytes in vitro and increases platelet counts in vivo. In murine, but not in human bone marrow cultures IL6 shows activities resembling those of GM-CSF.

Plasmacytoma cells produce IL6 and also the IL6 receptor. It has been suggested that these cells are stimulated in an autocrine fashion. A paracrine mechanism involving the presence of two different cell populations, one producing the factor and the other expressing the receptor, has been described also.

IL6 can be detected in bioassays employing IL6 responsive cell lines (e.g., 7TD1; B9; CESS, KPMM2, KT-3; M1, MH60-BSF-2, MO7E; Mono Mac 6; NFS-60; PIL-6; SKW6-C14; T1165; XG-1). IL6 can be assayed also by its activity as a hybridoma growth factor. Sensitive immunoassays and colorimetric tests are also available. An ELISA assay exists for detecting the receptor-associated gp130 protein.

In combination with other cytokines (for example, IL2) IL6 may be useful in the treatment of some tumor types. The transduction of murine tumor cells with a functional IL6 gene has been shown to lead to the rejection of the genetically modified cells by syngeneic hosts. Altered tumor cells expressing IL6 also increase systemic immunity. Mice vaccinated with transduced cells reject a subsequent challenge of non-transduced cells, and, in some cases, a pre-existing tumor.

Human IL10 is a homodimeric protein with subunits having a length of 160 amino acids. Human IL10 shows 73% amino acid homology with murine IL10. The human IL10 contains four exons. It is closely related to the product of the BCRF-1 gene (Bam HI C fragment rightward reading frame) of Epstein-Barr virus (84% homology at the protein level). These two proteins are more closely related to each other than human and murine IL10. BCRF-1 has therefore also been called viral IL10 (vIL10). The human IL10 gene maps to chromosome 1. The human IL10 shows 81% homology with murine IL10 at the nucleotide level.

A receptor has been identified on murine and human cells by using radiolabeled IL10 (e.g. polypeptides encoded by Genbank Accession No. L12120, U00672). Mouse IL10 is capable of blocking binding of human IL10 to mouse but not human cells. The murine IL10 receptor has been cloned. This receptor is a protein of approximately 110 kDa that binds murine IL10 specifically. This receptor is structurally related to receptors for IFN.

IL10 inhibits the synthesis of a number of cytokines such as IFN-gamma, IL2 and TNF-beta in Th1 subpopulations of T-cells but not of Th2 cells. This activity is antagonized by IL4. The inhibitory effect on IFN-gamma production is indirect and appears to be the result of a suppression of IL12 synthesis by accessory cells. In the human system, IL10 is produced by, and down-regulates the function of, Th1 and Th2 cells. In macrophages stimulated by bacterial lipopolysaccharides IL10 inhibits the synthesis of IL1, IL6 and TNF-alpha by promoting, among other things, the degradation of cytokine mRNA. It also leads to an inhibition of antigen presentation. In human monocytes IFN-gamma and IL10 antagonize each other's production and function. IL10 has been shown also to be a physiologic antagonist of IL12.

IL10 also inhibits mitogen- or anti-CD3-induced proliferation of T-cells in the presence of accessory cells and reduces the production of IFN-gamma and IL2. Exogenous IL2 and IL4 inhibit the proliferation-inhibitory effect but do not influence the production of IFN-gamma. In LPS-stimulated macrophages IFN-gamma increases the synthesis of IL6 by inhibiting the production of IL10. IL10 appears to be responsible for most or all of the ability of Th2 supernatants to inhibit cytokine synthesis by Th1 cells.

IL10 inhibits secretion of Ig by T-cell-independent antigens induced by IL5 but not that induced by IL2.

Murine Ly-1 B cells are the principal source of IL10. In contrast to other B-cells, Ly-1 B-cells express greatly elevated constitutive and inducible levels of IL10. These cells also have the distinctive property of continuous self-replenishment. The continuous treatment of newborn mice with anti-IL10 antibodies leads to a depletion of the Ly-1 B-cells while maintaining a normal population of splenic B-cells. These mice also contain greatly reduced serum immunoglobulin M levels and are also impaired in their antibody responses to specific antigens. IL10 is therefore a regulator of Ly-1 B-cell development. The mechanism of Ly-1 B-cell depletion appears to involve the increased production of IFN-gamma since co-administration of neutralizing anti-IFN-gamma antibodies substantially restores the number of peritoneal-resident Ly-1 B-cells in these mice.

IL10 is also a costimulator for the growth of mature and immature thymocytes (together with IL2, IL4 and IL7) and functions as a cytotoxic T-cell differentiation factor, promoting a higher number of IL2-activated cytotoxic T-lymphocyte precursors to proliferate and differentiate into cytotoxic effector cells. IL10 sustains viability of B-cells in vitro and also stimulates B-cells and promotes their differentiation. It enhances the expression of MHC class II antigens on B-cells whereas it inhibits MHC class II expression on monocytes. In B-cells activated via their antigen receptors or via CD40 IL10 induces the secretion of IgG, IgA and IgM. This effect is synergised by IL4 while the synthesis of immunoglobulins induced by IL10 is antagonized by TGF-beta. The activation of macrophages can be prevented by IL10.

It has been shown that human IL10 is a potent and specific chemoattractant for human T-lymphocytes. The chemotactic activity is directed towards cells expressing CD8 and not towards CD4 (+)cells. IL10 also inhibits the chemotactic response of CD4 (+)cells, but not of CD8 (+)cells, towards IL8. IL10 can be detected with a sensitive ELISA assay. The murine mast cell line D36 can be used to bioassay human IL10. The intracellular factor can be detected also by flow cytometry.

The introduction of an IL10 expression vector into CHO cells has been used to analyze the consequences of local IL10 production in vivo. These altered cells were no longer tumorigenic in nude mice or severe combined immunodeficient SCID mice and also suppressed the growth of equal numbers of co-injected normal CHO cells. While normal CHO tumors are usually substantially infiltrated by macrophages, these were virtually absent within CHO-IL10 tumor tissues, suggesting that IL10 indirectly suppresses tumor growth of certain tumors by inhibiting infiltration of macrophages which may provide tumor growth promoting activity.

Human IL12 is a heterodimeric 70 kDa glycoprotein consisting of a 40 kDa subunit (p40, 306 amino acids; 10% carbohydrate) and a 35 kDa subunit (p35, 197 amino acids; 20% carbohydrate) linked by disulfide bonds that are essential for the biological activity of IL12. p40 contains 10 cysteines and a binding site for heparin; p35 contains 7 cysteines.

The two subunits of IL12 are not related to any other known proteins. p40 shows some homology with the extracellular domain of the receptor for IL6, and p35 appears to be a homologue of IL6.

Bioactive murine and human IL12 fusion proteins combining the two IL12 subunits in a single molecule have been described. This designer cytokine retains antitumor activity in vivo. Flexi 12, a single chain protein retaining all of the biological characteristics of the dimeric recombinant IL12, has also been described.

The gene encoding the p40 subunit of IL12 (IL12B) maps to human chromosome 5q31-q33 in the same region that also harbors other cytokine genes. The gene encoding the p35 subunit of IL12 (IL12A) maps to human chromosome 3p12-q13.2. The expression of the two genes is regulated independently of each other.

The IL12 receptor appears to be a single protein of approximately 110 kDa (e.g. polypeptides encoded by Genbank Accession No. U03187, U23922, U64198, U64199). Up to 1000-9000 high affinity IL12 receptors/cell are expressed on peripheral blood mononuclear cells activated by various T-cell mitogens or by IL2. IL12 receptors are present on activated T-cells expressing CD4 and CD8 and on activated CD56 positive natural killer cells. Resting peripheral blood mononuclear cells, tonsillar B-cells, or tonsillar B-cells activated by anti-IgM/Dx, anti-IgM/Dx+IL2, or SAC+IL2 do not express the receptor. High affinity IL12 receptors are expressed constitutively on a transformed marmoset NK-like cell line, HVS.SILVA 40.

Binding of IL12 to its receptor can be prevented by monoclonal antibodies directed against the p40 subunit which therefore contains the binding site. The p40 subunit of IL12 shows homology with the extracellular domain of the IL6 receptor. A virus-encoded homologue of the p40 subunit is EBV-induced gene-3.

Human IL12 is not active in murine lymphocytes. Hybrid heterodimers consisting of murine p35 and human p40 subunits retain bioactivity on murine cells; however, the combination of human p35 and murine p40 is completely inactive on murine cells. Murine IL12 is active on both murine and human lymphocytes. The p40 subunit of murine IL12 subunit p40 (IL12p40) has been shown to specifically antagonize the effects of the IL12 heterodimer in different assay systems and to function as an endogenous specific inhibitor for the IL12 heterodimer.

IL12 stimulates the proliferation of human lymphoblasts activated by phytohaemagglutinin. IL12 activates NK-cells positive for CD56, and this activity is blocked by antibodies specific for TNF-alpha. IL12 promotes specific allogenic CTL reactions. IL12 synergizes also with anti-CD3 antibodies and with allogeneic stimulation in mixed lymphocyte cultures in inducing T-cell proliferation.

In peripheral lymphocytes of the Th1 type IL12 induces the synthesis of IFN-gamma and IL2, and TNF. TNF-alpha also appears to be involved in mediating the effects of IL12 on natural killer cells since the effects of IL12 are inhibited by an antibody directed against TNF-alpha. IL12 and TNF-alpha are costimulators for IFN-gamma production with IL12 maximizing the IFN-gamma response; the production of IL12, TNF, and IFN-gamma is inhibited by IL10. In Th2 helper cells IL12 reduces the synthesis of IL4, IL5, and IL10.

IL12 synergises with suboptimal amounts of IL2 in promoting the proliferation of mononuclear cells in the peripheral blood and in promoting the generation of LAK cells (lymphokine activated killer cells). Picomolar concentrations of IL12 are as effective as nanomolar concentrations of IL2 in augmenting the cytolytic activity of natural killer cells expanded in vivo by IL2. IL12 also acts as a co-mitogen and potentiates the proliferation of resting peripheral cells induced by IL2.

IL12 enhances myelopoiesis of primitive bone marrow progenitor cells induced by SCF (stem cell factor) and synergizes with colony stimulating factors to induce proliferation. IL12 also has synergistic effects on more committed bone marrow progenitors, synergising with IL3, IL11, or IL3 plus SCF.

IL12 is of potential clinical interest since it allows the reduction of doses of IL2 required for the generation of LAK cells (lymphokine-activated killer cells). IL12 has been shown to inhibit the growth of a variety of experimental tumors in vivo and to have antiangiogenic effects in vivo, which are, at least in part, mediated by IFN-gamma. IL12 therefore seems to be a potential candidate also for the treatment of angiogenesis-dependent malignancies.

IL19 and IL10 share 21 percent amino acid identity and are probably homologs. In monocytes treatment with bacterial lipopolysaccharides induces the synthesis of IL19 and this effect is potentiated in the presence of IL4 or IL13 but is unaffected by IFN-gamma. GM-CSF directly induces IL19 gene expression in monocytes. IL19 has been shown to bind to the IL20 receptor complex (Dumoutier L et al Cutting edge: STAT activation by IL-19, IL-20 and mda-7 through IL-20 receptor complexes of two types. Journal of Immunology 167(7): 3545-9 (2001); Gallagher G et al Cloning, expression and initial characterization of interleukin-19 (IL-19), a novel homologue of human interleukin-10 (IL-10). Genes Immun 1(7): 442-50 (2000)).

IL20 is structurally related to IL10. IL20 appears to be an autocrine factor for keratinocytes that regulates their participation in inflammation. Overexpression of IL20 in transgenic mice causes neonatal lethality with skin abnormalities characterized by an impairment of epidermal differentiation (Blumberg H et al Interleukin 20: discovery, receptor identification, and role in epidermal function. Cell 104(1): 9-19 (2001); Dumoutier L et al Cutting edge: STAT activation by IL-19, IL-20 and mda-7 through IL-20 receptor complexes of two types. Journal of Immunology 167(7): 3545-9 (2001); Rich B E and Kupper T S Cytokines: IL-20—a new effector in skin inflammation. Current Biology 11(13): R531-4 (2001)).

An IL20 receptor has been identified to consist of two orphan class 2 cytokine receptor subunits. The receptor is expressed in skin and its expression is upregulated dramatically in psoriatic skin. Engagement of the receptor in a keratinocyte cell line involves signaling by one member of the STAT proteins, STAT3.

The IL20 receptor complex has been shown to bind also IL19 and IL24.

IL21 has been isolated by Parrish-Novak et al from a cDNA library derived from activated CD3 (+) T-cells in a search for the ligand of a type-1 cytokine receptor isolated previously. The cDNA encodes a secreted protein of 131 amino acids protein most closely related to IL2 and IL15. The IL21 gene maps to human chromosome 4q26-q27 near the IL2 gene. IL21 mRNA is expressed in CD4 (+) but not in CD8 (+) T-cells after cell activation. It is not expressed also in B-cells and monocytes (Asao H et al Cutting edge: the common gamma-chain is an indispensable subunit of the IL-21 receptor complex. Journal of Immunology 167(1):1-5 (2001); Ozaki K et al Cloning of a type I cytokine receptor most related to the IL-2 receptor beta chain. Proceedings of the National Academy of Science (USA) 97: 11439-11444 (2000); Parrish-Novak J et al Interleukin 21 and its receptor are involved in NK cell expansion and regulation of lymphocyte function. Nature 408: 57-63 (2000)).

IL21 stimulates proliferation of B-cell stimulated by crosslinking of the CD40 antigen. It inhibits proliferation stimulated by IL4 plus anti-IgM. IL21 augments stimulation of the proliferation of naive (CD45RA (+)) but not memory (CD45RO (+)) T-cells mediated by engagement of CD3. IL21 stimulates the proliferation of bone marrow progenitor cells and the expression of the NK-cell marker CD56 in the presence of IL15.

The IL21 receptor has been isolated by Parrish-Novak et al and found to be expressed by CD23 (+)B-cells, B-cell lines, a T-cell leukemia line, and NK-cell lines. The receptor gene has been mapped to human chromosome 16p12. The same receptor has been isolated by Ozaki et al, who called it NILR (novel interleukin receptor). The receptor (538 amino acids) is most closely related to human IL2 beta receptor. The receptor contains a WSXWS motif in the extracellular region, typical of type-1 cytokine receptors. The receptor is expressed on NK-cells, T-cells, and B-cell lines.

The common gamma chain, which is an indispensable subunit of the functional receptor complexes for IL2, IL4, IL7, IL9, and IL15 has been shown also to be part of the IL21 receptor complex. The functional signalling complex activates Janus kinases JAK1, JAK3, and the STAT proteins STAT1, and STAT3 (Asao et al).

IL22 (180 amino acids including a signal sequence; 25 kDa; also called IL-TIF) was identified by a cDNA subtraction method as a gene induced specifically by IL9 in mouse T lymphocytes. The protein shows limited homology with IL10 (22 percent amino acid identity). Human and murine IL-TIF proteins share 79 percent amino acid identity.

The murine and human IL-TIF genes both consist of 6 exons. The human single-copy gene maps to chromosome 12q15 (90 Kb from the IFN-gamma gene, and 27 Kb from the AK155 gene encoding another IL10-related cytokine. In mice the gene is located also in the same region as the IFN-gamma gene. In BALB/c and DBA/2 mice the gene is a single copy gene. In C57Bl/6, FVB and 129 mice the gene is duplicated. The two copies, termed IL-TIF-alpha and IL-TIF-beta show 98 percent nucleotide identity in the coding region and differ by a deletion of 658 nucleotide in IL-TIF-beta. This gene may be inactive.

Expression of IL-TIF is induced by IL9 in thymic lymphomas, T-cells, and mast cells, and by lectins in freshly isolated splenocytes. IL-TIF expression in T-cells does not require protein synthesis, and depends on the activation Janus kinases and STAT proteins. IL-TIF is expressed constitutively in thymus and brain.

In HepG2 human hepatoma cells IL-TIF up-regulates the production of acute phase proteins. IL-TIF also acts as a pro-inflammatory cytokine in vivo because injection of the protein also induces the synthesis of acute phase proteins. Synthesis of IL-TIF is induced rapidly after injection of bacterial lipopolysaccharides. In contrast to IL10, IL22 does not inhibit the production of pro-inflammatory cytokines by monocytes in response to bacterial lipopolysaccharides. It also does not impair IL10 function on monocytes. IL-TIF has some inhibitory effects on IL4 production from Th2 T-helper cells.

IL10 and IL-TIF utilise a common receptor subunit. Antibodies directed against the beta chain of the IL10 receptor block the induction of acute phase proteins by IL-TIF. The functional IL-TIF receptor complex consists of two receptor chains. One chain has been identified as the orphan receptor CRF2-4 that is expressed in normal liver and kidney. The other chain is the IL10 receptor-2, the second chain of the IL10 receptor complex. Monkey COS expressing CRF2-9 alone respond to IL-TIF. In hamster cells both chains must be expressed to yield functional IL-TIF receptors. Although both receptor chains can bind IL-TIF independently binding of IL-TIF to the receptor complex is greater. This sharing of receptor subunits is similar to the shared use of the common gamma chain by cytokines such as IL2, IL4, IL7, IL9, and IL15. Some cell lines that do not respond to IL10 respond to IL-TIF by activation of STAT-1, STAT-3, and STAT-5.

A soluble secreted receptor (231 amino acids), designated IL22BP [IL22 binding protein] has been described (Kotenko et al). The protein demonstrates 34 percent amino acid identity with the extracellular domain of the IL22R1 chain and is known also as CRF2-10. The gene maps to human chromosome 6q24, 35 kb from the IFN-gamma R1 gene. It is expressed in various tissues with maximal expression in breast, lungs, and colon. The protein binds IL-TIF and inhibits its activity, blocking its interaction with the cell surface IL22 receptor complex and thus acting as a natural cytokine antagonist. IL22BP also blocks induction of the suppressors of cytokine signaling-3 (SOCS-3) gene expression by IL22 in HepG2 cells (Dumoutier L et al Cloning and characterization of IL-10-related T cell-derived inducible factor (IL-TIF), a novel cytokine structurally related to IL-10 and inducible by IL-9. Journal of Immunology 164(4): 1814-1819 (2000); Dumoutier L et al Human interleukin-10-related T cell-derived inducible factor: molecular cloning and functional characterization as an hepatocyte-stimulating factor. Proceedings of the National Academy of Science (USA) 97(18): 10144-9 (2000); Dumoutier L et al IL-TIF/IL-22: genomic organization and mapping of the human and mouse genes. Genes Immun 1(8): 488-494 (2000); Dumoutier L et al Cloning and characterization of il-22 binding protein, a natural antagonist of il-10-related t cell-derived inducible factor/il-22. Journal of Immunology 166 (12): 7090-5 (2001); Kotenko S V et al Identification, cloning, and characterization of a novel soluble receptor that binds IL-22 and neutralizes its activity. Journal of Immunology 166(12): 7096-7103 (2001); Kotenko S V et al Identification of the functional interleukin-22 (IL-22) receptor complex: the IL-10R2 chain (IL-10Rbeta) is a common chain of both the IL-10 and IL-22 (IL-10-related T cell-derived inducible factor, IL-TIF) receptor complexes. Journal of Biological Chemistry 276(4): 2725-32 (2001); Xie M H et al Interleukin (IL)-22, a novel human cytokine that signals through the interferon receptor-related proteins CRF2-4 and IL-22R. Journal of Biological Chemistry 275 (40): 31335-9 (2000)).

IL-23 is the name given to a factor that is composed of the p40 subunit of IL12 (IL12B) and another protein of 19 kDa, designated p19. p19 is structurally related to IL6, G-CSF, and the p35 subunit of IL12. In databanks the p19 subunit is found also under the acronym SGRF (IL6 G-CSF related factor).

p19 by itself is biologically inactive while the complex of p19 with p40 is active. The active complex is secreted by dendritic cells after cell activation.

Mouse memory T-cells (CD4 (+) CD45 Rb(low)) proliferate in response to IL23 but not in response to IL12. Human IL23 has been shown to stimulate the production of IFN-gamma by PHA blast T-cells and memory T-cells. It also induces proliferation of both cell types.

IL23 binds to the beta-1 subunit but not to the beta-2 subunit of the IL12 receptor, activating one of the STAT proteins, STAT4, in PHA blast T-cells.

Expression of p19 in transgenic mice leads to runting, systemic inflammation, infertility, and death before 3 months of age. The animals show high serum concentrations of the pro-inflammatory cytokines TNF-alpha and IL1. The number of circulating neutrophils is increased. Acute phase proteins are expressed constitutively. Animals expressing p19 specifically in the liver do not show these abnormalities. Expression of p19 is most likely due to hematopoietic cells as bone marrow transplantation of cells expressing p19 causes the same phenotype as that observed in the transgenic animals (Oppmann B et al Novel p19 protein engages IL-12p40 to form a cytokine, IL-23, with biological activities similar as well as distinct from IL-12. Immunity 13(5): 715-25 (2000); Wiekowski M T et al Ubiquitous Transgenic Expression of the IL-23 Subunit p19 Induces Multiorgan Inflammation, Runting, Infertility, and Premature Death. Journal of Immunology 166(12): 7563-70 (2001)).

IL24 is a name given to a protein that is known also as ST16 [suppression of tumorigenicity-16] and MDA-7 [melanoma differentiation-associated gene 7]. The rat counterpart of IL24 has been identified as mob-5 or C49a. The murine counterpart is FISP.

MDA-7 protein (206 amino acids) was identified initially as a melanoma differentiation-associated cDNA in a study using cultured human melanoma cells that lose proliferative capacity and terminally differentiate in response to human IFN-beta and mezerein. The expression of MDA-7 is upregulated as a consequence of terminal differentiation. H0-1 and C8161 human melanoma cells engineered to express MDA-7 show reduces growth and do not form colonies in a colony formation assay. MDA-7 selectively suppresses the growth of human breast cancer cells by promoting cell death by apoptosis. Ectopic expression of MDA-7 by means of a replication defective adenovirus results in growth suppression and induction of apoptosis in a broad spectrum of additional cancers, including melanoma, glioblastoma multiforme, osteosarcoma and carcinomas of the breast, cervix, colon, lung, nasopharynx and prostate. No apparent harmful effects are observed after expression of MDA-7 in normal epithelial or fibroblast cells.

In human hematopoietic cells MDA-7 expression is induced during megakaryocyte differentiation in response to treatment with TPA (12-O-tetradecanoyl-phorbol-13-acetate).

The human MDA-7 gene maps to chromosome 1q32 and is tightly linked (within a region of 195 kb) to the genes encoding IL10, IL19, and IL20.

The receptor for IL24 has been identified as the IL20 receptor complex. This receptor also binds to IL19 (Blumberg H et al Interleukin 20: discovery, receptor identification, and role in epidermal function. Cell 104(1): 9-19 (2001); Dumoutier L et al Cutting edge: STAT activation by IL-19, IL-20 and mda-7 through IL-20 receptor complexes of two types. Journal of Immunology 167(7): 3545-9 (2001); Huang E Y et al Genomic structure, chromosomal localization and expression profile of a novel melanoma differentiation associated (mda-7) gene with cancer specific growth suppressing and apoptosis inducing properties. Oncogene 20(48): 7051-63 (2001); Jiang H et al Subtraction hybridization identifies a novel melanoma differentiation associated gene, mda-7, modulated during human melanoma differentiation, growth and progression. Oncogene 11: 2477-2486 (1995); Jiang H et al The melanoma differentiation associated gene mda-7 suppresses cancer cell growth. Proceedings of the National Academy of Science (USA) 93: 9160-9165 (1996); Su Z et al The cancer growth suppressor gene mda-7 selectively induces apoptosis in human breast cancer cells and inhibits tumor growth in nude mice. Proceedings of the National Academy of Science (USA) 95: 14400-14405 (1998)).

IL25 (also known as SF20) has been identified in a search for factors that stimulate cell proliferation. The factor is secreted by bone marrow stromal cells The IL25 receptor has been identified as mouse thymic shared antigen-1 (TSA-1). Enforced expression of the receptor in one of the factor-dependent cell lines, BaF3, which does not express the receptor, causes cell proliferation. FDCP2 cells, which express the receptor, also proliferate in response to SF20/IL25. In both cases proliferation is abolished by specific blocking antibodies directed against the receptor.

SF20/IL-25 has no detectable myelopoietic activity but supports proliferation of cells in the lymphoid lineage (Tulin E E et al SF20/IL-25, a Novel Bone Marrow Stroma-Derived Growth Factor That Binds to Mouse Thymic Shared Antigen-1 and Supports Lymphoid Cell Proliferation. Journal of Immunology 167(11): 6338-47 (2001)).

The members of the TNF ligand superfamily (TNFalpha, TNF-beta, LT beta, CD27 ligand, CD30 ligand, CD40 ligand, CD95 ligand, 4 1BB, OX40 ligand, TRAIL) share common biological activities, but some properties are shared by only some ligands, while others are unique. Human TNF-alpha is a non-glycosylated protein of 17 kDa and a length of 157 amino acids. Murine TNF-alpha is N-glycosylated. Homology with TNF-beta is approximately 30%. TNF-alpha forms dimers and trimers. The 17 kDa form of the factor is produced by processing of a precursor protein of 233 amino acids. A TNF-alpha converting enzyme has been shown to mediate this conversion. A transmembrane form of 26 kDa has been described also.

TNF-alpha contains a single disulfide bond that can be destroyed without altering the biological activity of the factor. Mutations Ala84 to Val and Val91 to Ala reduce the cytotoxic activity of the factor almost completely. These sites are involved in receptor binding. The deletion of 7 N-terminal amino acids and the replacement of Pro8Ser9Asp 10 by ArgLysArg yields a mutated factor with an approximately 10-fold enhanced antitumor activity and increased receptor binding, as demonstrated by the L-M cell assay, while at the same time reducing the toxicity.

The gene has a length of approximately 3.6 kb and contains four exons. The primary transcript has a length of 2762 nucleotides and encodes a precursor protein of 233 amino acids. The aminoterminal 78 amino acids function as a presequence. The human gene maps to chromosome 6p23-6q12. It is located between class I HLA region for HLA-B and the gene encoding complement factor C. The gene encoding TNF-beta is approximately 1.2 kb downstream of the TNF-alpha gene. However, both genes are regulated independently. The two genes also lie close to each other on murine chromosome 17.

Approximately 500-10000 high-affinity receptors ($K_a=2.5 \times 10^{-9}$ M) for TNF-alpha are expressed on all somatic cell types with the exception of erythrocytes. Two receptors of 55 kDa (TNF-R1; new designation: CD120a) (e.g. polypeptides encoded by Genbank Accession No. X55313) and 75 kDa (TNF-R2; new designation: CD120b) (e.g. as described in Goodwin R G et al (1991) Molecular Cellular Biology 11: 3020-6) have been described. One receptor is a glycosylated protein of 455 amino acids that contains an extracellular domain of 171 and a cytoplasmic domain of 221 amino acids. Sequence homologies in the cysteine-rich domains of the extracellular portion reveal that the receptor is related to the low-affinity receptor of NGF and to human cell surface antigen CD40.

Deletion analysis in the C-terminal intracellular region of the 55 kDa receptor, TNF-R1 has revealed the existence of a so-called death domain, which is involved in signaling processes leading to programmed cell death. The death domain of TNF-R1 interacts with a variety of other signaling adaptor molecules, including TRADD, and RIP.

The two known receptors bind both TNF-alpha and TNF-beta. p55 is expressed particularly on cells susceptible to the cytotoxic action of TNF. p75 is also present on many cell types, especially those of myeloid origin (a virus-encoded homologue of the receptor subunit is EBV-induced gene-6). It is strongly expressed on stimulated T-cells and B-lymphocytes. The differential activities of TNF on various cell types, i.e. growth-promoting and growth-inhibiting activities, are probably mediated by the differential expression and/or regulation of multiple receptors in combination with other distinct receptor-associated proteins. p55 appears to play a critical role in host defenses against microorganisms and their pathogenic factors.

A third receptor subtype is expressed in normal human liver. It binds TNF-alpha but not TNF-beta. Some viruses contain genes encoding secreted proteins with TNF binding properties that are closely homologous to the p55 and p75 TNF receptors. Differential effects of the two receptor subtypes have been found also in TNF-mediated adhesion of leukocytes to the endothelium. It appears that engagement of the p55 receptor specifically leads to the induction of the cellular adhesion molecules ICAM-1, E-selectin, V-CAM-1, and CD44, while engagement of both the p55 and the p75 receptor induces expression of alpha-2 integrin.

Truncated soluble forms of the receptor have been found also. The soluble forms, in particular the soluble extracellular domain of the p60 receptor, block the antiproliferative effects of TNF and, therefore, may modulate the harmful effects of TNF.

Receptor densities are reduced by IL1 and tumor promoters such as phorbol esters. The expression of TNF-alpha receptor density is induced by IFN-alpha, IFN-beta, and IFN-gamma.

Signal transducers that associate with the cytoplasmic domains of members of the TNF receptor superfamily comprise TRAF (Tumor necrosis factor receptor-associated factors).

Human TNF-alpha is active on murine cells with a slightly reduced specific activity. In general, TNF-alpha and TNF-beta display similar spectra of biological activities in in-vitro systems, although TNF-beta is often less potent or displays apparent partial agonist activity.

TNF-alpha shows a wide spectrum of biological activities. It causes cytolysis and cytostasis of many tumor cell lines in vitro. Sensitive cells die within hours after exposure to picomolar concentrations of the factor and this involves, at least in part, mitochondria-derived second messenger molecules serving as common mediators of TNF cytotoxic and gene-regulatory signaling pathways. The factor induces hemorrhagic necrosis of transplanted tumors. Within hours after injection TNF-alpha leads to the destruction of small blood vessels within malignant tumors. The factor also enhances phagocytosis and cytotoxicity in neutrophilic granulocytes and also modulates the expression of many other proteins, including fos, myc, IL1 and IL6.

The 26 kDa form of TNF is found predominantly on activated monocytes and T-cells. It is also biologically active and mediates cell destruction by direct cell-to-cell contacts.

The chemotactic properties of fMLP (Formyl-Met-Leu-Phe) for neutrophils are enhanced by TNF-alpha. TNF-alpha induces the synthesis of a number of chemoattractant cytokines, including IP-10, JE, KC, in a cell-type and tissue-specific manner.

TNF-alpha is a growth factor for normal human diploid fibroblasts. It promotes the synthesis of collagenase and prostaglandin E2 in fibroblasts. It may also function as an autocrine growth modulator for human chronic lymphocytic leukemia cells in vivo and has been described to be an autocrine growth modulator for neuroblastoma cells. The autocrine growth-promoting activity is inhibited by IL4.

In resting macrophages TNF induces the synthesis of IL1 and prostaglandin E2. It also stimulates phagocytosis and the synthesis of superoxide dismutase in macrophages. TNF activates osteoclasts and thus induces bone resorption.

In leukocyte and lymphocyte progenitors TNF stimulates the expression of class I and II HLA and differentiation antigens, and the production of IL1, colony stimulating factors, IFN-gamma, and arachidonic acid metabolism. It also stimulates the biosynthesis of collagenases in endothelial cells and synovial cells.

IL6 suppresses the synthesis of IL1 induced by bacterial endotoxins and TNF, and the synthesis of TNF induced by endotoxins.

The neurotransmitter SP (substance P) induces the synthesis of TNF and IL1 in macrophages. IL1, like IL6, stimulates the synthesis of ACTH (corticotropin) in the pituitary. Glucocorticoids synthesized in response to ACTH in turn inhibit the synthesis of IL6, IL1 and TNF in vivo, thus establishing a negative feedback loop between the immune system and neuroendocrine functions.

TNF-alpha enhances the proliferation of T-cells induced by various stimuli in the absence of IL2. Some subpopulations of T-cells only respond to IL2 in the presence of TNF-alpha. In The presence of IL2 TNF-alpha promotes the proliferation and differentiation of B-cells.

The functional capacities of skin Langerhans cells are also influenced by TNF-alpha. These cells are not capable of initiating primary immune responses such as contact sensibilisation. They are converted into immunostimulatory dendritic cells by GM-CSF and also IL1. These cells therefore are a reservoir for immunologically immature lymphoid dendritic cells. The enhanced ability of maturated Langerhans cells to process antigens is significantly reduced by TNF-alpha.

Although TNF-alpha is also required for normal immune responses the overexpression has severe pathological consequences. TNF-alpha is the major mediator of cachexia observed in tumor patients (hence its name, cachectin). TNF is also responsible for some of the severe effects during Gram-negative sepsis.

TNF-alpha can be detected in bioassays involving cell lines that respond to it (e.g., BT-20, CT6, EL4; PK15; L929; L-M; MO7E; T1165; WEHI-3B). TNF-alpha can be detected also by a sensitive sandwich enzyme immunoassay, ELISA, an immunoradiometric assay (IRMA), and by an assay designated RELAY (receptor-mediated label-transfer assay). Intracellular factor is detected by two color immunofluorescence flow cytometry. Higuchi et al have described an assay based on the release of tritiated thymidine from cells undergoing apoptosis after treatment with either TNF-alpha or TNF-beta. IFN-alpha, IFN-beta, IFN-gamma, TGF-beta, IL4, LIF and GM-CSF have been shown not to interfere with this assay.

In contrast to chemotherapeutic drugs TNF specifically attacks malignant cells. Extensive preclinical studies have documented a direct cytostatic and cytotoxic effect of TNF-alpha against subcutaneous human xenografts and lymph node metastases in nude mice, as well as a variety of immunomodulatory effects on various immune effector cells, including neutrophils, macrophages, and T-cells.

Single- and multiple-dose phase I studies have confirmed that TNF can be administered safely to patients with advanced malignancies in a dose range associated with anticancer effect without concomitant serious toxicities such as shock and cachexia. However, clinical trials on the whole have unfortunately so far failed to demonstrate significant improvements in cancer treatment, with TNF-induced systemic toxicity being a major limitation for the use of TNF as an antineoplastic agent in most cases. The combined use of TNF and cytotoxic or immune modulatory agents, particularly IFN-gamma and possibly IL2, may be of advantage in the treatment of some tumors. In some cases intratumoral application of TNF has been found to be of advantage in tumor control.

Some mutant forms of TNF-beta with selective activity on the p55 receptor have been described recently. It has been shown that activation of the p55 receptor is sufficient to trigger cytotoxic activity towards transformed cells. Some of these mutants have been described to retain their antitumor activity in nude mice carrying transplanted human tumors.

TNF can also be used to increase the aggressiveness of lymphokine-activated killer cells. Studies with an experimental fibrosarcoma metastasis model have shown that TNF induces significant enhancement of the number of metastases in the lung. It has been suggested that low doses of endogenous TNF or administration of TNF during cytokine therapy may enhance the metastatic potential of circulating tumor cells. The transduction of murine tumor cells with a functional TNF-alpha gene has been shown to lead to the rejection of the genetically modified cells by syngeneic hosts.

The interferons are a family of cytokines that induce a virus-nonspecific antiviral state in target cells. Binding of an interferon to its receptor induces new protein synthesis which, in turn, results in the inactivation of initiation factor eIF-2. The inactivation is thought to contribute to the antiviral state induced by the interferons. Interferons also induce pathways that activate intracellular endonucleases which degrade viral mRNA. Many interferons also possess immunomodulatory activities, such as activation of macrophages and lymphocytes. Examples of interferons include IFN-gamma (e.g. polypeptides encoded by Genbank Accession No. K01900, J00209, M12350, J00213, J00216, J00214, M11003, M11026, M34913, M54886, X01974, L38698, M13710, K01238, M13660, M68944, X01972, X01971, X01973, X01969), IFN-gamma (e.g. polypeptides encoded by Genbank Accession No. M28622, X14029, X14455, K00020, J00218, E00171, X04430, A09363, M27327, M16656, M25460, K03196), IFN-gamma e.g. polypeptides encoded by Genbank Accession No. A34532, X87308, E00756, K00083), IFN-gamma e.g. polypeptides encoded by Genbank Accession No. X58822, A12140), bovine trophoblast protein-1 (IFN-gamma) e.g. polypeptides encoded by Genbank Accession No. M31556, M31557, M31558), and their homologues among species. Human IFN-gamma and IFN-gamma are thought to bind to a common receptor (e.g. polypeptides encoded by Genbank Accession No. X60459, M89641) which is distinct from the receptor for IFN-gamma (e.g. polypeptides encoded by Genbank Accession No. J03143, M28233).

At least 23 different variants of IFN-alpha are known. The individual proteins have molecular masses between 19-26 kDa and consist of proteins with lengths of 156-166 and 172 amino acids. All IFN-alpha subtypes possess a common conserved sequence region between amino acid positions 115-151 while the amino-terminal ends are variable. Many IFN-alpha subtypes differ in their sequences at only one or two positions. Naturally occurring variants also include proteins truncated by 10 amino acids at the carboxy-terminal end. Disulfide bonds are formed between cysteines at positions 1/98 and 29/138. The disulfide bond 29/138 is essential for biological activity while the 1/98 bond can be reduces without affecting bioactivity.

Human IFN-beta is a glycoprotein (approximately 20% sugar moiety) of 20 kDa and has a length of 166 amino acids. Glycosylation is not required for biological activity in vitro. The protein contains a disulfide bond Cys31/141) required for biological activity. At the DNA level IFN-beta displays 34% sequence homology with IFN-beta-2 and approximately 30% homology with other IFN-alpha subtypes. In contrast to IFN-gamma IFN-beta is stable at pH2.

Human IFN-gamma is a dimeric protein with subunits of 146 amino acids. The protein is glycosylated at two sites. The pI is 8.3-8.5. IFN-gamma is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-gamma with respect to molecular mass and charge are due to variable glycosylation patterns. 40-60 kDa forms observed under non-denaturing conditions are dimers and tetramers of IFN-gamma.

Members of the CSF family of cytokines allow the growth and differentiation of bone marrow cells immobilized on soft agar or methylcellulose. While hematopoietic progenitor cells can be maintained only for short periods of time in the absence of such factors, their presence allows the development of colonies containing erythroid cells, neutrophils, eosinophils, macrophages, and/or megakaryocytes, depending on the particular factor. The biochemical analysis of various activities stimulating colony formation supporting the growth and development of these cell types revealed that there existed many different and distinct factors of this sort.

Many of these factors are either N- or O-glycosylated. Glycosylation has been shown to enhance the solubility, stability and resistance to proteolytic enzymes. It does not appear to be required for the full spectrum of biological activities of these factors. The genes encoding many of the human colony stimulating factors have been cloned and mapped. Some of the genes are in close vicinity but they do not show great homology among each other with the exception of some conserved regions.

Colony stimulating factors are produced by many different cell types, including, for example, B-lymphocytes, epithelial cells, fibroblasts, endothelial cells, macrophages, Stromal cell line, T-lymphocytes. They are synthesized as precursor molecules containing a classical hydrophobic secretory signal sequence of approximately 25-32 amino acids. The secreted factors have an extremely high specific biological activity are active at very low concentrations (1-100 pM). These factors are absolutely required for the proliferation of hematopoietic progenitor cells. The concentrations required for mere maintenance of viability are usually orders of magnitude lower than those required to induce cell proliferation or to elicit specific functional activities of the cells.

The names of the individual factors usually indicate the cell types that respond to these factors. The classical colony stimulating factors include M-CSF (e.g. polypeptides encoded by Genbank Accession No. E03235, M64592, U22386, X05010) (macrophage-specific), G-CSF (granulocyte-specific), GM-CSF (macrophage/granulocyte-specific), IL3 (multifunctional) and MEG-CSF (e.g. polypeptides encoded by Genbank Accession No. D86370, U70136) (megakaryocyte-specific). G-CSF and M-CSF are lineage-specific while GM-CSF and IL3 are multifunctional hematopoietic growth factors acting on earlier stages of differentiation of hematopoietic progenitor cells.

Human GM-CSF is a monomeric protein of 127 amino acids with two glycosylation sites. The protein is synthesized as a precursor of 144 amino acids, which included a hydrophobic secretory signal sequence at the aminoterminal end. The sugar moiety is not required for the full spectrum of biological activities. Non-glycosylated and glycosylated GM-CSF show the same activities in vitro. Fully glycosylated GM-CSF is biologically more active in vivo than the non-glycosylated protein. The different molecular weight forms of GM-CSF (14 kDa, 35 kDa) described in the literature are the result of varying degrees of glycosylation. GM-CSF contains four cysteine residues (positions 54/96 and 88/121).

A comparison of the protein sequence of GM-CSF with those of the other colony stimulating factors reveals that they are not strongly homologous to each other. Human and murine GM-CSF display 60% homology at the protein level and 70% at the nucleotide level. The two factors do not, however, cross-react immunologically. GM-CSF can be associated with the extracellular matrix of cells as a complex with heparan sulfate proteoglycans. This allows storage of the factor in a biologically inactive form. The exact mechanism by which the factor is eventually released from these depots is not known.

The human gene has a length of approximately 2.5 kb and contains four exons. The distance between the GM-CSF gene and the IL3 gene is approximately 9 kb. The human GM-CSF gene maps to chromosome 5q22-31 in the vicinity of other genes encoding hematopoietic growth factors (M-CSF, IL3, IL4, IL5) and the gene encoding the M-CSF receptor. The 5' region of the GM-CSF gene contains several sequence elements known as CLE (conserved lymphokine element). They function as binding sites for transcription factors, modulating the expression of the GM-CSF gene.

GM-CSF receptors are expressed at densities of several 100 to several 1000 copies/cell on the cell surface of myeloid cells. The receptor is expressed also on non-hematopoietic cells such as endothelial cells and small cell lung carcinoma cells. In receptor-positive cell lineages the receptor density decreases with increasing degrees of maturation.

The receptor shows significant homologies with other receptors for hematopoietic growth factors, including IL2-beta, IL3, IL6, IL7, Epo and the prolactin receptors. One cloned subunit of the GM-CSF receptor (GM-R alpha, 45 kDa) binds GM-CSF with low affinity (e.g. polypeptides encoded by Genbank Accession No. SEG_HUMGRAS). The second subunit (GM-R beta, 120 kDa) does not bind GM-CSF. GM-R alpha is a protein of 400 amino acids that contains only a short cytoplasmic domain of 54 amino acids. The high affinity GM-CSF receptor is formed by the aggregation of the two receptor subunits. The GM-R beta subunit of the receptor (e.g. polypeptides encoded by Genbank Accession No. SEG_MUSAIC2B, M59941) is also a constituent of other cytokine receptor systems. It is a component of the high affinity receptors for IL3 and IL5, both of which also contain a cytokine-specific subunit (AIC2A).

Human GM-CSF is not active on murine cells and vice versa. GM-CSF was isolated initially as a factor stimulating the growth of macrophage/granulocyte-containing colonies in soft agar cultures (colony formation assay). GM-CSF is indispensable for the growth and development of granulocyte and macrophage progenitor cells. It stimulates myeloblasts and monoblasts and triggers irreversible differentiation of these cells. GM-CSF synergises with Epo in the proliferation of erythroid and megakaryocytic progenitor cells. In combination with another colony stimulating factor, M-CSF, one observes the phenomenon of synergistic suppression, i.e., the combination of these two factors leads to a partial suppression of the generation of macrophage-containing cell colonies.

For some types of blast cells from patients with acute myeloid leukemia GM-CSF acts as an autocrine mediator of growth. GM-CSF is a strong chemoattractant for neutrophils. It enhances microbicidal activity, oxidative metabolism, and phagocytotic activity of neutrophils and macrophages. It also improves the cytotoxicity of these cells. GM-CSF displays a less pronounced specificity than, for example, G-CSF. It stimulates the proliferation and differentiation of neutrophilic, eosinophilic, and monocytic lineages. It also functionally activates the corresponding mature forms, enhancing, for example, the expression of certain cell surface adhesion proteins (CD-11A, CD-11C). The overexpression of these proteins could be one explanation for the observed local accumulation of granulocytes at sites of inflammation. In addition, GM-CSF also enhances expression of receptors for fMLP (Formyl-Met-Leu-Phe) which is a stimulator of neutrophil activity.

At pico to nanomolar concentrations GM-CSF is chemotactic for eosinophils and also influences the chemotactic behavior of these cells in response to other chemotactic factors.

In granulocytes GM-CSF stimulates the release of arachidonic acid metabolites and the increased generation of reactive oxygen species. The activation of the Na+/H+ antiport system leads to a rapid alkalization of the cytosol. Phagocytotic activities of neutrophil granulocytes and the cytotoxicity of eosinophils is also enhanced considerably by GM-CSF. Since GM-CSF is produced by cells (T-lymphocytes, tissue macrophages, endothelial cells, mast cells) present at sites of inflammatory responses it can be assumed that it is an important mediator for inflammatory reactions.

The functional state of Langerhans cells of the skin is also influenced by GM-CSF. These cells are not capable of initiating primary immune responses, for example, contact sensibilization. They are converted to highly potent immunostimulatory dendritic cells by GM-CSF (and also IL1). Langerhans cells therefore form an in situ reservoir for immunologically immature lymphoid dendritic cells. The maturation of these cells which is seen as an increased ability to process antigens, can be down-regulated by TNF-alpha.

At nanomolar concentrations GM-CSF induces the expression of complement C3a receptors on basophils. Cells which normally do not respond to C3a and which have been activated by GM-CSF degranulate in response to the C3a stimulus. This is accompanied by the release of histamine and leukotriene C4. This process may be of significance in hypersensitivity reactions associated with inflammatory responses (T-lymphocytes, tissue macrophages, endothelial cells, mast cells). GM-CSF has been shown also to be a potent inducer of trophoblast interferon (TP-1).

GM-CSF synergises with some other cytokines, including IL1, IL3 and G-CSF. GM-CSF and G-CSF must act in concert to allow the development of neutrophil-containing colonies in vitro.

IL3 by itself only negligibly expands the number of circulating blood cells; a subsequent dose of GM-CSF, however, significantly increases cell numbers, probably because IL3 first leads to an expansion of those cells capable of responding to GM-CSF.

The observations that most IL3-dependent cell lines can also grow in the presence of GM-CSF and IL4 and that several synergistic effects are observed between GM-CSF and IL4 suggest that these three factors perform similar functions in controlling the growth of cells. There are some indications that the mechanism of signal transduction contains at least some common factors.

Experiments with tyrosine-specific protein kinases encoded by an oncogene have shown that the expression of this kinase activity in factor-dependent cells abolishes their dependence on GM-CSF, IL3 and IL4. The exact mechanism by which these factors regulate the proliferation and differentiation of cells is still unknown.

The consequences of a deregulated expression of GM-CSF have been studied in transgenic mice harboring a constitutively expressed GM-CSF gene. The overexpression of the transgene encoding GM-CSF leads to pathological alterations in the retina and causes blindness and also causes muscle deterioration. These mice are characterized by a very pronounced increase in activated macrophages. In addition, the overexpression of GM-CSF leads to the activation of mature macrophages secreting large amounts of IL1 and TNF, suggesting that these cytokines may be responsible for some aspects of the transgenic mouse disease.

Histopathological examination demonstrates a pronounced increase in the progenitor cell population of the monocytic lineage. GM-CSF-transgenic animals usually die within months from the massive tissue damage resulting from the overexpression of these factors. Similar results have been obtained with mice possessing a bone marrow manipulated to overexpress GM-CSF by transformation with suitable retrovirus vectors. These findings do not seem to be of clinical significance, though. The long-term treatment of primates and mice with GM-CSF has shown that life-threatening complications do not occur.

The biological consequences of GM-CSF gene disruption have been studied in mice generated from ES cells carrying a targeted deletion of the gene. Mice homozygous for a targeted disruption of the GM-CSF gene are characterized by an unimpaired steady-state hematopoiesis, demonstrating that GM-CSF is not essential for maintaining normal levels of the major types of mature hematopoietic cells and their precursors in blood, marrow, and spleen.

Most GM-CSF-deficient mice are superficially healthy and fertile but develop abnormal lungs. GM-CSF-deficient mice develop a progressive accumulation of surfactant lipids and proteins in the alveolar space, the defining characteristics of the idiopathic human disorder pulmonary alveolar proteinosis. Extensive lymphoid hyperplasia associated with lung airways and blood vessels is found also. These results demonstrate an unexpected, critical role for GM-CSF in pulmonary homeostasis.

Transgenic mice homozygous for null mutations of the gene encoding the common beta subunit (beta C) of the GM-CSF, IL3, and IL5 receptor complexes exhibit normal development and survive to young adult life. They develop pulmonary peribronchovascular lymphoid infiltrates and areas resembling alveolar proteinosis. Eosinophil numbers in peripheral blood and bone marrow of homozygous deletion mutants are reduced, while other hematological parameters are normal. Bone marrow cells from homozygous deletion mutants do not show high-affinity binding of GM-CSF, while cells from heterozygous animals show an intermediate number of high-affinity receptors. In clonal cultures of bone marrow cells derived from homozygous deletion mutants, even high concentrations of GM-CSF and IL5 do not stimulate colony formation in the colony formation assay. Differences in the systemic clearance and distribution of GM-CSF between mutant and wild-type littermates are not observed.

Nishinakamura et al have crossed beta-c mutant mice with mice deficient for IL3. The double-mutant mice lacking all IL3, GM-CSF, and IL5 functions are apparently normally fertile. The animals show the same reduced numbers of eosinophils and a lack of eosinophilic response to parasites as beta-c mutant mice. The immune response of the double mutant mice to *Listeria monocytogenes* is normal. Hematopoietic recovery after treatment with fluorouracil is also normal. These findings suggest the existence of alternative mechanism to produce blood cells that do not depend on the presence of IL3, GM-CSF, and IL5.

GM-CSF can be assayed in a colony formation assay by the development of colonies containing macrophages, neutrophils, eosinophils, and megakaryocyte's. GM-CSF is also detected in specific bioassays with cells lines that depend in their growth on the presence of GM-CSF or that respond to this factor (e.g., AML-193; B6SUt-A; BAC1.2F5; BCL1; Da; FDCP1; GF-D8; GM/SO; IC-2; MO7E; NFS-60; PT-18; TALL-103; TF-1; UT-7).

GM-CSF can be employed for the physiological reconstitution of hematopoiesis in all diseases characterized either by an aberrant maturation of blood cells or by a reduced production of leukocytes. The main and most important clinical application of GM-CSF is probably the treatment of life-threatening neutropenia following chemo and/or radiotherapy, which is markedly reduced under GM-CSF treatment. GM-CSF can be used also to correct chemotherapy-induced cytopenias and to counteract cytopenia-related predisposition to infections and hemorrhages.

In order to avoid potential complications following the administration of GM-CSF careful clinical monitoring is required in certain patient groups, for example those with myelodysplastic syndrome, acute myeloid leukemia, inflammatory disease, autoimmune thrombocytopenia or malfunctional immunological responsiveness.

Several studies have demonstrated that the use of GM-CSF enhances tolerance to cytotoxic drug treatment and can be used to prevent dose reductions necessitated by the side effects of cytotoxic drug treatment. GM-CSF treatment frequently permits to increase the doses of cytotoxic drugs per course. These studies have also revealed a significantly reduced morbidity under GM-CSF treatment.

The transduction of murine tumor cells with a functional GM-CSF gene has been shown to lead to the rejection of the genetically modified cells by syngeneic hosts. Moreover, vaccination with GM-CSF transduced tumor cells prevents growth of a subsequent inoculum of wild-type syngeneic tumor cells.

The chemokine family of cytokines consists of relatively small, structurally similar polypeptides that induce chemotaxis in leukocytes. Chemokines have molecular masses of 8-10 kDa and show approximately 20-50% sequence homology among each other at the protein level. The proteins also share common gene structures and tertiary structures. All chemokines possess a number of conserved cysteine residues involved in intramolecular disulfide bond formation.

According to the chromosomal locations of individual genes two different subfamilies of chemokines are distinguished. Members of the alpha-chemokines are referred to also as the 4q chemokine family because the genes encoding members of this family map to human chromosome 4q12-21. The first two cysteine residues of members of this family are separated by a single amino acids and these proteins, therefore, are called also C-X-C chemokines. This subfamily includes 9E3 (e.g. Genbank protein P08317), AMCF (e.g. polypeptides encoded by Genbank Accession No. M99367, M99368), beta-thromboglobulin (e.g. as disclosed in Begg G S et al (1978), Biochemistry 17: 1739-44), CINC family members (e.g. polypeptides encoded by Genbank Accession No. D21095), ENA-78 (e.g. polypeptides encoded by Genbank Accession No. X78686), eotaxin (e.g. polypeptides encoded by Genbank Accession No. U46572, U40672), GCP-2 (e.g. polypeptides encoded by Genbank Accession No. Y08770, U83303), IL8, IP-10 (e.g. polypeptides encoded by Genbank Accession No. L07417, X02530), KC (e.g. polypeptides encoded by Genbank Accession No. J04596), LIX (e.g. polypeptides encoded by Genbank Accession No. U27267), mig (e.g. polypeptides encoded by Genbank Accession No. M34815, Z24725), MGSA (e.g. polypeptides encoded by Genbank Accession No. X12510), mob-1 (e.g. polypeptides encoded by Genbank Accession No. U17035), NAP-2 (as described in Clark-Lewis I et al (1991) Biochemistry 30: 3128-35, Cohen A B et al (1992) American Journal of Physiology 263: L249-56), NAP-3 (as described in: Schrider J M et al (1991) Journal of Experimental Medicine 171: 1091-100), NAP-4 (as described in Schrider J M et al (1990) Biochemical and Biophysical Research Communications 172: 898-904), PBSF (SDF) (e.g. polypeptides encoded by Genbank Accession No. D21072, U16752, D50645), and PF4 (e.g. polypeptides encoded by Genbank Accession No. M25897).

IL8, MGSA, mouse KC, MIP-2 (e.g. polypeptides encoded by Genbank Accession No. X65647 and as described in Blum S et al Three human homologues of a murine gene encoding an inhibitor of stem cell proliferation. DNA Cell Biol. 9: 589-602 (1990); Clements J M et al Biological and structural properties of MIP-1 alpha expressed in yeast. Cytokine 4: 76-82 (1992); Devatelis G et al Cloning and characterization of a cDNA for murine macrophage inflammatory protein (MIP), a novel monokine with inflammatory and chemokinetic properties. Journal of Experimental Medicine 167: 1939-44 (1988) (erratum in JEM 170: 2189 (1989)); Farber J M A macrophage mRNA selectively induced by gamma-interferon encodes a member of the platelet factor 4 family of cytokines. Proceedings of the National Academy of Science (USA) 87: 5238-42 (1990); Haskill S et al Identification of three related human GRO genes encoding cytokine functions. Proceedings of the National Academy of Science (USA) 87: 7732-6 (1990); Poltorak A N et al (1995) Journal of Inflammation 45(3): 207-19; Rossi D L et al (1997) Journal of Immunology 158(3): 1033-1036; Sherry B et al (1988) Journal of Experimental Medicine 168: 2251-9; Tekamp-Olson P et al (1990) Journal of Experimental Medicine 172: 911-9; Wolpe S D et al (1989) Proceedings of the National Academy of Science (USA) 86: 612-16; Wolpe S D et al (1989) FASEB Journal 3: 2565-73), NAP-2, ENA-78, and GCP-2 comprise a subgroup of the human C-X-C-chemokines defined by the conserved ELR sequence motif (glutamic acid-leucine-arginine) immediately preceding the first cysteine residue near the amino-terminal end. Chemokines with an ELR sequence motif have been found to chemoattract and activate primarily neutrophils. Chemokines without the ELR sequence motif appear to chemoattract and activate monocytes, dendritic cells, T-cells, NK-cells, B-lymphocytes, basophils, and eosinophils.

Members of the beta-chemokines or 17q chemokine family map to human chromosome 17q11-32 (murine chromosome 11). The first two cysteine residues are adjacent and, therefore, these proteins are called also C-C chemokines. This subfamily includes ACT-2 (e.g. polypeptides encoded by Genbank Accession No. J04130), C10 (e.g. as described in Berger M S et al (1993) DNA Cell Biol. 12: 839-47; Berger M S et al (1996) 8: 439-447), CCF18 (e.g. as described in Hara T et al (1995) Journal of Immunology 155: 5352-8), DC-CK1 (e.g. as described in G J et al (1997) Nature 387: 713-717), ELC (e.g. polypeptides encoded by Genbank Accession No. AB000887, AF059208), Eotaxin-2 (e.g. as described in Forssmann U et al (1997) Journal of Experimental Medicine 185: 2171-2176), Exodus (e.g. polypeptides encoded by Genbank Accession No. U64197, U88320, U88321, U88322), FIC (e.g. polypeptides encoded by Genbank Accession No. L04694), GDCF and GDCF-2 (e.g. as described in Kuratsu J et al (1989) Journal of the National Cancer Institute 81: 347-51; Yoshimura T et al (1989) Journal of Experimental Medicine 169: 1449-59; Yoshimura T et al (1989) Journal of Immunology 142: 1956-62), HC-21 (e.g. as described in Chang H C & Reinherz E L (1989) European Journal of Immunology 19:1045-1051), HCC-1 (e.g. polypeptides encoded by Genbank Accession No. Z49270), 1-309 (e.g. polypeptides encoded by Genbank Accession No. M57502), JE (e.g. polypeptides encoded by Genbank Accession No. AF058786, M28226), LAG-1 (lymphocyte activation gene-1) (e.g. polypeptides encoded by Genbank Accession No. X53683), LARC D86955), LD78 E03130, E03131, MARC (e.g. as described in Thirion S et al (1994) Biochemical and Biophysical Research Communications 201: 493-499), MCAF M24545 and as described in Apella E et al (1990) Progress in Clinical and Biological Research 349: 405-17), MCP-1 (e.g. polypeptides encoded by Genbank Accession No. X14768), MCP-2 (e.g. polypeptides encoded by Genbank Accession No. Y16645), MCP-3 (e.g. polypeptides encoded by Genbank Accession No. X72308, S71251), MCP-4 (e.g. polypeptides encoded by Genbank Accession No. X98306), MCP-5 (e. g. polypeptides encoded by Genbank Accession No. U50712), MIP (macrophage inflammatory protein) (e.g. polypeptides encoded by Genbank Accession No. U77180, U77035, U49513, M35590), MRP-2 (e.g. as described in Youn B S et al (1995) Journal of Immunology 155: 2661-7), RANTES SDF (e.g. polypeptides encoded by Genbank Accession No. M21121, M77747), TARC (e.g. Genbank protein Accession No. Q92583).

In addition there are several other factors that are related to chemokines but that either have not been assigned yet to one of the two chemokine groups or that do not possess the classical features of either of the two chemokine groups (for example, ATAC (e.g. polypeptides encoded by Genbank Accession No. X86474), Ltn (e.g. polypeptides encoded by Genbank Accession No. U15607, U23772), SCM-1 (e.g. polypeptides encoded by Genbank Accession No. D63789, D63790, D43769). These have been referred to as C-type chemokines or gamma-chemokines.

Yet another group of chemokines has been identified that comprises neurotactin (e.g. polypeptides encoded by Genbank Accession No. AF010586, which is characterized by a CX(3)C cysteine signature motif. The existence of clearly defined subgroups of chemokines on the basis of structural and functional properties illustrates the importance of chemoattractant diversity in the regulation of leukocyte movement through the body.

The biological activities of chemokines are mediated by specific receptors and also by receptors with overlapping ligand specificities that bind several of these proteins which always belong either to the C-C-chemokines or the group of C-X-C-chemokines. Chemokine receptors belong to the large group of G-protein-coupled seven transmembrane domain receptors which contain seven hydrophobic alpha-helical segments that transverse the membrane. These receptors form a structurally related group within the superfamily of G-protein-coupled receptors which mediate signalling via heterotrimeric G-proteins.

The receptors that bind C-X-C chemokines are designated CXCR followed by a number (e.g., CXCR-1 (e.g. polypeptides encoded by Genbank Accession No. L19591), CXCR-2 (e.g. polypeptides encoded by Genbank Accession No. M94582), CXCR-3 (e.g. polypeptides encoded by Genbank Accession No. X95876), CXCR-4 (e.g. polypeptides encoded by Genbank Accession No. D87747, AF025375) while those binding C-C chemokines are designated CCR followed by a number (e.g., CCR-1 (e.g. polypeptides encoded by Genbank Accession No. L09230, U29678), CCR-2 (e.g. polypeptides encoded by Genbank Accession No. U29677, U95626), CCR-3 (e.g. polypeptides encoded by Genbank Accession No. U51241), CCR-4 (e.g. polypeptides encoded by Genbank Accession No. X90862, X85740), CCR-5 (e.g. polypeptides encoded by Genbank Accession No. U54994, U83327), CCR-6 (e.g. polypeptides encoded by Genbank Accession No. U95626), CCR-7 (e.g. polypeptides encoded by Genbank Accession No. L31581), CCR-8 (e.g. polypeptides encoded by Genbank Accession No. Z98206, U45983). Viral chemokine receptor homologues include ECRF-3, EBI-1 (EBV-induced gene-1), and US28.

It is now assumed that the combinatorial effects of multiple chemokines and other mediators are responsible for the cellular composition at inflammatory sites. In addition, many chemokines also directly activate cells. Some of them activate granulocytes and/or monocytes and cause respiratory bursts, degranulation, and the release of lysosomal enzymes. Others prime immune cells to respond to suboptimal amounts of other inflammatory mediators. Yet others have been shown to be potent histamine releasing factors for basophils. It has been proposed that erythrocytes through their promiscuous chemokine receptor play an important role in regulating the chemokine network. Chemokines bound to the erythrocyte receptor are known to be inaccessible to their normal target cells. This appears to provide a sink for superfluous chemokines and may serve to limit the systemic effects of these mediators without disrupting localized processes taking place at the site of inflammation.

Certain C-C chemokines exhibit biological activities other than mere chemotaxis. Some chemokines have been shown to be capable of inducing the proliferation and activation of killer cells known as CHAK (C-C-chemokine-activated killer), which are similar to cells activated by IL2.

Another particularly useful cytokine according to the invention is flt-3 ligand (e.g., polypeptides encoded by Genbank Accession Nos. U04806, U04807, U03858, L23636, U29874, U29875, U44024). This cytokine binds to the flt-3 tyrosine kinase (e.g., polypeptides encoded by Genbank Accession Nos. Z26652, X59398). The human flt-3 ligand also stimulates the proliferation of cells expressing murine flt-3 receptors.

The effects of flt-3 ligand are synergized by coexpression of G-CSF, GM-CSF, M-CSF, IL3, PIXY-321, and SCF. In combination with SCF and IL3 flt-3 ligand can cause expansion of cells with the marker spectrum CD34 (+)CD38 (−). Alone flt-3 ligand supports the survival of precursor cell types in the lineage of blood-forming cells such as CFU-GM, CFU-GEMM, and the very primitive high proliferative potential colony-forming cells. flt-3 ligand only has marginal effects on erythroid and megakaryocyte progenitor cells.

In the mouse, flt-3 ligand potently enhances growth of various types of progenitor/precursor cells in synergy with G-CSF, GM-CSF, M-CSF, IL3, IL6, IL7, IL11, IL12 and SCF. flt-3 ligand supports growth of LTC-IC (long-term culture-initiating cells). The ability of flt-3 ligand to promote the survival of hematopoietic progenitor cells is abrogated by TGF-beta and counteracted by TNF-alpha.

A study of the expression of functional flt-3 receptor and the responses to the ligand in AML (acute myeloid leukemia) and ALL (acute lymphoblastic leukemia) shows a considerable heterogeneity. BCP-ALL in particular fails to proliferate in the presence of flt-3 ligand despite strong expression of surface flt-3 receptor.

It has been shown that in patients with aplastic anemia and in cancer patients with chemotherapy-induced transient suppression of hematopoiesis, serum levels of flt-3 ligand fluctuate in an inverse relationship to the degree of bone marrow failure. flt-3 ligand levels in serum inversely correlate with the colony forming ability in vitro of bone marrow precursors from patients with aplastic anemia. flt-3 ligand treatment of mice challenged with syngeneic fibrosarcoma cells has been shown to result in complete tumor regression and in decreased tumor growth rates.

Antitumor cytokines are especially useful in the methods and compositions of the invention. According to the invention, an "antitumor cytokine" is a cytokine that can limit the growth or metastasis of tumor cells in vitro or in vivo, or can prolong the survival of a tumor-bearing animal, when either admixed with the cells or administered to the animal. The cytokine can be formulated as a solution in a biologically compatible buffer, e.g. PBS, and admixed with tumor cells in vitro. The concentration of cytokine may be from about the picomolar range to about the micromolar range. An antitumor cytokine will, for example, reduce the growth rate of the cells, e.g. by at least 10% compared to buffer alone, or inhibit metastatic properties of the cells, as may be evidenced by, e.g., increased cell adhesiveness or decreased ability to invade an extracellular matrix substrate, such as an artificial basement membrane. Alternatively, an antitumor cytokine may inhibit the growth or metastasis of a tumor in vivo, or may prolong the survival of a tumor-bearing animal. To evaluate the in vivo antitumor effects of a cytokine, the cytokine may be formulated in a pharmaceutically acceptable carrier and administered, e.g., by intravenous, intratumoral, or intraperitoneal injection. The cytokine may also be administered in association with cells, such as tumor cells that express or are coated with the cytokine.

Assays for Bioactivity

According to the invention, it is preferred that a cytokine be "bioactive", "highly bioactive", "extremely bioactive", "natively bioactive", or "suprabioactive". Different levels of bioactivity relate to the ability to induce a change in a leukocyte (other than mere occupancy of the leukocyte's receptors for the cytokine). According to the invention, all naturally occurring cytokines are natively bioactive. Many types of assay can demonstrate the bioactivity of a non-naturally occurring cytokine. For example, a cytokine may be shown to induce survival and/or proliferation of a particular cell type. As another example, a cytokine may change the concentration of an intracellular second messenger, such as cAMP, arachidonic acid, calcium ions, or inositol triphosphate. The following are examples of assays for bioactivity:

Assay 1

Each well of one or more 60-well Lux microtiter trays is loaded with 200 FDC-P1 cells in 10 ul Dulbecco's modified Eagle's medium with a final concentration of 10% newborn calf serum. Cytokine in a concentration in at most the micromolar range is added to each well in a volume of 5 ul. The tray is incubated for 48 h at 37° C. in 10% $CO_2$. Viable cell counts are performed. The average number of viable cells/well is counted. This assay is useful, for example, for identifying bioactivity mediated through a murine GM-CSF receptor.

Assay 2

Cytokine sample and a recombinant standard identical to a naturally occurring cytokine are each diluted serially in complete RPMI-10 in 96-well flat-bottom microtiter plates. Each dilution is plated in triplicate. CT.4S cells in active log-phase growth are collected, washed at least twice in complete RPMI-10, and resuspended in complete RPMI-10 at $1\times10^5$ cells/ml. 50 ul of the cell suspension is added to each well of the plate, which is then incubated for 24 h at 37° C. in 5% $CO_2$. Tritiated thymidine is added to each well and the plate is incubated for an additional 24 h. The cells are then harvested and tritium incorporation is measured by liquid scintillation counting. This assay is useful, for example, for identifying bioactivity mediated through an IL-4 receptor.

Assay 3 (Colony Formation Assay)

Agar (4% w/v) is melted in sterile water by boiling 3 min. The agar is then cooled to 42° C. and added to 42° C. RPMI-15 to a final concentration of 0.4%. The solution is maintained at 42° C. Femurs are removed from young mice using sterile technique. Marrow is collected by flushing the opened ends of the bones with sterile Hank's Balanced Salt Solution (HBSS) using a syringe equipped with a 23G needle. Marrow is placed in a 15 ml tissue culture tube and vortexed into a cell suspension. Bone fragments are allowed to settle for 5 min, and the supernatant suspension is removed. The suspension is adjusted to $7.5\times10^6$ nucleated cells/ml and diluted 1:100 by adding the 42° C. RPMI with 0.4% agar. 2-fold serial dilutions of cytokine are added to 35 mm tissue culture dishes in a volume <=0.2 ml. Control dishes have no cytokine added. 1 ml warm cell suspension is added to each dish and the agar is allowed to set at room temperature. The cultures are incubated for 5-7 days at 37° C. in 5% $CO_2$. Colony formation is then evaluated by microscopy. The average number of colonies of a given type (or aggregate number of colonies of given different types) on the cytokine plates and the average number on the control plates is counted. This assay is useful, for example, for identifying bioactivity mediated through CSF receptors.

Assay 4

Cytokine is diluted serially in RPMI 1640/25 mM HEPES/1% BSA. 25 ul of each dilution is plated in triplicate in a multiwell chemotaxis chamber bottom. Wells containing medium alone serve as negative controls and wells containing chemotaxis-inducing naturally occurring cytokine serve as positive controls. A polycarbonate membrane is placed over the chamber bottom and the chamber is assembled. 50 ul of peripheral blood mononuclear cells at $1.5\times10^6$ cells/ml in the RPMI/HEPES/BSA is added to each of the upper wells of the chamber. The chamber is incubated for 90 min at 37° C. in 5% $CO_2$. The membrane is removed, washed, and stained. Migrated cells in 3-5 random fields of each well are counted by microscopy.

Assay 5

Naturally-occurring cytokine reference standard is diluted to 2 ng/ml in a 17×100 mm tube using supplemented medium. 3 further 5-fold serial dilutions are also prepared.

Serial dilutions of cytokine are prepared in 17×100 mm tubes from 2 ng/ml to 20 pg/ml. 50 ul of PHA-activated human lymphoblasts 4×10$^5$ cells/ml in supplemental medium is added to each well of a 96-well flat-bottom microtiter plate. 50 ul of each dilution of reference standard or cytokine is added to triplicate wells. Negative control wells receive 50 ul of supplemented media alone. The plate is incubated for 48 h at 37° C. in 5% CO$_2$ and the cells are labeled with tritiated thymidine Incorporation is measured by liquid scintillation counting. This assay is useful, for example, for identifying bioactivity mediated through an IL-12 receptor.

Assay 6

In another assay for bioactivity, an immunocompetent animal is vaccinated with on the order of 10$^4$-10$^8$ irradiated cytokine-transduced or cytokine-coated tumor cells, and challenged with on the order of 10$^4$-10$^8$ live wild-type tumor cells (in any temporal sequence). Readouts of the assay are survival, tumor onset, or number of metastases.

Further examples of cytokine assays can be found, e.g., in: Callard R E et al Assay for human B cell growth and differentiation factors. in: Clemens M J et al (eds) Lymphokines and Interferons. A practical Approach, pp. 345-64, IRL Press, Oxford 1987; Coligan J E et al Current protocols in immunology. Grene and Wiley-Interscience, New York 1991); Dotsika E N Assays for mediators affecting cellular immune functions. Current Opinion in Immunology 2: 932-5 (1989); Feldmann M et al Cytokine assays: role in evaluation of the pathogenesis of autoimmunity. Immunological Reviews 119: 105-123 (1991); Guiguet M et al Misinterpretation of the biological activity of cytokine-containing preparations attributable to unrecognized interacting components. Analytical Biochemistry 247(2): 441-442 (1997); Hamblin A S & O'Garra A Assays for interleukins and other related factors. In: Lymphocytes, a practical approach, Klaus G G B (edt), pp. 209-28, IRL Press, Oxford, (1987); Laska E M & Meisner M J Statistical methods and applications of bioassay. Annu. Rev. Pharmacol. Toxicol. 27: 385-97 (1987); Mosman T R & Fong T A T Specific assays for cytokine production by T cells Journal of Immunological Methods 116: 151-8 (1989); Newton R C & Uhl J Assays relevant to the detection and quantitation of cytokines and their inhibitors. Modern Methods in Pharmacol. 5: 83-99 (1989); Thorpe R et al Detection and measurement of cytokines. Blood Rev. 6: 133-48 (1992); van Zoelen E J The use of biological assays for detection of polypeptide growth factors. Progress in Growth Factor Research 2: 131-52 (1990); Winstanley F P Cytokine bioassay. In: Gallagher G et al (eds) Tumor Immunobiology, A practical Approach. Oxford University Press, pp. 179-303 (1993); Wadha M et al Quantitative biological assays for individual cytokines. In: Balkwill F R (edt) Cytokines, A practical approach. Oxford University press, pp. 309-330 (1991)

According to the invention, if a non-naturally occurring cytokine gives a readout in a bioactivity assay that is at least 10% but not more than 29% (to the nearest 1%) of the readout yielded by an equimolar amount of a naturally occurring cytokine (the latter giving a positive result in the assay), then the non-naturally occurring cytokine is "bioactive". According to the invention, if a non-naturally occurring cytokine gives a readout in a bioactivity assay that is at least 30% but not more than 49% (to the nearest 1%) of the readout yielded by an equimolar amount of a naturally occurring cytokine (the latter giving a positive result in the assay), then the non-naturally occurring cytokine is "highly bioactive". According to the invention, if a non-naturally occurring cytokine gives a readout in a bioactivity assay that is at least 50% but not more than 69% (to the nearest 1%) of the readout yielded by an equimolar amount of a naturally occurring cytokine (the latter giving a positive result in the assay), then the non-naturally occurring cytokine is "extremely bioactive". According to the invention, if a non-naturally occurring cytokine gives a readout in a bioactivity assay that is at least 70% but not more than 100% (to the nearest 1%) of the readout yielded by an equimolar amount of a naturally occurring cytokine (the latter giving a positive result in the assay), then the non-naturally occurring cytokine is "natively bioactive". According to the invention, if a non-naturally occurring cytokine gives a readout in a bioactivity assay that is greater than 100% of the readout yielded by an equimolar amount of a naturally occurring cytokine (the latter giving a positive result in the assay), then the non-naturally occurring cytokine is "suprabioactive".

Ligands for CD40 Useful According to the Invention

Nucleotide sequences encoding the CD40 proteins of various species are provided by, e.g., Genbank Accession Nos. Y10507, M83312, and U57745. Human CD40 is a transmembrane glycoprotein with a length of 277 amino acids (48 kDa). CD40 is a phosphoprotein and can be expressed as a homodimer. A soluble form of CD40 (28 kDa) has also been described. CD40 protein is expressed on all B-lymphocytes during various stages of development, activated T-cells and monocytes, follicular dendritic cells, thymic epithelial cells, and various carcinoma cell lines. It is expressed on most mature B-cell malignancies and on some early B-cell acute lymphocytic leukemias. CD40 has been demonstrated on the majority of myeloma cell lines and myeloma cells from patients with plasma cell dyscrasia.

Induction of CD40 mRNA and enhancement of cell surface protein expression in primary human monocytes is observed after treatment with GM-CSF, IL3, or IFN-gamma. The human CD40 gene maps to chromosome 20.

CD40 has been proposed to play a role in the development of memory cells. It also plays a role in cell activation, functioning as a competence factor and progression factor. Crosslinking of the CD40 antigen (in combination with cytokines such as IL4 and IL5) leads to B-cell proliferation and induces immunoglobulin class switching from IgM to the synthesis of IgG, IgA, and IgE in the absence of activated T-cells. CD40 is one of the obligatory signals required for commitment of naive B-cells to IgA secretion; the mechanism of IgA induction requires the cooperation of IL10 and TGF-beta. Soluble CD40 inhibits T-cell-dependent B-cell proliferation.

Monoclonal antibodies against CD40 mediate a variety of effects on B-lymphocytes, including induction of intercellular adhesion (via CD11a/CD18 (LFA-1)), short- and long-term proliferation, differentiation and enhanced tyrosine phosphorylation of proteins. Germinal center centrocytes are prevented from undergoing cell death by apoptosis by activation through CD40 and antigen receptors.

In human resting B-cells expression of CD40 is induced by IL4. Treatment of human B-cells with IL6 leads to the phosphorylation of the intracellular CD40 domain. CD40 does not, however, function as a receptor for IL6. In activated human B-cells the synthesis of IL6 is induced by treatment of the cells with monoclonal antibodies directed against CD40, suggesting that CD40 participates in signal transduction mechanisms dependent on IL6.

Some limited sequence homologies have been found with receptors for Nerve Growth Factor, TNF-alpha and CD27 and it has been assumed that CD40 may be involved also in modulating the biological activity of these and other cytokines.

CD40 has biological functions also in non-immune cells although these are still largely unknown. CD40 ligation has been shown to induce cell death by apotosis in transformed cells of mesenchymal and epithelial origin. In part these processes are mediated through the death domain present in the cytoplasmic domain of CD40.

A particularly useful ligand for CD40 is CD154. CD154 ("CD40 ligand"; human protein 29.3 kDa, 261 amino acids) is a member of the TNF family of proteins. The human protein shows 82.8% and 77.4% identity at the cDNA and protein level, respectively, with a similar protein isolated from murine EL4 thymoma cells. Both proteins are the ligands for the CD40 cell surface antigen expressed on resting B-cells. The human gene encoding CD154 maps to chromosome Xq26.3-q27. Nucleotide sequences encoding the native CD40 ligands of various species are provided by, e.g., Genbank Accession Nos. X67878, X96710, X68550, X65453, Z48469, and L07414. Amino acid sequences of the CD154 molecules of various species are provided, e.g., by Entrez protein database Accession Nos. 1705713, 231718, 560693, 3047129, 116000, 1518170, 38412, 109639, 1083014, 38484, and 37270.

CD154 is naturally synthesized as a transmembrane polypeptide. Nevertheless, a biologically active soluble fragment of human CD154 has been described (Pietravalle et al, 1996, J Biol Chem 271:5965-5967.) Mazzei et al (1995, J Biol Chem 270:7025-7028) identified a biologically active soluble fragment of CD154 as a homotrimer of polypeptides consisting of amino acids Glu 108 through Leu 261 of intact transmembrane CD154. Graf et al (1995, Eur J Immunol 25:1749) describe another active fragment consisting of the C-terminal fragment produced by proteolyttic cleavage at Met 113. Aruffo et al disclose soluble forms of CD154 and their use to stimulate B cells in vitro in U.S. Pat. No. 5,540,926. In the present invention, particularly useful ligands for CD40 include polypeptides that comprise a sequence as set forth in SEQ ID NO. 2 of the '926 patent, from amino acid residues 47 to 261. These residues are comprised by the extracellular domain of human CD154.

Another particularly useful type of ligand for CD40 is an antibody to CD40. Examples of such antibodies include the monoclonal antibodies designated product numbers MCA1143 and MCA1590 of Harlan Bioproducts for Science (Indianapolis, Ind.); monoclonal antibodies designated catalog numbers P61640F (produced by clone 14G7), P42374M (produced by clone MAB89), P61046M (produced by clone BL-C4), and P54486M (produced by clone B-B20) of Biodesign International (Kennebunk, Me.); monoclonal antibody designated catalog number 05-422 (produced by clone 626.1) of Upstate Biotechnology (Lake Placid, N.Y.); monoclonal antibody designated catalog number 3601 (produced by clone S2C6) of Mabtech (Nacka, Sweden); monoclonal antibodies designated catalog numbers RDI-CBL486 (produced by clone BB20), RDI-M1691clb (produced by clone CLB-14G7), RDI-mCD40-323 (produced by clone 3/23) of Research Diagnostics (Flanders, N.J.); monoclonal antibodies described in Schwabe et al, 1997, Hybridoma 16:217-226; monoclonal antibodies described in Bjorck et al, 1994, Immunology 83:430-437; monoclonal antibody G28-5 described by Ledbetter et al, 1994, Circ Shock 44:67-72; and monoclonal antibodies described in Buske et al, 1997, Exp Hematol 25:329-337.

Opsonins Useful According to the Invention

As defined hereinabove, "opsonin" refers to naturally occurring and non-naturally occurring molecules which bind to both antigens and antigen presenting cells (APCs), such as, for example, phagocytic leukocytes (including monocytes and macrophages), dendritic cells (for example, Langerhans cells of the skin), B lymphocytes and, in humans, endothelial cells, or molecules which can be processed such that at least one product of the processing step or steps can bind to both antigens and antigen presenting cells (APCs), such as, for example, phagocytic leukocytes, dendritic cells, B lymphocytes, and, in humans, endothelial cells.

Without being bound to any one mechanism of action, it is believed that opsonin-enhanced cells provide a beneficial effect according to the invention because the opsonin portion acts as a link or coupling agent between the antigen and the APC to allow more efficient binding, engulfment, and internalization of the antigen. In addition, the opsonin itself can be internalized with the antigen. "Internalization" refers to the cellular uptake of a molecule such that it is brought into the cytoplasm or a compartment within the cytoplasm of the cell. Phagocytosis is a process by which a molecule is internalized by a cell.

Preferred opsonins are non-rodent opsonins, e.g., primate, e.g., human, opsonins. Opsonins useful according to the invention bind to receptors on APCs (e.g., phagocytic leukocytes, e.g., macrophages and other cells of the phagocytic system) such as receptors on cells which play a role in innate immunity, as described herein.

Some sets of opsonins can be regarded as structurally and functionally similar. For example, one family comprises fragments of complement components C3 and C4. These two components are highly structurally homologous, and each possesses an intramolecular thiolester bond that is broken when a peptide (C3a or C4a respectively) is proteolytically cleaved from the native molecule. Disruption of the thiolester makes available a chemical structure that can form an ester linkage with an antigen. The moiety of C3 on which this ester bond resides, i.e. the non-C3a moiety, is designated C3b, and C4b is the analogous product of C4 cleavage. C3b can be further proteolysed by proteins such as factor I to yield fragments such as C3bi and C3d, which also remain linked to the antigen via the ester bond.

There are four structurally unique proteins that are known to function as high affinity receptors for biologically active, membrane-bound fragments of C3 and/or C4. CR1 is the major receptor for the C3b fragment of C3 and C4b fragment of C4. It is expressed on monocytes and monocyte-derived APCs, among other cell types. CR2 is the major receptor for the fragment of C3 known as C3d, and is expressed on, e.g., mature B lymphocytes, but not on cells of monocytic lineage. The major role of CR2 on B lymphocytes is believed to be direct costimulation of B cells in concert with their cognate antigens.

CR3 is expressed primarily by neutrophils and monocytes and is also expressed on FDC, Kupffer cells, and NK cells. CR3 is a C3 fragment receptor with a primary specificity for C3bi. CR3 has been proposed as an important organizer of cytoskeletal events necessary for adhesive interactions and membrane reorganization during processes such as phagocytosis.

CR4 is a member of the beta2 integrin family, and its alpha chain is structurally similar to the alpha chain of CR3 and LFA-1. Its primary physiologic ligands are believed to be C3d and C3d,g, however, its biologic activities are less well understood than CR3.

Another example of a family of innate opsonins is the collectins, a group of collagenous C-type lectins that comprises complement component C1q, mannose binding protein, surfactant proteins A and D, and conglutinin. Each molecule comprises a lectin domain that can bind to an antigen, and a collagenous domain that can bind to receptors on phagocytic mononuclear cells, including receptors that are wholly or partially identical to the C1q receptor (Nepomuceno et al, Immunity 6:11'9-29; Tenner et al, Immunity 3:485-93; Guan et al, J Immunol 152:4005-16; Geertsma et al, Am J Physiol 267:L578-84; Miyamura et al, Biochem J 300:237-42; Malhotra et al, J Exp Med 172:955-9; Malhotra et al, Biochem J 293:15-19). Most known collectins comprise multiple polypeptide chains, in some cases homomeric and in others heteromeric, that are assembled post-translationally, in part by covalent cross-linkage of hydroxyproline and hydroxylysine residues. Collectins are demonstrated to be opsonins in, for example, Pikaar et al, J Infect Dis 172:481-9; Alvarez-Dominguez et al, Infection & Immunity 61:3664-72; Kuhlman et al, J Exp Med 169:1733-45; and Geertsma et al, op cit.

Among the other innate opsonins useful according to the invention are C-reactive protein (CRP), alpha-2 macroglobulin, and fibronectin. CRP, a member of the pentraxin family of molecules, binds to receptors on cells of monocytic lineage and has been shown to be an opsonin (Tebo and Mortenson, J Immunol 144:231-8; Holzer et al, J Immunol 133:1424-30). Alpha-2 macroglobulin, like C3 and C4, comprises an internal thiolester bond that can be disrupted when the molecule is proteolysed. Such disruption allows covalent binding of the molecule to an antigen, and binding of alpha-2 macroglobulin to an APC can promote uptake of the conjugate. Fibronectin binds to the alpha 5 beta 1 integrin and can also bind to various antigens, allowing it to function as an opsonin (Cosio, J Lab Clin Med 103:613-9; Czop and Austen, J Immunol 129:2678-81).

Immunoglobulins (antibodies) can function as opsonins by binding antigens via their variable regions and APCs via their constant regions. Typically, an immunoglobulin comprises two heavy chains which are covalently bound to each other and each of which is bound to one light chain. These heterotetramers can further assemble into higher-order structures, such as the pentamers of IgM. Both heavy and light chain variable regions can contribute to the structure of the antigen binding site, whereas the APC binding site is located on the heavy chain constant region. Recombinant single-chain antibodies have also been described. APC receptors for immunoglobulins include Fc alpha, Fc gamma, Fc epsilon, and Fc mu receptors for IgA, IgG, IgE, and IgM, respectively.

Opsonins that are naturally expressed by multicellular eukaryotic organisms are secreted. The latter characteristic distinguishes opsonins from adhesion molecules. A non-naturally occurring molecule containing a naturally occurring APC-binding moiety shall be considered an opsonin if it contains a moiety through which it can be stably bound or attached to a cell such that the APC-binding moiety is located in the extracellular space, whether or not the molecule contains an antigen-binding moiety of a naturally occurring antigen. Moieties through which molecules can be stably bound to a cell include crosslinking moieties, trans-membrane sequences, and lipid moieties. The preparation of proteins containing these sequences or moieties is well-known to one of skill in the art.

An "APC binding moiety of an opsonin" is a sequence or domain of an opsonin which when included in a chimeric molecule permits binding of the chimeric molecule to a receptor that is physiologically expressed on an APC with an affinity at least in the nanomolar range.

There are a number of examples of opsonin fragments that comprise APC binding moieties. Such a fragment may be any length so long as it retains an APC binding function; for example, it may be about 40 amino acids, 100 amino acids, 150 amino acids, 500 amino acids, 800 amino acids, or even as long as 3000 amino acids. For example, Las Holtet et al, 1994, FEBS Lett 344:242 describe a carboxy-terminal fragment of human α2m (val1299-ala1451) that binds with high affinity to the α2m receptor. Fragments comprising amino acids 1314-1451 of human α2m and the corresponding domain of rat α2m also bind to α2m receptors, albeit with 1-2% of the affinities of native α2m (Van Leuven et al, 1986, J Biol Chem 261:11369; Enghild et al, 1989, Biochemistry 28:1406; Salvesen et al, 1992, FEBS Lett 313:198; Sottrup-Jensen et al, 1986, FEBS Lett 205:20).

Becherer and Lambris, 1988, J Biol Chem 263:14586 describe fragments of C3b that bind to CR1, e.g., C3c, fragments of C3 generated by elastase treatment and comprising the N-terminal of the alpha' chain of C3b, and a synthetic peptide comprising the 42 N-terminal amino acids of the C3b alpha' chain. A binding sequence in C3 for CR3 has also been described (Wright et al, 1987, PNAS 84:4235).

"Collagen stalks" of C1q, which are N-terminal fragments obtained by pepsin digestion, bind to the C1q receptor (Reid, 1981, Methods Enzymol 80:16; Malhotra et al, 1993, Biochem J 293:15). Malhotra et al, ibid., also provide evidence that an APC binding moiety of conglutinin is comprised by its 55 N-terminal amino acids. Ezekowitz (U.S. Pat. No. 5,270,199) offers a putative APC binding site in human mannose binding protein consisting of nucleotides 370-438 of FIG. 2 in the '199 patent. In addition, by homology with conglutinin, exon 1 disclosed in the '199 patent may comprise an APC binding moiety.

An APC binding moiety of IgG comprises the CH2 domain and the lower hinge region, including residues 234-237, as described by Canfield and Morrison, 1991, J Exp Med 173:1483-91; Lund et al, 1991, J Immunol 147: 2657-62; and Sarmay et al, 1992, Mol Immunol, 29:633-9.

Examples of opsonins which can be used in the compositions and methods of the invention include fibronectin (e.g., Genbank accessions X02761, K00799, K02273, X82402, X00307, X00739), CRP (e.g., Genbank accessions X17496, M11880, M11881, M11882), complement components such as C1q (e.g., Genbank accessions X66295, M22531, X03084, X58861, and Swiss-Prot accessions P02747, P02745), complement fragments such as C3b and C3d (e.g., Genbank accessions K02782, K02765), mannose binding protein (e.g., Genbank accessions S42292, S42294, X15422), conglutinin (e.g., Genbank accession X71774), alpha-2-macroglobulin (e.g., Genbank accessions M93264, M11313), and surfactant proteins A (e.g., Genbank accessions M68519, S48768) and D (e.g., Genbank accessions L40156, X65018, S38981), immunoglobulins, and their homologues among species.

TABLE 2

Exemplary Opsonin, APC binding moiety/APC receptor pairs useful according to the invention.

| Opsonin | Exemplary APC Binding Moiety | Receptor |
|---|---|---|
| α-2 macroglobulin | Val(1299)-Ala(1451) of human α-2m | α-2m receptor, CD91 |
| C3b | 42 N-terminal amino acids of the α' chain of human C3b | CR1 |
| C3bi | C3bi | CR2, CR3 |
| C3d | C3d | CR2, CR4 |
| C1q | Collagen stalks (Reid, 1981, Methods Enzymol. 80: 16) | Collectin receptor (Nepomuceno et al., 1997, Immunity 6: 119), CD93 |
| Conglutinin | 55 N-terminal amino acids of bovine conglutinin | Collectin receptor |
| MBP | 1. Polypeptide encoded by nt 370-438 of FIG. 2, U.S. Pat. No. 5,270,199<br>2. Polypeptide encoded by Econ . . . I of FIG. 2, U.S. Pat. No. 5,270,199 | Collectin receptor, CD35, CD14 |
| CRP | CRP | CRP receptor, FcγRI, FcγRIIa (CD32) |
| Fibronectin | Fibronectin | α5b1 integrin |
| IgG | CH2 domain plus lower hinge including amino acids 234-237, as described by Lund et al., 1991, J. Immunol. 147: 2657 | FcγRI, FcγRII, FcγRIII |
| Surfactant Protein A | Surfactant Protein A | Collectin receptor, CD14 |
| Surfactant Protein D | Surfactant Protein D | |

Determination of Opsonicity According to the Invention

A given naturally occurring opsonin is considered useful according to the invention if it is determined to possess opsonicity according to one or more of the following assays, and if it is a secreted molecule.

Assay 1

In one assay of opsonicity, as described by O'Rear and Ross in Current Protocols in Immunology, 1994, John Wiley & Sons, pp. 13.4.5-9, SRBC bound via a physiologically occurring linkage to the candidate opsonin molecule are obtained. APCs from the species to which the candidate opsonin is native are suspended at $4\times10^6$/ml in ice-cold HBSS with 1% (w/v) Cohn fraction of BSA. If the candidate opsonin is a fragment of C3, the APCs are freshly drawn, uncultivated peripheral blood monocytes. SRBC linked to the candidate opsonin or control SRBC (identical to the former but not linked to the candidate opsonin) are suspended in the same solution at $2\times10^8$/ml. 100 ul of SRBC suspension and 100 ul of APC suspension are mixed in a 10×75 mm plastic tube. The tube is rotated at 40 rpm at 37° C. for 2-20 min. A small drop of the suspension is placed on a slide, covered with a coverslip, and allowed to stand for 5-10 min. Excess fluid can be removed by pressure on the coverslip, and the coverslip can be sealed to the slide, e.g. with clear nail polish. The slide is examined microscopically, and the percentage of APCs visibly adherent to 4 or more SRBCs is determined. If the percentage is 50% or greater when there are up to $4\times10^4$ candidate opsonin molecules/SRBC', the candidate opsonin can be an opsonin.

Assay 2 (for Protease-activated Candidate Opsonin)

Candidate opsonin or radiolabeled Candidate opsonin is treated with a 1.5-3 fold molar excess of protease (0.05 M triethanolamine-0.1 M NaCl, pH 8.0, room temperature overnight). In this assay, the protease can serve as the antigen or an excess of another antigen can be added. Prior to binding studies, the candidate opsonin-antigen complex is dialyzed against HBSS (4° C.).

Candidate opsonin-antigen complex binding to monocytes is measured by incubating labeled ligand at a concentration up to 1.0 M with $(1.5-4.0)\times10^6$ monocytes in 200 ml volume on ice. Nonspecific binding of radiolabeled ligands is determined in the presence of a 100-fold molar excess labeled candidate opsonin-antigen complex. The unbound ligand is separated from the cells and cell-bound ligand by rapid vacuum filtration on glass fiber filters. Studies are performed on ice to avoid potential complications due to endocytosis. Binding constants and the number of sites per cell are determined by analysis and by nonlinear curve fit. If candidate opsonin-antigen complex affinity for a monocyte binding site is in at least the nanomolar range, the candidate opsonin is an opsonin.

Assay 3

Part I

To directly evaluate whether candidate opsonin is bound to the surface of *P. carinii*, immunoelectron microscopy is performed. *P. carinii* are isolated from bronchoaveolar lavage (BAL) of moribund infected rats using TBS with 1 mM calcium to preserve surface-bound candidate opsonin. Isolated organisms are fixed in periodate-lysine-paraformaldehyde buffer and embedded in Lowacryl mounting medium (Ted Pella, Inc., Redding, Calif.). Ultrathin sections are obtained, blocked with normal goat serum (2%) for 1 h, and incubated with either rabbit anti-candidate opsonin or nonimmune rabbit IgG (25 mg/ml) overnight. After washing, the sections are subsequently incubated with goat and rabbit IgG conjugated to 15 nM colloidal gold (Amersham Corp., Arlington Heights, Ill.). The sections are washed again and examined on a transmission electron microscope (model 6400:JEOL USA, Inc., Peabody, Mass.).

Part II

The attachment of *P. carinii* to cultured alveolar macrophages in the presence or absence of antibody to the candidate opsonin or with the addition of purified candidate is quantified as follows. Adherence of *P. carinii* to alveolar macrophages is assayed by $^{51}$Cr-labeling the organisms. *P. carinii* are isolated from infected rats with TBS containing 1 mM calcium to prevent loss of surface-bound candidate opsonin. The organisms are radiolabeled by incubation for 8 h at 37° C. in 2 ml of DME containing 20% FCS and 200 mCi of $^{51}$Cr-sodium chromate (New England Nuclear). Normal alveolar macrophages are lavaged from healthy rats and plated in tissue culture plates ($1\times10^5$) cells/well) which are been precoated with normal rat IgG (100 mg/ml×60 min) in order to ensure firm adherence of the macrophages. After 1 h, the macrophages are gently washed with HBSS to remove nonadherent cells. >95% of macrophages are adherent after this wash. $^{51}$Cr-*P. carinii* ($1\times10^6$) containing surface-associated candidate opsonin are added to the macrophages and incubated at 37° C. for an additional hour. Subsequently, nonadherent *P. carinii* are removed by washing. The macrophage monolayers containing adherent *P. carinii* are solubilized in 1 N NaOH and quantified. Adherence of *P. carinii* is defined as: percentage of adherence= (A/A+B)×100, where A=$^{51}$Cr-*P. carinii* associated with the monolayer, and B=unattached $^{51}$Cr-*P. carinii*. To assess the effect of candidate opsonin on the attachment of *P. carinii* to alveolar macrophage lung cells in culture, *P. carinii* adherence assays are conducted in the presence or absence of a polyclonal rabbit antibody generated against the candidate opsonin (100 mg/ml).

If candidate opsonin binding to *P. carinii* is apparent in Part I and if, in Part II, % adherence is diminished in the presence of anti-candidate opsonin with statistical significance of P<0.05, the candidate opsonin is an opsonin.

Assay 4

Association of bacteria with adherent monocytes is measured as follows. Endotoxin level in the modified PBS and in all buffers used is below 50 pg/ml as determined by the Limulus assay. $5\times10^3$ monocytes in modified PBS are allowed to adhere to the wells of a Terasaki plate for 2 h at 37° C. After nonadherent cells are removed by three washes with PBS, $5\times10^4$ FITC-labeled bacteria in 0.5 ml buffer with or without 10-50 micrograms/ml of candidate opsonin are added. A bacteria-to-monocyte ratio of 10:1 to 50:1 is used. After 30 min of incubation at 37° C. in the dark, the nonadherent bacteria are removed by five washes with warm PBS. Assays are performed in quadruplicate; in each well, the number of bacteria associated with 100 monocytes is counted under a fluorescence microscope using ×400 magnification. Results are expressed as the number of bacteria associated with 100 monocytes. If this number with candidate opsonin can be at least twice that without candidate opsonin, the candidate opsonin is an opsonin.

Assay 5

Part I

About $1\times10^7$ to $6\times10^7$ bacteria per ml are incubated (20 min, 0° C.) with 10 mcg/ml of $^{125}$I-candidate opsonin in a total volume of 0.7 ml. of PBS aliquots, 100 ml, of the reaction mixtures are layered over 150 ml of an oil cushion (60% dibutyl phthalate, 40% dioctyl phthalate [Eastman Kodak Co., Rochester, N.Y.]), and the mixtures are centrifuged (10,000×g, 60 s, 4° C.). The tip of the tube, containing the cell pellet, is cut with a Mozart razor blade, and the radioactivity is counted.

Part II

APCs are plated in 96-well tissue culture plates (Costar, Cambridge, Mass.) at $2\times10^5$ cells per ml the evening before use. $2\times10^6$ bacteria per well (0.1 ml per well) are added to the culture plates with or without 100 mcg/ml of candidate opsonin. The plates are then centrifuged at 1,000×g for 7 min. After 15 min at 37° C. to allow the uptake of bacteria, free bacteria are removed by several washes with cold PBS. They are then incubated (45 min, 37° C.) in RPMI 1640 plus an amount of antibiotic that, when present in the culture for 45 min, kills all extracellular bacteria. The end of this incubation period is considered time zero. Monolayers are washed three times with Hanks' balanced saline solution, and the same volume of RPMI 1640 (RO) is added. The cells are lysed by using several cycles of freezing and thawing. The number (CFU) of viable bacteria per well is determined by quantitative plate counts on blood agar plates (Columbia blood agar; Becton Dickinson, San Jose, Calif.) after 24 h of incubation. Each result is given as the mean of three determinations.

If, in Part I, candidate opsonin-treated bacterial pellet has >75 KCPM and this incorporation can be inhibited by unlabeled candidate opsonin, and if in Part II the CFU with candidate opsonin is greater than without (P<0.05), the candidate opsonin can be an opsonin.

Assay 6

200 µl of GHBSS (Hanks Balanced Salt Solution)+0.1% of gelatin containing 10 m mol $CaCl_2$) containing 10' bacteria is prepared. The bacteria are then incubated at 4° C. with 20-100 µg/ml of candidate opsonin. Binding assays are done in the presence or absence of a competitive inhibitor. After incubation for 30 minutes, the bacteria are washed five times in a GHBSS+10 mmol $CaCl_2$ at room temperature in a microfuge at 1,300 g for 3 minutes. Thereafter, a 1:1,000 dilution of rabbit anti-candidate opsonin antiserum is incubated with the bacteria for 1 h in PBS+5% FCS and 10 mmol $CaCl_2$ and then the bacteria are washed three times in GHBSS+10 mmol $CaCl_2$ plus 0.05% Tween 20. Binding of anti-serum to bacteria is detected by a 1:1,000 dilution of goat anti-rabbit IgG conjugated to rhodamine (Fisher Pharmaceuticals, Orangeburg, N.Y.). After incubation, the bacteria are washed five times in GHBSS+10 mmol $CaCl_2$ plus 0.05% Tween 20, smeared onto glass slides and allowed to air dry. Thereafter bacteria are fixed with 100% ice cold methanol for 5 minutes. Negative controls included the absence of candidate opsonin and no first step antibody. Numerous fields of triplicate assays are examined by fluorescence microscopy.

Part II Association of Radiolabeled Bacteria with Cells.

$10^7$ radiolabeled bacteria are resuspended in 200 µl of GHBSS+10 mmol $CaCl_2$ and are incubated with or without candidate opsonin ranging from 2 µg/ml to 40 µg/ml at 4° C. for 30 min. The bacteria are then washed three times in GHBSS+10 mmol $CaCl_2$ for 3 min at room temperature in a microfuge at 1,300 g, resuspended in 50 µl of GHBSS and added to a 1-ml suspension containing on the order of $10^6$ APCs (GHBSS). The bacteria and APCs are gently rocked at 37° C. for 20 min and thereafter the unattached bacteria are removed by five washes using differential centrifugation at 82 g in a microfuge. Before the last wash, an aliquot from each sample is plated on a Labtek slide and cells are adhered for 10 min, fixed in methanol, stained with Giemsa, and scored by light microscopy. To score the cells plated on the Labtek slides, at least 400 cells are counted. The phagocytic index represented the number of attached or ingested particles per 100 PMNs. The pellet from above containing cells and radiolabeled bacteria is then lysed in 100 µl PBS+0.5% Triton X-100 and the radioactivity is measured in a scintillation counter. If, in Part I, specific binding of candidate opsonin to bacteria is evident, and in Part II the specific uptake of bacteria, in cpm, is more than three times greater with candidate opsonin than without, the candidate opsonin can be an opsonin.

Assay 7

Part I

To investigate binding to *L. donovani* promastigotes cultures are seeded at $5 \times 10^5$ parasites $ml^{-1}$. At regular time points up to 9 days, a fraction of parasites are counted, washed, and resuspended in 1% BSA, 0.5 mM $Ca^{2+}$. 0.05% $NaN_3$, Tris-buffered saline (TBS), (10 mM Tris-HCl, 0.15 M NaCl, pH 8.0) (diluent) to $2 \times 10^5$ $ml^{-1}$. Fifty microliters of this suspension are then added to 200-μl microfuge tubes containing 70 μl 5 μg/ml radiolabeled candidate opsonin (0.12 μCi/μg) in diluent without EDTA, which had been layered over 150 μl of a dinonyl phthalate/dibutyl phthalate (40:60 v/v) oil mixture. Parasites are incubated for 1 h and centrifuged through the oil layer, the cell pellet is cut off, and associated candidate is detected by gamma counting. Each assay is performed in triplicate. The concentration dependency of candidate binding to promastigotes is also measured as above, using an activity of 0.045 μCi/μg and a twofold dilution series from 60 to 0.015 μg/ml candidate.

Part II

APCs are plated out at $1 \times 10^6$ cells/well on glass coverslips in a 24-well tissue culture plate. Cells are incubated in RPMI 1640 (Life Technologies) supplemented with 10% PCS, 1 mM glutamine, 200 U/ml penicillin and 200 μg/ml streptomycin in a humidified incubator at 37° C. After 24 h, nonadherent cells are removed and remaining cells are used after 6 days. Promastigotes are incubated with or without candidate at 30 μg/ml in RPMI 1640 for 1 h and then washed three times before adding to the APC cultures at $10^6$/well. Promastigotes are allowed to infect APCs for 1 h, then cells are washed, fixed with methanol, and Geimsa stained (BDH, Poole, Dorset, U.K.) before counting. The percentage of APCs infected and the number of parasites/100 macrophages is determined from quadruplicate cultures.

If in Part I the affinity of candidate opsonin for parasites is at least in the nanomolar range and in Part II the number of parasites taken up/100 APCs is, with candidate opsonin, at least twice that without candidate opsonin, the candidate opsonin can be an opsonin.

Assay 8

Part I

Portions (0.5 ml) of [$^{35}$S]methionine-labeled culture medium containing 5 percent fetal calf serum and the candidate opsonin are incubated for 30 minutes at room temperature with 0.1 ml or 0.2 ml of a 10 percent suspension of a microorganism). The microorganisms tested may include, for example, *Salmonella typhimurium, Bacillus subtilis, Staphylococcus aureus, Escherichia coli*, and *Saccharomyces cerevisiae*. Bound proteins are released by boiling in buffer containing 2 percent SDS and 0.1 M dithiothreitol and are analyzed on a 5 percent SDS gel.

Part II

Fixed bacteria (0.1 ml; 10 percent by volume; $10^{'10}$ organisms per milliliter), labeled with [$^3$H]thymidine, are incubated with 0.1 ml of serum with or without depletion of the candidate opsonin. After being washed with PBS, the bacteria are incubated with on the order of $1 \times 10^7$ APCs in a final volume of 0.9 ml PBS containing divalent cations. At intervals 0.2 ml is removed to ice-cold PBS with N-ethyi-maleimide (2 mM) to block further endocytosis, and the cells are washed (at about 100 g for 10 seconds)

If in Part I a band corresponding to the candidate opsonin is apparent, and if in Part II the CPM after 6-10 min of incubation is at least three times greater for undepleted samples with serum than with depleted serum, the candidate opsonin can be an opsonin.

In lieu of results form Parts I of assays 3, 5, 6, 7, 8, a candidate opsonin that satisfies Part II of an assay can be an opsonin if it can bind to the antigen of the assay with an affinity in at least the nanomolar range.

Assay 9

SRBC coated with at least $1.2 \times 10^4$ molecules/cell of a fragment of C3 are prepared as described by O'Rear and Ross in Current Protocols in Immunology, 1994, John Wiley & Sons, pp. 13.4.5-9. 250 ul of monocytes at $2 \times 10^5$ cells/ml of RPMI with 10% fetal calf serum are added to each well of an 8-well glass tissue culture plate and incubated at 37° C., 5% $CO_2$ for 3 h. The monocytes are washed twice with HBSS, and 50 ul of the SRBC at $1.5 \times 10^8$/ml of $DVBS^{2+}$ are added to each well. The plate is centrifuged at 50 g for 5 min and then incubated at 37° C., 5% $CO_2$ for 3 h. The walls are washed twice with HBSS, fixed with 0.5% glutaraldehyde, and stained with Giemsa stain. If >40% of the monocytes form rosettes with at least 1 SRBC as determined by light microscopy, the candidate can be an opsonin.

Heat Shock Proteins Useful in the Invention

Heat shock proteins (HSPs) are associated in cells with a broad spectrum of peptides, polypeptides, denatured proteins and antigens with which they form complexes. Such HSP-peptide complexes have been described as being useful in vaccines against cancers and infectious diseases by Srivastava et al., "Heat shock protein-peptide complexes in cancer immunotherapy" in Current Opinion in Immunology (1994), 6:728-732; Srivastava, "Peptide-Binding Heat Shock Proteins in the Endoplasmic Reticulum" in Advances in Cancer Research (1993), 62:153-177. The HSP-peptide complexes appear to work as vaccines, because they may function as antigen carrying and presentation molecules. The development of vaccines using such antigens has been described by Baltz, "Vaccines in the treatment of Cancer" in Am. J Health-Syst. Pharm. (1995), 52:2574-2585. The antigenicity of heat shock proteins appears to derive not from the heat shock protein itself, but from the associated peptides, see Udono et al., "Heat Shock Protein 70-associated Peptides Elicit Specific Cancer Immunity" in J. Exp. Med. (1993), 178:1391-1396; Srivastava et al., "Heat shock proteins transfer peptides during antigen processing and CTL priming" in Immunogenetics (1994), 39:93-98; Srivastava, "A Critical Contemplation on the Roles of Heat Shock Proteins in Transfer of Antigenic Peptides During Antigen Presentation" in Behring Inst. Mitt. (1994), 94:37-47. HSPs appear to be part of the process by which peptides are transported to the Major Histocompatibility Complex (MHC) molecules for surface presentation.

A number of different HSPs have been shown to exhibit immunogenicity, and are useful in the present invention, including, but not limited to: gp96, hsp90, hsp100, hsp60, hsp 25 and hsp70, see Udono et al., supra. and Udono et al., "Comparison of Tumor-Specific Immunogenicities of Stress-Induced Proteins gp96, hsp90, and hsp 70" in Journal of Immunology (1994), 5398-5403; gp96 and grp94, Li et al., "Tumor rejection antigen gp96/grp94 is an ATPase: implications for protein folding and antigen presentation" in The EMBO Journal, Vol. 12, No. 8 (1993), 3143-3151; and gp96, hsp90 and hsp70, Blachere et al., "Heat Shock Protein Vaccines Against Cancer" in Journal Of Immunotherapy (1993), 14:352-356.

Heat shock proteins may be purified for use in the present invention using a procedure employing DE52 ionexchange chromatography followed by affinity chromatography on ATP-agarose, see Welch et al., "Rapid Purification of Mammalian 70,000-Dalton Stress Proteins: Affinity of the Proteins for Nucleotides" in Molecular and Cellular Biology (June 1985), 1229-1237.

Adhesion Molecules Useful in the Invention

Adhesion molecules useful in the present invention include any cell-surface protein which is involved in bediating the recognition and adhesion of cell sto their substrate and to other cells. Cellular adhesion molecules can be divided into two primary classes: $Ca^{2+}$ dependent (cadherins) and $Ca^{2+}$ independent.

There are over a dozen different types of $Ca^{2+}$ dependent adhesion molecules called cadherins. Most cadherins are single-pass transmembrane glycoproteins composed of about 700-750 amino acid residues. The large extracellular part of the molecule is usually folded into five domains, each containing about 100 amino acid residues. Four of these domains contain presumptive $Ca^{2+}$ binding sites. Cadherins are often present in the cell membrane as dimers.

Cadherens useful in the present invention include, but are not limited to cadherin E, cadherin N, cadherin BR, cadherin P, cadherin R, cadherin M, cadherin VE, cadherin T&H, cadherin OB, cadherin K, cadherin 7, cadherin 8, cadherin KSP, cadherin LI, cadherin 18, fibroblast 1, cadherin, fibroblast 2, cadherin, fibroblast 3, cadherin 23, desmocollin 1, desmocollin 2, desmoglein 1, desmoglein 2, desmoglein 3, and protocadherin 1, 2, 3, 7, 8, and 9.

The remaining adhesion molecules are $Ca^{2+}$ independent, and, like the cadherins, may be used as ligands of a cell surface protein on an APC in the present invention. General classes of adhesion molecules as well as specific adhesion molecules useful in the present invention are shown below in Table 3.

Counter-receptors of T Cell Co-stimulatory Molecules of the Invention

In one embodiment of the invention the portion of the multifunctional molecule which is a ligand of a cell surface protein of an APC is a counter-receptor of a T cell co-stimulatory molecule. Costimulation is defined as a signaling pathway that does more than simply augment antigen receptor-proximal activation events, but that intersects with antigen-specific signals synergistically to allow lymphocyte activation. Accordingly, a counter-receptor of a co-stimulatory molecule, useful in the present invention includes, but is not limited to a receptor for one or more of B7-1, B7-2, ICOS:B7 h, PD-1:PD-L1/PD-L2, CD48, CD40 ligand, and OX40. Counter-receptors useful in the present invention include, but are not limited to CD28, CTLA-4, ICOS, PD-1, members of the TNF receptor family, CD40, the major B cell costimulatory molecule, as well as OX-40, 4-1BB, CD30, and CD27.

Peptide Linkers

In one embodiment, the multifunctional molecule is a fusion polypeptide which comprises one or more amino acids interposed between the first and second parts which bind to cells, e.g. a fusion polypeptide which comprises a first amino acid sequence which can bind to an antigen bearing target and a second amino acid sequence which can bind to a leukocyte, and which further comprises at least one amino acid interposed between the first and second parts. The interposed amino acids may comprise, e.g., a linker sequence intended to lessen steric hindrance or other undesirable interactions between the aforementioned first and second parts. For, example, one such type of sequence takes the form $(Gly_xSer)_n$, wherein n is an integer from between 1 and 15, and x is an integer between 1 and 10. Additional useful linkers include, but are not limited to (Arg-Ala-Arg-Asp-Pro-Arg-Val-Pro-Val-Ala-Thr)$_{1-5}$ (Xu et al., 1999, Proc. Natl. Acad. Sci. U.S.A. 96: 151-156), $(Gly-Ser)_n$ (Shao et al.,

TABLE 3

| | |
|---|---|
| Selectins | L-selectin; E-selectin; P-selectin |
| Integrins | α1β1; α2β1; α3β1; α4β1; α5β1; α6β1; α7β1; α8β1; α9β1; αvβ1; αLβ2; αMβ2; αXβ2; αIIbβ3; αvβ3; α6β4; αvβ5; αvβ6; αvβ7; αIELβ7; α11 |
| Immunoglobulin Superfamily | Neural Specific: Adhesion molecule on glia (AMOG); L1CAM; Myelin-associated glycoprotein (MAG); Myelin-oligodendrocyte glycoprotein (MOG); NCAM-1 (CD-56); NrCAM; OBCAM; P$_0$protein; PMP-22protein; Neurofascin; NgCAM<br>Systemic IgCAMS: ALCAM; Basigin (CD147); BL-CAM (CD22); CD44; ICAM-1 (CD54); ICAM-3 (CD50); Lymphocyte function antigen-2 (LFA-2); LFA-3 (CD58); MHC molecules; MAdCAM-1; PECAM (CD31); T-cell receptor; VACM-1 |
| Other Adhesion Molecules | Agrin; CD34; GlyCAM-1; Oligodendrocyte-myelin glycoprotein (OMGP) |

Defensins Useful in the Invention

In one embodiment, the portion of the multifunctional molecule which is a ligand of a cell surface protein of an APC is a defensin. Defensins are a large family of broad-spectrum antimicrobial peptides, identified originally in leukocytes of rabbits and humans. Defensins, cationic, polar peptides (30-35 aa, 3-4 kDa), are distinguished by a conserved tri-disulfide and largely beta sheet structure. When expressed at the cell surface, defensins have been hypothesized to function as a biochemical barrier against microbial invention by inhibiting colonization of the epithelium by a wide range of pathogenic microorganisms. Defensins useful in the present invention include, but are not limited to human alpha defensins 1-6, human neutrophil peptides 1-4, human beta defensin 1 and 2, and rat beta defensin 1 and 2.

2000, Bioconjug. Chem. 11: 822-826), (Thr-Ser-Pro), (Kroon et al., 2000, Eur. J. Biochem. 267: 6740-6752), $(Gly-Gly-Gly)_n$ (Kluczyk et al., 2000, Peptides 21: 1411-1420), and (Glu-Lys) (Klyczyk et al., 2000, supra), wherein n is 1 to 15 (each of the preceding references is also incorporated herein by reference). In another embodiment, no amino acids are interposed between the first and second parts.

Antigens Useful According to the Invention

1. Viral Antigens

Examples of viral antigens include, but are not limited to, retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B. and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpl, gpII, and other varicella zoster viral antigen components; Japanese encephalitis viral antigens such as proteins E, M-E, M-E-NS 1, NS 1, NS 1-NS2A, 80% E, and other Japanese encephalitis viral antigen components; rabies viral antigens such as rabies glycoprotein, rabies nucleoprotein and other rabies viral antigen components. See Fundamental Virology, Second Edition, e's. Fields, B. N. and Knipe, D. M. (Raven Press, New York, 1991) for additional examples of viral antigens.

2. Bacterial Antigens

Bacterial antigens which can be used in the compositions and methods of the invention include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diphtheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; hemophilus influenza bacterial antigens such as capsular polysaccharides and other hemophilus influenza bacterial antigen components; anthrax bacterial antigens such as anthrax protective antigen and other anthrax bacterial antigen components; rickettsiae bacterial antigens such as romps and other rickettsiae bacterial antigen component. Also included with the bacterial antigens described herein are any other bacterial, mycobacterial, mycoplasmal, rickettsial, or chlamydial antigens.

3. Fungal Antigens

Fungal antigens which can be used in the compositions and methods of the invention include, but are not limited to, *candida* fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

4. Parasite Antigens

Examples of protozoa and other parasitic antigens include, but are not limited to, *plasmodium falciparum* antigens such as merozoite surface antigens, sporozoite surface antigens, circumsporozoite antigens, gametocyte/gamete surface antigens, blood-stage antigen pf 1 55/RESA and other plasmodial antigen components; *toxoplasma* antigens such as SAG-1, p30 and other *toxoplasma* antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

5. Tumor Antigens.

Tumor antigens which can be used in the compositions and methods of the invention include, but are not limited to, telomerase components; multidrug resistance proteins such as P-glycoprotein; MAGE-1, alpha fetoprotein, carcinoembryonic antigen, mutant p53, immunoglobulins of B-cell derived malignancies, fusion polypeptides expressed from genes that have been juxtaposed by chromosomal translocations, human chorionic gonadotrpin, calcitonin, tyrosinase, papillomavirus antigens, gangliosides or other carbohydrate-containing components of melanoma or other tumor cells. It is contemplated by the invention that antigens from any type of tumor cell can be used in the compositions and methods described herein.

6. Antigens Relating to Autoimmunity.

Antigens involved in autoimmune diseases, allergy, and graft rejection can be used in the compositions and methods of the invention. For example, an antigen involved in any one or more of the following autoimmune diseases or disorders can be used in the present invention: diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjigren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. An antigen can also be an altered peptide ligand useful in treating an autoimmune disease.

Examples of miscellaneous antigens which can be can be used in the compositions and methods of the invention include endogenous hormones such as luteinizing hormone, follicular stimulating hormone, testosterone, growth hormone, prolactin, and other hormones, drugs of addiction such as cocaine and heroin, and idiotypic fragments of antigen receptors such as Fab-containing portions of an anti-leptin receptor antibody.

Determination of Binding of a Multifunctional Molecule to a Antigen Bearing Target or APC Multiple techniques are known to those of skill in the art for detecting protein-protein binding. That is, the binding of a multifunctional molecule of the invention to either or both of an antigen bearing target and an APC.

The association between the multifunctional molecule and an antigen bearing target and/or an APC may be measured for example by Fluorescent Resonance Energy Transfer (FRET), wherein one peptide (i.e., the multifunctional molecule) comprises a fluorescent label moiety, and the antigen bearing target or APC harbours a second such moiety, and where excitation at an appropriate wavelength may result in absorption of photons by one label, followed by FRET, and emission at a second wavelength characteristic of the second fluorophore, this emission being measured and corresponding to the amount of antigen bearing target or APC which is associated with the multifunctional molecule. Alternatively, this association may be measured in one of many other ways which are described more fully below.

A "fluorescent tag" or "fluorescent group" refers to either a fluorophore or a fluorescent protein or fluorescent fragment thereof, or refers to a fluorescent amino acid such as tryptophan which may be incorporated into a polypeptide. "Fluorescent protein" refers to any protein which fluoresces when excited with appropriate electromagnetic radiation. This includes proteins whose amino acid sequences are either natural or engineered.

It is additionally preferred that the fluorophores comprise fluorescein and tetramethylrhodamine or another suitable pair. In another preferred embodiment, the label comprises two different fluorescent proteins. It is preferred that fluorescent proteins comprise any protein selected from the group consisting of green fluorescent protein (GFP), blue fluorescent protein, red fluorescent protein and other engineered forms of GFP.

Preferably, the polypeptide comprises a cysteine amino acid through which the label is attached via a covalent bond. More preferably, the label may be attached via a primary amine group such as via a lysine residue. As will be apparent to a person skilled in the art, it is preferable to avoid using the same chemistry for both labelling and immobilising polypeptides of the invention. For example, if the polypeptide is immobilised via cysteine residues, the label is advantageously attached via lysine residues.

Preferably, the measuring is performed by fluorescent resonance energy transfer (FRET), fluorescence anisotropy or fluorescence correlation spectroscopy, or by measuring the binding of a fluorescent partner polypeptide to an immobilised polypeptide. Techniques for performing such measurements are well known to those of skill in the art.

It is preferred that the fluorescence emitting means comprise two different fluorophores, and particularly preferred that the fluorophores comprise fluorescein and tetramethylrhodamine or another suitable pair.

As used herein with regard to fluorescent labels for use in FRET, the term "appropriate combination" refers to a choice of reporter labels such that the emission wavelength spectrum of one (the "donor" moiety) is within the excitation wavelength spectrum of the other (the "acceptor" moiety).

Methods of detection without use of label are known in the art. These include detection using surface plasmon resonance to detect changes in the mass of, for example the multifunctional molecule, which would occur if binding of the partner polypeptide increased or decreased. Such measurements may be made for example using a BIACORE machine. In this embodiment, the multifunctional molecule is immobilized on a solid support prior to contacting the molecule with the antigen bearing moiety and/or APC.

In addition to the above methods, one technique for determining the binding of a multifunctional molecule of the invention to an antigen bearing moiety and/or and APC involves the use of antibodies specifically directed to the multifunctional molecule. Briefly, antigen bearing cells, for example, are incubated with the multifunctional molecule of the invention in RPMI 1640, or other suitable buffer, for 1-4 hours at 37° C. with shaking. The cells are then washed in PBS containing 2% FBS, or other cell culture serum. The antigen bearing cells are then incubated with, for example, an FITC labeled anti-multifunctional molecule antibody for 1 hour at 4° C. After additional washing in PBS, the cells are analyzed by flow cytometry, wherein the identification of labeled cells is indicative of the binding of the multifunctional molecule of the invention to the antigen bearing cell.

Preparation of a Cell Containing a Recombinant Nucleic Acid According to the Invention In one embodiment of the present invention, a nucleic acid molecule encoding a multifunctional molecule of the present invention is introduced into a host cell capable of expressing the nucleic acid molecule so as to produce the multifunctional molecule. In one embodiment, the host cell is permitted to express the nucleic acid ex vivo. In an alternate embodiment, the host cell is transfected with the nucleic acid molecule encoding the multifunctional molecule, and then placed back into the host animal from which it was obtained, wherein the multifunctional polypeptide molecule is expressed in vivo in the host animal.

Host cells are transfected, as taught herein, via conventional methods well-known in the art. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals. Additional examples of methods of introducing nucleic acid molecules encoding multifunctional molecules are described below. The cells containing the introduced nucleic acid molecules encoding, for example, multifunctional molecule and/or an antigen, can themselves be administered to a subject (as the antigen) according to the methods of the invention, e.g., in a vaccine composition.

A. Introduction of Naked Nucleic Acid into Cells

1. Transfection Mediated by DEAE-Dextran: Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce nucleic acid transiently into cells but is not preferred for creating stably transfected cells. Thus, this method can be used for short term production of a gene product but is not a method of choice for long-term production of a gene product. Protocols for DEAE-dextran-mediated transfection can be found in *Current Protocols in Molecular Biology*, Ausubel, F. M. et al. (e's.) Greene Publishing Associates, (1989), Section 9.2 and in *Molecular Cloning: A Laboratory Manual. 2nd Edition*. Sambrook et al. Cold Spring Harbor Laboratory Press, (1989), Sections 16.41-16.46 or other standard laboratory manuals.

2. Electroporation: Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the nucleic acid and the ionic composition of the media. Electroporation can be used to stably (or transiently) transfect a wide variety of cell types and is only applicable to in vitro modification of cells. Protocols for electroplating cells can be found in *Current Protocols in Molecular Biology*, Ausubel, F. M. et al. (e's.) Greene Publishing Associates, (1989), Section 9.3 and in *Molecular Cloning: A Laboratory Manual, 2nd Edition*, Sambrook et al. Cold Spring Harbor Laboratory Press, (1989), Sections 16.54-16.55 or other standard laboratory manuals.

3. Liposome-Mediated Transfection ("Lipofection"): Naked nucleic acid can be introduced into cells by mixing the nucleic acid with a liposome suspension containing cationic lipids. The nucleic acid/liposome complex is then incubated with cells. Liposome mediated transfection can be used to stably (or transiently) transfect cells in culture in vitro. Protocols can be found in *Current Protocols in Molecular Biology*, Ausubel, F. M. et al. (e's.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157-176; Wang and Huang (1987) *Proc. Natl. Acad Sci. SA* 84:7851-785S; Brigham et al. (1989) *Am. J. Med. Sci.* 298:278; and Gould-Fogerite et al. (1989) *Gene* 84:429-438.

4. Direct Injection: Naked nucleic acid can be introduced into cells by directly injecting the nucleic acid into the cells. For an in vitro culture of cells, nucleic acid can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the nucleic acid is stably introduced into a fertilized oocyte which is then allowed to develop into an animal. The resultant animal contains cells carrying the nucleic acid introduced into the oocyte. Direct injection has also been used to introduce naked nucleic acid into cells in vivo (see e.g., Acsadi et al. (1991) *Nature* 332: 815-818; Wolff et al. (1990) *Science* 247:1465-1468). A delivery apparatus (e.g., a "gene gun") for injecting DNA into cells in vivo can be used. Such an apparatus is commercially available (e.g., from BioRad).

5. Receptor-Mediated DNA Uptake: Naked nucleic acid can also be introduced into cells by complexing the nucleic acid to a cation, such as polylysine, which is coupled to a ligand for a cell-surface receptor (see for example Wu, G. and Wu, C. H. (1988) *J. Biol. Chem* 263:14621; Wilson et al. (1992) *J. Biol. Chem.* 267:963-967; and U.S. Pat. No. 5,166,320). Binding of the nucleic acid-ligand complex to the receptor facilitates uptake of the nucleic acid by receptor-mediated endocytosis. Receptors to which a nucleic acid-ligand complex have targeted include the transferrin receptor and the asialoglycoprotein receptor. A nucleic acid-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc.* Natl. Acad. Sci USA 90:2122-2126). Receptor-mediated nucleic acid uptake can be used to introduce nucleic acid into cells either in vitro or in vivo and, additionally, has the added feature that nucleic acid can be selectively targeted to a particular cell type by use of a ligand which binds to a receptor selectively expressed on a target cell of interest.

Generally, when naked nucleic acid is introduced into cells in culture (e.g., by one of the transfection techniques described above) only a small fraction of cells (about 1 out of 105) typically integrate the transfected nucleic acid into their genomes (i.e., the nucleic acid is maintained in the cell episomally). Thus, in order to identify cells which have taken up exogenous nucleic acid, it is advantageous to transfect nucleic acid encoding a selectable marker into the cell along with the nucleic acid(s) of interest. Preferred selectable markers include those which confer resistance to drugs such as G418, hygromycin and methotrexate. Alternatively, a selectable marker maybe one which emits a detectable signal upon expression such as green fluorescen protein or blue fluorescent protein. Selectable markers may be introduced on the same plasmid as the gene(s) of interest or may be introduced on a separate plasmid.

B. Viral-Mediated Gene Transfer

A preferred approach for introducing nucleic acid encoding a gene product into a cell is by use of a viral vector containing nucleic acid, e.g. a cDNA, encoding the gene product. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are expressed efficiently in cells which have taken up viral vector nucleic acid and viral vector systems can be used either in vitro or in vivo.

1. Retroviruses: Defective retroviruses are well characterized for use in gene transfer for gene therapy purposes (for a review see Miller, A. D. (1990) *Blood* 76:271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ϕCrip, ϕCre, _2, and_Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci.*

USA 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad Sci. USA* 88:8377-8381; Chowdhury et al. (1991) *Science* 254:1802-1805; van Beusechem et al. (1992) *Proc. Natl. Acad Sci. USA* 89:7640-7644; Kay et al. (1992) *Human Gene Therapy* 3:641-647; Dai et al. (1992) *Proc. Natl. Acad Sci. USA* 89:10892-10895; Hwu et al. (1993) *J. Immunol.* 150:4104-115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

2. Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Adz, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral nucleic acid (and foreign DNA contained therein) is not integrated into the genome of a host cell but remains episomal, thereby avoiding potential problems that can occur as a result of insertional mutagenesis in situations where introduced nucleic acid becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

3. Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) J. Virol. 63:3822-3828; and McLaughlin et al. (1989) J. Virol 62:1963-1973). Vectors containing as little as 300 base pairs of AAV can be packaged and can integrate. Space for exogenous nucleic acid is limited to about 4.5 kb. An AAV vector such as that described in Tratschin et al. (1985) *Mol. Cell. Biol.* 5:3251-3260 can be used to introduce nucleic acid into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) J. Virol. 51:611-619; and Flotte et al. (1993) J. Biol. Chem. 268:3781-3790).

The efficacy of a particular expression vector system and method of introducing nucleic acid into a cell can be assessed by standard approaches routinely used in the art. For example, nucleic acid introduced into a cell can be detected by a filter hybridization technique (e.g., Southern blotting) and RNA produced by transcription of introduced nucleic acid can be detected, for example, by Northern blotting, RNase protection or reverse transcriptase-polymerase chain reaction (RI-PCR). The gene product can be detected by an appropriate assay, for example by immunological detection of a produced protein, such as with a specific antibody, or by a functional assay to detect a functional activity of the gene product, such as an enzymatic assay. If the gene product of interest to be expressed by a cell is not readily assayable, an expression system can first be optimized using a reporter gene linked to the regulatory elements and vector to be used. The reporter gene encodes a gene product which is easily detectable and, thus, can be used to evaluate the efficacy of the system. Standard reporter genes used in the art include genes encoding beta-galactosidase, chloramphenicol acetyl transferase, luciferase and human growth hormone.

Cells Useful According to the Invention

The invention provides for host cells transfected with nucleic acid constructs encoding a multifunctional molecule of the invention. Host cells useful in the invention include but are not limited to the following.

A host cell can be any cell which is able to act as a carrier for an antigen according to the invention and thus may be a nucleated cell or a procaryotic cell into which nucleic acid can be artificially introduced. Procaryotic cells useful according to the invention include bacterial cells. Eucaryotic (nucleated) cells useful according to the invention include cells of a yeast, fungus, cells of a parasite and mammalian cells. Mammalian cells useful according to the invention include but are not limited to fibroblasts, including specialized mesenchymal cells such as a synoviocytes; keratinocytes, epithelial cells, endothelial cells, leukocytes and tumor cells.

Cell lines useful according to the invention include but are not limited to B16, CMS-5 fibrosarcoma cells, Cos1 cells and CHO cells, TS/A, Lewis lung carcinoma, RENCA, Dunning rat prostate carcinoma, and cell lines included in the catalogue of the American Type Culture Collection (Manassas, Va.).

Host cells comprising a nucleic acid molecule encoding a multifunctional molecule of the invention can be prepared from pathogenic cells according to the invention. Pathogenic cells include tumor cells (e.g. B16 cells, CMS-5 fibrosarcoma cells, and cells derived from the tumors included in the section entitled "Tumors for which the Invention is Useful"), and cells derived from pathogenic bacterium, pathogenic fungus, pathogenic virus, pathogenic parasite, or a pathogenic arthropod.

Methods of Detecting Expression From an Artificially Introduced Recombinant Nucleic Acid Sequence The invention provides for methods of detecting a protein (e.g., a multifunctional molecule) that is expressed from a recombinant nucleic acid molecule that has been artificially introduced into a cell.

Preparation of Antibodies

Antibodies specific for a protein useful according to the invention (e.g., a multifunctional molecule) are useful for protein purification, and for the detection of expression of these proteins from cells into which a recombinant nucleic acid molecule expressing these proteins has been artificially introduced. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Although a protein product (or fragment or oligopeptide thereof) of a protein according to the invention (e.g., a multifunctional molecule according to the invention) that is useful for the production of antibodies does not require biological activity, it must be antigenic. Antibodies may be directed to any portion of the multifunctional molecule of the invention. For example, an antibody may be directed to the lecting portion of the multifunctional molecule or to the ligand portion of the multifunctional molecule. Peptides used to induce specific antibodies may have an amino acid sequence consisting of at least five amino acids and preferably at least 10 amino acids. Preferably, they should be identical to a region of the natural protein and may contain the entire amino acid sequence of a small, naturally occurring molecule. Short stretches of amino acids corresponding to the protein product of a recombinant nucleic acid encoding a protein useful according to the invention (e.g., a multifunctional molecule according to the invention) may be fused with amino acids from another protein such as keyhole limpet hemocyanin or GST, and antibody will be produced against the chimeric molecule. Procedures well known in the art can be used for the production of antibodies to the protein products of recombinant nucleic acids of the invention.

For the production of antibodies, various hosts including goats, rabbits, rats, mice etc. . . . may be immunized by injection with the protein products (or any portion, fragment, or oligonucleotide thereof which retains immunogenic properties) of the recombinant nucleic acid molecules encoding proteins useful according to the invention. Depending on the host species, various adjuvants may be used to increase the immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

I. Polyclonal Antibodies.

The antigen protein may be conjugated to a conventional carrier in order to increase its immunogenicity, and an antiserum to the peptide-carrier conjugate will be raised. Coupling of a peptide to a carrier protein and immunizations may be performed as described (Dymecki et al., 1992, *J. Biol. Chem.*, 267: 4815). The serum can be titered against protein antigen by ELISA (below) or alternatively by dot or spot blotting (Boersma and Van Leeuwen, 1994, *J. Neurosci. Methods*, 51: 317). At the same time, the antiserum may be used in tissue sections prepared as described. A useful serum will react strongly with the appropriate peptides by ELISA, for example, following the procedures of Green et al., 1982, *Cell*, 28: 477.

2. Monoclonal Antibodies.

Techniques for preparing monoclonal antibodies are well known, and monoclonal antibodies may be prepared using a candidate antigen (e.g., a mulispecific molecule or a lectin whose level is to be measured or which is to be either inactivated or affinity-purified, preferably bound to a carrier, as described by Arnheiter et al., 1981, *Nature*, 294; 278.

Monoclonal antibodies are typically obtained from hybridoma tissue cultures or from ascites fluid obtained from animals into which the hybridoma tissue was introduced.

Monoclonal antibody-producing hybridomas (or polyclonal sera) can be screened for antibody binding to the target protein.

3. Antibody Detection Methods

Particularly preferred immunological tests rely on the use of either monoclonal or polyclonal antibodies and include enzyme-linked immunoassays (ELISA), immunoblotting and immunoprecipitation (see Voller, 1978, *Diagnostic Horizons*, 2:1, Microbiological Associates Quarterly Publication, Walkersville, Md.; Voller et al., 1978, *J. Clin. Pathol.*, 31: 507; U.S. Reissue Pat. No. 31,006; UK Patent 2,019,408; Butler, 1981, *Methods Enzymol.*, 73: 482; Maggio, E. (ed.), 1980, *Enzyme Immunoassay*, CRC Press, Boca Raton, Fla.) or radioimmunoassays (RIA) (Weintraub, B., *Principles of radioimmunoassays*, Seventh Training Course on Radioligand Assay Techniques, The Endocrine Society, March 1986, pp. 1-5, 46-49 and 68-78). For analysing tissues for the presence or absence of a protein produced by a recombinant nucleic acid encoding a protein useful according to the invention (e.g., multifunctional molecule or portion thereof), immunohistochemistry techniques may be used. It will be apparent to one skilled in the art that the antibody molecule may have to be labelled to facilitate easy detection of a target protein. Techniques for labelling antibody molecules are well known to those skilled in the art (see Harlow and Lane, 1989, *Antibodies*, Cold Spring Harbor Laboratory).

Determining Whether an Immune Response is Modulated According to the Invention

The multifunctional molecules described herein are useful according to the invention to modulate an immune response in a mammalian, preferably a human, to an antigen or antigens contained in the antigen bearing target which is bound to the lectin portion of the multifunctional molecule. In one embodiment, a composition comprising a multifunctional molecule bound to an antigen bearing target is administered to an animal, preferably a human. The second portion of the multifunctional molecule comprising a ligand for a cell-surface molecule of an APC targets the composition to antigen presenting cells in the animal to which the composition has been administered. The antigen bearing target is taken up (i.e., ingested or phagocytosed) by antigen presenting cells. Alternatively, the multifunctional molecule/antigen bearing target complex is contacted with antigen presenting cells in vitro under conditions which allow phagocytosis, wherein the APCs are subsequently returned to the host organism from which they were derived.

The present invention thus provides a method for modulating an immune response in an mammal comprising administering to the mammal a composition comprising at least a multifunctional molecule as described herein. In one embodiment, the composition further comprises an antigen bearing target. In a further embodiment, the composition still further comprises an APC.

An "immune response" refers to stimulation/activation of a selected response involving the immune system, or suppression, elimination, or attenuation of a selected response. In a preferred embodiment, an immune response refers to stimulation/activation of a selected response involving the immune system by about at least 5%, or preferably between 5 and 50% or more preferably between 50 and 100% or at least 100% or greater, or suppression, elimination, or attenuation of a selected response by about at least 5%, or preferably between 5 and 50% or more preferably between 50 and 100% or at least 100% or greater, as compared to control cells that are not CD 40-ligand enhanced cells. Thus, to modulate an immune response means that the desired response is more efficient, more rapid, greater in magnitude, and/or more easily induced than when an antigen bearing target is contacted with an APC in the absence of a multifunctional molecule. Different immune responses in the subject may be modulated differentially, e.g., the cellular immune response may be selectively enhanced while the humoral response may be selectively attenuated, and vice versa.

The following in vitro and in vivo assays are useful for determining whether an immune response is modulated according to the invention. The assays described in detail below measure stimulation or suppression of cellular or humoral immune responses to an antigen. The antigens referred to in the following assays are representative. It will be apparent to one of skill in the art that an immune response to a selected antigen useful according to the invention may be measured using one or more of the following assays by adapting the assay to that antigen.

I. Detection of Increased Phagocytosis

The following assay may be used in order to determine whether opsonin-enhanced cells stimulate phagocytosis by antigen presenting cells.

Phagocytosis is examined using monocytes that have been adhered at 37° for 30 min in RPMI without added FCS. Sheep erythrocytes are incubated with an opsonin, or its precursor, under conditions such that there are no more than 300 of such molecules, on average, are deposited on each erythrocyte. If a precursor is used, coated erythrocytes are then processed to convert all precursors to the actual candidate molecule (e.g., See Carlo et al., J. Immunol. 123:523-8(1979)). Fresh monocytes are isolated from the subject, and $5\times10^4$-$1\times10^5$ of these cells suspended in 0.25-0.5 ml of RPMI medium with 1% BSA. This aliquot is placed in a tissue culture well and incubated for 30 min at 37° C. An excess of coated erythrocytes, suspended at $1.2\times10^8$ cells/ml, is overlain on the monocytes, the plate is centrifuged for 5 min at 50 g, and incubated for 30 min at 37° C. Non-ingested material is removed in two hypotonic lysis steps using ice-cold lysing buffer before fixing and staining the adherent cells, and examining the cells under light microscopy. Phagocytosis is quantified by determining the percentage of 100 monocytes ingesting one or more target cells, and the total number of ingested E/100 monocyptes (PI) is recorded. Stimulation of phagocytosis according to the invention is indicated by a phagocytic index of equal to or greater than 40.

Another assay for phagocytosis is as follows: Cells of the murine macrophage line are harvested and suspended in DMEM-10 at $4\times10^5$/ml. 2.0 ml of this suspension is aliquoted into individual 3.5 cm cell culture plates, and the dishes incubated at 37° C. in 5% $CO_2$ overnight. Target cells, as well as control cells, are harvested on the same day as the macrophages, washed in PBS, and resuspended 2 min in PKH26 dye (a 2 µM solution in 1 ml of the supplied diluent) at $5\times10^6$ cells/ml. The fluorescent PKH26 dye emits in the red spectrum when excited, whereas the FITC label that is used for the phagocytes emits in the green spectrum. PKH26 is stable in the endosomal/lysosomal compartment of phagocytes. The dyed target cells are washed 3 times with PBS and cultured overnight to allow leaching of PKH26 out into the medium. This minimizes leakage of dye during the assay. The following day the target cells are harvested, washed 3 times with PBS, and resuspended in serum-free DMEM at $5\times10^5$/ml. The phagocytic cells are rinsed vigorously with PBS on the culture plates in order to remove serum, and 2 ml of target cells is added to each plate After 0, 2, 4, or 8 h, the plates are rinsed 3 times with PBS to remove all non-adhered cells and the remaining cells are incubated with 2 mM EDTA to release them from the plate. The released cells are washed with 1% FBS/PBS, and suspending in 100 µl of the same buffer. 2 µg anti-phagocyte (e.g. anti-CR3) antibody is added and the cells placed on ice for 25 min. The cells are washed 3 times with 1% FBS/PBS, resuspended in 100 µl of this solution, and stained with a 1:25 dilution of FITC-conjugated secondary IgG for 25 min on ice. Cells are washed 3 times and resuspended in 500 µl 1% FBS/PBS, then analyzed on a Becton Dickinson FACScan with CellQuest software.

FL-1 (green) fluorescence is used to gate phagocytes. The FL-2 (red) fluorescence of these cells, which reflects internalization of PKH26-labeled target cells, is then measured. Phagocytosis induced by, e.g., an opsonin is indicated by the difference between mean FL-2 fluorescence of macrophages incubated with opsonin-coated versus non-opsonin-coated target cells. Use of an opsonin will increase mean FL-2 fluorescence by, e.g. at least 10%., or enough to obtain a p value less than or equal to 0.05 by student t-test.

II. Amplification of the Immune Response Usually Involves Proliferation of Particular Subpopulations of Lymphoid Cells that are Normally in the Resting State.

Proliferative assays have the following applications in clinical studies: (1) Assessment of overall immunologic competence of T cells or B cells as manifested in their ability to respond to polyclonal proliferation signals such as mitogens or anti-CD3 antibodies. Defects in the proliferation may be indicative of fundamental cellular immunologic defect. Low proliferation is often found as a nonspecific secondary effect of chronic disease. (2) Assessment of an individual's response to specific antigens, where low responses are indicative of general or specific immunologic defect. (3) Determination of MHC compatibility by the mixed lymphocyte reaction (MLR).

In addition, proliferative assays are useful for estimating lymphokine production, investigating signal transduction, and assessing growth factor requirements (e.g., lymphokines) for T or B cells. The procedure outlined here measures incorporation of [$^3$H]thymidine into DNA, which usually correlates well with cell growth as measured by changes in cell number. However, when the activation stimulus is toxic, as with chemical activators such as ionomycin plus phorbol myristate acetate (PMA), the burst of new DNA synthesis following activation may not be accompanied with a net increase in viable cells, and, in fact, a decline in cell number may be observed. In this instance, [$^3$H]thymidine incorporation in DNA is more indicative of initial cell stimulation than estimation of cell number. In addition, [$^3$H]thymidine incorporation provides information on cell populations, not on individual cells. Alternate methods, such as flow cytometry may be used for studies requiring that type of information.

Assay for Antigen-Induced T Cell Proliferation

This protocol is designed to test the proliferation of T cells in response to a specific antigen—tetanus toxoid. It can be modified to test T cell proliferation in response to any protein or polysaccharide antigen. Materials: (T cell suspension, autologous antigen-presenting cell suspension (non-T cells), Tetanus toxoid solution (Connaught or State Laboratory Institute of Massachusetts)). (1) Count T cells and adjust to $1 \times 10^6$ cells/ml with complete RPMI-10 AB. (2) Treat antigen-presenting cells with mitomycin C (or irradiate with 2500 rad) as in step 2 of one-way MLR protocol. Adjust concentration of antigen-presenting cells to $2 \times 10^5$ cells/ml. Antigen-presenting cells can consist of autologous non-T cells or autologous monocytes/macrophages. (3) Add 100 ul T cell suspension and 50 ul antigen-presenting cell population to wells; mix just before dispensing. (4) Add 50 ul tetanus toxoid solution to give final concentrations of 0, 1, 5, 10, and 20 ug/ml. Prepare three wells for each dilution. (5) Incubate 6 days in a humidified 37° C., 5% $CO_2$ incubator. (6) Pulse with [$^3$H]thymidine and harvest as described in support protocol.

Assay for Lymphokine-Dependent Cell Proliferation

This protocol assays the lymphokine-dependent proliferation of a lymphocyte population, in this case, the IL-4 dependent proliferation of B cells. Materials: (Tonsil B cell suspension, Anti-IgM cross-linked to Sepharose beads (Bio-Rad), 10,000 U/ml human rIL-4 (Genzyme) in complete RPMI-10). (1) Count tonsil B cells and adjust concentration to $1 \times 10^6$ cells/ml with complete RPMI-10. (2) Dispense 100 ul of tonsil B cells into each well. Prepare three wells for each experimental condition. (3) Dilute 10,000 U/ml rIL-4 solution 1:10, 1:100, and 1:1000. Add 20 ul of the stock or dilution to appropriate wells to yield 1000 U/ml, 100 U/ml, 10 U/ml, and 1 U/ml. Include a control well with no rIL-4. (4) Pipet anti-IgM beads into appropriate wells.

Determine the optimal concentration of beads with pilot experiments. It is best to include several concentrations of beads in each experiment to "bracket" the optimal dose. Prepare wells with tonsil B cells and IL-4 dilutions alone, anti-IgM beads alone, culture medium alone, and all the combinations of IL-4 and anti-IgM bead dilutions. (5) Increase the volume of each well to 200 ul with complete RPMI-10 as necessary. (6) Culture 5 days in a humidified 37° C., 5% $CO_2$ incubator. (7) Pulse with [$^3$H]thymidine and harvest as described in support protocol.

[$^3$H]Thymidine Pulse and Harvest of Cell Cultures

This protocol is used in conjunction with the preceding protocols to complete the [$^3$H]thymidine incorporation assay. (1) Add 20 ul of 50 uCi/ml [$^3$H]thymidine to each culture (1.0 uCi) at a fixed time before terminating the culture (usually 6 or 18 hr). (2) Harvest cell cultures using an automated multiwell harvester that aspirates cells, lyses cells, and transfers DNA onto filter paper, while allowing unincorporated [$^3$H]thymidine to wash out. Fill and aspirate each row of the microtiter plate ten times to ensure complete cell transfer and complete removal of unincorporated thymidine. Wash each filter strip with 100% ethanol to facilitate drying. Transfer to scintillation vials. For semiautomated harvester, transfer filter dots for each well into scintillation counting vials. For manual transfer, dry filters under lamp and transfer to scintillation vial with forceps. Add scintillation fluid to each vial. (3) Count samples in scintillation counter until standard deviation is less than 2%. Calculate mean cpm for background cultures and for each experimental condition. There should be less than 20% variation in replicate cultures.

III. Induction and Measurement of In Vitro Antibody Responses

The capacity of the human immune system to mount an antibody response following in vivo immunization with a protein or polysaccharide antigen is a revealing indication of the overall integrity of both the B and T cell arms of the immune system. As such, in vivo immunization followed by measurement of the antibody response is an appropriate test of immune function in the various acquired and congenital immunodeficiencies and in a host of other conditions affecting the immune system. The following procedures are for in vivo immunization and for the measurement of the subsequent immune response using an ELISA technique.

Immuno-Enzymetric Assay for Cytokines Using NIP- and HRPO-Labeled Antibodies

This protocol describes an immunonoenzymetric assay for cytokines using a heterogeneous, noncompetitive immunoassay reaction in which the cytokine is immobilized by a coating antibody bound to a microtiter plate. Unbound material is washed free, and detection is carried out using a different anti-cytokine antibody labeled with the hapten nitroiodophenyl (NIP). This is in turn detected by a horseradish peroxidase (HRPO) conjugate of an anti-NIP antibody, which is revealed with the chromogenic substrate ABTS. In this noncompetitive immunoassay, the immunoassay signal ($A_{405}$) increases as a direct function of the amount of cytokine present in the sample. Antibodies are prepared as described in Current Protocols in Immunology, 1995, 6.20.2-6.20.10.

Coat assay plate. (1) Using a multichannel pipettor, transfer 100 ul of an appropriate dilution of coating antibody into all wells of the assay plate that are to be used. (2) Seal plates with microtiter plate sealer or Parafilm and incubate 2 hr. At 37° C. Prepare samples and standards in preparation plate. (3) Dilute each sample (or aliquot of conditioned medium) to be assayed with an equal volume of immunoassay diluent. (4) Pipet less than or equal to 1 ml of each diluted sample to be assayed into the upper chamber of a separate Spin-X microfiltration device. Microcentifuge 5 min. At 10,000 rpm and save the filtrates that collect in the lower chambers. (5) Add 65 ul of each diluted sample to the appropriate well of a preparation plate (i.e., a separate 96-well microtiter plate). (6) Thaw an aliquot of cytokine standard at room temperature and make sure that it is well mixed. Pipet 130 ul into the well of the preparation plate representing the highest concentration on the standard curve. Transfer 65 ul from this well into the next, then continue performing serial 1:1 dilutions in immunoassay diluent so that 65 ul of each concentration represented on the standard curve is placed in appropriate well of the preparation plate. (7) Thaw an aliquot of calibrator at room temperature (if used). Dilute with an equal volume of immunoassay diluent, then pipet 65 ul of diluted calibrator into appropriate well or wells of preparation plate.

Incubate with coating antibody. (8) Remove coated assay plate from incubator. Dip in 2-liter beaker filled with 1× wash buffer, then invert over sink and flick to remove liquid. Repeat two more times, then bang dry on paper towel. (9) Transfer 50 ul of solution from each well of preparation plate to corresponding well of the assay plate using multichannel pipettor. (10) Seal plate with microtiter plate sealer or Parafilm and incubate 2 hr. at room temperature.

Incubate with detecting antibody. (11) Dilute NIP-labeled detecting antibody specific to cytokine of interest to 1 ug/ml in detecting buffer. (12) Wash assay plate as in step 8. (13) Add 75 ul diluted detecting antibody from step 11 to all wells of assay plate, including unused outer walls. (14) Reseal plate with microtiter plate sealer or Parafilm and incubate 1 hr. at room temperature.

Incubate with HRPO-conjugated anti-NIP antibody. (15) Dilute HRPO-conjugated anti-NIP Mab 1:3000 in detecting buffer. (16) Wash assay plate as in step 8. (17) Add 75 ul of diluted HRPO-labeled anti-NIP antibody from step 15 to all wells of assay plate. (18) Reseal plate with microtiter plate sealer or Parafilm and incubate 1 hr. at room temperature.

Incubate with chromogenic substrate. (19) Wash assay plate as in step 8. (20) Add 100 ul ABTS substrate working solutions to all wells of assay plate. Cover plate and incubate at room temperature until color development reaches desired level (generally until $A_{405}$ for wells containing the highest concentration of standard is between 1.5 and 2). This protocol usually produces an assay that can be read after 30 to 60 min.

Read plate and analyze data. (21) Using microtiter plate reader with computer interface, measure absorbance in all wells at 405 nm in single-wavelength mode or at 405 and 650 nm in dual-wavelength mode. (22) Fit standard data to a curve described by a first-degree (linear), second degree (quadratic), or four-parameter (nonlinear) mathematical function using curve-fitting software. (23) Interpolate absorbance data from unknown cytokine samples to fitted standard curve, and calculate cytokine concentrations.

IV. Induction of an in vivo Antibody Response Provides an Approach to the Evaluation of the Overall Integrity of the Immune System.

In the protocols presented here, diptheria and tetanus toxoids are used as representative protein antigens and pneumococcal polysaccharides are used as representative polysaccharide antigens because of their safety and availability. It should be noted, however, that the responses elicited by these antigens are likely to be secondary responses because of past vaccination or natural exposure. To obtain a primary response, an unusual antigen such as keyhole limpet hemocyanin should be used.

When antigens are administered by the intramuscular or subcutaneous route, as they are here, a "systemic" immune response is induced and measurement of circulating antibody is most appropriate. It is, however, sometimes of interest to evaluate "local" or mucosal immune responses. In this case, the antigen is given either intranasally to stimulate respiratory lymphoid tissue or orally to stimulate gastrointestinal lymphoid tissue and bronchial washings or intestinal fluids, rather than blood, is assayed for antibody content; in addition, antigens are used that are more appropriate for stimulation of the local/mucosal response (i.e., influenza virus antigen for respiratory responses and cholera toxin for gastrointestinal responses).

In assaying the in vivo antibody response, it is important to determine responses to both protein and polysaccharide antigens because these antigens stimulate different components of the immune system. In this regard, the major antibody response to protein antigen is composed of IgG1 and IgG3 subclass antibodies, whereas the major antibody response to polysaccharide antigen is composed of IgG2 subclass antibody.

A variety of immunoassay techniques have been used to measure antibody responses in materials obtained after in vivo immunization. Of these, the ELISA assay is perhaps the most useful because it yields a stable, easily measurable, reproducible, and safe readout.

Induction of In Vivo Antibody Responses to Protein/Polysaccharide Antigens

In this protocol antigens are administered by the intramuscular or subcutaneous route and serum is collected for measurement of responses. (1) Draw preimmunized blood sample, allow blood to clot, and separate serum from clot by centrifugation. Store serum at $-20°$ C. to $-70°$ C. in appropriately labeled plastic tubes. (2) Inject 0.5 ml of toxoid mixture into an appropriately prepared intramuscular site (deltoid or thigh), taking care not to inject material intravenously. (3) Inject 0.5 ml polyvalent pneumococcal vaccine into an appropriately prepared subcutaneous site, taking care not to inject material intravenously. (4) Draw post-immunization blood samples at desired intervals, usually at 1, 2, and 3 weeks. Separate serum and store at $-20°$ C. to $-70°$ C. (5) After all serum samples are collected, assay samples for presence of antibodies using ELISA.

The ELISA offers a rapid, sensitive, reproducible, nonradioactive method for measuring in vivo antibody responses to a variety of antigens, including protein and polysaccharide antigens in sera obtained from individuals vaccinated with tetanus and diphtheria boosters and the polyvalent pneumococcal polysaccharide vaccine. Assays specific for tetanus, diphtheria and the pneumococcal polysaccharide types I, II, and III are detailed in Current Protocols in Immunology, 1995, Vols. 6 and 7.

Assay Using Tumor Rejection

In another assay for immunomodulation, an immunocompent animal is vaccinated with on the order of $10^4$-$10^8$ irradiated cytokine-coated tumor cells, and challenged with on the order of $10^4$-$10^8$ live wild-type tumor cells (in any temporal sequence). If survival or tumor onset in these animals differs from that of animal vaccinated, using identical parameters, with irradiated non-cytokine coated cells instead of opsonin-enhanced cells, immunomodulation has occurred. For example, if at least 10% of the animals in the test group survive 100% longer than mean survival in the control group, the test is positive. As another example, onset of tumors in 20% of the test animals might be 50% later than mean onset in the control animals.

Dosage and Administration

The invention encompasses methods of modulating an immune response in a mammal to a selected antigen, the method comprising administering to a mammal a therapeutic amount of a composition comprising a multifunctional molecule as described herein, or a composition comprising a multifunctional molecule of the invention and an antigen bearing target, or administering a composition comprising a therapeutic amount of APCs which have been contacted with a multifunctional molecule and antigen bearing target in vitro.

Compositions described herein may be prepared as injectables, either as liquid solutions or suspensions; solid forms suitable for solution in or suspension in, liquid prior to infection can also be prepared. The preparation can also be emulsified, or encapsulated in liposomes. The active immunogenic ingredients are often mixed with carriers which are pharmaceutically acceptable and compatible with the active ingredient. The term "pharmaceutically acceptable carrier" refers to a carrier that does not cause an allergic reaction or other untoward effect in subjects to whom it is administered. As used herein, a "pharmaceutically acceptable carrier" does not include culture medium, or any solution containing about 0.2-2% serum or greater. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl- D-isoglutaminyl-alanine-2-1'-2'-dipalmitoyl-sn-glycero-3-hydroxyphosphoryloxy)-ethylamine (COP) 19835A, referred to as MTP-PE), and RIBI, which contains three components extracted from bacteria, monophosporyl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-, IL-2 and IL-12) or synthetic IFN-inducers such as poly I:C can be used in combination with adjuvants described herein.

Compositions of the invention can be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulations can result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

The compositions of the invention can be formulated into the vaccine compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Any cellular component of such vaccine compositions can, in preparation for inclusion in such compositions, be subjected to treatments which involve attenuation or inactivation of the cells of the vaccine, including, for example, exposure to ionizing radiation, which can inhibit cell division, antiproliferative agents such as cyclophosphamide, cytochalasin D, or colchicine, or killing with or without fixation.

The compositions, including antigen bearing targets and APCs are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection desired. Suitable dose ranges are on the order of several hundred micrograms active ingredient per vaccination with a preferred range from about 0.1 µg to 1000 µg, such as in the range from about 1 µg to 300 µg, and preferably in the range from about 10 µg to 50 µg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of cells of this invention will depend, inter alia, upon the administration schedule, the unit dose of antigen administered, whether the cells are administered in combination with other therapeutic agents, the immune status and health of the recipient, and the therapeutic activity of the particular composition.

The compositions can be given in a single dose schedule, or preferably in a multiple dose schedule. A multiple dose schedule is one in which a primary course of vaccination can include 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are preferable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-released from the primed lymphocytes. The assays can be performed using conventional labels, such as radionucleotides, enzymes, fluorescent labels and the like. These techniques are known to one skilled in the art and can be found in U.S. Pat. Nos. 3,791,932, 4,174,384 and 3,949,064, which are hereby incorporated by reference.

Tumors for which the Invention is Applicable

The invention contemplates treatment of tumors including but not limited to the following:

Melanomas, squamous cell tumors, basal cell carcinomas, astrocytomas, gliomas, glioblastoma multiforme, meningiomas, ependymomas, schwannomas, neuroblastomas, retinoblastomas, meningiomas, glomus tumors, sarcomas, including, e.g., osteosarcomas, Ewing's sarcomas, chondrosarcomas, myosarcomas, synovial cell sarcomas, fibrosarcomas, spindle cell tumors, angiosarcomas, primitive neuroectodermal cell tumors, and Kaposi's sarcomas, lymphomas, acute and chronic leukemias, tumors of the head and neck, nasopharyngeal carcinomas, carcinomas of the pharynx, laryngeal carcinomas, carcinomas of the thyroid, carcinomas of the parathyroids, thymomas, esophageal carcinomas, gastric carcinomas, tumors of the small bowel, carcinomas of the colon and rectum, mesotheliomas, lung carcinomas, including adenocarcinomas, squamous cell carcinomas, bronchoalveolar carcinomas, and small cell tumors, pancreatic carcinomas, islet cell and non-islet cell tumors, carcinomas of the breast, cardiac myxomas, pituitary tumors, carcinoid tumors, hepatomas, cholangiocarcinomas, hepatoblastomas, renal cell carcinomas, nephroblastomas, Wilms' tumors, adrenal carcinomas, pheochromocytomas, germ cell tumors, choriocarcinomas, ovarian carcinomas, testicular tumors, seminomas, endometrial tumors, carcinomas of the prostate, carcinomas of the seminal vesicles, vaginal tumors, carcinomas of the penis, hydatiform moles, carcinomas of the gall bladder, and carcinomas of the urinary bladder.

Subjects for Treatment According to the Invention

The present invention provides a method for reducing the size and/or number of metastases in a subject. The method comprises administering to the subject a vaccine composition comprising a multifunctional molecule of the invention. A "subject" as used herein, may refer to an organism of the Kingdom animalia, preferably a mammal, and still more preferably a human. A "subject", according to the invention may also be an animal in need of anti-metastases therapy, e.g., a patient with malignant metastases to one or more organs or tissues, e.g., a human patient with lung or lymph node metastases. A "subject", according to the invention may also be an animal model of metastases, in which the animal is manipulated, either genetically, or by injection of malignant cells, or by other methods known to those of skill in the art, to simulate the appearance of foci of malignant cells or infected cells which are observed in a similar animal with naturally occurring metastases. The generation of animal models of metastasis is well known in the art, and examples of such models may be found in, for example, Ryan M H et al., *J Immunol.* 2001; 167:4286-92; Specht J M et al., *J Exp Med.* 1997; 186:1213-21; Nakanishi et al., *Tumour Biol.* 2003 24:70-6; Wang et al., *Int J Gastrointest Cancer,* 2001; 29(1):37-46; Muralidharan et al., *J Clin Laser Med Surg.* 2003 21(2):75-83; Tanaka et al., *Chest* 2003, 123(4):1248-53; Huang et al., *Clin Exp Metastasis* 2002; 19(4):359; and Irvine K R et al., *J Immunol.* 1996; 156:238-45. One of skill in the art would be able to readily adapt the animal models of metastasis known in the art to generate a metastasis model of interest for any given application.

Detection of Metastases

The present invention provides a method of reducing the number and/or size of metastases in a subject comprising administering to a subject, a multifunctional molecule as described herein. One of skill in the art will recognize that the detection and measurement of metastases is routine in the art and may be accomplished using well established methods. For example, metastases may be detected using gross examination of a subject, such as exploratory surgery (e.g., laparotomy). Alternatively, metastases may be detected, measure, and/or observed using less invasive techniques and methods such as thorascopy, mediastinoscopy, and laparoscopy. One of skill in the art may also detect the presence of metastases using imaging techniques known to those of skill in the art. Such techniques include, but are not limited to radiographic imaging, computerized tomography (CT scan), magnetic resonance imaging (MRI), positron emission tomography (PET scan), single photon excitation (SPECT), and radionuclide scintigraphy (e.g., bone scan). The sensitivity of many of the above imaging methods may be enhanced, as known by those of skill in the art by injection or IV administration of contrast agents (e.g., iodine or barium) to a subject to be imaged. Additional methods for assessing the presence of, or detecting, or measuring metastasis is through the use of gross or histological pathologic examination (i.e., in which a tissue sample is removed from a subject an examined at either or both of the gross anatomical level, or at the histological or ultrastructural level according to methods which are well known in the art). The above methods for the detection, measurement, and imaging of metastases are known to those of skill in the art and may be adapted according to the knowledge in the art to particular tissues, organs, or cells which one of skill in the art wishes to asses according to the methods of the invention. More detailed descriptions of such methods may be found in the art, for example, the *Oxford Textbook of Oncology, $2^{nd}$* Ed., New York, Oxford University Press, 2002.

According to the invention, metastasis is detected if any amount of metastasis is detected in a subject. That is, upon the detection of even a single foci in a subject, metastasis may be said to have been detected. Preferably, metastasis is detected as plural metastatic foci, in one or preferably one or more organs in a subject.

Transgenic Animals According to the Invention

A nucleic acid molecule encoding a multifunctional molecule as described herein can be used to produce nonhuman transgenic animals, and cells of such transgenic animals can be isolated and used in a vaccine formulation in animal or human vaccination.

For example, in one embodiment, a nucleic acid molecule is introduced into a fertilized oocyte or an embryonic stem cell. Such cells can then be used to create non-human transgenic animals in which exogenous nucleic acid molecules encoding the polypeptides of the invention have been introduced into their genome or homologous recombinant animals in which endogenous nucleic acid molecules have been altered. Such animals are useful for studying the function and/or activity of the molecules of the invention and for identifying and/or evaluating modulators of the activity of the molecules of the invention. As used herein, a "transgenic animal" is a non-human animal, prefers mammal, more preferably a mouse, in which one or more of the cells of the animal includes a transgene. A transgene is exogenous nucleic acid which is integrated into the genome of a cell from which a transgenic animal develops and which remains in the genome of the mature animal, thereby directing the expression of an encoded gene product in one or more cell types or tissues of the transgenic animal.

A transgenic animal of the invention can be created by introducing nucleic acid molecules encoding the polypeptides described herein (i.e., a multifunctional molecule) into the male pronuclei of a fertilized oocyte, e.g., by microinjection, and allowing the oocyte to develop in a pseudo-pregnant female foster animal. Intronic sequences and polyadenylation signals can also be included in the transgene to increase the efficiency of expression of the transgene. A tissue-specific regulatory sequence(s) can be operably linked to the transgene to direct expression of a polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the nucleic acid molecule of the invention, e.g., the transgene in its genome and/or expression of the transgene mRNA in tissues or cells of the animals. A transgenic founder animal can then be used to breed additional animals carrying the transgene. Moreover, transgenic animals carrying a transgene encoding polypeptides of the invention can further be bred to other transgenic animals carrying other transgenes.

The invention is further illustrated by the following exemplifications which should not be construed as being further limiting.

EXAMPLES

Example 1

Cloning of a Murine GM-CSF Fused to the *S. Cerevesiae* Gas1 GPI Modification Signal Sequence The starting point for producing a yeast expression vector was the pUC19-GM-CSF-mammalian GPI signal sequence plasmid (pUC19-GM-CSF-GPI). This plasmid encodes murine GM-CSF (upstream) fused in-frame to the human Thy-1 GPI modification signal sequence (downstream). The following two oligonucleotides were purchased from Midland Certified Reagent Company (Midland, Tex.):

```
GTX-5
5'pAATTCCGCGCCGGCACAGTGCTCAGAGACAAACTGGTCAAGT

GTGAGGGCATCAGCCTGCTGGCTCAGAACACCTCGTGGCTGCTGC

TGCTCCTGCTGTCCCTCTCCCTCCTCCAGGCCACGGATTTCATGT

CCCTGTGACTGGGTAC3'
```

GTX-5 comprises:
a. Sequences at the 5' end suitable for ligating to an EcoRI site (bases 1-5)
b. An NgoM1 site for creating an in-frame chimeric coding sequence (bases 9-14)
c. The coding sequence for the GPI modification sequence of human Thy-1 (Genbank Accession No. M11749) (bases 15-137)
d. A termination codon (bases 138-140)
e. Sequences at the 3' end for ligating to a KpnI site (bases 144-148)

```
GTX-6
5'pCCAGTCACAGGGACATGAAATCCGTGGCCTGGAGGAGGGAGA

GGGACAGCAGGAGCAGCAGCAGCCACGAGGTGTTCTGAGCCAGCA

GGCTGATGCCCTCACACTTGACCAGTTTGTCTCTGAGCACTGTGC

CGGCGCGG3'
```

This oligonucleotide is complementary to GTX-5, except for staggered ends.

GTX-5 and GTX-6 were dissolved in individual tubes in sterile water at a final concentration of 1 microgram/lambda. GTX-5 and GTX-6 were mixed at a final concentration of 100 ng/lambda and allowed to anneal for 60 minutes at room temperature.
The GTX-5:GTX-6 double stranded oligonucleotide was then cloned into the plasmid pUC19. Four micrograms of pUC19 DNA was digested with EcoRI and KpnI. After electrophoresis, the linear DNA was purified from a 0.7% agarose gel using a Qiagen (Santa Clarita, Calif.) gel purification kit according to instructions provided by the manufacturer. 100 ng of the GTX-5:GTX-6 oligonucleotide was ligated to 200 ng of the EcoRI-KpnI digested pUC19 in a final volume of 20 microliters at room temperature for 60 minutes.

The plasmid was transformed into competent AG-1 cells, which were purchased from Stratagene. Transformed E. coli were inoculated onto LB-amp plates. Bacterial colonies grown on LB plates containing ampicillin (100 micrograms/ml) were picked and inoculated into one ml of LB with amp and grown overnight at 370 with shaking.

Plasmid DNA was isolated using a standard alkaline lysis miniprep protocol and DNA was digested with EcoRI and KpnI. DNA was electrophoresed on 1.6% agarose gels stained with ethidium bromide, and colonies containing an EcoRI-KpnI fragment of approximately 148 bp were thus identified. Positive colonies were inoculated into 100 ml of LB with ampicillin and grown overnight. Plasmid DNA was again purified using kits purchased from Qiagen.

The nucleotide sequence of a Thy-GPI positive clone, designated pUC-GPI 21, was sequenced, confirming its identity.

The GM-CSF coding sequence was amplified by PCR from a mouse lung cDNA library purchased from Clontech. PCR was performed for 35 cycles using pfu polymerase and the following primers:

```
Upstream
5'CCGAATTCATGTGGCTGCAGAATTTACTTTTCCTGGGCATTGT
GGTCTAC3'

Downstream
5'CAGCCGGCTTTTTGGACTGGTTTTTTGCATTCAAAGGGGATAT
CAGTCAG3'
```

PCR parameters were denaturation at 90° for 1 minute, annealing at 60° for 1 minute, and extension at 720 for 1 minute.

The GM-CSF chain PCR product was purified after electrophoresis through a 1% agarose gel. The DNA band was excised and the DNA fragment purified using a kit purchased from Qiagen.

The purified GM-CSF DNA fragment was digested with EcoRI and NgoM1. After digestion, the reaction mix was extracted with phenol:chloroform (1:1) followed by chloroform. The aqueous phase was adjusted to 0.3M sodium acetate pH 5.2 and the DNA was precipitated with 2 volumes of ethanol at −800 for 2 hours. The DNA was pelleted by centrifugation, ethanol was removed, and the pellet was rinsed with 70% ethanol. The pellet was dried under vacuum.

The GM-CSF DNA was resuspended in sterile water and ligated to pUC19-GPI 21 that had been digested with EcoRI-NgoM1. Ligation was for one hour at room temperature. PUC19 GPI 21 ligated to GM-CSF DNA was used to transform competent AG-1 cells. Transformed AG-1 cells were selected on LB plates with ampicillin. Plasmid DNA was isolated and analyzed as above. Restriction digests were performed to confirm the pUC19 GPI-GM-CSF chimeric construct. The DNA from several positive clones was isolated and sequenced.

This plasmid was digested with NgoMIV and KpnI, and the larger resulting fragment isolated after electrophoresis through a 1% agarose gel.

The 280 bp GPI modification signal sequence from the yeast protein Gas1 was amplified by PCR from the yeast cosmid clone C9952 (ATCC). This PCR employed pfu polymerase and the primers:

```
Upstream Primer
5'GTAGCCGGCGCTAGCTCGGGGTCTTCTTCCAAGTCTA

Downstream Primer
5'TACGGTACCCCTAGGCCACAATGAAATAAGATACCATACC3'
```

These primers add a 5' NgoMIV site and a 3' KpnI site to the Gas1 fragment.
Conditions for PCR were:

| Denaturation | 90° one minute |
|---|---|
| Annealing | 60° one minute |
| Extension | 72° one minute |
| Cycles | 25 |

The PCR product was purified after electrophoresis through a 1% agarose gel and digested with NgoM IV and KpnI. The Gas1 GPI signal sequence was then ligated into the pUC19-GM-CSF-GPI plasmid prepared above so that the Gas1 signal sequence was fused in-frame downstream of the GM-CSF sequence, replacing the Thy-1 sequence. This vector is termed pUC19-GMCSF-Gas1.1. The resultant plasmid was then transformed into AG-1 competent *E. coli* (Stratagene) and plasmid clones were isolated by alkaline lysis mini-prep. Plasmids were then screened for inserts by restriction digest. DNA from a positive clone was sequenced to confirm the identity of the GAS1 coding region.

A yeast expression plasmid for GPI-GM-CSF was then generated utilizing the pITY-4 vector, which was kindly provided by Dr. K. Dane Wittrup (University of Illinois). This plasmid stably integrates into the yeast genome and allows high-level expression of heterologous genes. Features of pITY-4 include: a delta sequence (LTR of Ty element) that enables multiple integration events by homologous recombination; a neo/kanamycin resistance gene that provides for selection in *E. coli* and tunable selection in yeast; the Gall promoter for high-level inducible transcription; a unique EagI cloning site; a synthetic Pre-Pro sequence optimized for efficient secretion of expressed genes; the alpha factor termination sequence; and an origin of replication for propagation in *E. coli*. In this system, yeast are grown in dextrose-containing media for 3 days, then are switched to media containing galactose to induce transcription of genes inserted downstream of the Gall promoter.

The GMCSF-Gas1 insert described above was amplified by PCR from pUC19-GMCSF-Gas1.1 using pfu polymerase and the primers:

```
Upsteam
5'TACGGCCGGCACCCACCCGCTCACCC3'

Downstream
5'TACGGCCGCCACAATGAAAATAAGATACCAT3'
```

These primers add EagI sites at both ends for cloning into the pITY-4 plasmid.
Conditions for PCR were:

| Denaturation | 90° one minute |
| Annealing | 60° one minute |
| Extension | 72° one minute |
| Cycles | 25 |

The PCR product was purified after electrophoresis through a 1% agarose gel and digested with EagI. The EagI-flanked GMCSF-Gas1 fragment was ligated into EagI-digested pITY-4 and used to transform *E. coli* AG1 cells. *E. coli* were then grown on kanamycin-containing LB plates (100 ug/ml). Plasmids from kanamycin resistant colonies were purified by mini-prep and mapped by restriction digests for presence and correct orientation of inserts. The identity of a positive clone was confirmed by sequencing. This plasmid is termed pITY-GMCSF-Gas1.1.

Example 2

Expression of Murine GM-CSF Fused to the Gas1 GPI Modification Signal Sequence in Yeast A 50 ml culture of the *E. coli* clone containing pITY-GMCSF-Gas1.1 was grown in LB with 100 ug/ml kanamycin and the plasmid purified using a Midi-Prep Kit from Qiagen. The *S. cerevesiae* strain BJ5464 (ATCC) was then transformed with pITY-GMCSF-Gas1.1 using a lithium acetate (LiAc) protocol. A 10 ml overnight culture of BJ5464 in YPD (Per liter: 20 g Bactotryptone, 10 g yeast extract, 20 g dextrose) was used to inoculate a 100 ml flask. Yeast were grown for 3 hours at 30° and then harvested by centrifugation at 12,000×g for 2 minutes at room temperature. Cells were washed with sterile water and centrifuged again. The cells were resuspended in 1.0 ml of 100 mM LiAc, transferred to a 1.5 ml microfuge tube and centrifuged in an Eppendorf microfuge at top speed for 15 seconds. The cells were then resuspended in 0.5 ml of 100 mM LiAc and 50 uL samples were aliquoted to individual tubes. The cells were pelleted. 240 uL of PEG (50% w/v), 36 uL 1.0 M LiAc, 5 uL (10 mg/ml) boiled carrier DNA (salmon sperm DNA, Sigma), and 2 ug plasmid in 75 uL water, were then added in that order. After the addition of plasmid, the tube was vortexed, incubated at 300 for 30 minutes and heat-shocked at 42° for 15 minutes. The cells were then pelleted, resuspended in sterile water and plated on YPD plates containing 1 mg/ml G418.

Individual colonies of G418-resistant yeast were picked and grown in one ml of YPD with 1 mg/ml G418 for 3 days. The cells were then pelleted by centrifugation in a microfuge and the YPD (dextrose-containing, galactose-free) media was replaced with YPG (20 g bactotryptone, 10 g yeast extract, 20 g galactose per liter) with 1 mg/ml G418. Yeast were grown in YPG for 3 days to allow full induction of transcription from the Gall promoter. After induction, cells were pelleted, washed with TN (0.15M NaCl, 25 mM Tris pH 7.4) and lysed in TN containing 20 mM octyl glucopyranoside (OGP), 1 mM PMSF, and 1 ug/ml each aprotinin, leupeptin and pepstatin. Yeast were lysed by vortexing with acid-washed glass beads (425-600 microns, Sigma). Insoluble material was pelleted and the supernatant assayed using a murine GM-CSF ELISA (Endogen). A colony expressing high levels of GPI-GM-CSF was identified. Based on standard curve of soluble GMCSF, we estimate expression to be approximately 25 ug/L, a significant improvement over mammalian expression and sufficient for in vivo experiments. This yeast clone is designated SC-GM-GPI.

One of the advantages of stably integrating vectors for expression in yeast is that, after the initial cloning and colony isolation, antibiotic maintenance is no longer required. To confirm this, cells were grown with and without G418 and tested for GPI-GM-CSF expression. We have seen no decrease in expression levels in the absence of G418 over 8 months.

To produce GPI-GM-CSF on a scale suitable for in vitro and in vivo functional characterization, 500 ml of YPD was inoculated with SC-GM-GPI and grown for three days at 30° with shaking. Cells were pelleted by centrifugation at 12,000×g for 2 minutes at room temperature and transferred to an equal volume of YPG for an additional three days of growth. Cells were then pelleted, washed with TN and lysed in 25 ml of TN containing 20 mM OGP, 1 mM PMSF, and 1 ug/ml each aprotinin, leupeptin and pepstatin. Cells were then lysed by vortexing with acid washed glass beads, 20 g/500 ml culture, (425-600 microns, Sigma). Insoluble material was pelleted at 8,000×g for 10 minutes at room temperature and the soluble material was applied to an immunoaffinity column of anti-murine GMCSF monoclonal antibody (Endogen) linked to cyanogen bromide-activated Sepharose 4B (Sigma). Coupling of the monoclonal to the Sepharose was performed according to the manufacturer's instructions. Efficiency of coupling was monitored using $OD_{280}$ and binding of murine GM-CSF to immobilized antibody was confirmed using commercially available, recombinant cytokine.

Soluble yeast-derived material was applied to the column and allowed to flow by gravity. The column was washed sequentially with: (a) 20 volumes of TN with 1% Triton X-100; (b) 5 volumes of 50 mM Tris pH 8.0, 1 mM OGP; (c) 20 volumes TN with 1 mM OGP. Bound material was then eluted with 10 volumes of 0.15M NaCl, 25 mM Tris pH 2.5 with 1 mM OGP. Eluted material was neutralized with 1/200 volume of 1.5M Tris pH8.8. The purified material was concentrated using a Microsep 3K centrifugal device (Pall Gelman Laboratory). Yields of GPI-GM-CSF were determined by ELISA (Endogen) to be 25 ug/L of culture. Final concentration was adjusted to 40 ug/ml by addition of 0.15M NaCl, 25 mM Tris pH 7.4 with 1 mM OGP.

Purified GPI-GM-CSF was analyzed by stained gel and western blot. Approximately 1 ug of purified GPI-GM-CSF or recombinant soluble murine GM-CSF per lane were electrophoresed. Gels were then stained with silver nitrate using the Sigma silver staining kit according to the manufacturer's directions (Sigma). For western blots, gels were transferred to Protran BA83 (Schleicher and Schuell) using an Owl Scientific electric transblotter and blocked with TBS (Tris Buffered Saline) containing 0.05% Tween 20 and 2% nonfat dry milk overnight at room temperature. The blot was then incubated with primary antibody (rat monoclonal anti-murine GMCSF, Endogen) at 1:5000 dilution in blocking buffer for 2 hours at room temperature. The blot was washed with TBS-0.05% Tween 20, and incubated with a secondary antibody, alkaline phosphatase conjugated goat anti-rat IgG (Sigma) at 1:10,000 for 1 hour at room temperature. After washing, color was developed with NBT-BCIP (Sigma). A single dominant band migrating at approximately the same rate as a recombinant soluble GM-CSF standard was clearly present on both the gel and the blot (the molecular weight of the GPI moiety is only approximately 1500 compared to approximately 14,000 for the protein moiety]. Given the immunoreactivity with anti-GM-CSF and the ability of this material to bind to tumor cell membranes, these bands appear to represent GPI-GM-CSF. While some high molecular weight material, possibly representing aggregates, is visible in the blot, this material is not visible in the less sensitive silver stain, indicating that it is present in lower amount than the dominant band.

Example 3

Attachment of Murine GM-CSF Fused to the Gas1 GPI Modification Signal Sequence to Cells Wild type CMS-5 murine fibrosarcoma cells grown in DMEM, 10% FBS, Pen-Strep were harvested, washed twice with RPMI 1640 (Life Technologies) and resuspended in RPMI 1640 at a concentration of $5 \times 10^5$ cells/ml. 0.9 ml aliquots of the cell suspension were dispensed to Eppendorf siliconized microfuge tubes. Each aliquot received either 1 ug of purified GPI-GM-CSF prepared as in Example 2, 1 ug of soluble recombinant murine GM-CSF (Intergen, supplied as lyophilized powder and reconstituted at 40 ug/ml in the same buffer as GPI-GM-CSF), or media alone. Cells were then incubated for 3 hours at 37° C. with shaking and then washed 3 times with PBS containing 2% FBS.

For detection of GPI-GM-CSF by flow cytometry, cells were incubated with a rat anti-murine GM-CSF monoclonal antibody (Endogen) for one hour at 4° C. The cells were then washed 3 times with PBS containing 2% FBS, and incubated with FITC-labeled goat anti-rat IgG antibody (Sigma) for one hour at 4° C., and again washed 3 times with PBS containing 2% FBS. The cells were analyzed by flow cytometry on a Becton-Dickinson Facscalibur. Decoration with GPI-GM-CSF caused an approximately 10-fold increase in peak and mean FL-1 fluorescence relative to cells incubated with media alone. In contrast, cells incubated with soluble GM-CSF had virtually the same profile as the negative control cells. This data indicates that GPI-GM-CSF, but not soluble recombinant GM-CSF, can bind to tumor cells.

GPI-GM-CSF attached to CMS-5 cells was also detected and quantitated by ELISA. CMS-5 cells were harvested and washed as described above. $1\times10^6$ cells in 1 ml of RPMI 1640 were incubated with 1 ug of purified GPI-GM-CSF. After incubation for 2 hours at 37° C., the cells were washed 3 times with PBS containing 2% FBS. The cell pellet was lysed with 50 microliters of PBS containing 0.15% deoxycholate and the detergent subsequently diluted by the addition of 200 microliters of PBS. The material was serially diluted with PBS and amounts of GM-CSF determined using an ELISA kit (Endogen) against a soluble, recombinant GM-CSF standard provided by the manufacturer. Based on this data, the mean number of GPI-GM-CSF molecules incorporated/cell over five experiments was 37,000+/−33,000. The large standard deviation was due to one experiment in which the number of molecules/cell was 66,000. Excluding this experiment, the mean was 29,500+/−4,500.

"Decoration" of B16 murine melanoma cells with GPI-GM-CSF was also quantitated by ELISA. Decoration and ELISA were performed exactly as described for CMS-5 cells. The mean number of molecules/cell over three experiments was 21,000+/−11,500.

Example 4

Stability of Murine GM-CSF Fused to the Gas1 GPI Modification Signal Sequence on Cells To study the stability of incorporated GPI-GM-CSF on cells, CMS-5 cells were harvested and decorated as described above in Example 3. After decoration, the cells were washed 3 times with PBS containing 2% FBS and then resuspended at $4\times10^6$ cells/ml in RPMI 1640. The cells were irradiated at 3500 rads from a $^{137}Cs$ source. The cells were then incubated at 37° C. in 5% $CO_2$ and aliquots were removed at hourly intervals, washed three times, and lysed in 50 ul PBS with 0.15% deoxycholate. 200 ul of PBS was then added to dilute the deoxycholate. Cell-associated GM-CSF was measured by ELISA. Even at 6 hours, cells showed only about a 20% loss of cell-surface GPI-GM-CSF. After 6 hours, viability of irradiated cells (both decorated and non-decorated) as measured by microscopic inspection with trypan blue staining was significantly compromised. However, in vivo data (see below) indicates that both cell-surface retention of GPI-GM-CSF and post-irradiation cellular viability are sufficient to sustain a biological effect.

Example 5

Bioactivity of Murine GM-CSF Fused to the Gas1 GPI Modification Signal Sequence to Cells The bioactivity of GPI-GM-CSF was assayed by determining the molecule's ability to support the proliferation of the FDC-P1 cell line, a murine bone-marrow derived, GM-CSF dependent cell line. Proliferation of FDC cells was measured with the Biotrak Cell Proliferation ELISA (Amersham Pharmacia), an assay that utilizes the thymidine analogue 5-bromo-2'-deoxyuridine (BrdU). WEHI cells (ATCC) were grown in Iscove MEM, 10% FBS, Penicillin-streptomycin, as a source of conditioned media for FDC-P1 cells. FDC-P1 cells were grown in DMEM, 10% FBS, Penicillin-streptomycin with 25% WEHI conditioned media, harvested, and washed 3 times with DMEM, 10% FBS, Penicillin-streptomycin. The cells were resuspended at $1 \times 10^5$/ml in DMEM, 10% FBS, Penicillin-streptomycin and 100 uL was aliquoted to individual wells of a 96 well microtitre plate. Groups, done in triplicate, were as follows:
  A. Media-No Cells
  B. FDC-PI Cells-Unstimulated
  C. FDC-P1 Cells+10 ng soluble GM-CSF
  D. FDC-PI Cells+10 ng GM-CSF as GPI-GM-CSF (as determined by ELISA against GM-CSF standard)
  E. FDC-PI Cells+10 ng GPI-GM-CSF (as in "D") denatured by extraction of the protein with chloroform:methanol (3:1) followed by acetone precipitation and resuspension.

All protein solutions were diluted to 100 ng/ml in 0.15M NaCl, 25 mM Tris pH 7.4 with 1 mM OGP, so that the volume added to each well was 100 uL.

The non-isotopic proliferation assay was performed according to the manufacturer's instructions. The plated cells were grown for two days at 37° C. in 5% $CO_2$. On day 3, 10 ul of the BrdU solution was added to individual wells and the cells incubated for 3 more hours. The plate was then centrifuged at 300×g for 10 minutes and the supernatant removed. The plate was dried by incubating at 60° C. for one hour. The plate was then fixed and blocked according to the manufacturer's instructions. The fixed cells were then incubated with peroxidase-labelled anti-BrdU for 90 minutes. The wells were then washed and color developed with TMB according to the manufacturer's instructions. In two experiments, GPI-GM-CSF consistently sustained proliferation at a level somewhat (about 25%) higher than did soluble recombinant GM-CSF, indicating that GPI-GM-CSF is suprabioactive. The effect of GPI-GM-CSF was not due to the GPI moiety alone, since denatured GPI-GM-CSF did not support proliferation. The GPI moiety remained linked to the protein after denaturation, since the protein was still able to decorate cells as demonstrated by ELISA, which recognizes linear epitopes on GM-CSF.

Example 6

Effective Immunization with Cells Admixed with GPI-GM-CSF

These experiments included mice vaccinated with:
(a) Wild-type cells (WT)
(b) Cells incubated with soluble GM-CSF-Unwashed (total GM-CSF in dose: 1 microgram)
(c) Cells decorated with GPI-GM-CSF-Unbound GPI-GM-CSF Washed off Following Incubation (total GPI-GM-CSF in dose: 0.74 nanograms by ELISA [mean of 2 experiments; 73 and 75 ng individually)
(d) Cells decorated with GPI-GM-CSF-Unwashed (total GM-CSF in dose: 1 microgram)
GPI-GM-CSF mass and concentration values are expressed in terms of equivalence to GM-CSF as determined by ELISA against a soluble GM-CSF standard.

CMS-5 cells were grown to 70% confluence in DMEM, 10% FBS, Penicillin-streptomycin, harvested trypsinization, and washed 3 times with RPMI 1640. Viability was determined by trypan blue staining of an aliquot and the cells were then resuspended at a concentration of $4 \times 10^6$ cells/ml a 1 ul aliquots dispensed into siliconized microfuge tubes. The cells were incubated with 1 ug GPI-GM-CSF or 1 ug soluble recombinant murine GM-CSF per $10^6$ cells for 3 hours at 37° C. "Washed" groups were then washed 3 times with PBS, 2% FBS and resuspended at $4 \times 10^6$ cells/ml in RPMI 1640. An aliquot of the washed GPI-GM-CSF decorated cells was removed and the amount of cell-associated GM-CSF measured by ELISA as described above. There were approximately 31,000 and 32,000 GPI-GM-CSF molecules/cell in the washed decorated groups in the two experiments, respectively.

The cells were irradiated at 3500 rads from a $^{137}Cs$ source. 8-10 week-old female Balb/c mice (which are syngeneic for CMS-5) were anesthetized by metofane inhalation and vaccinated subcutaneously in the left inguinal fold with $1 \times 10^6$ cells in 0.25 ml. Seven days later, wild-type CMS-5 cells at 70% confluence were harvested and washed 3 times in HBSS. Viability was determined by trypan blue staining of an aliquot and cells were adjusted to $4 \times 10^6$/ml in HBSS. The previously vaccinated mice were then injected subcutaneously behind the neck, under metofane anesthesia, with $2 \times 10^6$ live, wild-type CMS-5 cells in 0.5 ml HBSS.

Tumor development was assessed daily by palpation and visual inspection. "Onset" was defined as the first day on which a tumor mass was both palpable and visible. The observer was blinded to the vaccine received by each set of mice to ensure against bias. Mice were sacrificed by CO2 asphyxiation when tumors become unwieldy. Experiments were terminated 70 days after tumor challenge, as planned in advance.

Data is pooled from three experiments for GPI-GM-CSF unwashed, soluble GM-CSF, and wild-type vaccine groups. Data for these groups includes that from undepleted controls in a lymphocyte subset depletion experiment. Data for the GPI-GM-CSF washed group is pooled from two experiments, since this group was not included in the initial depletion experiment. The depletion experiment had 4 mice/group, and the other experiments had 5/group. In terms of total mouse numbers, n=14 for GPI-GM-CSF unwashed; 10 for GPI-GM-CSF washed; 14 for soluble GM-CSF unwashed; and 14 for WT. Approximate percentages of mice surviving tumor-free to day 70 after challenge were: WT, 15%; soluble GM-CSF, 50%; GPI-GM-CSF washed, 60%; GPI-GM-CSF unwashed, 85%. Thus, even though the GPI-GM-CSF washed vaccine contained over a thousand-fold less GM-CSF than the unwashed soluble, administration of cells decorated with GPI-GM-CSF was more effective. Furthermore, the GPI-GM-CSF unwashed vaccine, in which some molecules were not attached to a cell, was even more effective.

Example 7

Cloning and Expression of Human GM-CSF Fused to the Gas1 GPI Modification Signal Sequence Human GM-CSF is amplified by PCR from a human T cell cDNA library (Clontech) using Pfu polymerase (Stratagene). The following primers are used:

```
Upstream
5'GCGAATCCCGGCCGGCACCCGCCCGCTCGCCCAGCCCC

Downstream
5'CAGCCGGCCTCCTGGACTGGCTCCCAGCAGTC
```

The upstream primer contains EcoR1 and Eag1 restriction sites immediately preceding the first amino acid found in the mature human GM-CSF protein. Since expression in *S. cerevisiae* utilizes a yeast leader sequence, cloning of the human GM-CSF begins at the N terminus of the mature protein. Each downstream primer omits the native stop codon to allow in-frame ligation to the sequence encoding the Gas1 GPI modification signal. The downstream primer contains an NgoM IV restriction site, consistent with restriction sites used in other constructs.

PCR parameters are denaturation at 97° C. for 1 minute, annealing at 56° C. for 1 minute, and extension at 72° C. for 2 minutes.

PCR is performed for the least number of cycles yielding a visible band on agarose gel electrophoresis. After amplification, the reaction mix is allowed to cool at 4° for 10 minutes.

The PCR product is isolated by electrophoresis through a 1% agarose gel and eluted from the excised agarose band using a commercially available kit (Qiagen). The purified hGM-CSF DNA fragment is digested with EcoR1 and NgoM IV and ligated to the (murine) pUC19 GM-CSF-GPI plasmid that has been digested with EcoR1 and NgoM IV. This replaces the murine GM-CSF with its human counterpart. The pUC19-hGM-CSF GPI plasmid is then transformed into competent AG-1 *E. coli* cells, 30 colonies are picked for mini-culture, and plasmid clones are isolated and purified using commercially available kits (Qiagen). Positive clones are identified by restriction enzyme test digest and agarose gel electrophoresis. Positive *E. coli* colonies are grown overnight in maxi-culture and their plasmids purified using Qiagen maxi-prep kits. Inserts are sequenced.

To clone GM-CSF GAS1 g into the pITY-4 expression vector, PCR of this construct from the pUC19 vector is performed. The primers are:

```
5' TACGGCCGGCACCCGCCCGCTCGCCCAGCCCC

3' TACGGCCGCCACAATGAAAATAAGATACCAT
```

The upstream primer has an EagI site immediately preceding the first codon of the mature GM-CSF. This removes the mammalian secretion signal and allows for in-frame ligation to the yeast signal sequence. The same restriction site can be used as for the mouse construct because it is absent in the human sequence. The downstream primer appends an EagI site at the 3' end. PCR is performed using Pfu polymerase for 25 cycles. Conditions for PCR are: denaturation 90° one minute, annealing 60° one minute, extension 72° one minute. After amplification, the reaction mix is allowed to cool at 4° for 10 minutes.

The PCR product is isolated by electrophoresis through a 1% agarose gel and eluted from the excised agarose band using a commercially available kit (Qiagen). The purified GM-CSF GAS1 g DNA fragment is digested with EagI, ligated to pITY-4, and transformed into AG-1 chemically competent bacteria (Stratagene). 30 colonies are picked for mini-culture and plasmid clones are isolated and purified using commercially available kits (Qiagen). Positive clones are identified by restriction enzyme test digest and agarose gel electrophoresis. Positive *E. coli* colonies are grown overnight in maxi-culture and their plasmids purified using Qiagen maxi-prep kits. Inserts are sequenced.

The GPI-human GM-CSF molecule is expressed in *S. cerevesiae* as described for the murine molecule in Example 2. Immunoaffinity purification is performed as described in Example 2, substituting an anti-human GM-CSF antibody for the anti-murine GM-CSF antibody. ELISA to detect and quantitate the molecule, whether in isolation or bound to an antigen bearing target, is performed using an anti-human GM-CSF monoclonal antibody, as is flow cytometry on cells decorated with the molecule.

Example 8

Cloning of GM-CSF/Influenza Hemagglutinin Chimeric Proteins pUC19 GMCSF-K-GAS1.1 pUC19 GM-CSF-K-HA was cloned starting with pUC19 GM-CSF-K-Gas1.1, which we produced in our laboratory. This plasmid includes a sequence that encodes murine GM-CSF. fused to a downstream glycosylphosphatidylinositol modification sequence derived from the yeast GAS1 protein (the latter obtained from Dr. D. Wittrup, University of Illinois). A linker sequence is interposed between the GM-CSF and GAS1 portions. To insert the linker sequence, the plasmid pUC19 GMCSF-Gas1.1, also previously produced in our lab, was digested with NgoM IV and NheI. These restriction enzymes cut at the 3' end of the GM-CSF molecule and at the 5' end of the Gas1.1 sequence, respectively. The resulting plasmid was purified after electrophoresis through agarose gel using a kit manufactured by Qiagen. The following oligonucleotides were purchased:

```
5' CCGGCACTAGTGGCGGAGGGGGCTCCGGCGGCGGGGGCAGCG

5' CTAGCGCTGCCCCCGCCGCCGGCGCCCCCTCCGCCACTAGTG
```

The synthetic oligonucleotides contain:

1. 5' overhang that anneals to NgoM IV digested plasmid DNA
2. 3' overhang that anneals to Nhe I digested plasmid DNA
3. DNA sequence coding for the peptide GGGGSGGGGS where G stands for glycine and S stands for serine. This 10 amino acid sequence $(G_4S)_2$ is designed to insert a kink/spacer in the protein between the GMCSF and the Gas1.1 moieties.
4. SpeI site to allow confirmation of cloning of the small fragment and for further manipulations.

The two oligonucleotides were mixed in equimolar concentrations, boiled for 2 minutes and allowed to anneal at room temperature. The oligonucleotide was ligated into the NgoM IV-Nhe I digested plasmid and the plasmid was used to transform the *E. coli* strain AG-1. Transformants were selected on LB plates containing 100 ug/ml ampicillin. Plasmid DNA was isolated, digested with Spe I, and electrophoresed on agarose gels to confirm the presence of the $(G_4S)_2$ sequence.

pUC19 GM-CSF-K-hemagglutinin (HA)

The plasmid pUC19 GM-CSF-K-HA was produced, which encodes a chimeric protein containing (from amino terminal to carboxy terminal): (1) murine GM-CSF; (2) the $(G_4S)_2$ linker described above; and (3) the HA1 domain of the H1 HA from the A/PR/8/34 influenza A isolate. The HA1 sequence used (amino acids 18 to 344 of the HA precursor) omits the N-terminal leader sequence and the downstream HA2 domain. A termination codon was added after amino acid 344.

pUC19 GM-CSF-K-Gas1.1. was digested with Nhe I and Kpn I. Nhe I cuts at the 5' end of the Gas1.1 coding sequence and Kpn I cuts at the 3' end of the Gas1.1 coding sequence, respectively. The resulting plasmid with the GPI coding region removed, was purified after electrophoresis through agarose gel using a kit manufactured by Qiagen. The HA1 coding sequence was cloned by PCR from a plasmid encoding the HA gene of the A/PR/8/34 strain of influenza. The HA1 sequence used begins at amino acid 18, the start of the mature protein, i.e. lacking the secretion signal sequence. The 3' end corresponds to amino acid 344, eliminating the transmembrane region and substituting a termination codon. Primers for PCR of the HA1 sequence were as follows:

```
Upstream HA1 Primer
5' ATGCTAGCGACACAATATGTATAGGC

Downstream HA1 Primer
5' ATGGTACCCGGCCGTTATCATCTGGATTGAATGGACGG
```

Conditions for PCR were:

| Denaturation | 90° one minute |
|---|---|
| Annealing | 60° one minute |
| Extension | 72° one minute |

PCR was performed for 20 cycles using vent polymerase.

Following PCR, the product was electrophoresed through a 1.0% agarose gel and the HA1 cDNA was extracted from the gel using a Qiagen kit according to the manufacturer's instructions. The purified HA1 DNA fragment was digested with Nhe I and Kpn I. To make the fusion protein, the purified Nhe I-Kpn I HA fragment was ligated into the pUC19 GM-CSF-K-Gas1.1 vector that had been digested with Nhe I and Kpn I to remove the Gas1.1 coding region. The DNA was used to transform *E. coli* AG1 and transformants selected on LB-ampicillin plates. Plasmid DNA from individual colonies was isolated and digested with restriction enzymes. Restriction digests identified a pUC19 GM-CSF-K-HA plasmid.

The pUC19 GM-CSF-K-HA plasmid was purified according to the manufacturer's instructions using a kit purchased from Qiagen.

Example 9

Cloning of GM-CSF-K-HA into Yeast Expression Vector

PCR of pUC19 GM-CSF-K-HA was used to isolate a DNA fragment encoding GM-CSF-K-HA for cloning into a yeast expression vector. The PCR product contains Eag I cloning sites for in frame insertion into the yeast expression vector.

```
Upstream Primer
5' TACGGCCGGCACCCACCCGCTCACCC

Downstream Primer
5' ATGGTACCCGGCCGTTATCATCTGGATTGAATGGACGG
```

Conditions for PCR were:

| | |
|---|---|
| Denaturation | 90° one minute |
| Annealing | 60° one minute |
| Extension | 72° one minute |

PCR was performed for 20 cycles using vent polymerase.

Following PCR, the product was electrophoresed through a 1.0% agarose gel and the GM-CSF-K-HA gene was extracted from the gel using a Qiagen kit according to the manufacturers instructions. The purified DNA fragment was digested with Eag I and ligated to the yeast expression vector ITK that had been digested with Eag I. The ITK vector is designed for (1) replication in *E. coli* and (2) expression of genes in the yeast *Saccharomyces cerevisiae* after stable integration using homologous recombination. The vector contains:

1. Sequences for replication of the plasmid in *E. coli*
2. Yeast Gal promoter for expression of heterologous genes in yeast grown in media containing galactose.
3. PrePro—Synthetic DNA sequence, optimized for secretion and signal sequence cleavage of distal genes in yeast.
4. Unique Eag I site for cloning genes to be expressed.
5. Alpha terminator-DNA sequence for efficient termination of proximal genes.
6. Delta sequence that allows for stable integration of the plasmid by recombination with endogenous delta sequences in the yeast chromosome.
7. Antibiotic resistance gene allowing for selection in *E. coli* with kanamycin and selection in yeast with G418.

This plasmid was used to transform *E. coli* strain AG-1. Transformants were selected by growth on LB plates containing 100 ug/ml kanamycin. Individual colonies were grown in LB media containing kanamycin and plasmids were purified. Restriction digests determined orientation of inserts. The resulting plasmid ITK GM-CSF-K-HA was purified using a kit purchased from Qiagen according to the manufacturer's instructions.

Example 10

Expression of GM-CSF-K-HA in Yeast

The purified plasmid was linearized with Mfe 1 and used to transform the yeast strain *Saccharomyces cerevisiae* WDHY131 using lithium acetate (LiAc). A 10 ml culture of *S. cerevisiae* grown to saturation at 30° in YPD media (per liter/20 g Bactotryptone; 20 g dextrose; 10 g yeast extract) was used to inoculate 100 ml of YPD. The culture was grown at 300 with shaking for 3 hours. The yeast were harvested by centrifugation at 11,000×g for 2 minutes and resuspended in 25 ml of sterile water. The yeast were centrifuged as above and resuspended in 1.0 ml of 100 mM lithium acetate and transferred to a 1.5 ml microfuge tube. The yeast were pelleted by centrifugation at 12,000×g for 15 seconds and the supernatant removed. The cells were resuspended in 0.5 ml of 100 mM LiAc. 50 uL of cell suspension was added to individual microfuge tubes and centrifuged as above. Supernatant was removed.

Transformation mix added to the yeast pellet consisted of: 240 uL PEG (50% w/v); 36 uL 1.0 M LiAc; 5 uL single stranded DNA (10 mg/ml) and 1 ug of linearized ITK GM-CSF-K-HA in 75 uL of water. The mixture was vortexed to resuspend the cell pellet and incubated at 30° for 30 minutes. The cells were then shocked at 42° for 15 minutes, centrifuged to pellet cells and resuspended in 0.5 ml of YPD. Yeast were incubated in YPD media for 3 hours and plated on YPD plates containing 2 mg/ml G418. Plates were grown at 300 for 3 days until individual colonies appeared. To screen for expression of GM-CSF-K-HA, individual colonies were grown in 1 ml of YPD media at 300 for 2 days. The cells were centrifuged at 8,000×g for 2 minutes and the YPD media removed and replaced with 1 ml of YPG media (per liter/20 g Bactotryptone; 20 g galactose; 10 g yeast extract) for induction from the gal promoter. Yeast were grown in YPG media for 2 days. At this time, an aliquot was removed and cells were pelleted. The supernatant was tested for GM-CSF expression using an ELISA kit purchased from Endogen. Protocol was according to the manufacturer. A high-expressing yeast clone secreting the chimeric protein GM-CSF-K-HA was identified. Based on standard curve of soluble GMCSF, expression level was approximately 2.4 mg/L of GM-CSF moiety.

Example 11

Production of pUC19 HA (hemagglutinin)-K-GM-CSF

The plasmid pUC19 HA-K-GM-CSF was also produced, which encodes a chimeric protein containing (from amino terminal to carboxy terminal): (1) an HA1 domain (2) K, the $(G_4S)_2$ linker described above, and (3) murine GM-CSF, The HA1 begins at the amino terminus of the mature protein, amino acid 18, eliminating the leader sequence. The 3' end terminates at amino acid 344. The $(G_4S)_2$ has been added to supply a flexible linker. The GM-CSF begins at amino acid 18 of the GM-CSF protein, corresponding to the first amino acid of the mature protein.

The HA-K sequence was first cloned by PCR of the HA1 coding sequence from a plasmid encoding the HA gene of the A/PR/8/34 strain of influenza.

```
Upstream Primer
5' CTGAATTCCGGCCGGACACAATATGTATAGGC

Downstream Primer
5' ATGGTACCGCTGCCCCCGCCGCCGGAGCCCCCTCCGCCACTTC
TGGATTGAATGGACGGAAT
```

The oligonucleotides for PCR generate a nucleic acid with:
1. A 5' EcoRI site at the amino terminus of the mature HA
2. The $(G_4S)_2$ linker at the carboxy terminus of the HA1 domain (amino acid 344 of the HA precursor)
3. A Kpn I site distal to the end of the $(G_4S)_2$ sequence
Conditions for PCR were:

| Denaturation | 90° one minute |
| Annealing | 60° one minute |
| Extension | 72° one minute |

PCR was performed for 20 cycles using vent polymerase.

Following PCR, the product was electrophoresed through a 1.0% agarose gel and the HA1-K DNA was extracted from the gel using a Qiagen kit according to the manufacturer's instructions. The purified HA-K DNA fragment was digested with EcoRI and Kpn I and the fragment was cloned into pUC19 that had been digested with EcoRI and KpnI. The plasmid was used to transform E. coli AG-1 to amp$^r$. Individual colonies were picked and grown in LB-amp. The identity of plasmids with the correct insert was determined by restriction mapping. The resulting plasmid termed pUC19 HA-K was purified using a Qiagen kit according to the manufacturer's instructions.
The GM-CSF fragment was cloned by PCR.

```
Upstream Primer
5' ACGGTACCGCACCCACCCGCTCACCCATC

Downstream Primer
5' TAGGATCCCGGCCGTCATTTTTGGACTGGTTTTTTGCACG
```

The PCR primers generate a GM-CSF fragment with
1. 5' KpnI site that allows in frame translation from the $(G_4S)_2$ portion of the HA-K molecule to the start of the mature GM-CSF molecule at amino acid 18.
2. A termination codon at the 3' end of the GM-CSF
3. 3' BamHI site
Conditions for PCR were:

| Denaturation | 90° one minute |
| Annealing | 60° one minute |
| Extension | 72° one minute |

PCR was performed for 20 cycles using vent polymerase.

Following PCR, the product was electrophoresed through a 1.0% agarose gel and the GM-CSF gene was extracted from the gel using a Qiagen kit according to the manufacturer's instructions. The purified fragment was digested with Kpn I and BamHI and the fragment was ligated into pUC19 HA-K plasmid that had been digested with KpnI and BamHI. The plasmid was used to transform E. coli AG-1 to amp$^r$. Individual colonies were picked and grown in LB-amp. The identity of plasmids with the correct insert was determined by restriction mapping. The resulting plasmid termed pUC19 HA-K-GM-CSF was purified using a Qiagen kit according to the manufacturer's instructions.

Example 12

Cloning of HA-K-GM-CSF into Yeast Expression Vector

PCR of pUC19 HA-K-GM-CSF was used to generate a DNA fragment encoding HA-K-GM-CSF for cloning into a yeast expression vector. The PCR product contains Eag I cloning sites for in-frame insertion into the yeast expression vector.

```
Upstream Primer
5' CTGAATTCCGGCCGGACACAATATGTATAGGC

Downstream Primer
5' TAGGATCCCGGCCGTCATTTTTGGACTGGTTTTTTGCACG
```

Conditions for PCR were:

| Denaturation | 90° one minute |
| Annealing | 60° one minute |
| Extension | 72° one minute |

PCR was performed for 20 cycles using vent polymerase.

Following PCR, the product was electrophoresed through a 1.0% agarose gel and the HA-K-GM-CSF gene was extracted from the gel using a Qiagen kit according to the manufacturers instructions. The purified DNA fragment was digested with Eag I and ligated to the yeast expression vector ITK, that had been digested with Eag I. The ITK vector is designed for (1) replication in E. coli and (2) expression of genes in the yeast Saccharomyces cerevisiae after stable integration using homologous recombination. The vector contains:
1. Sequences for replication of the plasmid in E. coli
2. Yeast Gal promoter for expression of heterologous genes in media containing galactose.
3. PrePro—Synthetic DNA sequence, optimized for secretion and signal sequence cleavage of distal genes in yeast.

4. Unique Eag I site for cloning genes to be expressed.
5. Alpha terminator-DNA sequence for efficient termination of proximal genes.
6. Delta sequence that allows for stable integration of the plasmid by recombination with endogenous delta sequences in the yeast chromosome.
7. Antibiotic resistance gene allowing for selection in *E. coli* with kanamycin and selection in yeast with G418.

This plasmid was used to transform *E. coli* strain AG-1. Transformants were selected by growth on LB plates containing 100 ug/ml kanamycin. Individual colonies were grown in LB media containing kanamycin and plasmids were purified. Restriction digests determined orientation of inserts. The resulting plasmid ITK HA-K-GM-CSF was purified using a kit purchased from Qiagen according to the manufacturer's instructions.

The purified plasmid was linearized with Mfe 1 and used to transform the yeast strain *Saccharomyces cerevisiae* WDHY131 using lithium acetate (LiAc). A 10 ml culture of *S. cerevisiae* grown to saturation at 30° C. in YPD media (per liter/20 g Bactotryptone; 20 g dextrose; 10 g yeast extract) was used to inoculate 100 ml of YPD. The culture was grown at 30° C. with shaking for 3 hours. The yeast were harvested by centrifugation at 11,000×g for 2 minutes and resuspended in 25 ml of sterile water. The yeast were centrifuged as above and resuspended in 1.0 ml of 100 mM lithium acetate and transferred to a 1.5 ml microfuge tube. The yeast were pelleted by centrifugation at 12,000×g for 15 seconds and the supernatant removed. The cells were resuspended in 0.5 ml of 100 mM LiAc. 50 uL of cell suspension was added to individual microfuge tubes and centrifuged as above. Supernatant was removed. Transformation mix added to the yeast pellet consisted of: 240 uL PEG (50% w/v); 36 uL 1.0 M LiAc; 5 uL single stranded DNA (10 mg/ml) and 1 ug of linearized ITK HA-K-GM-CSF in 75 uL of water. The mixture was vortexed to resuspend the cell pellet and incubated at 30° for 30 minutes. The cells were then shocked at 42° C. for 15 minutes, centrifuged to pellet cells and resuspended in 0.5 ml of YPD. Yeast were incubated in YPD media for 3 hours and plated on YPD plates containing 2 mg/ml G418. Plates were grown at 30° C. for 3 days until individual colonies appeared. To screen for expression of HA-K-GM-CSF, individual colonies were grown in 1 ml of YPD media at 30° C. for 2 days. The cells were centrifuged at 8,000×g for 2 minutes and the YPD media removed and replaced with 1 ml of YPG media (per liter/20 g Bactotryptone; 20 g galactose; 10 g yeast extract) for induction from the gal promoter. Yeast were grown in YPG media for 2 days. At this time, an aliquot was removed and cells were pelleted. The supernatant was tested for GM-CSF expression using an ELISA kit purchased from Endogen. The protocol was according to the manufacturer.

A colony expressing high levels of the chimeric protein was identified. Based on standard curve of soluble GMCSF, expression level is approximately 2.0 mg/L of soluble material. There is no decrease in expression levels in the absence of G418.

Example 13

Scale Up Purification of GM-CSF-K-HA

For scaled-up purification of the chimeric protein, yeast were inoculated into 500 ml of YPD and grown for three days at 30° C. Cells were pelleted by centrifugation at 12,000×g for 2 minutes and transferred to an equal volume of YPG for an additional three days of growth. The cells were then pelleted by centrifugation at 12,000×g for 2 minutes and the supernatant collected. The soluble material was applied to an immunoaffinity column of anti-murine GMCSF monoclonal antibody (Endogen) linked to cyanogen bromide-activated Sepharose 4B (Sigma). Coupling of the monoclonal to the Sepharose was performed according to the manufacturer. Efficiency of coupling was monitored using $OD_{280}$ and of binding of GMCSF to immobilized antibody was tested using soluble, commercially available material.

Soluble yeast-derived material was applied to the column and allowed to flow by gravity. The column was washed with: (a) 20 volumes of 0.15M NaCl, 25 mM Tris pH 7.4 (TN) (b) 5 volumes of 50 mM Tris pH 8.0 (c) 20 volumes TN. Bound material was then eluted with 10 volumes of 0.15M NaCl, 25 mM Tris pH 2.5. Eluted material was neutralized with 1/200 volume of 1.5M Tris pH8.8. The purified material was concentrated using a Microsep 3K centrifugal devise (Pall Gelman Laboratory). Yields of chimeric protein were determined by ELISA (Endogen) according to the manufacturer's instructions.

Purified GM-CSF-K-HA

Purified GM-CSF-K-HA was analyzed by western blot. Approximately 1 ug of GM-K-HA per lane was electrophoresed along with soluble GMCSF. For western blot, gels were transferred to Protran BA83 (Schleicher and Schuell), blocked with TBS (Tris Buffered Saline) containing 0.05% Tween 20 and 2% Nonfat Dry Milk. The blot was incubated with primary antibody (rat monoclonal anti-murine GMCSF, Endogen) at 1:5000 dilution in blocking buffer for 2 hours at room temperature. The blot was washed with TBS-0.05% Tween 20. Secondary antibody, alkaline phosphatase conjugated anti-rat IgG (Sigma) was incubated at 1:10,000 for 1 hour at room temperature.

Example 14

Decoration of Cells with GM-K-HA

Purified GM-CSF-K-HA was used to decorate CMS 5 murine fibrosarcoma cells. CMS 5 cells were grown in DMEM, 10% FBS, Penicillin-streptomycin, harvested by trypsinization and washed 3 times with RPMI 1640 (Gibco). Cells were diluted to $1 \times 10^6$/ml in RPMI 1640 and 0.9 ml were aliquoted to siliconized tubes. Cells were incubated for 2 hours at 37° C. with shaking and then washed 3 times with PBS containing 2% FBS. Primary antibody, rat anti-murine GMCSF monoclonal, was incubated for one hour at 4° C. Cells were washed as above, treated with FITC labeled anti-rat antibody (Sigma), and incubated for one hour at 4° C. After additional washing, the cells were analyzed by flow cytometry, which confirmed the presence of GM-CSF-K-HA on the surface of the tumor cells.

Example 15

Quantitation of GM-CSF-K-HA on the Cell Surface of CMS 5 Cells after Decoration

CMS 5 cells were harvested and washed as described above. $1 \times 10^6$ cells in 1 ml of RPMI 1640 were incubated with 1 ug of purified GM-K-HA. After incubation for 15 min, 30 min, 1 hour, or 2 hours at 4° C., room temperature, or 37° C., the cells were washed 3 times with PBS containing 2% FBS. The cell pellet was lysed with 50 microliters of PBS containing 0.15% deoxycholate and the detergent subsequently diluted by the addition of 200 microliters of PBS.

The material was serially diluted with PBS and tested by ELISA (Endogen). Based on the amount of GM-CSF detected in the cell lysates, it was possible to quantitate the average number of GM-CSF molecules associated with each cell. For example, after a 15 min incubation at 4° C., 58,700 molecules were present per cell. After a 15 min incubation at room temperature, 25,700 molecules were present per cell. After a 15 min incubation at 37° C., 17,200 molecules were present per cell.

Example 16

Effective Immunization with Tumor Cells Admixed with GM-CSF/Hemagglutinin Fusion Polypeptides CMS-5 murine fibrosarcoma cells were grown to 70% confluence in DMEM, 10% FBS, Penicillin-streptomycin, harvested by trypsinization, and washed 3 times with RPMI 1640. Viability was determined by trypan blue staining of an aliquot and the cells were then resuspended at a concentration of $4 \times 10^6$ cells/ml and 1 ml aliquots dispensed into siliconized microfuge tubes. The cells were incubated with 1 ug (microgram) murine GM-CSF-K-HA or 10 ng (nanograms) HA-K-murine GM-CSF per $10^6$ cells for 3 hours at 37° C. Cells were then washed 3 times with RPMI 1640 and resuspended at $4 \times 10^6$ cells/ml in RPMI 1640. An aliquot of the cells was removed and the amount of cell-associated GM-CSF measured by ELISA as described above. There were approximately 20,240 and 18,000 molecules/cell in the GM-CSF-K-HA and HA-K-GM-CSF groups, respectively. Cells for a control vaccine, to be administered without a molecule of the invention (or any other immunomodulator), were prepared in parallel.

The cells were irradiated at 3500 rads from a $^{137}$Cs source. 8 week-old female Balb/c mice (which are syngeneic for CMS-5) were anesthetized by metofane inhalation and vaccinated subcutaneously in the left inguinal fold with $1 \times 10^6$ cells in 0.25 ml. Each mouse received cells from only one vaccine type. Seven days later, wild-type CMS-5 cells at 70% confluence were harvested and washed 3 times in HBSS. Viability was determined by trypan blue staining of an aliquot and cells were adjusted to $4 \times 10^6$/ml in HBSS. The previously vaccinated mice were then injected subcutaneously behind the neck, under metofane anesthesia, with $2 \times 10^6$ live, wild-type CMS-5 cells in 0.5 ml HBSS. The groups receiving the HA-K-GM-CSF and control vaccines each consisted of 5 mice, whereas the group receiving the GM-CSF-K-HA vaccine consisted of 4 mice because 1 mouse failed to awaken from anesthesia.

Tumor development was assessed daily by palpation and visual inspection. The observer was blinded to the vaccine received by each set of mice to ensure against bias. Mice were sacrificed by C02 asphyxiation when tumors become unwieldy. All mice that had received the control vaccine developed tumors within 18 days after challenge with live tumor cells. In contrast, 100% of mice that had received the GM-CSF-K-HA vaccine and 60% of mice that had received the HA-K-GM-CSF vaccine remained tumor-free at the end of the experiment, 40 days after challenge. Thus, immunization with a composition comprising tumor cells and a molecule of the invention confers significantly longer tumor-free survival than immunization with a composition comprising tumor cells but not comprising a molecule of the invention.

Example 17

Cloning of Human GM-CSF-K-HA pUC19 human GM-CSF-K-HA (hGM-CSF-K-HA) is cloned starting with pUC19 GM-CSF-K-HA. pUC19 GM-CSF-K-HA. is digested with EcoRI and NgoM IV. EcoRI cuts at the 5' end of the murine GM-CSF coding sequence and Ngo M IV cuts at the 3' end of the murine GM-CSF molecule. The resulting plasmid with the murine GM-CSF coding region removed is purified after electrophoresis through agarose gel using a kit manufactured by Qiagen. The human GM-CSF coding segment is generated by PCR from a commercially available human cDNA library (Clontech). The human sequence begins at amino acid 18, the start of the mature protein, i.e. lacking the secretory signal sequence. The 3' end corresponds to amino acid 144, eliminating the endogenous termination codon.

```
Upstream hGM-CSF Primer
5' GCGAATTCCGGCCGGCACCCGCCCGCTCGCCCAGC

Downstream hGM-CSF Primer
5' TAGCCGGCCTCCTGGACTGGCTCCCAGCA
```

Conditions for PCR are:

| Denaturation | 90° one minute |
|---|---|
| Annealing | 60° one minute |
| Extension | 72° one minute |

PCR is performed for 20 cycles using vent polymerase.

Following PCR, the product is electrophoresed through a 1.0% agarose gel and the hGM-CSF gene is extracted from the gel using a Qiagen kit according to the manufacturer's instructions. The purified hGM-CSF DNA fragment is digested with Eco RI and NgoM IV and ligated into the pUC19 murine GM-CSF-K-HA vector that has been digested with EcoRI and NgoM IV to remove the murine GM-CSF sequence. The DNA is used to transform *E. coli* AG1 and transformants are selected on LB-ampicillin plates. Plasmid DNA from individual colonies is isolated and digested with restriction enzymes to identify clone harboring a pUC19 hGM-CSF-K-HA plasmid.

The pUC19 hGM-CSF-K-HA plasmid is purified according to the manufacturer's instructions using a kit purchased from Qiagen. PCR of pUC19 hGM-CSF-K-HA is used to generate a DNA fragment encoding hGM-CSF-K-HA for cloning into a yeast expression vector. The PCR product contains Eag I cloning sites for in frame insertion into the yeast expression vector.

```
Upstream Primer
5' GCGAATTCCGGCCGGCACCCGCCCGCTCGCCCAGC

Downstream Primer
5' ATGGTACCCGGCCGTTATCATCTGGATTGAATGGACGG
```

Conditions for PCR are:

| Denaturation | 90° one minute |
|---|---|
| Annealing | 60° one minute |
| Extension | 72° one minute |

PCR is performed for 20 cycles using vent polymerase.

Following PCR the product is electrophoresed through a 1.0% agarose gel and the hGM-CSF-K-HA gene is extracted from the gel using a Qiagen kit according to the manufacturer's instructions. The purified DNA fragment is digested with Eag I and ligated to the yeast expression vector ITK that has been digested with Eag I. The ITK vector is designed for (1) replication in *E. coli* and (2) expression of genes in the yeast *Saccharomyces cerevisiae* after stable integration using homologous recombination. The vector contains:

1. Sequences for replication of the plasmid in *E. coli*
2. Yeast Gal promoter for expression of heterologous genes in yeast grown in media containing galactose.
3. PrePro—Synthetic DNA sequence, optimized for secretion and signal sequence cleavage of distal genes in yeast.
4. Unique Eag I site for cloning genes to be expressed.
5. Alpha terminator-DNA sequence for efficient termination of proximal genes.
6. Delta sequence that allows for stable integration of the plasmid by recombination with endogenous delta sequences in the yeast chromosome.
7. Antibiotic resistance gene allowing for selection in *E. coli* with kanamycin and selection in yeast with G418.

This plasmid is used to transform *E. coli* strain AG-1. Transformants are selected by growth on LB plates containing 100 ug/ml kanamycin. Individual colonies are grown in LB media containing kanamycin and plasmids are purified. Restriction digests determine orientation of inserts. The resulting plasmid ITK hGM-CSF-K-HA is purified using a kit purchased from Qiagen according to the manufacturer's instructions.

The purified plasmid is linearized with Mfe 1 and used to transform the yeast strain *Saccharomyces cerevisiae* WDHY131 using lithium acetate (LiAc). A 10 ml culture of *S. cerevisiae* grown to saturation at 30° in YPD media (per liter/20 g Bactotryptone; 20 g dextrose; 10 g yeast extract) is used to inoculate 100 ml of YPD. The culture is grown at 30° with shaking for 3 hours. The yeast are harvested by centrifugation at 11,000×g for 2 minutes and resuspended in 25 ml of sterile water. The yeast are centrifuged as above and resuspended in 1.0 ml of 100 mM lithium acetate and transferred to a 1.5 ml microfuge tube. The yeast are pelleted by centrifugation at 12,000×g for 15 seconds and the supernatant removed. The cells are resuspended in 0.5 ml of 100 mM LiAc. 50 uL of cell suspension is added to individual microfuge tubes and centrifuged as above. Supernatant is removed. Transformation mix added to the yeast pellet consists of: 240 uL PEG (50% w/v); 36 uL 1.0 M LiAc; 5 uL single stranded DNA (10 mg/ml) and 1 ug of linearized ITK hGM-CSF-K-HA in 75 uL of water. The mixture is vortexed to resuspend the cell pellet and incubated at 30° for 30 minutes. The cells are then shocked at 420 for 15 minutes, centrifuged to pellet, and resuspended in 0.5 ml of YPD. Yeast are incubated in YPD media for 3 hours and plated on YPD plates containing 2 mg/ml G418. Plates are grown at 30° for 3 days until individual colonies appear.

To screen for expression of hGM-CSF-K-HA, individual colonies are grown in 1 ml of YPD media at 300 for 2 days. The cells are centrifuged at 8,000×g for 2 minutes and the YPD media removed and replaced with 1 ml of YPG media (per liter/20 g Bactotryptone; 20 g galactose; 10 g yeast extract) for induction from the gal promoter. Yeast are grown in YPG media for 2 days. An aliquot is then removed and the cells are pelleted. The supernatant is tested for hGM-CSF expression using an ELISA kit purchased from Endogen. Protocol is according to the manufacturer.

Example 18

Reduction of Metastases in a Mouse Model

B16F10 murine melanoma cells were harvested and washed three times in PBS. Cells were then suspended at $5 \times 10^5$ viable cells/ml in PBS, with viability determined by staining an aliquot of cells with Trypan blue. 100 ul of this suspension was injected into the tail veins of 8-10 week old female C57BL/6 mice. On day 1 or day 3 after tumor challenge, mice were immunized with $1 \times 10^6$ irradiated B16F10 cells subcutaneously in the left inguinal fold. Groups (3 mice each) received either cells alone, cells mixed with 1 ug soluble recombinant murine GM-CSF (Serologicals Corp.), or cells mixed with 1 ug of a multifunctional molecule of the invention comprising murine GM-CSF at the N terminus, a $(Gly_4Ser)_2$ flexible linker, and the HA1 domain of influenza A/PR/8/34 hemagglutinin at the C terminus. The latter composition comprised both free and cell-bound multifunctional molecule.

Mice were sacrificed on day 12, the thoracic cavity opened with dissecting scissors, and the lungs removed en bloc by tracheal transection. Metastases were enumerated with a hand lens. In the mice immunized 1 day after challenge, the average number of metastases/mouse was as follows:

Cells alone: 30.00
Cells+GM-CSF: 14.33
Cells+multifunctional molecule: 0.67

In the mice immunized 3 days after challenge, the average number of metastases/mouse was as follows:

Cells alone: 36.33
Cells+GM-CSF: 10.33
Cells+multifunctional molecule: 1.00

Thus, administration of the composition comprising a multifunctional molecule of the invention was able to effectively reduce metastases and treat disease.

Example 19

GM-CSF-HA1-Mediated Protection Against Tumor Challenge In Vivo

As an allogeneic tumor vaccine model, C57BL/6 mice (haplotype b) were immunized with C3H (haplotype k)-derived K1735 melanoma cells, followed by challenge with C57BL/6-derived B16F10 melanoma cells. K1735 cells were grown to 70% confluence in DMEM with 10% FBS and penicillin-streptomycin, harvested by trypsinization, and washed 3 times with RPMI 1640. Viability was determined by trypan blue staining of an aliquot and the cells were then resuspended at a concentration of $4 \times 10^6$ cells/ml for K1735. One ml aliquots were then dispensed into siliconized microfuge tubes. The cells were incubated with 1 ug mGM-CSF-HA1 (a fusion polypeptide consisting of murine GM-CSF at the N terminus, a $(Gly_4Ser)_2$ linker, and the HA1 domain of influenza A/PR/8/34) per $10^6$ cells for 2 hours at 4° C. An aliquot of the cells was removed for measurement of cell-associated GM-CSF by ELISA. Mean cell-associated GM-CSF across two experiments was approximately 60,000. Cells that were not admixed with any polypeptide and, in one experiment, cells mixed with 1 ug soluble murine GM-CSF (Serologicals Corp.) were prepared in parallel as control vaccines.

The cells were irradiated at 3500 rads from a $^{137}Cs$ source. 8 week-old female C57BL/6 mice were anesthetized by metofane inhalation and vaccinated subcutaneously in the left inguinal fold with or 1×10$^6$ cells in 0.25 ml RPMI, along with a total of 1 ug GM-CSF-HA1 (including bound and free fusion polypeptide). Each mouse received cells from only one vaccine type. Seven days later, B16F10 cells, as appropriate, at 70% confluence were harvested and washed 3 times in HBSS. Viability was determined by trypan blue staining of an aliquot and cells were adjusted in HBSS to 1×10$^5$/ml. The previously vaccinated mice were then challenged subcutaneously behind the neck, under metofane anesthesia, with 0.5 ml of the B16F10 cell suspension.

Tumor development was assessed daily by palpation and visual inspection. "Onset" was defined as the first day on which a tumor mass was both palpable and visible. The observer was blinded to the vaccine received by each set of mice to ensure against bias. Mice were sacrificed by CO2 asphyxiation when tumors become unwieldy. Experiments were terminated 70 days after tumor challenge, as planned in advance.

In pooled results from two experiments, 70 days after challenge, 7/10 mice that had been vaccinated with cells admixed with fusion polypeptide remained tumor-free. In contrast, 10/10 mice that had been vaccinated with cells alone developed tumors, as did 4/5 mice vaccinated with cells admixed with soluble murine GM-CSF.

Other Embodiments

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

The invention claimed is:

1. A vaccine composition comprising an antigen bearing target and further comprising a fusion polypeptide, said fusion polypeptide comprising: a first amino acid sequence which can bind to a carbohydrate and is HA; and a second amino acid sequence comprising a ligand for a cell surface polypeptide of a leukocyte, wherein said ligand is GM-CSF, wherein said vaccine composition comprises said fusion polypeptide bound to a carbohydrate on said antigen bearing target and further comprises some of said polypeptide which is not bound to said antigen bearing target.

2. The vaccine composition of claim 1, wherein said antigen bearing target is chosen from the group consisting of: a tumor cell, a virus, a bacterial cell, a fungal cell, a cell of a parasite, a prion, a mammalian cell, an insect cell, and a polypeptide free of other cell-derived material.

3. The vaccine composition of claim 2, wherein said antigen bearing target is pathogenic.

4. The vaccine composition of claim 2, wherein said antigen bearing target is attenuated.

5. The vaccine composition of claim 1, wherein said antigen bearing target is a cell which is unable to divide.

6. The vaccine composition of claim 1, wherein said leukocyte is an antigen presenting cell.

7. The vaccine composition of claim 6, wherein said leukocyte is a professional antigen presenting cell.

8. The vaccine composition of claim 6, wherein said leukocyte is a dendritic cell.

* * * * *

SEQUENCE LISTING

```
<160> NUMBER OF SEQ ID NOS: 31

<210> SEQ ID NO 1
<211> LENGTH: 11
<212> TYPE: PRT
<213> ORGANISM: Artificial
<220> FEATURE:
<223> OTHER INFORMATION: Synthetic Peptide Spacer

<400> SEQUENCE: 1

Arg Ala Arg Asp Pro Arg Val Pro Val Ala Thr
1               5                   10

<210> SEQ ID NO 2
<211> LENGTH: 11
<212> TYPE: DNA
<213> ORGANISM: Homo sapiens

<400> SEQUENCE: 2
cgaaaatttc c                                                           11

<210> SEQ ID NO 3
<211> LENGTH: 148
<212> TYPE: DNA
<213> ORGANISM: Artificial
<220> FEATURE:
<223> OTHER INFORMATION: Synthetic Oligonucleotide

<400> SEQUENCE: 3
aattccgcgc cggcacagtg ctcagagaca aactggtcaa gtgtgagggc atcagcctgc      60
tggctcagaa cacctcgtgg ctgctgctgc tcctgctgtc cctctccctc ctccaggcca     120
cggatttcat gtccctgtga ctgggtac                                        148

<210> SEQ ID NO 4
<211> LENGTH: 140
<212> TYPE: DNA
<213> ORGANISM: Artificial
<220> FEATURE:
<223> OTHER INFORMATION: Synthetic Oligonucleotide

<400> SEQUENCE: 4
ccagtcacag ggacatgaaa tccgtggcct ggaggaggga gagggacagc aggagcagca      60
```
gcagccacga ggtgttctga gccagcaggc tgatgccctc acacttgacc agtttgtctc    120
tgagcactgt gccggcgcgg                                                140

<210> SEQ ID NO 5
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 5
ccgaattcat gtggctgcag aatttacttt tcctgggcat tgtggtctac                50

<210> SEQ ID NO 6
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 6
cagccggctt tttggactgg tttttttgcat tcaaagggga tatcagtcag               50

<210> SEQ ID NO 7
<211> LENGTH: 37
<212> TYPE: DNA
<213> ORGANISM: Artificial
<220> FEATURE:
<223> OTHER INFORMATION: Synthetic Oligonucleotide

<400> SEQUENCE: 7
gtagccggcg ctagctcggg gtcttcttcc aagtcta                             37

<210> SEQ ID NO 8
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 8
tacggtaccc ctaggccaca atgaaataag ataccatacc                          40

<210> SEQ ID NO 9
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 9
tacggccggc acccacccgc tcaccc                                         26

<210> SEQ ID NO 10
<211> LENGTH: 31
<212> TYPE: DNA
<213> ORGANISM: Artificial
<220> FEATURE:
<223> OTHER INFORMATION: Synthetic Oligonucleotide

<400> SEQUENCE: 10
tacggccgcc acaatgaaaa taagatacca t                                   31

<210> SEQ ID NO 11

```
<211> LENGTH: 38
<212> TYPE: DNA
<213> ORGANISM: Artificial
<220> FEATURE:
<223> OTHER INFORMATION: Synthetic Oligonucleotide

<400> SEQUENCE: 11
gcgaatcccg gccggcaccc gcccgctcgc ccagcccc                              38

<210> SEQ ID NO 12
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 12
cagccggcct cctggactgg ctcccagcag tc                                    32

<210> SEQ ID NO 13
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 13
tacggccggc acccgcccgc tcgcccagcc cc                                    32

<210> SEQ ID NO 14
<211> LENGTH: 31
<212> TYPE: DNA
<213> ORGANISM: Artificial
<220> FEATURE:
<223> OTHER INFORMATION: Synthetic Oligonucleotide

<400> SEQUENCE: 14
tacggccgcc acaatgaaaa taagatacca t                                     31

<210> SEQ ID NO 15
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 15
ccggcactag tggcggaggg ggctccggcg gcggggcag cg                          42

<210> SEQ ID NO 16
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 16
ctagcgctgc ccccgccgcc ggcgccccct ccgccactag tg                         42

<210> SEQ ID NO 17
<211> LENGTH: 10
<212> TYPE: PRT
<213> ORGANISM: Artificial
<220> FEATURE:
<223> OTHER INFORMATION: Synthetic Peptide Spacer

<400> SEQUENCE: 17
```

Gly Gly Gly Gly Ser Gly Gly Gly Gly Ser
1               5                   10

<210> SEQ ID NO 18
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 18
atgctagcga cacaatatgt ataggc                                    26

<210> SEQ ID NO 19
<211> LENGTH: 38
<212> TYPE: DNA
<213> ORGANISM: Artificial
<220> FEATURE:
<223> OTHER INFORMATION: Synthetic Oligonucleotide

<400> SEQUENCE: 19
atggtacccg gccgttatca tctggattga atggacgg                       38

<210> SEQ ID NO 20
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 20
tacggccggc acccacccgc tcaccc                                    26

<210> SEQ ID NO 21
<211> LENGTH: 38
<212> TYPE: DNA
<213> ORGANISM: Artificial
<220> FEATURE:
<223> OTHER INFORMATION: Synthetic Oligonucleotide

<400> SEQUENCE: 21
atggtacccg gccgttatca tctggattga atggacgg                       38

<210> SEQ ID NO 22
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 22
ctgaattccg gccggacaca atatgtatag gc                             32

<210> SEQ ID NO 23
<211> LENGTH: 62
<212> TYPE: DNA
<213> ORGANISM: Artificial
<220> FEATURE:
<223> OTHER INFORMATION: Synthetic Oligonucleotide

<400> SEQUENCE: 23
atggtaccgc tgcccccgcc gccggagccc cctccgccac ttctggattg aatggacgga   60
at                                                                 62

```
<210> SEQ ID NO 24
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 24
acggtaccgc acccacccgc tcacccatc                                           29

<210> SEQ ID NO 25
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 25
taggatcccg gccgtcattt ttggactggt tttttgcacg                               40

<210> SEQ ID NO 26
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 26
ctgaattccg gccggacaca atatgtatag gc                                       32

<210> SEQ ID NO 27
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 27
taggatcccg gccgtcattt ttggactggt tttttgcacg                               40

<210> SEQ ID NO 28
<211> LENGTH: 35
<212> TYPE: DNA
<213> ORGANISM: Artificial
<220> FEATURE:
<223> OTHER INFORMATION: Synthetic Oligonucleotide

<400> SEQUENCE: 28
gcgaattccg gccggcaccc gcccgctcgc ccagc                                    35

<210> SEQ ID NO 29
<211> LENGTH: 29
<212> TYPE: DNA
<213> ORGANISM: Artificial
<220> FEATURE:
<223> OTHER INFORMATION: Synthetic Oligonucleotide

<400> SEQUENCE: 29
tagccggcct cctggactgg ctcccagca                                           29

<210> SEQ ID NO 30
<211> LENGTH: 35
<212> TYPE: DNA
<213> ORGANISM: Artificial
<220> FEATURE:
<223> OTHER INFORMATION: Synthetic Oligonucleotides
```

-continued

```
<400> SEQUENCE: 30
gcgaattccg gccggcaccc gcccgctcgc ccagc                            35

<210> SEQ ID NO 31
<211> LENGTH: 38
<212> TYPE: DNA
<213> ORGANISM: Artificial
<220> FEATURE:
<223> OTHER INFORMATION: Synthetic Oligonucleotide

<400> SEQUENCE: 31
atggtacccg gccgttatca tctggattga atggacgg                         38
```